(12) United States Patent
Caravatti et al.

(10) Patent No.: US 8,940,771 B2
(45) Date of Patent: *Jan. 27, 2015

(54) ORGANIC COMPOUNDS

(75) Inventors: Giorgio Caravatti, Basel (CH); Robin Alec Fairhurst, Horsham (GB); Pascal Furet, Basel (CH); Vito Guagnano, Basel (CH); Patricia Imbach, Basel (CH)

(73) Assignee: Novartis AG, Basel (CH)

( * ) Notice: Subject to any disclaimer, the term of this patent is extended or adjusted under 35 U.S.C. 154(b) by 742 days.

This patent is subject to a terminal disclaimer.

(21) Appl. No.: 12/338,432

(22) Filed: Dec. 18, 2008

(65) Prior Publication Data
US 2009/0163469 A1    Jun. 25, 2009

(30) Foreign Application Priority Data

Dec. 20, 2007 (EP) .................................. 07150228

(51) Int. Cl.
A61K 31/4439 (2006.01)
A61K 31/427 (2006.01)
C07D 417/14 (2006.01)
C07D 417/12 (2006.01)

(52) U.S. Cl.
CPC ............ C07D 417/14 (2013.01); C07D 417/12 (2013.01); A61K 31/427 (2013.01); A61K 31/4439 (2013.01)
USPC ......... 514/342; 514/371; 546/270.4; 548/196

(58) Field of Classification Search
CPC . C07D 417/14; A61K 31/4439; A61K 31/427
USPC ................ 514/342, 371; 546/270.4; 548/196
See application file for complete search history.

(56) References Cited

U.S. PATENT DOCUMENTS

| | | | |
|---|---|---|---|
| 4,649,146 A | 3/1987 | Takaya et al. | |
| 4,735,957 A | 4/1988 | Takaya et al. | |
| 6,187,797 B1 | 2/2001 | Pruitt et al. | |
| 8,293,753 B2 * | 10/2012 | Fairhurst et al. | 514/256 |
| 2009/0036654 A1 | 2/2009 | Jacobs et al. | |

FOREIGN PATENT DOCUMENTS

| | | |
|---|---|---|
| EP | 0 117 082 A2 | 8/1984 |
| EP | 0 280 873 A1 | 9/1988 |
| EP | 0 373 226 B1 | 6/1990 |
| EP | 1 256 578 A1 | 11/2002 |
| EP | 1 256 578 B1 | 11/2002 |
| GB | 2 361 236 A | 10/2001 |
| WO | WO 89/09767 A1 | 10/1989 |
| WO | 98/27108 A2 | 6/1998 |
| WO | 99/21555 A2 | 5/1999 |
| WO | WO 99/65884 A1 | 12/1999 |
| WO | 0117995 A1 | 3/2001 |
| WO | 0172745 A1 | 10/2001 |
| WO | 02/32872 A1 | 4/2002 |
| WO | 03015773 A2 | 2/2003 |
| WO | WO 03/015778 A1 | 2/2003 |
| WO | 03029248 A1 | 4/2003 |
| WO | WO 03/072557 A1 | 9/2003 |
| WO | 2004041813 A1 | 5/2004 |
| WO | WO 2004/045518 A2 | 6/2004 |
| WO | WO 2004/078754 A1 | 9/2004 |
| WO | WO 2004/096797 A1 | 11/2004 |
| WO | WO 2004096797 A1 * | 11/2004 |
| WO | WO 2005/021519 A2 | 3/2005 |
| WO | WO 2005/026137 A2 | 3/2005 |
| WO | WO 2005/068444 A2 | 7/2005 |
| WO | WO 2006/051270 A1 | 5/2006 |
| WO | WO 2006/125805 A1 | 11/2006 |
| WO | WO 2006/125807 A1 | 11/2006 |
| WO | WO 2007/033780 A2 | 3/2007 |
| WO | WO 2007/068473 A2 | 6/2007 |
| WO | WO 2007/070600 A2 | 6/2007 |
| WO | WO 2007/082956 A1 | 7/2007 |
| WO | WO 2007/134827 A8 | 11/2007 |
| WO | WO 2008/064218 A2 | 5/2008 |
| WO | WO 2008/124000 A2 | 10/2008 |
| WO | WO 2008/145616 A1 | 12/2008 |
| WO | WO 2009/003009 A1 | 12/2008 |
| WO | WO 2009/012482 A2 | 1/2009 |

OTHER PUBLICATIONS

Berge et al. J. Pharm. Sci. 1977, 66, 1-19.*
Giron, D. J. Therm. Anal. Cal. 2001, 64, pp. 37-60.*
Giron, D. J. Therm. Anal. Cal. 2002, 68, pp. 335-357.*
B. Rodriquez-Spong et al. Advanced Drug Delivery Reviews, 2004, 56, pp. 241-274.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Luo et al. Cell, 2009, 136, pp. 823-837.*
Fry, M. J., "Phosphoinositide 3-kinase signalling in breast cancer: how big a role might it play?" Breast Cancer Res., vol. 3, pp. 304-312, 2001.
Kulkarni, S. E. et al., "Reactions of o-Aminothiophenol, Guanidine, Thiourea, Hydrazine Hydrate & Hydroxylamine with Acryloylthiazoles & Microbial Activities of the Reaction Products" Indian Journal of Chem., vol. 25B, pp. 452-455, 1986.
Reddy, B. R. et al., CAPLUS Abstract 105:39172, 1986.
Simone, J. V., "Oncology: Introduction, Cecil Textbook of Medicine" 20th Ed., vol. 1, pp. 1004-1010, 1996.

* cited by examiner

*Primary Examiner* — Joseph Kosack
*Assistant Examiner* — Matthew Coughlin
(74) *Attorney, Agent, or Firm* — Scott W. Reid

(57) ABSTRACT

The present invention relates to compounds of formula I

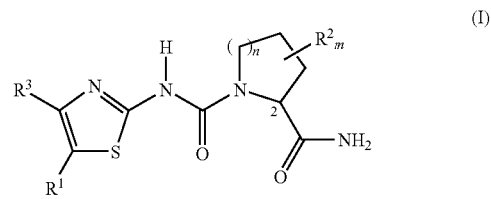

(I)

and its salts, wherein the substituents are as defined in the description, to compositions and use of the compounds in the treatment of diseases ameloriated by inhibition of phosphatidylinositol 3-kinase.

8 Claims, No Drawings

ORGANIC COMPOUNDS

This application claims priority to E.P. Application Serial No. 07150228.0 filed 20 Dec. 2007, the contents of which are incorporated herein by reference in their entirety.

The present invention relates to 2-carboxamide cycloamino urea derivatives, as new phosphatidylinositol (PI) 3-kinase inhibitor compounds, their pharmaceutically acceptable salts, prodrugs thereof and processes for their production. This invention also relates to compositions of these compounds, either alone or in combination with at least one additional therapeutic agent, and optionally in combination with a pharmaceutically acceptable carrier. This invention still further relates to methods of use of these compounds, either alone or in combination with at least one additional therapeutic agent, in the prophylaxis or treatment of a number of diseases, in particular, those mediated by one or more of abnormal activity of growth factors, receptor tyrosine kinases, protein serine/heroine kinases, G protein coupled receptors and phospholipid kinases and phosphatases.

Phosphatydylinositol 3-kinases (PI3Ks) comprise a family of lipid kinases that catalyze the transfer of phosphate to the D-3' position of inositol lipids to produce phosphoinositol-3-phosphate (PIP), phosphoinositol-3,4-diphosphate ($PIP_2$) and phosphoinositol-3,4,5-triphosphate ($PIP_3$) that, in turn, act as second messengers in signaling cascades by docking proteins containing pleckstrin-homology, FYVE, Phox and other phospholipid-binding domains into a variety of signaling complexes often at the plasma membrane ((Vanhaesebroeck et al., *Annu. Rev. Biochem* 70:535 (2001); Katso et al., *Annu. Rev. Cell Dev. Biol.* 17:615 (2001)). Of the two Class 1 PI3Ks, Class 1A PI3Ks are heterodimers composed of a catalytic p110 subunit (α, β, δ isoforms) constitutively associated with a regulatory subunit that can be p85α, p55α, p50α, p85β or p55γ. The Class 1B sub-class has one family member, a heterodimer composed of a catalytic p110γ subunit associated with one of two regulatory subunits, p101 or p84 (Fruman et al., *Annu Rev. Biochem.* 67:481 (1998); Suire et al., *Curr. Biol.* 15:566 (2005)). The modular domains of the p85/55/50 subunits include Src Homology (SH2) domains that bind phosphotyrosine residues in a specific sequence context on activated receptor and cytoplasmic tyrosine kinases, resulting in activation and localization of Class 1A PI3Ks. Class 1B PI3K is activated directly by G protein-coupled receptors that bind a diverse repertoire of peptide and non-peptide ligands (Stephens et al., *Cell* 89:105 (1997); Katso et al., *Annu. Rev. Cell Dev. Biol.* 17:615-675 (2001)). Consequently, the resultant phospholipid products of class I PI3K link upstream receptors with downstream cellular activities including proliferation, survival, chemotaxis, cellular trafficking, motility, metabolism, inflammatory and allergic responses, transcription and translation (Cantley et al., *Cell* 64:281 (1991); Escobedo and Williams, *Nature* 335:85 (1988); Fantl et al., *Cell* 69:413 (1992)).

In many cases, PIP2 and PIP3 recruit Akt, the product of the human homologue of the viral oncogene v-Akt, to the plasma membrane where it acts as a nodal point for many intracellular signaling pathways important for growth and survival (Fantl et al., *Cell* 69:413-423(1992); Bader et al., *Nature Rev. Cancer* 5:921 (2005); Vivanco and Sawyer, *Nature Rev. Cancer* 2:489 (2002)). Aberrant regulation of PI3K, which often increases survival through Akt activation, is one of the most prevalent events in human cancer and has been shown to occur at multiple levels. The tumor suppressor gene PTEN, which dephosphorylates phosphoinositides at the 3' position of the inositol ring and in so doing antagonizes PI3K activity, is functionally deleted in a variety of tumors. In other tumors, the genes for the p110α isoform, PIK3CA, and for Akt are amplified and increased protein expression of their gene products has been demonstrated in several human cancers. Furthermore, mutations and translocation of p85α that serve to up-regulate the p85-p110 complex have been described in human cancers. Finally, somatic missense mutations in PIK3CA that activate downstream signaling pathways have been described at significant frequencies in a wide diversity of human cancers (Kang et al., *Proc. Natl. Acad. Sci. USA* 102:802 (2005); Samuels et al., *Science* 304:554 (2004); Samuels et al., *Cancer Cell* 7:561-573 (2005)). These observations show that deregulation of phosphoinositol-3 kinase and the upstream and downstream components of this signaling pathway is one of the most common deregulations associated with human cancers and proliferative diseases (Parsons et al., *Nature* 436:792 (2005); Hennessey at el., *Nature Rev. Drug Disc.* 4:988-1004 (2005)).

In view of the above, inhibitors of PI3Ks would be of particular value in the treatment of proliferative disease and other disorders.

WO2004/096797 discloses certain thiazole derivatives as inhibitors of PI3 kinase and their use as pharmaceutical.

WO 2005/021519 also discloses certain thiazole derivatives as inhibitors of PI3 kinase and their use as pharmaceutical.

It has now been found that the 2-carboxamide cycloamino urea derivatives of the formula I given below have advantageous pharmacological properties and inhibit, for example, the PI3 kinases (phosphatidylinositol 3-kinase). In particular, preferably these compounds show a high degree of selectivity for PI3K alpha with respect to beta and/or delta and/or gamma subtypes in the biochemical and/or in the cellular assay. Hence, the compounds of formula I are suitable, for example, to be used in the treatment of diseases depending on the PI3 kinase (in particular PI3K alpha), especially proliferative diseases such as tumor diseases, leukaemias, polycythemia vera, essential thrombocythemia, and myelofibrosis with myeloid metaplasia.

In a first aspect, the present invention provides compounds of the formula I

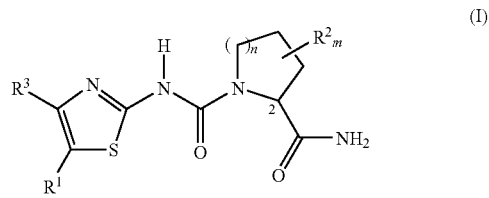

(I)

wherein n represents 1 and m represents 1, 2, 3 or 4
 or
n represents 0 and m represents 0, 1, 2 or 3;

$R^1$ represents optionally substituted aryl or optionally substituted heterocyclyl;

$R^2$ represents halo, cyano, nitro, hydroxy, phenyl, lower alkyl, lower alkoxy, lower alkylamino, lower dialkylamino, lower dialkylamino lower alkyl, cycloalkyl, cycloalkoxy wherein each alkyl or cycloalkyl may be mono or poly-substituted by halo, cyano, nitro, hydroxy, phenyl and wherein each phenyl may be mono or poly-substituted by halo, cyano, nitro, hydroxy, lower alkyl
 or
two $R^2$ substituents together form an alkandiyl or alkenediyl, each optionally substituted by hydroxy or halo, to form a cyclic moiety or two vicinal $R^2$ substituents together form a bond to form a double bond;

$R^3$ represents hydrogen, lower alkyl, mono-, poly- or per-deutero lower alkyl, halo, halo lower alkyl, hydroxy lower alkyl, lower dialkylamino lower alkyl, or salts thereof.

The invention may be more fully appreciated by reference to the following description, including the following glossary of terms and the concluding examples. For the sake of brevity, the disclosures of the publications cited in this specification are herein incorporated by reference. As used herein, the terms "including", "containing" and "comprising" are used herein in their open, non-limiting sense.

Any formula given herein is intended to represent compounds having structures depicted by the structural formula as well as certain variations or forms. In particular, compounds of any formula given herein may have asymmetric centers and therefore exist in different enantiomeric forms. If at least one asymmetrical carbon atom is present in a compound of the formula I, such a compound may exist in optically active form or in the form of a mixture of optical isomers, e.g. in the form of a racemic mixture. All optical isomers and their mixtures, including the racemic mixtures, are part of the present invention. Thus, any given formula given herein is intended to represent a racemate, one or more enantiomeric forms, one or more diastereomeric forms, one or more atropisomeric forms, and mixtures thereof. Furthermore, certain structures may exist as geometric isomers (i.e. cis and trans isomers), as tautomers, or as atropisomers.

Any formula given herein is intended to represent hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{31}P$, $^{32}P$, $^{18}F$ $^{35}S$, $^{36}Cl$, $^{125}I$ respectively. Various isotopically labeled compounds of the present invention, for example those into which radioactive isotopes such as $^3H$, $^{13}C$, and $^{14}C$ are incorporated. Such isotopically labelled compounds are useful in metabolic studies (preferably with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium, for example in the ranges given above.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula (where one or more up to all more general expressions in embodiments characterized as preferred above or below can be replaced with a more specific definition, thus leading to a more preferred embodiment of the invention, respectively).

Where the plural form (e.g. compounds, salts) is used, this includes the singular (e.g. a single compound, a single salt). "A compound" does not exclude that (e.g. in a pharmaceutical formulation) more than one compound of the formula I (or a salt thereof) is present.

The salts of compounds of formula I are preferably pharmaceutically acceptable salts; such salts are known in the field.

The following general definitions shall apply in this specification, unless otherwise specified:

Halogen (or halo) denotes fluorine, bromine, chlorine or iodine, in particular fluorine, chlorine. Halogen-substituted groups and moieties, such as alkyl substituted by halogen (halogenalkyl) can be mono-, poly- or per-halogenated.

Hetero atoms are atoms other than Carbon and Hydrogen, preferably nitrogen (N), oxygen (O) or sulfur (S), in particular nitrogen.

Carbon containing groups, moieties or molecules contain 1 to 7, preferably 1 to 6, more preferably 1 to 4, most preferably 1 or 2, carbon atoms. Any non-cyclic carbon containing group or moiety with more than 1 carbon atom is straight-chain or branched.

The prefix "lower" or "$C_1$-$C_7$" denotes a radical having up to and including a maximum of 7, especially up to and including a maximum of 4 carbon atoms, the radicals in question being either linear or branched with single or multiple branching.

"Alkyl" refers to a straight-chain or branched-chain alkyl group, preferably represents a straight-chain or branched-chain $C_{1-12}$alkyl, particularly preferably represents a straight-chain or branched-chain $C_{1-7}$alkyl; for example, methyl, ethyl, n- or iso-propyl, n-, iso-, sec- or tert-butyl, n-pentyl, n-hexyl, n-heptyl, n-octyl, n-nonyl, n-decyl, n-undecyl, n-dodecyl, with particular preference given to methyl, ethyl, n-propyl, iso-propyl and n-butyl and iso-butyl. Alkyl may be unsubstituted or substituted. Exemplary substituents include, but are not limited to hydroxy, alkoxy, halogen and amino. An example of a substituted alkyl is trifluoromethyl. Cycloalkyl may also be a substituent to alkyl. An example of such a case is the moiety (alkyl)-cycloalkyl, such as (alkyl)-cyclopropyl or (alkyl)-cyclobutyl, e.g. methyl-cyclopropyl or methyl-cyclobutyl. A more specific example of an (alkyl)-cycloalkyl moiety includes geminal-type of substitution pattern, e.g. 1-alkyl cycloalkyl, such as 1-methyl cyclopropyl. Another example of cycloalkyl as a substituent to alkyl is alkandiyl-cycloalkyl, such as alkandiyl-cyclopropyl, e.g. —$CH_2$-cyclopropyl. $C_1$-$C_7$-alkyl is preferably alkyl with from and including 1 up to and including 7, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or preferably methyl.

Each alkyl part of other groups like "alkoxy", "alkoxyalkyl", "alkoxycarbonyl", "alkoxy-carbonylalkyl", "alkylsulfonyl", "alkylsulfoxyl", "alkylamino", "halogenalkyl" shall have the same meaning as described in the above-mentioned definition of "alkyl".

"Alkandiyl" refers to a straight-chain or branched-chain alkandiyl group bound by two different Carbon atoms to the moiety, it preferably represents a straight-chain or branched-chain $C_{1-12}$ alkandiyl, particularly preferably represents a straight-chain or branched-chain $C_{1-6}$ alkandiyl; for example, methandiyl (—$CH_2$—), 1,2-ethanediyl (—$CH_2$—$CH_2$—), 1,1-ethanediyl ((—$CH(CH_3)$—), 1,1-, 1,2-, 1,3-propanediyl and 1,1-, 1,2-, 1,3-, 1,4-butanediyl, with particular preference given to methandiyl, 1,1-ethanediyl, 1,2-ethanediyl, 1,3-propanediyl, 1,4-butanediyl.

"Alkenediyl" refers to a straight-chain or branched-chain alkendiyl group bound by two different Carbon atoms to the molecule, it preferably represents a straight-chain or branched-chain $C_{2-6}$ alkenediyl; for example, —CH=CH—, —CH=C($CH_3$)—, —CH=CH—$CH_2$—, —C($CH_3$)=CH—$CH_2$—, —CH=C($CH_3$)—$CH_2$—, —CH=CH—C($CH_3$)H—, —CH=CH—CH=CH—, —C($CH_3$)=CH—CH=CH—, —CH=C($CH_3$)—CH=CH—, with particular preference given to —CH=CH—$CH_2$—, —CH=CH—CH=CH—. Alkendiyl may be substituted or unsubstituted "Cycloalkyl" refers to a saturated or partially saturated, monocyclic, fused polycyclic, or Spiro polycyclic, carbocycle having from 3 to 12 ring atoms per carbocycle. Illustrative examples of cycloalkyl groups include the following moieties: cyclopropyl, cyclobutyl, cyclopentyl and cylclohexyl. Cycloalkyl may be unsubstituted or substituted; exemplary substituents are provided in the definition for alkyl.

"Aryl" refers to an aromatic homocyclic ring system with 6 or more carbon atoms; aryl is preferably an aromatic moiety with 6 to 14 ring carbon atoms, more preferably with 6 to 10 ring carbon atoms, such as phenyl or naphthyl, preferably phenyl. Aryl may be unsubstituted or substituted by one or more, preferably up to three, more preferably up to two substituents independently selected from the group consisting of unsubstituted or substituted heterocyclyl as described below, especially pyrrolidinyl, such as pyrrolidino, oxopyrrolidinyl, such as oxo-pyrrolidino, $C_1$-$C_7$-alkyl-pyrrolidinyl, 2,5-di-($C_1$-$C_7$-alkyl)pyrrolidinyl, such as 2,5-di-($C_1$-$C_7$-alkyl)-pyrrolidino, tetrahydrofuranyl, thiophenyl, $C_1$-$C_7$-alkylpyrazolidinyl, pyridinyl, $C_1$-$C_7$ alkylpiperidinyl, piperidino, piperidino substituted by amino or N-mono- or N,N-di-[lower alkyl, phenyl, $C_1$-$C_7$-alkanoyl and/or phenyl-lower alkyl)-amino, unsubstituted or N-lower alkyl substituted piperidinyl bound via a ring carbon atom, piperazino, lower alkylpiperazino, morpholino, thiomorpholino, S-oxo-thiomorpholino or S,S-dioxothiomorpholino; $C_1$-$C_7$-alkyl, amino-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, phenyl, naphthyl, mono- to tri-[$C_1$-$C_7$-alkyl, halo and/or cyano]-phenyl or mono- to tri-[$C_1$-$C_7$-alkyl, halo and/or cyano]-naphthyl; $C_3$-$C_8$-cycloalkyl, mono- to tri-[$C_1$-$C_7$-alkyl and/or hydroxy]-$C_3$-$C_8$-cycloalkyl; halo, hydroxy, lower alkoxy, lower-alkoxy-lower alkoxy, (lower-alkoxy)-lower alkoxy-lower alkoxy, halo-$C_1$-$C_7$-alkoxy, phenoxy, naphthyloxy, phenyl- or naphthyl-lower alkoxy; amino-$C_1$-$C_7$-alkoxy, lower-alkanoyloxy, benzoyloxy, naphthoyloxy, formyl (CHO), amino, N-mono- or N,N-di-($C_1$-$C_7$-alkyl)-amino, $C_1$-$C_7$-alkanoylamino, $C_1$-$C_7$-alkanesulfonylamino, carboxy, lower alkoxy carbonyl, e.g.; phenyl- or naphthyl-lower alkoxycarbonyl, such as benzyloxycarbonyl; $C_1$-$C_7$-alkanoyl, such as acetyl, benzoyl, naphthoyl, carbamoyl, N-mono- or N,N-disubstituted carbamoyl, such as N-mono- or N,N-di-substituted carbamoyl wherein the substitutents are selected from lower alkyl, (lower-alkoxy)-lower alkyl and hydroxy-lower alkyl; amidino, guanidino, ureido, mercapto, lower alkylthio, phenyl- or naphthylthio, phenyl- or naphthyl-lower alkylthio, lower alkyl-phenylthio, lower alkyl-naphthylthio, halogen-lower alkylmercapto, sulfo (—$SO_3H$), lower alkanesulfonyl, phenyl- or naphthyl-sulfonyl, phenyl- or naphthyl-lower alkylsulfonyl, alkylphenylsulfonyl, halogen-lower alkylsulfonyl, such as trifluoromethanesulfonyl; sulfonamido, benzosulfonamido, azido, azido-$C_1$-$C_7$-alkyl, especially azidomethyl, $C_1$-$C_7$-alkanesulfonyl, sulfamoyl, N-mono- or N,N-di-($C_1$-$C_7$-alkyl)-sulfamoyl, morpholinosulfonyl, thiomorpholinosulfonyl, cyano and nitro; where each phenyl or naphthyl (also in phenoxy or naphthoxy) mentioned above as substituent or part of a substituent of substituted alkyl (or also of substituted aryl, heterocyclyl etc. mentioned herein) is itself unsubstituted or substituted by one or more, e.g. up to three, preferably 1 or 2, substituents independently selected from halo, halo-lower alkyl, such as trifluoromethyl, hydroxy, lower alkoxy, azido, amino, N-mono- or N,N-di-(lower alkyl and/or $C_1$-$C_7$-alkanoyl)-amino, nitro, carboxy, lower-alkoxy-carbonyl, carbamoyl, cyano and/or sulfamoyl.

"Heterocyclyl" refers to a heterocyclic radical that is unsaturated (=carrying the highest possible number of conjugated double bonds in the ring(s)), saturated or partially saturated and is preferably a monocyclic or in a broader aspect of the invention bicyclic, tricyclic or spirocyclic ring; and has 3 to 24, more preferably 4 to 16, most preferably 5 to 10 and most preferably 5 or 6 ring atoms; wherein one or more, preferably one to four, especially one or two carbon ring atoms are replaced by a heteroatom, the bonding ring preferably having 4 to 12, especially 5 to 7 ring atoms. The heterocyclic radical (heterocyclyl) may be unsubstituted or substituted by one or more, especially 1 to 3, substituents independently selected from the group consisting of the substituents defined above for substituted alkyl and/or from one or more of the following substituents: oxo (=O), thiocarbonyl (=S), imino (=NH), imino-lower alkyl. Further, heterocyclyl is especially a heterocyclyl radical selected from the group consisting of oxiranyl, azirinyl, aziridinyl, 1,2-oxathiolanyl, thienyl (=thiophenyl), furanyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidinyl, piperazinyl, pyridazinyl, morpholinyl, thiomorpholinyl, (S-oxo or S,S-dioxo)-thiomorpholinyl, indolizinyl, azepanyl, diazepanyl, especially 1,4-diazepanyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, beta-carbolinyl, phenanthridinyl, acridinyl, perimidinyl, phenanthrolinyl, furazanyl, phenazinyl, phenothiazinyl, phenoxazinyl, chromenyl, isochromanyl, chromanyl, benzo[1,3]dioxol-5-yl and 2,3-dihydrobenzo[1,4]di-oxin-6-yl, each of these radicals being unsubstituted or substituted by one or more, preferably up to three, substituents selected from those mentioned above for substituted aryl and/or from one or more of the following substituents: oxo (=O), thiocarbonyl (=S), imino(=NH), imino-lower alkyl.

"Arylalkyl" refers to an aryl group bound to the molecule via an alkyl group, such as a methyl or ethyl group, preferably phenethyl or benzyl, in particular benzyl. Similarly, cycloalkylalkyl and heterocyclyl represents a cycloalkyl group bound to the molecule via an alkyl group or a heterocyclyl group bound to the molecule via an alkyl group. In each instance, aryl, heterocyclyl, cycloalkyl and alkyl may be substituted as defined above.

"Treatment" includes prophylactic (preventive) and therapeutic treatment as well as the delay of progression of a disease or disorter.

"PI3 kinase mediated diseases" (especially PI3K alpha mediated diseases) are especially such disorders that respond in a beneficial way (e.g. amelioration of one or more symptoms, delay of the onset of a disease, up to temporary or complete cure from a disease) to the inhibition of a PI3 kinase, especially inhibition of PI3Kalpha (where among the diseases to be treated, especially proliferative diseases such as tumor diseases, leukaemias, polycythemia vera, essential thrombocythemia, and myelofibrosis with myeloid metaplasia may be mentioned).

"Salts" (which, what is meant by "or salts thereof" or "or a salt thereof"), can be present alone or in mixture with free compound of the formula I and are preferably pharmaceutically acceptable salts. Such salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, e.g., carboxylic acids or sulfonic acids, such as fumaric acid or methansulfonic acid. For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred. In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

Combination refers to either a fixed combination in one dosage unit form, or a kit of parts for the combined administration where a compound of the formula I and a combination partner (e.g. an other drug as explained below, also referred to as "therapeutic agent" or "co-agent") may be administered independently at the same time or separately within time intervals, especially where these time intervals allow that the combination partners show a cooperative, e.g. synergistic effect. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a combination partner, are both administered to a patient simultaneously in the form of a single entity or dosage. The term "non-fixed combination" means that the active ingredients, e.g. a compound of formula I and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

In preferred embodiments, which are preferred independently, collectively or in any combination or sub-combination, the invention relates to a compound of the formula I, in free base form or in acid addition salt form, wherein the substituents are as defined herein.

In an embodiment, the invention relates to a compound of formula I, having the following defined stereochemistry at position-2 of the nitrogen-containing heterocyclic ring, represented by formula I':

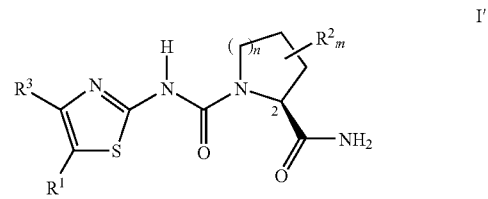

In another embodiment, the invention relates to a compound of formula I, wherein n is 1, and which is represented by formula IA:

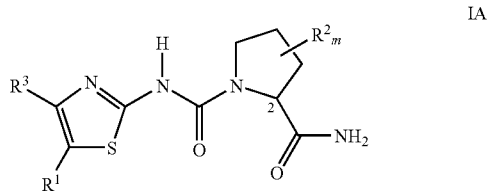

wherein the substituents are as defined for a compound of formula I and m represents 1 or 2.

In a further embodiment, the invention relates to a compound of formula I, wherein n is 0, and which is represented by formula IB:

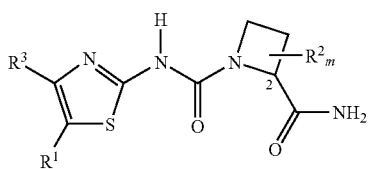

IB wherein the substituents are as defined for a compound of formula I and m represents 0 or 1.

Preferred embodiments of formulae IA and IB include the same stereochemistry at position 2 of the pyrrolidine and azetidine rings respectively as that shown for the pyrrolidine ring in formula I'.

The following preferred features apply to any of the formulas herein, in particular to formulae I, IA, IB, IC and/or (I').
$R^1$ preferably represents unsubstituted or substituted heterocyclyl or unsubstituted or substituted aryl
wherein said heterocyclyl is selected from unsaturated, saturated or partially saturated heterocycles which are monocyclic, bicyclic, tricyclic or spirocyclic and have 4 to 16, ring atoms wherein one to four heteroatoms are present;
wherein said aryl is selected from aromatic moieties with 6 to 14 ring carbon atoms;
wherein said substituents are independently selected from one or more, preferably one to four of the following moieties: $C_1$-$C_7$-alkyl; mono-, poly-, per-deutero $C_1$-$C_7$-alkyl; (phenyl-, $C_1$-$C_7$-alkylphenyl-, $C_1$-$C_7$-alkoxyphenyl-, halophenyl- or N,N-dialkylamino alkoxyphenyl)$C_1$-$C_7$-alkyl; (phenoxy-, $C_1$-$C_7$-alkylphenoxy-, $C_1$-$C_7$-alkoxyphenoxy- or halophenoxy-)$C_1$-$C_7$-alkyl; $C_3$-$C_{12}$-cycloalkyl; mono-, poly-, per-deutero $C_3$-$C_{12}$-cycloalkyl; ($C_1$-$C_7$-alkyl)-$C_3$-$C_{12}$ cycloalkyl; (mono-, poly-, per-deutero $C_1$-$C_7$-alkyl)-$C_3$-$C_{12}$-cycloalkyl; (phenyl-, $C_1$-$C_7$ alkylphenyl-, $C_1$-$C_7$-alkoxyphenyl- or halophenyl-,)$C_3$-$C_{12}$-cycloalkyl; (halo$C_1$-$C_7$-alkyl)-$C_3$-$C_{12}$ cycloalkyl; cyano $C_3$-$C_{12}$-cycloalkyl; amino-$C_1$-$C_7$-alkyl; halo-$C_1$-$C_7$-alkyl; N—$C_1$-$C_7$-alkanoylamino-$C_1$-$C_7$-alkyl; N—$C_1$-$C_7$-alkanesulfonyl-amino-$C_1$-$C_7$-alkyl; pyrrolidino-$C_1$-$C_7$-alkyl; oxo-pyrrolidino-$C_1$-$C_7$-alkyl; N-mono- or N,N-di-($C_1$-$C_7$-alkyl)-amino pyrrolidinyl; piperidino-$C_1$-$C_7$-alkyl; 4-($C_1$-$C_7$-alkyl)-piperidino; 4-[N-mono- or N,N-di-($C_1$-$C_7$-alkyl)-amino]-piperidino; piperazin-1-yl-$C_1$-$C_7$-alkyl; 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)piperazin-1-yl; 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)piperazin-1-yl-$C_1$-$C_7$-alkyl; 4-(amino-$C_1$-$C_7$-alkyl)-piperazin-1-yl-$C_1$-$C_7$-alkyl; 4-[N-mono- or N,N-di-($C_1$-$C_7$-alkylamino)-$C_1$-$C_7$-alkyl]-piperazin-1-yl-$C_1$-$C_7$-alkyl; morpholino-$C_1$-$C_7$-alkyl; thiomorpholino-$C_1$-$C_7$-alkyl; S-mono- or S,S-dioxo-thiomorpholino-$C_1$-$C_7$-alkyl; carbamoyl-$C_1$-$C_7$-alkyl; [N-mono- or N,N-di-($C_1$-$C_7$-alkyl)-carbamoyl]-$C_1$-$C_7$-alkyl; $C_1$-$C_7$-alkanesulfinyl-$C_1$-$C_7$-alkyl, $C_1$-$C_7$-alkanesulfonyl-$C_1$-$C_7$-alkyl, halo, hydroxy, $C_1$-$C_7$-alkoxy, amino, N-mono- or N,N-di-($C_1$-$C_7$-alkyl)-amino; N-mono- or N,N-di-($C_3$-$C_7$-cycloalkyl)-amino; N-mono- or N,N-di-[N-mono- or N,N-di-($C_1$-$C_7$-alkyl)-amino-$C_1$-$C_7$-alkyl]-amino; N,N—[N-mono- or N,N-di-($C_1$-$C_7$-alkyl)-amino-$C_1$-$C_7$-alkyl][$C_1$-$C_7$-alkyl]-amino; aza-bi-cyclo[2.2.1]heptan7-yl; $C_1$-$C_7$-alkanoylamino; pyridinamino; imidazolinyl; 2-methyl imidazolinyl; pyrrolidino; oxo-pyrrolidino; piperidino; piperazin-1-yl; 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl; 4-(amino-$C_1$-$C_7$-alkyl)-piperazin-1-yl; 4-[N-mono- or N,N-di-($C_1$-$C_7$-alkylamino)-$C_1$-$C_7$-alkyl]-piperazin-1-yl; morpholino; thiomorpholino; S-oxo- or S,S-dioxothiomorpholino; $C_1$-$C_7$-alkanesulfonylamino; carbamoyl; N-mono- or N,N-di-($C_1$-$C_7$-alkyl, $C_1$-$C_7$-alkoxy-$C_1$-$C_7$ alkyl, amino-$C_1$-$C_7$-alkyl and/or (N'-mono- or N',N'-di-($C_1$-$C_7$-alkyl)-amino-$C_1$-$C_7$-alkyl)-carbamoyl; pyrrolidin-1-carbonyl; piperidin-1-carbonyl; piperazin-1-carbonyl; 4-($C_1$-$C_7$-alkyl)piperazin-1-carbonyl; tetrahydro-pyran-4-yl; $C_1$-$C_7$-alkyl-tetrahydro-pyran-4-yl (especially 4-($C_1$-$C_7$-alkyl)-tetrahydro-pyran-4-yl); morpholin-1-carbonyl; thiomorpholin-1-carbonyl; S-oxo- or S,S-dioxothiomorpholin-1-carbonyl; sulfo; $C_1$-$C_7$-alkanesulfonyl; $C_1$-$C_7$ alkanesulfinyl; sulfamoyl; N-mono- or N,N-di-($C_1$-$C_7$-alkyl)-sulfamoyl; morpholinosulfonyl; thiomorpholinosulfonyl; $C_1$-$C_7$-alkylsulphanyl; cyano; nitro and thiazolyl.

$R^1$ further preferably represents unsubstituted or substituted heterocyclyl or unsubstituted or substituted aryl
wherein said heterocyclyl or aryl is selected from the group consisting of phenyl, naphthyl, indanyl, pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, furazane (oxadiazole), dioxolane, thiophene, dihydrothiophene, tetrahydrothiophene, oxazole, oxazoline, oxazolidine, isoxazole, isoxazoline, isoxazolidine, thiazole, thiazoline, thiazolidine, isothiazole, istothiazoline, isothiazolidine, thiadiazole, thiadiazoline, thiadiazolidine, pyridine, piperidine, pyrimidine, pyridazine, pyrazine, piperazine, triazine, pyrane, tetrahydropyrane, thiopyrane, tetrahydrothiopyrane, oxazine, thiazine, dioxine, morpholine, purine, pterine, and the corresponding benz-annelated heterocycles, e.g. indole, isoindole, cumarine, cumaronecinoline, isochinoline, cinnoline, benzoimidazol and
wherein said heterocyclyl or aryl is substituted by one or more, preferably one to three moieties independently selected from the group consisting of halogen, hydroxy, cyano, nitro, $C_1$-$C_7$-alkyl, per-deutero $C_1$-$C_7$-alkyl, $C_3$-$C_{12}$-cycloalkyl, amino-$C_1$-$C_7$-alkyl, halo-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, pyrrolidino-$C_1$-$C_7$-alkyl, oxo-pyrrolidino-$C_1$-$C_7$-alkyl, $C_1$-$C_7$-alkanesulfinyl, $C_1$-$C_7$-alkanesulfonyl, $C_1$-$C_7$-alkoxy, amino, N-mono- or N,N-di-($C_1$-$C_7$-alkyl)-amino, N-mono- or N,N-di-($C_1$-$C_7$-cycloalkyl)-amino $C_1$-$C_7$-alkanoylamino, pyrrolidino, oxo-pyrrolidino, piperidino, piperazin-1-yl, 4-($C_1$-$C_7$-alkyl, $C_1$-$C_7$-alkoxy-$C_1$-$C_7$ alkyl, halo-$C_1$-$C_7$-alkyl or $C_3$-$C_{10}$-cycloalkyl)-piperazin-1-yl, 4-(amino-$C_1$-$C_7$-alkyl)-piperazin-1-yl, 4-[N-mono- or N,N-di-($C_1$-$C_7$-alkylamino)-$C_1$-$C_7$-alkyl]-piperazin-1-yl, morpholino, thiomorpholino, S-oxo- or S,S-dioxothiomorpholino, $C_1$-$C_7$-alkanesulfonylamino, carbamoyl, N-mono- or N,N-di-($C_1$-$C_7$-alkyl, $C_1$-$C_7$-alkoxy-$C_1$-$C_7$-alkyl, amino-$C_1$-$C_7$-alkyl and/or (N'-mono- or N',N'-di-($C_1$-$C_7$-alkyl)-amino-$C_1$-$C_7$-alkyl)-carbamoyl, pyrrolidin-1-carbonyl, piperidin-1-carbonyl, piperazin-1-carbonyl, 4-($C_1$-$C_7$-alkyl)piperazin-1-carbonyl, morpholin-1-carbonyl, thiomorpholin-1-carbonyl, S-oxo- or S,S-dioxothiomorpholin-1-carbonyl, sulfo, $C_1$-$C_7$-alkanesulfonyl, $C_1$-$C_7$-alkanesulfinyl, sulfamoyl, N-mono- or N,N-di-($C_1$-$C_7$-alkyl)-sulfamoyl, morpholinosulfonyl, thiomorpholinosulfonyl, thiazolyl.

$R^1$ very preferably represents heterocyclyl or aryl in each case unsubstituted or substituted by one or more (preferably 0, 1, 2 or 3 substituents),
  wherein said heterocyclyl or aryl is selected from the group consisting of phenyl, 2-, 3-, 4-pyridyl (especially 2- or 4-, particularly, 4-pyridyl), 2-, 4-, 5-pyrimidinyl (especially 4-pyrimidinyl), pyrazinyl, 3-, 4-pyridazinyl, benzoimidazol (e.g. alkyl-3H-benzoimidazol-5-yl, such as 3-methyl-, 3-ethyl, 3-tert-butyl-3H-benzoimidazol-5-yl), thiazol-4-yl and wherein said substituent(s) is (are) selected from the group consisting of fluoro, chloro, cyano, $C_1$-$C_4$-alkyl (in particular methyl, ethyl, iso-propyl, sec-butyl, tert.-butyl, 1,1,2-trimethyl-propyl, 1,1-dimethyl-propyl), per-deutero $C_1$-$C_7$-alkyl (in particular —$CD_3$, $d_9$-tert-butyl), $C_3$-$C_6$-cycloalkyl (in particular cyclopropyl, cyclobutyl, cyclopentyl), $C_3$-$C_6$-cycloalkyl-$C_1$-$C_4$-alkyl (in particular cyclopropylmethyl, cyclobutylmethyl),
  1-($C_1$-$C_4$-alkyl)-$C_3$-$C_6$-cycloalkyl (in particular 1-methyl-cyclopropyl, 2-methyl-cyclopropyl, 1-methyl-cyclobutyl), 1-(halo-$C_1$-$C_4$-alkyl)-$C_3$-$C_6$-cycloalkyl (in particular 1-trifluoromethyl-cyclopropyl, 1-trifluoromethyl-cyclobutyl), 1-(per-deutero-$C_1$-$C_4$-alkyl)-$C_3$-$C_6$-cycloalkyl (in particular 1-$d_3$-methyl-cyclopropyl, 1-$d_3$-methyl-cyclobutyl), 1-cyano-$C_3$-$C_6$-cycloalkyl (in particular 1-cyano-cyclopropyl, 1-cyano-cyclobutyl), $C_1$-$C_4$-alkyloxy (in particular methoxy, ethoxy), hydroxy-$C_1$-$C_4$-alkyl (in particular 2-hydroxyethyl), halo-$C_1$-$C_4$-alkyl (in particular $CF_3$, 2-fluoro-1,1-dimethyl-ethyl, 2,2,2-trifluoro-1,1-dimethyl-ethyl), $C_1$-$C_4$-alkyloxy-$C_1$-$C_4$-alkyl (in particular methoxymethyl), cyclopropyl, cyclobutyl, cyclopentyl, cyclopropyloxy, cyclopentyloxy, $C_1$-$C_4$-alkylsulfonyl (in particular methylsulfonyl), $C_1$-$C_4$-alkylsulfanyl (in particular methylsulfanyl); amino-substituents such as, in particular, dimethylamino, diethylamino, ethyl-methyl-amino, ethyl-propyl-amino, cyclopropyl amino, 2-methoxy-ethyl-amino, 4-dimethylamino-piperidin-1-yl, methyl-(1-methyl-piperidin-4-yl)-amino, 4-methyl-piperazin-1-yl, 3-dimethylamino-pyrrolidin-1-yl(specifically (R)- or (S)-3-dimethylamino-pyrrolidin-1-yl, isopropyl-methyl-amino, 2-dimethylamino-ethyl)-methyl-amino, 2-azetidin-1-yl, 7-aza-bicyclo[2.2.1]hept-7-yl, 3-aza-bicyclo[3.2.2]non-3-yl, benzyl-ethyl-amino, 1-(4-$C_1$-$C_4$-alkyloxy-phenyl)-$C_3$-$C_6$-cycloalkyl (in particular 1-(4-methoxy-phenyl)-cyclopropyl), (4-$C_1$-$C_4$-alkyloxy-phenyl)-$C_1$-$C_4$-alkyl (in particular 1-(4-methoxy-phenyl)-1-methyl-ethyl), 1-phenyl-$C_3$-$C_6$-cycloalkyl (in particular 1-phenyl-cyclopentyl), $C_1$-$C_7$-alkylphenyl (in particular 1,1-dimethyl-2-p-tolyl-ethyl), $C_1$-$C_7$-alkoxyphenyl $C_1$-$C_7$-alkyl (in particular (4-methoxy-phenyl)-1,1-dimethyl-ethyl), $C_1$-$C_7$-alkoxyphenoxy (in particular 4-methoxy-phenoxymethyl), N,N-dialkylamino alkoxy phenyl (in particular 1-[4-(3-dimethylamino-propoxy)-phenyl]-1-methyl-ethyl), 4-($C_1$-$C_7$-alkyl)-tetrahydro-pyran-4-yl (in particular 4-ethyl-tetrahydro-pyran-4-yl),
  benzyl, phenyl or an aromatic heterocycle with 5 or 6 ring atoms (in particular pyrrole, pyrazole, imidazole (in particular imidazol-1-yl), triazole, pyridine, pyrazine, pyridazine, thiazol-4-yl) which benzyl, phenyl or aromatic heterocycle is optionally substituted (preferably, for benzyl, on the phenyl ring) by one or two substituents selected from the group consisting of halogen (in particular chloro or fluoro), $C_1$-$C_4$-alkyl (in particular methyl, ethyl, n-propyl, tert.-butyl), $C_1$-$C_4$-alkyloxy (in particular methoxy), halo-$C_1$-$C_4$-alkyl (in particular $CF_3$), in particular, 2-methyl-imidazol-1-yl, 2-propyl-imidazol-1-yl, 2-fluorophenyl, 2,6-dichlorophenylmethyl.

It is preferred that when $R^1$ is substituted pyridyl, e.g. 4-pyridyl, substituted by at least one substituent (as defined herein above), said substituent is at least at the 2-position of the pyridyl group.

It is preferred that when $R^1$ is substituted pyrimidinyl, e.g. 4-pyrimidinyl, substituted by at least one substituent (as defined herein above), said substituent is at least at the 2-position of the pyrimidinyl group.

$R^2$ preferably represents halo, cyano, nitro, hydroxy, $C_1$-$C_7$-alkyl, $C_1$-$C_7$-alkyloxy, $C_3$-$C_6$-cycloalkyl, $C_3$-$C_6$-cycloalkyloxy, $C_1$-$C_7$-alkylamino, di-$C_1$-$C_7$-alkylamino, di-$C_1$-$C_7$-alkylamino $C_1$-$C_7$-alkyl, phenyl wherein each alkyl, cycloalkyl or phenyl may be mono or disubstituted by fluoro, chloro, cyano, hydroxy, phenyl. In this aspect $R^2$ in particular represents hydroxy, methyl, fluoro, chloro.

$R^2$ preferably represents, together with a further substituent $R^2$, a group —$CH_2$—; —$CH(CH_3)$—, —$C(CH_3)_2$—; —$CH_2$—$CH_2$—, —CH=CH— thereby forming a cyclic moiety, and thus, together with the nitrogen-containing ring, a bicyclic moiety.

$R^2$ preferably represents, together with a further substituent $R^2$, a bond, particularly when n is 1, to form a double bond. Thus the nitrogen-containing ring is then an unsaturated moiety.

The $R^2$ may be substituted at the 2- and/or 3- and/or 4-position of the nitrogen-containing heterocycle to which it is attached (e.g. the pyrrolidine ring of formula IA (n=1 in formula I) or the azetidine ring of formula IB (n=0 in formula I)). Most preferably, when n=1 and m=1, the $R^2$ substituent is substituted at the 2-position of the pyrrolidine ring, i.e. on the same carbon which is simultaneously substituted by the carboxamide group.

In formula I, preferably, when n=1, m=1 or 2; and when n=0, m=0 or 1, most preferably, when n=0, m=0.

Typically, when n=1 and m=2, the two $R^2$ substituents together form an alkandiyl or alkenediyl (especially an alkandiyl, most especially a methano group, e.g. a 2,3-methano group). Alternatively when n=1 and m=2, the two $R^2$ groups may be separate and substituted at the 2- and 4-positions respectively of the pyrrolidine ring, or both at a single position (i.e. geminal): 2,2-, 3,3- or 4,4- (especially 4,4-), e.g. when $R^2$ is halo, such as fluoro). Most preferably, when n=1 then m=1.

$R^3$ preferably represents hydrogen, lower alkyl, mono-, poly- or per-deutero lower alkyl, halo, fluoro lower alkyl, hydroxy lower alkyl, lower dialkylamino lower alkyl.

$R^3$ preferably represents hydrogen, methyl, mono-, di- or tri-deutero methyl, chloro, fluoromethyl, hydroxymethyl, dimethylamino lower alkyl, lower dialkylamino methyl.

$R^3$ most preferably represents hydrogen, methyl, $d_3$-methyl (that is —$CD_3$), chloro, dimethylamino methyl.

$R^3$ may also represent methyl, fluoromethyl (that is —$CH_2F$), hydroxymethyl (that is —$CH_2OH$).

An embodiment of the present invention includes compounds of the formula IC:

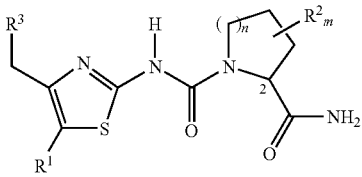

(IC)

wherein
n represents 1 and m represents 1, 2, 3 or 4
or
n represents 0 and m represents 0, 1, 2 or 3;
$R^1$ represents optionally substituted aryl or optionally substituted heterocyclyl;
$R^2$ represents halo, cyano, nitro, hydroxy, phenyl, lower alkyl, lower alkoxy, lower alkylamino, lower dialkylamino, cycloalkyl, cycloalkoxy wherein each alkyl or cycloalkyl may be mono or poly-substituted by halo, cyano, nitro, hydroxy, phenyl and wherein each phenyl may be mono or poly-substituted by halo, cyano, nitro, hydroxy, lower alkyl
or
two substituents together form an alkandiyl or alkenediyl, each optionally substituted by hydroxy or halo, to form a bicyclic moiety
or
two substituents together form a bond to form a unsaturated moiety;
$R^3$ represents hydrogen, fluoro, hydroxy
or salts thereof.

Another embodiment of the present invention relates to compounds of formula (I) or (IC), excluding one or more of the specific compounds according to formula (ID) listed in table 2.

Another embodiment of the present invention relates to compounds of formula (I) or (IC), excluding one or more of the specific compounds according to formula (ID) listed in table 2A.

Another embodiment of the present invention relates to compounds of formula (I) or (IC), excluding compounds according to formula ID:

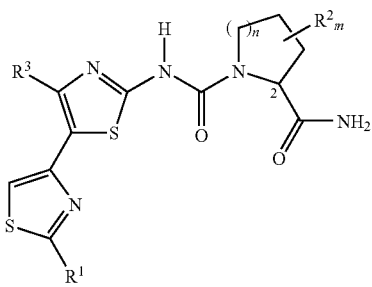

(ID)

wherein $R^1$ is as defined herein, $R^3$ represents methyl, n represents 1, m represents 0, 1 or 2, chirality at Pos. 2 is S.

Another embodiment of the present invention relates to compounds of formula (I), (I') and/or (IC), excluding compounds wherein $R^1$ is thiazol-4-yl.

The invention further relates to pharmaceutically acceptable prodrugs of a compound of formula (I), (IA), (IB), (IC) and/or (I').

The invention further relates to pharmaceutically acceptable metabolites of a compound of formula (I), (IA), (IB), (IC) and/or (I').

The invention relates especially to the compounds of the formula (I), (IA), (IB), (IC) and/or (I') given in the Examples, as well as the methods of manufacture described therein.

The present invention also relates to processes for the production of a compound of formula (I), (IA), (IB), (IC) and/or (I'). In principle all known processes which convert two different amines into a corresponding urea derivative are suitable and may be applied by using the respective starting material.

Thus, the invention in particular relates to a process which comprises reacting a compound of formula II

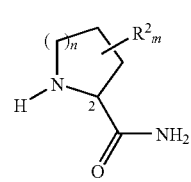

(II)

wherein the substituents are as defined above, either with a compound of formula IIIA

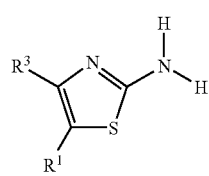

(IIIA)

wherein the substituents are as defined above and $R^3$ may additionally represent halomethyl, e.g. bromomethyl or chloromethyl, in the presence of an activating agent ("method A") or with a compound of formula IIIB

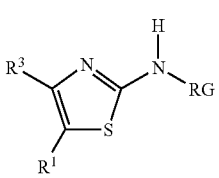

(IIIB)

wherein $R^1$ is as defined above; RG represents a reactive group (such as imidazolylcarbonyl) and $R^3$ is as defined above and may additionally represent, halomethyl, e.g. bromomethyl or chloromethyl ("method B"),
in each case optionally in the presence of a diluent and optionally in the presence of a reaction aid and
recovering the resulting compound of formula I in free form or in form of a salt and, optionally converting a compound of the formula I obtainable according to method A or method B into a different compound of the formula I, and/or converting an obtainable salt of a compound of the formula I into a different salt thereof, and/or converting an obtainable free compound of the formula I into a salt thereof, and/or separating an obtainable isomer of a compound of the formula I from one or more different obtainable isomers of the formula I.

Reaction Conditions

The process may be performed according to methods known in the art, or as disclosed below in the Examples. For example a compound of formula II may be reacted with a compound of formula III in a solvent, e.g. dimethylformamide, in the presence of a base e.g. an organic amine, e.g. triethylamine.

Where temperatures are given hereinbefore or hereinafter, "about" has to be added, as minor deviations from the numeric values given, e.g. variations of ±10%, are tolerable. All reactions may take place in the presence of one or more diluents and/or solvents. The starting materials may be used in equimolar amounts; alternatively, a compound may be used in excess, e.g. to function as a solvent or to shift equilibrium or to generally accelerate reaction rates.

Reaction aids, such as acids, bases or catalysts may be added in suitable amounts, as known in the field, required by a reaction and in line with generally known procedures.

Protecting Groups

If one or more other functional groups, for example carboxy, hydroxy, amino, sulfhydryl or the like are or need to be protected in a starting material as described herein or any other precursor, because they should not take part in the reaction or disturb the reaction, these are such groups as are usually used in the synthesis of peptide compounds, and also of cephalosporins and penicillins, as well as nucleic acid derivatives and sugars. Protecting groups are such groups that are no longer present in the final compounds once they are removed, while groups that remain as substituents are not protecting groups in the sense used here which are groups that are added at a starting material or intermediate stage and removed to obtain a final compound. Also in the case of conversions of a compound of the formula (I), (IA), (IB), (IC) and/or (I') into a different compound of the formula (I), (IA), (IB), (IC) and/or (I'), protecting groups may be introduced and removed, if useful or required.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by acetolysis, protonolysis, solvolysis, reduction, photolysis or also by enzyme activity, for example under conditions analogous to physiological conditions, and that they are not present in the end-products. The specialist knows, or can easily establish, which protecting groups are suitable with the reactions mentioned above and below.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/I, Georg Thieme Verlag, Stuttgart 1974, in H.-D. Jakubke and H. Jescheit, "Aminosauren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide and Derivate" (Chemistry of carbohydrates: monosaccharides and derivatives), Georg Thieme Verlag, Stuttgart 1974.

Optional Reactions and Conversions

A compound of the formula (I), (IA), (IB), (IC) and/or (I') may be converted into a different compound of the formula (I), (IA), (IB), (IC) and/or (I').

In a compound of the formula (I), (IA), (IB), (IC) and/or (I') wherein $R^3$ represents fluoromethyl or hydroxymethyl; such compound may be obtained by converting the corresponding chlorine derivative into the hydroxy or fluoro compound. Such reactions are known and referred to as substitution reactions. This conversion may take place at the step of the starting material of formula (IIIA or B) or by converting a corresponding compound of formula (I), (IA), (IB), (IC) and/or (I').

In a compound of the formula (I), (IA), (IB), (IC) and/or (I') wherein a substituent carries an amino or amino-$C_1$-$C_7$-alkyl substituent, the amino can be converted into acylamino, e.g. $C_1$-$C_7$-alkanoylamino or $C_1$-$C_7$-alkanesulfonylamino, by reaction with a corresponding $C_1$-$C_7$al-kanoylhalogenide or $C_1$-$C_7$-alkanesulfonylhalogenide, e.g. a corresponding chloride, in the presence of a tertiary nitrogen base, such as triethylamine or pyridine, in the absence or presence of an appropriate solvent, such a methylene chloride, for example at temperatures in the range from −20 to 50° C., e.g. at about room temperature.

In a compound of the formula (I), (IA), (IB), (IC) and/or (I') wherein a substituent carries a cyano substituent, the cyano may be converted to an aminomethyl group, e.g. by hydrogenation in the presence of an appropriate metal catalyst, such as Raney Nickel or Raney Cobalt, in an appropriate solvent, e.g. a lower alkanol, such as methanol and/or ethanol, for example at temperatures in the range from −20 to 50° C., e.g. at about room temperature.

Salts of a compound of formula (I), (IA), (IB), (IC) and/or (I') with a salt-forming group may be prepared in a manner known per se. Acid addition salts of compounds of formula (I), (IA), (IB), (IC) and/or (I') may thus be obtained by treatment with an acid or with a suitable anion exchange reagent. A salt with two acid molecules (for example a dihalogenide of a compound of formula (I), (IA), (IB), (IC) and/or (I')) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of formula (I), (IA), (IB), (IC) and/or (I'). Salts can usually be converted to free compounds, e.g. by treating with suitable basic compounds, for example with alkali metal carbonates, alkali metal hydrogencarbonates, or alkali metal hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula (I), (IA), (IB), (IC) and/or (I') itself. Enantiomers may be separated through the formation of diastereomeric salts, for example by salt formation with an enantiomer-pure chiral acid, or by means of chromatography, for example by HPLC, using chromatographic substrates with chiral ligands.

It should be emphasized that reactions analogous to the conversions mentioned in this chapter may also take place at the level of appropriate intermediates (and are thus useful in the preparation of corresponding starting materials).

Starting Materials:

The starting materials of the formulae II and III, as well as other starting materials mentioned herein, e.g. below, can be prepared according to or in analogy to methods that are known in the art, are known in the art and/or are commercially available. Insofar as the production of the starting materials is not particularly described, the compounds are either known or may be prepared analogously to methods known in the art, e.g. in WO 05/021519 or WO04/096797, or as disclosed hereinafter. Novel starting materials, as well as processes for the preparation thereof, are likewise an embodiment of the present invention. In the preferred embodiments, such starting materials are used and the reaction chosen are selected so as to enable the preferred compounds to be obtained.

In the starting materials (including intermediates), which may also be used and/or obtained as salts where appropriate and expedient, the substituents are preferably as defined for a compound of the formula (I), (IA), (IB), (IC) and/or (I').

The compounds of formula (I), (IA), (IB), (IC) and/or (I') as disclosed herein are useful as pharmaceuticals. The invention therefore relates in one embodiment to compositions for human or veterinary use where inhibition of PI3K is indicated.

In one embodiment, the invention relates to the treatment of cellular proliferative diseases such as tumor and/or cancerous cell growth mediated by PI3K. In particular, the compounds are useful in the treatment of human or animal (e.g., murine) cancers, including, for example, lung and bronchus; prostate; breast; pancreas; colon and rectum; thyroid; liver and intrahepatic bile duct; hepatocellular; gastric; glioma/glioblastoma; endometrial; melanoma; kidney and renal pelvis; urinary bladder; uterine corpus; uterine cervix; ovary; multiple myeloma; esophagus; acute myelogenous leukemia; chronic myelogenous leukemia; lymphocytic leukemia; myeloid leukemia; brain; oral cavity and pharynx; larynx; small intestine; non-Hodgkin lymphoma; melanoma; and villous colon adenoma.

In other embodiments, the PI3K-mediated condition or disorder is selected from the group consisting of: asthma, COPD, ARDS, Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, psoriasis, contact dermatitis, atopic dermatitis, alopecia areata, erythema multiforme, dermatitis herpetiformis, *scleroderma*, vitiligo, hypersensitivity angiitis, urticaria, bullous pemphigoid, lupus erythematosus, pemphisus, epidermolysis bullosa acquisita, autoimmune haematogical disorders (e.g. haemolytic anaemia, aplastic anaemia, pure red cell anaemia and idiopathic thrombocytopenia), systemic lupus erythematosus, polychondritis, *scleroderma*, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), interstitial lung fibrosis, psoriatic arthritis, glomerulonephritis, cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease, reperfusion injuries, retinopathy, such as diabetic retinopathy or hyperbaric oxygen-induced retinopathy, and conditions characterized by elevated intraocular pressure or secretion of ocular aqueous humor, such as glaucoma.

For the above uses the required dosage will of course vary depending on the mode of administration, the particular condition to be treated and the effect desired. In general, satisfactory results are indicated to be obtained systemically at daily dosages of from about 0.03 to 10.0 mg/kg per body weight. An indicated daily dosage in the larger mammal, e.g. humans, is in the range from about 0.5 mg to about 1 g, conveniently administered, for example, in divided doses up to four times a day or in retard form. Suitable unit dosage forms for oral administration comprise from ca. 0.1 to 500 mg active ingredient.

The compounds of formula (I), (IA), (IB), (IC) and/or (I') may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, by inhalation, intranasally, or in a suppository form.

The compounds of formula (I), (IA), (IB), (IC) and/or (I') may be administered in free form or in pharmaceutically acceptable salt form e.g. as indicated above. Such salts may be prepared in conventional manner and exhibit the same order of activity as the free compounds.

Consequently, the invention also provides:

a method for preventing or treating conditions, disorders or diseases mediated by the activation of the PI3 kinase alpha enzyme e.g. such as indicated above, in a subject in need of such treatment, which method comprises administering to said subject an effective amount of a compound of formula (I), (IA), (IB), (IC) and/or (I') or a pharmaceutically acceptable salt thereof a compound of formula (I), (IA), (IB), (IC) and/or (I'), in free form or in a pharmaceutically acceptable salt form as a pharmaceutical, e.g. in any of the methods as indicated herein.

a compound of the formula (I), (IA), (IB), (IC) and/or (I') in free form or in pharmaceutically acceptable salt form for use as pharmaceutical, e.g. in any of the methods as indicated herein, in particular for the use in one or more phosphatidylinositol 3-kinase mediated diseases.

the use of a compound of formula (I), (IA), (IB), (IC) and/or (I') in free form or in pharmaceutically acceptable salt form in any of the methods as indicated herein, in particular for the treatment of one or more phosphatidylinositol 3-kinase mediated diseases.

the use of a compound of formula (I), (IA), (IB), (IC) and/or (I') in free form or in pharmaceutically acceptable salt form in any of the methods as indicated herein, in particular for the manufacture of a medicament for the treatment of one or more phosphatidylinositol 3-kinase mediated diseases.

PI3K serves as a second messenger node that integrates parallel signaling pathways, evidence is emerging that the combination of a PI3K inhibitor with inhibitors of other pathways will be useful in treating cancer and proliferative diseases in humans.

Approximately 20-30% of human breast cancers overexpress Her-2/neu-ErbB2, the target for the drug trastuzumab. Although trastuzumab has demonstrated durable responses in some patients expressing Her2/neu-ErbB2, only a subset of these patients respond. Recent work has indicated that this limited response rate can be substantially improved by the combination of trastuzumab with inhibitors of PI3K or the PI3K/AKT pathway (Chan et al., Breast Can. Res. Treat. 91:187 (2005), Woods Ignatoski et al., Brit. J. Cancer 82:666 (2000), Nagata et al., Cancer Cell 6:117 (2004)).

A variety of human malignancies express activating mutations or increased levels of Her1/EGFR and a number of antibody and small molecule inhibitors have been developed against this receptor tyrosine kinase including tarceva, gefitinib and erbitux. However, while EGFR inhibitors demonstrate anti-tumor activity in certain human tumors (e.g., NSCLC), they fail to increase overall patient survival in all patients with EGFR-expressing tumors. This may be rationalized by the fact that many downstream targets of Her1/EGFR are mutated or deregulated at high frequencies in a variety of malignancies, including the PI3K/Akt pathway. For example, gefitinib inhibits the growth of an adenocarcinoma cell line in in vitro assays. Nonetheless, sub-clones of these cell lines can be selected that are resistant to gefitinib that demonstrate increased activation of the PI3/Akt pathway. Down-regulation or inhibition of this pathway renders the resistant sub-clones sensitive to gefitinib (Kokubo et al., Brit. J. Cancer 92:1711 (2005)). Furthermore, in an in vitro model of breast cancer with a cell line that harbors a PTEN mutation and over-expresses EGFR inhibition of both the PI3K/Akt pathway and EGFR produced a synergistic effect (She et al., Cancer Cell 8:287-297(2005)). These results indicate that the combination of gefitinib and PI3K/Akt pathway inhibitors would be an attractive therapeutic strategy in cancer.

The combination of AEE778 (an inhibitor of Her-2/neu/ErbB2, VEGFR and EGFR) and RAD001 (an inhibitor of mTOR, a downstream target of Akt) produced greater combined efficacy that either agent alone in a glioblastoma xenograft model (Goudar et al., Mol. Cancer. Ther. 4:101-112 (2005)).

Anti-estrogens, such as tamoxifen, inhibit breast cancer growth through induction of cell cycle arrest that requires the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to anti-estrogen resistance (Donovan, et al, J. Biol. Chem. 276:40888, (2001)). As reported by Donovan et al., inhibition of MAPK signaling through treatment with MEK inhibitor reversed the aberrant phosphorylation status of p27 in hormone refractory breast cancer cell lines and in so doing restored hormone sensitivity. Similarly, phosphorylation of p27Kip by Akt also abrogates its role to arrest the cell cycle (Viglietto et al., Nat Med. 8:1145 (2002)).

Accordingly, in a further aspect, the compounds of formulas (I), (IA), (IB), (IC) and/or (I') are used in the treatment of hormone dependent cancers, such as breast and prostate cancers. By this use, it is aimed to reverse hormone resistance commonly seen in these cancers with conventional anticancer agents.

In hematological cancers, such as chronic myelogenous leukemia (CML), chromosomal translocation is responsible for the constitutively activated BCR-Abl tyrosine kinase. The afflicted patients are responsive to imatinib, a small molecule tyrosine kinase inhibitor, as a result of inhibition of Abl kinase activity. However, many patients with advanced stage disease respond to imatinib initially, but then relapse later due to resistance-conferring mutations in the Abl kinase domain. In vitro studies have demonstrated that BCR-Ab1 employs the Ras-Raf kinase pathway to elicit its effects. In addition, inhibiting more than one kinase in the same pathway provides additional protection against resistance-conferring mutations.

Accordingly, in another aspect, the compounds of formulas (I), (IA), (IB), (IC) and/or (I') are used in combination with at least one additional agent selected from the group of kinase inhibitors, such as Gleevec®, in the treatment of hematological cancers, such as chronic myelogenous leukemia (CML). By this use, it is aimed to reverse or prevent resistance to said at least one additional agent.

Because activation of the PI3K/Akt pathway drives cell survival, inhibition of the pathway in combination with therapies that drive apoptosis in cancer cells, including radiotherapy and chemotherapy, will result in improved responses (Ghobrial et al., CA Cancer J. Clin 55:178-194 (2005)). As an example, combination of PI3 kinase inhibitor with carboplatin demonstrated synergistic effects in both in vitro proliferation and apoptosis assays as well as in in vivo tumor efficacy in a xenograft model of ovarian cancer (Westfall and Skinner, Mol. Cancer Ther. 4:1764-1771 (2005)).

In addition to cancer and proliferative diseases, there is accumulating evidence that inhibitors of Class 1A and 1B PI3 kinases would be therapeutically useful in others disease areas. The inhibition of p110β, the PI3K isoform product of the PIK3CB gene, has been shown to be involved in shear-induced platelet activation (Jackson et al., Nature Medicine 11:507-514 (2005)). Thus, a PI3K inhibitor that inhibits p110β would be useful as a single agent or in combination in anti-thrombotic therapy. The isoform p110δ, the product of the PIK3CD gene, is important in B cell function and differentiation (Clayton et al., J. Exp. Med. 196:753-763 (2002)), T-cell dependent and independent antigen responses (Jou et al., Mol. Cell. Biol. 22:8580-8590 (2002)) and mast cell differentiation (Ali et al., Nature 431:1007-1011 (2004)). Thus, it is expected that p110δ-inhibitors would be useful in the treatment of B-cell driven autoimmune diseases and asthma. Finally, the inhibition of p110γ, the isoform product of the PI3KCG gene, results in reduced T, but not B cell, response (Reif et al., J. Immunol. 173:2236-2240 (2004)) and its inhibition demonstrates efficacy in animal models of autoimmune diseases (Camps et al., Nature Medicine 11:936-943 (2005), Barber et al., Nature Medicine 11:933-935 (2005)).

The invention further provides pharmaceutical compositions comprising at least one compound of formula (I), (IA), (IB), (IC) and/or (I'), together with a pharmaceutically acceptable excipient suitable for administration to a human or animal subject, either alone or together with other anticancer agents.

The invention further provides methods of treating human or animal subjects suffering from a cellular proliferative disease, such as cancer. The invention thus provides methods of treating a human or animal subject in need of such treatment, comprising administering to the subject a therapeutically effective amount of a compound of formula (I), (IA), (IB), (IC) and/or (I') either alone or in combination with one or more other anticancer agents. In particular, compositions will either be formulated together as a combination therapeutic or administered separately. Suitable anticancer agents for use with a compound of formula I include, but are not limited to, one or more compounds selected from the group consisting of kinase inhibitors, anti-estrogens, anti androgens, other inhibitors, cancer chemotherapeutic drugs, alkylating agents, chelating agents, biological response modifiers, cancer vaccines, agents for antisense therapy as set forth below:

A. Kinase Inhibitors:

Kinase inhibitors for use as anticancer agents in conjunction with the compound of the formula (I), (IA), (IB), (IC) and/or (I') include inhibitors of Epidermal Growth Factor Receptor (EGFR) kinases such as small molecule quinazolines, for example gefitinib (U.S. Pat. No. 5,457,105, U.S. Pat. No. 5,616,582, and U.S. Pat. No. 5,770,599), ZD-6474 (WO 01/32651), erlotinib (Tarceva®, U.S. Pat. No. 5,747,498 and WO 96/30347), and lapatinib (U.S. Pat. No. 6,727,256 and WO 02/02552); Vascular Endothelial Growth Factor Receptor (VEGFR) kinase inhibitors, including SU-11248 (WO 01/60814), SU 5416 (U.S. Pat. No. 5,883,113 and WO 99/61422), SU 6668 (U.S. Pat. No. 5,883,113 and WO 99/61422), CHIR-258 (U.S. Pat. No. 6,605,617 and U.S. Pat. No. 6,774,237), vatalanib or PTK-787 (U.S. Pat. No. 6,258, 812), VEGF-Trap (WO 02/57423), B43-Genistein (WO-09606116), fenretinide (retinoic acid p-hydroxypheny-lamine) (U.S. Pat. No. 4,323,581), IM-862 (WO 02/62826), bevacizumab or Avastin® (WO 94/10202), KRN-951, 3-[5-(methylsulfonylpiperadine methyl)-indolyl]-quinolone, AG-13736 and AG-13925, pyrrolo[2,1-f][1,2,4]triazines, ZK-304709, Veglin®, VMDA-3601, EG-004, CEP-701 (U.S. Pat. No. 5,621,100), Cand5 (WO 04/09769); Erb2 tyrosine kinase inhibitors such as pertuzumab (WO 01/00245), trastuzumab, and rituximab; Akt protein kinase inhibitors, such as RX-0201; Protein Kinase C (PKC) inhibitors, such as LY-317615 (WO 95/17182), and perifosine (US 2003171303); Raf/Map/MEK/Ras kinase inhibitors including sorafenib (BAY 43-9006), ARQ-350RP, LErafAON, BMS-354825 AMG-548, and others disclosed in WO 03/82272; Fibroblast Growth Factor Receptor (FGFR) kinase inhibitors; Cell Dependent Kinase (CDK) inhibitors, including CYC-202 or roscovitine (WO 97/20842 and WO 99/02162); Platelet-Derived Growth Factor Receptor (PDGFR) kinase inhibitors such as CHIR-258, 3G3 mAb, AG-13736, SU-11248 and SU6668; and Bcr-Abl kinase inhibitors and fusion proteins such as STI-571 or Gleevec® (imatinib).

B. Anti-Estrogens:

Estrogen-targeting agents for use in anticancer therapy in conjunction with the compoound of formula (I), (IA), (IB), (IC) and/or (I') include Selective Estrogen Receptor Modulators (SERMs) including tamoxifen, toremifene, raloxifene; aromatase inhibitors including Arimidex® or anastrozole; Estrogen Receptor Downregulators (ERDs) including Faslodex® or fulvestrant.

C. Anti-Androgens:

Androgen-targeting agents for use in anticancer therapy in conjunction with the compound of formula (I), (IA), (IB), (IC) and/or (I') include flutamide, bicalutamide, finasteride, aminoglutethamide, ketoconazole, and corticosteroids.

D. Other Inhibitors:

Other inhibitors for use as anticancer agents in conjunction with the compound of formula (I), (IA), (IB), (IC) and/or (I') include protein farnesyl transferase inhibitors including tipifarnib or R-115777 (US 2003134846 and WO 97/21701), BMS-214662, AZD-3409, and FTI-277; topoisomerase inhibitors including merbarone and diflomotecan (BN-80915); mitotic kinesin spindle protein (KSP) inhibitors including SB-743921 and MKI-833; proteasome modulators such as bortezomib or Velcade® (U.S. Pat. No. 5,780,454), XL-784; and cyclooxygenase 2 (COX-2) inhibitors including non-steroidal antiinflammatory drugs I (NSAIDs).

E. Cancer Chemotherapeutic Drugs:

Particular cancer chemotherapeutic agents for use as anticancer agents in conjunction with the compound of formula (I), (IA), (IB), (IC) and/or (I') include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNUO), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®, US 2004073044), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

F. Alkylating Agents:

Alkylating agents for use in conjunction with the compound of formula (I), (IA), (IB), (IC) and/or (I') include VNP-40101M or cloretizine, oxaliplatin (U.S. Pat. No. 4,169, 846, WO 03/24978 and WO 03/04505), glufosfamide, mafosfamide, etopophos (U.S. Pat. No. 5,041,424), prednimustine; treosulfan; busulfan; irofluven (acylfulvene); penclomedine; pyrazoloacridine (PD-115934); 06-benzylguanine; decitabine (5-aza-2-deoxycytidine); brostallicin; mitomycin C (MitoExtra); TLK-286 (Telcyta®); temozolomide; trabectedin (U.S. Pat. No. 5,478,932); AP-5280 (Platinate formulation of Cisplatin); porfiromycin; and clearazide (meclorethamine).

G. Chelating Agents:

Chelating agents for use in conjunction with the compound of formula (I), (IA), (IB), (IC) and/or (I') include tetrathiomolybdate (WO 01/60814); RP-697; Chimeric T84.66 (cT84.66); gadofosveset (Vasovist®); deferoxamine; and bleomycin optionally in combination with electorporation (EPT).

H. Biological Response Modifiers:

Biological response modifiers, such as immune modulators, for use in conjunction with the compound of formula (I), (IA), (IB), (IC) and/or (I') include staurosprine and macrocyclic analogs thereof, including UCN-01, CEP-701 and midostaurin (see WO 02/30941, WO 97/07081, WO 89/07105, U.S. Pat. No. 5,621,100, WO 93/07153, WO 01/04125, WO 02/30941, WO 93/08809, WO 94/06799, WO 00/27422, WO 96/13506 and WO 88/07045); squalamine (WO 01/79255); DA-9601 (WO 98/04541 and U.S. Pat. No. 6,025,387); alemtuzumab; interferons (e.g. IFN-a, IFN-b etc.); interleukins, specifically IL-2 or aldeskulin as well as IL-1, IL-3, IL-4, IL-5, IL-6, IL-7, IL-8, IL-9, IL-10, IL-11, IL-12, and active biological variants thereof having amino acid sequences greater than 70% of the native human sequence; altretamine (Hexalen®); SU 101 or leflunomide (WO 04/06834 and U.S. Pat. No. 6,331,555); imidazoquinolines such as resiquimod and imiquimod (U.S. Pat. Nos. 4,689,338, 5,389,640, 5,268, 376, 4,929,624, 5,266,575, 5,352,784, 5,494,916, 5,482,936, 5,346,905, 5,395,937, 5,238,944, and 5,525,612); and SMIPs, including benzazoles, anthraquinones, thiosemicarbazones, and tryptanthrins (WO 04/87153, WO 04/64759, and WO 04/60308).

I. Cancer Vaccines:

Anticancer vaccines for use in conjunction with the compound of formula (I), (IA), (IB), (IC) and/or (I') include Avicine® (Tetrahedron Lett. 26:2269-70 (1974)); oregovomab (OvaRex®); Theratope® (STn-KLH); Melanoma Vaccines; GI-4000 series (GI-4014, GI-4015, and GI-4016), which are directed to five mutations in the Ras protein; GlioVax-1; MelaVax; Advexin® or INGN-201 (WO 95/12660); Sig/E7/LAMP-1, encoding HPV-16 E7; MAGE-3 Vaccine or M3TK (WO 94/05304); HER-2VAX; ACTIVE, which stimulates T-cells specific for tumors; GM-CSF cancer vaccine; and *Listeria monocytogenes*-based vaccines.

J. Antisense Therapy:

Anticancer agents for use in conjunction with the compound of formula (I), (IA), (IB), (IC) and/or (I') also include antisense compositions, such as AEG-35156 (GEM-640); AP-12009 and AP-11014 (TGF-beta2-specific antisense oligonucleotides); AVI-4126; AVI-4557; AVI-4472; oblimersen (Genasense®); JFS2; aprinocarsen (WO 97/29780); GTI-2040 (R2 ribonucleotide reductase mRNA antisense oligo) (WO 98/05769); GTI-2501 (WO 98/05769); liposome-encapsulated c-Raf antisense oligodeoxynucleotides (LErafAON) (WO 98/43095); and Sirna-027 (RNAi-based therapeutic targeting VEGFR-1 mRNA).

A compound of formula (I), (IA), (IB), (IC) and/or (I') can also be combined in a pharmaceutical composition with bronchiodilatory or antihistamine drugs substances. Such bronchiodilatory drugs include anticholinergic or antimuscarinic agents, in particular glycopyrrolate, ipratropium bromide, oxitropium bromide, and tiotropium bromide, OrM3, aclidinium, CHF5407, GSK233705 and β-2-adrenoreceptor agonists such as salbutamol, terbutaline, salmeterol, carmoterol, milveterol and, especially, indacaterol and formoterol. Cotherapeutic antihistamine drug substances include cetirizine hydrochloride, clemastine fumarate, promethazine, loratadine, desloratadine diphenhydramine and fexofenadine hydrochloride.

The invention provides in a further aspect a combination comprising a compound of formula (I), (IA), (IB), (IC) and/or (I') and one or more compounds that are useful for the treatment of a thrombolytic disease, heart disease, stroke, etc. Such compounds include aspirin, a streptokinase, a tissue plasminogen activator, a urokinase, a anticoagulant, antiplatelet drugs (e.g, PLAVIX; clopidogrel bisulfate), a statin (e.g., LIPITOR or Atorvastatin calcium), ZOCOR (Simvastatin), CRESTOR (Rosuvastatin), etc.), a Beta blocker (e.g., Atenolol), NORVASC (amlodipine besylate), and an ACE inhibitor (e.g., lisinopril).

The invention provides in a further aspect a combination comprising a compound of formula (I), (IA), (IB), (IC) and/or (I') and one or more compounds that are useful for the treatment of antihypertension. Such compounds include ACE inhibitors, lipid lowering agents such as statins, LIPITOR (Atorvastatin calcium), calcium channel blockers such as NORVASC (amlodipine besylate).

The invention provides in a further aspect a combination comprising a compound of formula (I), (IA), (IB), (IC) and/or (I') and one or more compounds selected from the group consisting of fibrates, beta-blockers, NEPI inhibitors, Angiotensin-2 receptor antagonists and platelet aggregation inhibitors.

The invention provides in a further aspect a combination comprising a compound of formula (I), (IA), (IB), (IC) and/or (I') and a compound suitable for the treatment of inflammatory diseases, including rheumatoid arthritis. Such compound may be selected from the group consisting of TNF-α inhibitors such as anti-TNF-α monoclonal antibodies (such as REMICADE, CDP-870) and D2E7 (HUMIRA) and TNF receptor immunoglobulin fusion molecules (such as ENBREL), IL-1 inhibitors, receptor antagonists or soluble IL-1Rα☐ (e.g. KINERET or ICE inhibitors), nonsterodial anti-inflammatory agents (NSAIDS), piroxicam, diclofenac, naproxen, flurbiprofen, fenoprofen, ketoprofen ibuprofen, fenamates, mefenamic acid, indomethacin, sulindac, apazone, pyrazolones, phenylbutazone, aspirin, COX-2 inhibitors (such as CELEBREX (celecoxib), PREXIGE (lumiracoxib)), metalloprotease inhibitors (preferably MMP-13 selective inhibitors), p2x7 inhibitors, α2α☐ inhibitors, NEUROTIN, pregabalin, low dose methotrexate, leflunomide, hydroxyxchloroquine, d-penicillamine, auranofin or parenteral or oral gold.

The invention provides in a further aspect a combination comprising a compound of formula (I), (IA), (IB), (IC) and/or (I') and a compound suitable for the treatment of osteoarthritis. Such compound may be selected from the group consisting of standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, lumiracoxib and etoricoxib, analgesics and intraarticular therapies such as corticosteroids and hyaluronic acids such as hyalgan and synvisc.

The invention provides in a further aspect a combination comprising a compound of formula (I), (IA), (IB), (IC) and/or (I') and an antiviral agent and/or an antisepsis compound. Such antiviral agent may be selected from the group consisting of Viracept, AZT, acyclovir and famciclovir. Such antisepsis compound may be selected from the group consisting of Valant.

The invention provides in a further aspect a combination comprising a compound of formula (I), (IA), (IB), (IC) and/or (I') and one or more agents selected from the group consisting of CNS agents such as antidepressants (sertraline), anti-Parkinsonian drugs (such as deprenyl, L-dopa, Requip, Mirapex; MAOB inhibitors (such as selegine and rasagiline); comP inhibitors (such as Tasmar); A-2 inhibitors; dopamine reuptake inhibitors; NMDA antagonists; Nicotine agonists; Dopamine agonists; and inhibitors of neuronal nitric oxide synthase).

The invention provides in a further aspect a combination comprising a compound of formula (I), (IA), (IB), (IC) and/or (I') and one or more anti-Alzheimer's drugs. Such anti-Alzheimer Drug may be selected from the group consisting of donepezil, tacrine, α2δinhibitors, NEUROTIN, pregabalin, COX-2 inhibitors, propentofylline or metryfonate.

The invention provides in a further aspect a combination comprising a compound of formula (I), (IA), (IB), (IC) and/or (I') and anosteoporosis agents and/or an immunosuppressant agent. Such osteoporosis agents ma be selected from the group consisting of EVISTA (raloxifene hydrochloride), droloxifene, lasofoxifene or fosomax. Such immunosuppressant agents may be selected from the group consisting of FK-506 and rapamycin.

In another aspect of the preferred embodiments, kits that include one or more compound of formula (I), (IA), (IB), (IC) and/or (I') an a combination partner as disclosed herein are provided. Representative kits include a PI3K inhibitor compound (e.g., a compound of formula (I), (IA), (IB), (IC) and/or (I')) and a package insert or other labeling including directions for treating a cellular proliferative disease by administering a PI3K inhibitory amount of the compound(s).

In general, the compounds of formula (I), (IA), (IB), (IC) and/or (I') will be administered in a therapeutically effective amount by any of the accepted modes of administration for agents that serve similar utilities. The actual amount of the compound of formula (I), (IA), (IB), (IC) and/or (I'), i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day. All of these factors are within the skill of the attending clinician. Therapeutically effective amounts of compounds of formulas I may range from about 0.05 to about 50 mg per kilogram body weight of the recipient per day; preferably about 0.1-25 mg/kg/day, more preferably from about 0.5 to 10 mg/kg/day. Thus, for administration to a 70 kg person, the dosage range would most preferably be about 35-70 mg per day.

In general, compounds of formula (I), (IA), (IB), (IC) and/or (I') will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of the formula I is inhalation. This is an effective method for delivering a therapeutic agent directly to the respiratory tract.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI).

Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

The inventions also relates to formulations wherein the particle size of a compound of formula I between 10-1000 nm, preferably 10-400 nm. Such pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability. Both documents are included by reference.

In a further aspect, the invention provides pharmaceutical compositions comprising a (therapeutically effective amount) of a compound of formula (I), (IA), (IB), (IC) and/or (I'), and at least one pharmaceutically acceptable excipient. Acceptable excipients are non-toxic, aid administration, and do not adversely affect the therapeutic benefit of the compound of formula (I), (IA), (IB), (IC) and/or (I'). Such excipient may be any solid, liquid, semi-solid or, in the case of an aerosol composition, gaseous excipient that is generally available to one of skill in the art. Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like.

Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of the formula I in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01-99.99 wt % of a compound of formula I based on the total formulation, with the balance being one or more suitable pharmaceutical excipients. Preferably, the compound is present at a level of about 1-80 wt %.

The invention further relates to pharmaceutical compositions comprising (i.e. containing or consisting of) at least one compound of formula (I), (IA), (IB), (IC) and/or (I') and at least one pharmaceutically acceptable excipient.

Pharmaceutical compositions comprising a compound of formula (I), (IA), (IB), (IC) and/or (I') in free form or in pharmaceutically acceptable salt form in association with at least one pharmaceutical acceptable excipient (such as a carrier and/or diluent) may be manufactured in conventional manner by mixing the components.

Combined pharmaceutical compositions comprising a compound of formula (I), (IA), (IB), (IC) and/or (I') in free form or in pharmaceutically acceptable salt form and further comprising a combination partner (either in one dosage unit form or as a kit of parts) in association with at least one pharmaceutical acceptable carrier and/or diluent may be manufactured in conventional manner by mixing with a pharmaceutically acceptable carrier and/or diluent with said active ingredients.

Consequently, the invention provides in further aspects
- a combined pharmaceutical composition, e.g. for use in any of the methods described herein, comprising a compound of formula (I), (IA), (IB), (IC) and/or (I') in free form or pharmaceutically acceptable salt form in association with a pharmaceutically acceptable diluent and/or carrier.
- a combined pharmaceutical composition comprising a compound of formula (I), (IA), (IB), (IC) and/or (I') in free form or in pharmaceutically acceptable salt form as active ingredient; one or more pharmaceutically acceptable carrier material(s) and/or diluents and optionally one or more further drug substances. Such combined pharmaceutical composition may be in the form of one dosage unit form or as a kit of parts.
- a combined pharmaceutical composition comprising a therapeutically effective amount of a compound of formula (I), (IA), (IB), (IC) and/or (I') in free form or in pharmaceutically acceptable salt form and a second drug substance, for simultaneous or sequential administration.

a method as defined above comprising co-administration, e.g. concomitantly or in sequence, of a therapeutically effective non-toxic amount of a compound of formula (I), (IA), (IB), (IC) and/or (I') or a pharmaceutically acceptable salt thereof, and at least a second drug substance, e.g. as indicated above.

a pharmaceutical combination, e.g. a kit, comprising a) a first agent which is a compound of formula (I), (IA), (IB), (IC) and/or (I') as disclosed herein, in free form or in pharmaceutically acceptable salt form, and b) at least one co-agent, e.g. as indicated above; whereby such kit may comprise instructions for its administration.

The following examples of compounds formula (I), (IA), (IB), (IC) and/or (I') illustrate the invention without limiting the scope thereof and are shown in Table 1 and Table 2. Methods for preparing such compounds are described hereinafter.

Table 1 relates to compounds of formula (IC)

TABLE 1

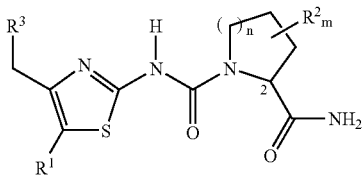
(IC)

| Example | R¹ | R² | m | R³ | n | Chirality at position 2 |
|---|---|---|---|---|---|---|
| 1 | (3-(methylsulfonyl)-2-(2-propyl-1H-imidazol-1-yl)phenyl) | α-4-hydroxy | 1 | H | 1 | S |
| 2 | (3-(methylsulfonyl)-2-(2-propyl-1H-imidazol-1-yl)phenyl) | β-4-hydroxy | 1 | H | 1 | S |
| 3 | (2-tert-butylpyrimidin-4-yl) | α-4-hydroxy | 1 | H | 1 | S |
| 4 | (2-tert-butylpyrimidin-4-yl) | β-4-hydroxy | 1 | H | 1 | S |
| 5 | (2-tert-butylpyrimidin-4-yl) | 3,4-dehydro | 2 | H | 1 | S |

TABLE 1-continued
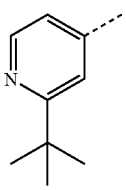
(IC)
| Example | R¹ | R² | m | R³ | n | Chirality at position 2 |
|---|---|---|---|---|---|---|
| 6 | 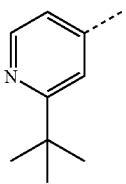 | α-4-hydroxy | 1 | H | 1 | S |
| 7 | 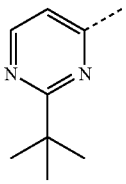 | β-4-hydroxy | 1 | H | 1 | S |
| 8 | 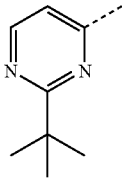 | α-4-fluoro | 1 | H | 1 | S |
| 9 | 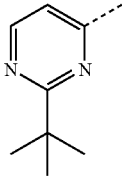 | α-3-hydroxy | 1 | H | 1 | S |
| 10 | 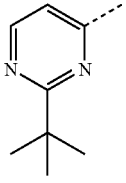 | α-3-methyl | 1 | H | 1 | S |
| 11 | 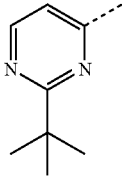 | β-3,4-methano | 2 | H | 1 | S |
| 12 | 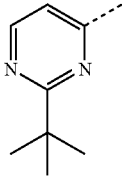 | α-2-methyl | 1 | H | 1 | S |

TABLE 1-continued (IC)

| Example | R¹ | R² | m | R³ | n | Chirality at position 2 |
|---|---|---|---|---|---|---|
| 13 | (pyrimidin-4-yl)-CH₂-(2,6-dichlorophenyl) | α-3-methyl | 1 | H | 1 | S |
| 14 | 2-cyclopropylpyrimidin-4-yl | α-3-methyl | 1 | H | 1 | S |
| 15 | 2-(2-fluorophenyl)pyrimidin-4-yl | α-3-methyl | 1 | H | 1 | S |
| 16 | 2-tert-butylpyrimidin-4-yl | — | 0 | H | 0 | R, S |
| 17 | 2-methylpyrimidin-4-yl | α-2-methyl | 1 | H | 1 | S |
| 18 | 2-tert-butylpyridin-4-yl | α-2-methyl | 1 | H | 1 | S |

TABLE 1-continued (IC)

| Example | R¹ | R² | m | R³ | n | Chirality at position 2 |
|---|---|---|---|---|---|---|
| 19 | 6-(1H-imidazol-1-yl)pyridin-2-yl | α-2-methyl | 1 | H | 1 | S |
| 20 | 2-(methoxymethyl)pyrimidin-4-yl | α-3-methyl | 1 | H | 1 | S |
| 21 | 2-isobutylpyrimidin-4-yl | α-3-methyl | 1 | H | 1 | S |
| 22 | 2-benzylpyrimidin-4-yl | α-2-methyl | 1 | H | 1 | S |
| 23 | 2-ethylpyrimidin-4-yl | α-2-methyl | 1 | H | 1 | S |
| 24 | 2-cyclopropylpyrimidin-4-yl | α-2-methyl | 1 | H | 1 | S |

TABLE 1-continued
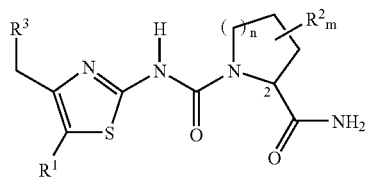
(IC)
| Example | R¹ | R² | m | R³ | n | Chirality at position 2 |
|---|---|---|---|---|---|---|
| 25 | 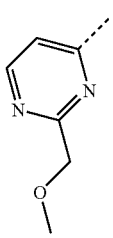 | α-2-methyl | 1 | H | 1 | S |
| 26 | 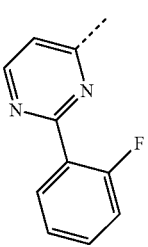 | α-2-methyl | 1 | H | 1 | S |
| 27 | 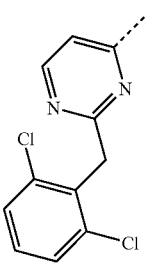 | α-2-methyl | 1 | H | 1 | S |
| 28 | 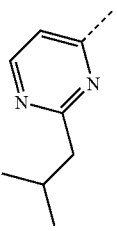 | α-2-methyl | 1 | H | 1 | S |
| 29 | 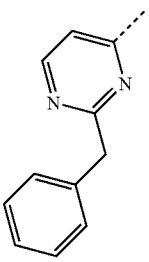 | α-3-methyl | 1 | H | 1 | S |

TABLE 1-continued (IC) Structure: R³-substituted thiazole with R¹, connected via NH-C(O)-N to pyrrolidine with (R²)ₘ and position 2 carboxamide.

| Example | R¹ | R² | m | R³ | n | Chirality at position 2 |
|---|---|---|---|---|---|---|
| 30 | 4-pyrimidinyl-ethyl | α-3-methyl | 1 | H | 1 | S |
| 31 | 4-(2-trifluoromethyl)pyrimidinyl | α-3-methyl | 1 | H | 1 | S |
| 32 | 3-tert-butylphenyl | α-2-methyl | 1 | H | 1 | S |

Table 2 relates to compounds of formula ID wherein R³ represents methyl, n represents 1, chirality at Pos. 2 is S

TABLE 2

(ID) Structure: bis-thiazole system with R³, R¹, connected via NH-C(O)-N to pyrrolidine with (R²)ₘ and position 2 carboxamide.

| Example | R¹ | R² | m |
|---|---|---|---|
| 33 | tert-butyl | α-4-hydroxy | 1 |
| 34 | tert-butyl | β-4-hydroxy | 1 |
| 35 | tert-butyl | α-3-hydroxy | 1 |
| 36 | tert-butyl | α-2-methyl | 1 |
| 37 | tert-butyl | α-3-methyl | 1 |
| 38 | tert-butyl | α-4-fluoro | 1 |

TABLE 2-continued (ID)

| Example | R¹ | R² | m |
|---------|-----|-----|---|
| 39 | 3-pyridyl-NH- | α-2-methyl | 1 |

Table 2A relates to further compounds of formula (ID) wherein R³ represents methyl, n represents 1, chirality at Pos. 2 is S

TABLE 2A

| Example | R¹ | R² | m |
|---------|-----|-----|---|
| 130 | 2-methyl-thiazol-4-yl | α-2-methyl | 1 |
| 131 | 2-methyl-imidazol-4-yl | α-2-methyl | 1 |
| 132 | cyclopropyl-NH- | α-2-methyl | 1 |
| 133 | (CH₃)₂N- | α-2-methyl | 1 |
| 134 | quinuclidinyl | α-2-methyl | 1 |
| 135 | ethyl | α-2-methyl | 1 |
| 136 | 3-pyridyl | α-2-methyl | 1 |
| 137 | 1-methyl-cyclopropyl | α-2-methyl | 1 |
| 138 | 1-methyl-cyclopropyl | α-4-hydroxy | 1 |
| 139 | 1-methyl-cyclopropyl | β-4-hydroxy | 1 |
| 140 | tert-butyl | α-4-N,N-dimethylamino | 1 |
| 141 | 1-methyl-cyclopropyl | α-4-N,N-dimethylamino | 1 |
| 142 | tert-butyl | β-4-N,N-dimethylamino | 1 |
| 143 | 1-methyl-cyclopropyl | β-4-N,N-dimethylamino | 1 |
| 144 | cyclobutyl | α-2-methyl | 1 |
| 145 | 1-(trifluoromethyl)cyclopropyl | α-2-methyl | 1 |
| 146 | tert-butyl | α-2,3-methano | 2 |
| 147 | cyclobutyl | α-2,3-methano | 2 |
| 148 | sec-butyl | α-2-methyl | 1 |
| 149 | sec-butyl | α-2,3-methano | 2 |
| 150 | (CH₃)₂N-CH₂- | α-2-methyl | 1 |
| 151 | cyclopropylmethyl | α-2-methyl | 1 |

Table 3 relates to further compounds of formula (IC)

TABLE 3

(IC)

| Example | R¹ | R² | m | R³ | n | Chirality at position 2 |
|---|---|---|---|---|---|---|
| 40 | 2-(1-methylcyclopropyl)pyridin-4-yl | α-2-methyl | 1 | H | 1 | S |
| 41 | 2-cyclopropylpyridin-4-yl | α-2-methyl | 1 | H | 1 | S |
| 42 | 2-(2-fluorophenyl)pyridin-4-yl | α-2-methyl | 1 | H | 1 | S |
| 43 | 2-cyclobutylpyridin-4-yl | α-2-methyl | 1 | H | 1 | S |
| 44 | 2-(1-methylcyclobutyl)pyridin-4-yl | α-2-methyl | 1 | H | 1 | S |
| 45 | 2-isopropylpyridin-4-yl | α-2-methyl | 1 | H | 1 | S |

TABLE 3-continued
(IC)
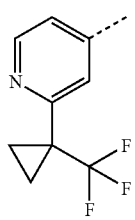
| Example | R¹ | R² | m | R³ | n | Chirality at position 2 |
|---|---|---|---|---|---|---|
| 46 | 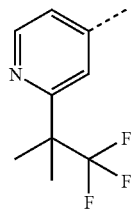 | α-2-methyl | 1 | H | 1 | S |
| 47 | 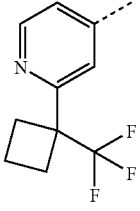 | α-2-methyl | 1 | H | 1 | S |
| 48 | 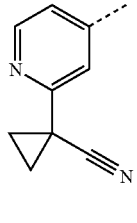 | α-2-methyl | 1 | H | 1 | S |
| 49 | 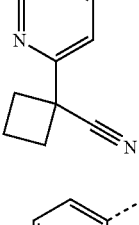 | α-2-methyl | 1 | H | 1 | S |
| 50 | 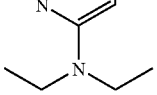 | α-2-methyl | 1 | H | 1 | S |
| 51 |  | α-2-methyl | 1 | H | 1 | S |

TABLE 3-continued (IC)

| Example | R¹ | R² | m | R³ | n | Chirality at position 2 |
|---------|----|----|----|----|----|-------------------------|
| 52 | 1-ethylbenzimidazol-7-yl | α-2-methyl | 1 | H | 1 | S |
| 53 | 2-[2-(4-methoxyphenyl)propan-2-yl]pyridin-4-yl | α-2-methyl | 1 | H | 1 | S |
| 54 | 2-[1-(4-methoxyphenyl)cyclopropyl]pyridin-4-yl | α-2-methyl | 1 | H | 1 | S |
| 55 | 2-{2-[4-(3-dimethylaminopropoxy)phenyl]propan-2-yl}pyridin-4-yl | α-2-methyl | 1 | H | 1 | S |
| 56 | 2-[1-(trideuteromethyl)cyclobutyl]pyridin-4-yl | α-2-methyl | 1 | H | 1 | S |
| 57 | 2-[1-(trideuteromethyl)cyclobutyl]pyridin-4-yl | α-2-methyl | 1 | NMe2 | 1 | S |

TABLE 3-continued (IC)

| Example | R¹ | R² | m | R³ | n | Chirality at position 2 |
|---|---|---|---|---|---|---|
| 58 | pyridine with C(CH₃)₂CH₂F substituent | α-2-methyl | 1 | H | 1 | S |
| 59 | pyridine with 1-methylcyclopropyl substituent | 4,4-difluoro | 2 | H | 1 | S |
| 60 | pyridine with imidazol-1-yl substituent | α-2-methyl | 1 | H | 1 | S |
| 61 | pyrimidine with isopentyl (C(CH₃)₂CH(CH₃)₂) substituent | α-3-methyl | 1 | H | 1 | S |
| 62 | pyrimidine with 4-methoxyphenoxymethyl substituent | α-2-methyl | 1 | H | 1 | S |
| 63 | pyrimidine with 2-(4-methoxyphenyl)-1,1-dimethylethyl substituent | α-2-methyl | 1 | H | 1 | S |

TABLE 3-continued (IC)

| Example | R¹ | R² | m | R³ | n | Chirality at position 2 |
|---|---|---|---|---|---|---|
| 64 | pyrimidin-2-yl with 2,3-dimethylbutan-2-yl | α-2-methyl | 1 | H | 1 | S |
| 65 | pyrimidin-2-yl with tert-butyl | α-2-methyl and α-4-hydroxy | 2 | H | 1 | S |
| 66 | pyrimidin-2-yl with tert-butyl | β-4-fluoro | 1 | H | 1 | S |
| 67 | pyrimidin-2-yl with 4-ethyltetrahydropyran-4-yl | α-2-methyl | 1 | H | 1 | S |
| 68 | pyrimidin-2-yl with 1-phenylcyclopentyl | α-2-methyl | 1 | H | 1 | S |
| 69 | pyrimidin-2-yl with 2-methyl-1-(p-tolyl)propan-2-yl | α-2-methyl | 1 | H | 1 | S |

TABLE 3-continued (IC)

| Example | R¹ | R² | m | R³ | n | Chirality at position 2 |
|---|---|---|---|---|---|---|
| 70 | 2-tert-butyl-pyrimidin-4-yl | α-4-N,N-dimethylamino | 1 | H | 1 | S |
| 71 | 2-(N,N-diethylamino)-pyrimidin-4-yl | α-2-methyl | 1 | H | 1 | S |
| 72 | 2-tert-butyl-pyrimidin-4-yl | β-4-N,N-dimethylamino | 1 | H | 1 | S |
| 73 | 2-isopropyl-pyrimidin-4-yl | α-2-methyl | 1 | H | 1 | S |
| 74 | 2-methylthio-pyrimidin-4-yl | α-2-methyl | 1 | H | 1 | S |
| 75 | 2-[4-(N,N-dimethylamino)piperidin-1-yl]-pyrimidin-4-yl | α-2-methyl | 1 | H | 1 | S |

TABLE 3-continued (IC)

| Example | R¹ | R² | m | R³ | n | Chirality at position 2 |
|---|---|---|---|---|---|---|
| 76 | (4-pyrimidinyl with 2-(N-methyl-N-(1-methylpiperidin-4-yl))amino) | α-2-methyl | 1 | H | 1 | S |
| 77 | (4-pyrimidinyl with 2-(4-methylpiperazin-1-yl)) | α-2-methyl | 1 | H | 1 | S |
| 78 | (4-pyrimidinyl with 2-((3R)-3-(dimethylamino)pyrrolidin-1-yl)) | α-2-methyl | 1 | H | 1 | S |
| 79 | (4-pyrimidinyl with 2-(N-methyl-N-isopropyl)amino) | α-2-methyl | 1 | H | 1 | S |
| 80 | (4-pyrimidinyl with 2-(N-methyl-N-(2-(dimethylamino)ethyl))amino) | α-2-methyl | 1 | H | 1 | S |

TABLE 3-continued (IC)

| Example | R¹ | R² | m | R³ | n | Chirality at position 2 |
|---------|----|----|---|----|----|------------------------|
| 81 | 2-cyclobutyl-pyrimidin-4-yl | α-2-methyl | 1 | H | 1 | S |
| 82 | 2-isopropyl-pyrimidin-4-yl | α-4-N,N-dimethylamino | 1 | H | 1 | S |
| 83 | 2-[(3R)-3-(dimethylamino)pyrrolidin-1-yl]pyrimidin-4-yl | α-2-methyl | 1 | H | 1 | S |
| 84 | 2-(azetidin-1-yl)pyrimidin-4-yl | α-2-methyl | 1 | H | 1 | S |
| 85 | 2-isopropyl-pyrimidin-4-yl | β-4-fluoro | 1 | H | 1 | S |
| 86 | 2-tert-butyl-pyrimidin-4-yl | α-2,3-methano | 2 | H | 1 | S |

TABLE 3-continued (IC)

| Example | R¹ | R² | m | R³ | n | Chirality at position 2 |
|---|---|---|---|---|---|---|
| 87 | 2-isopropyl-pyrimidin-4-yl | α-2,3-methano | 2 | H | 1 | S |
| 88 | 2-(diethylamino)-pyrimidin-4-yl | α-2,3-methano | 2 | H | 1 | S |
| 89 | 2-isobutyl-pyrimidin-4-yl | α-2,3-methano | 2 | H | 1 | S |
| 90 | 2-(tert-pentyl)-pyrimidin-4-yl | α-2,3-methano | 2 | H | 1 | S |
| 91 | 2-cyclopropyl-pyrimidin-4-yl | α-2,3-methano | 2 | H | 1 | S |
| 92 | 2-(7-azabicyclo[2.2.1]heptan-7-yl)-pyrimidin-4-yl | α-2-methyl | 1 | H | 1 | S |
| 93 | 2-(diethylamino)-pyrimidin-4-yl | β-4-hydroxy | 1 | H | 1 | S |

TABLE 3-continued (IC)

| Example | R¹ | R² | m | R³ | n | Chirality at position 2 |
|---------|-----|-----|---|-----|---|------------------------|
| 94 | pyrimidine-N(ethyl)(ethyl) | α-4-hydroxy | 1 | H | 1 | S |
| 95 | pyrimidine-N(ethyl)(ethyl) | β-4-fluoro | 1 | H | 1 | S |
| 96 | pyrimidine-N(ethyl)(ethyl) | α-4-fluoro | 1 | H | 1 | S |
| 97 | pyrimidine-N(ethyl)(methyl) | α-2-methyl | 1 | H | 1 | S |
| 98 | pyrimidine-N(benzyl)(ethyl) | α-2-methyl | 1 | H | 1 | S |
| 99 | pyrimidine-imidazole | α-2-methyl | 1 | H | 1 | S |
| 100 | pyrimidine-N(propyl)(ethyl) | α-2-methyl | 1 | H | 1 | S |

TABLE 3-continued (IC)

| Example | R¹ | R² | m | R³ | n | Chirality at position 2 |
|---------|----|----|---|----|---|------------------------|
| 101 | pyrimidine with N(ethyl)(2-methoxyethyl) | α-2-methyl | 1 | H | 1 | S |
| 102 | pyrimidine with 2-methylimidazol-1-yl | α-2-methyl | 1 | H | 1 | S |
| 103 | pyrimidine with 1-methylcyclopropyl | α-2-methyl | 1 | H | 1 | S |
| 104 | pyrimidine with cis-2-methylcyclopropyl | α-2-methyl | 1 | H | 1 | S |
| 105 | pyrimidine with trans-2-methylcyclopropyl | α-2-methyl | 1 | H | 1 | S |
| 106 | pyrimidine with tert-butyl | α-2-benzyl | 1 | H | 1 | R |

TABLE 3-continued (IC)

| Example | R¹ | R² | m | R³ | n | Chirality at position 2 |
|---|---|---|---|---|---|---|
| 107 | 2-tert-butyl-pyrimidin-4-yl | α-2-(N,N-dimethyl-amino)-methyl | 1 | H | 1 | R |
| 108 | 2-(sec-butyl)-pyrimidin-4-yl | α-2-methyl | 1 | H | 1 | S |
| 109 | 2-tert-butyl-pyrimidin-4-yl | α-4-cyano | 1 | H | 1 | S |
| 110 | 2-(cyclopropylmethyl)-pyrimidin-4-yl | α-2-methyl | 1 | H | 1 | S |
| 111 | 2-(tert-butyl-d9)-pyrimidin-4-yl | α-2-methyl | 1 | H | 1 | S |
| 112 | 2-tert-butyl-pyrimidin-4-yl | α-2-methoxy-methyl | 1 | H | 1 | R |

TABLE 3-continued (IC)

| Example | R¹ | R² | m | R³ | n | Chirality at position 2 |
|---------|----|----|---|-----|---|-------------------------|
| 113 | 2-tert-butyl-pyrimidin-4-yl | — | 0 | H | 0 | S |
| 114 | 2-tert-butyl-pyrimidin-4-yl | α-2-difluoro-methyl | 1 | H | 1 | S |

Table 4 relates to compounds of formula (I')

TABLE 4

(I')

| Example | R¹ | R² | m | R³ | n |
|---------|----|----|---|-----|---|
| 115 | 2-tert-butyl-pyridin-4-yl | α-2-methyl | 1 | H | 1 |
| 116 | 2-cyclobutyl-pyridin-4-yl | α-2-methyl | 1 | H | 1 |
| 117 | 2-(1-methylcyclopropyl)-pyridin-4-yl | α-2-methyl | 1 | H | 1 |
| 118 | 2-(1-trifluoromethyl-cyclopropyl)-pyridin-4-yl | α-2-methyl | 1 | H | 1 |
| 119 | 2-(1,1,1-trifluoro-2-methylpropan-2-yl)-pyridin-4-yl | α-2-methyl | 1 | H | 1 |
| 120 | 2-(1-trifluoromethyl-cyclobutyl)-pyridin-4-yl | α-2-methyl | 1 | H | 1 |

TABLE 4-continued

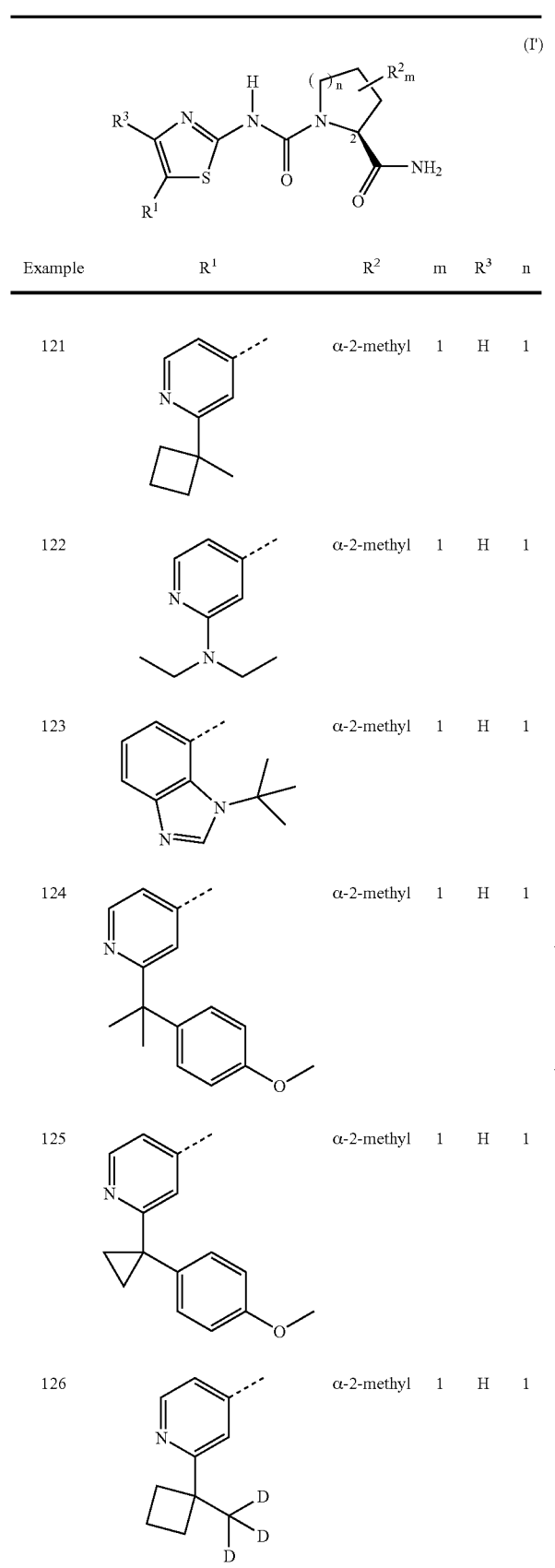

| Example | R¹ | R² | m | R³ | n |
|---|---|---|---|---|---|
| 121 | | α-2-methyl | 1 | H | 1 |
| 122 | | α-2-methyl | 1 | H | 1 |
| 123 | | α-2-methyl | 1 | H | 1 |
| 124 | | α-2-methyl | 1 | H | 1 |
| 125 | | α-2-methyl | 1 | H | 1 |
| 126 | | α-2-methyl | 1 | H | 1 |

TABLE 4-continued

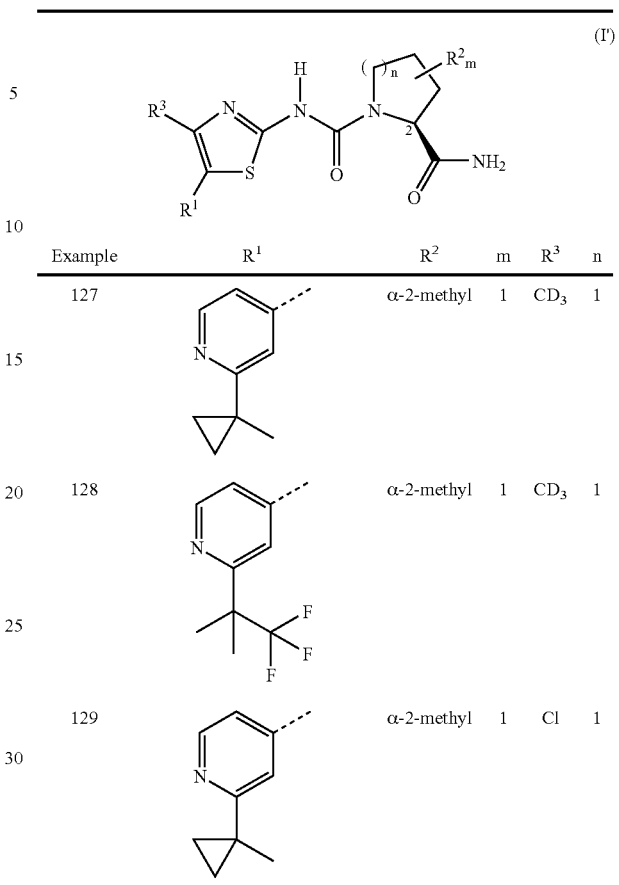

| Example | R¹ | R² | m | R³ | n |
|---|---|---|---|---|---|
| 127 | | α-2-methyl | 1 | CD₃ | 1 |
| 128 | | α-2-methyl | 1 | CD₃ | 1 |
| 129 | | α-2-methyl | 1 | Cl | 1 |

Temperatures are measured in degrees Celsius. Unless otherwise indicated, the reactions take place at rt. The following Hplc/MS and MS methods are used in the preparation of the Intermediates and Examples:

Method A (analytical Hplc/MS) Instrument: Hewlett Packard Agilent 1100 series, column: XBridge™ C18 2.5 microm 3.0×30 mm, temperature: 50° C., eluent, 2 channel system: Channel A 5% acetonitrile in water, Channel B acetonitrile containing 0.2% formic acid

| Time (minutes) | % channel B | Flow (ml/minute) |
|---|---|---|
| 0 | 1 | 0.6 |
| 0.5 | 1 | 0.6 |
| 2.5 | 30 | 0.6 |
| 3.5 | 95 | 0.7 |
| 4.0 | 95 | 0.7 |
| 4.5 | 95 | 0.8 | detection: Agilent 1100 DAD 210-350 nm and Waters Micromass ZQ 2000 ESI+ and ESI−.

Method B (preparative Hplc/MS) Instrument: Gilson preparative HPLC system, column: Sunfire™ Prep C18 OBD™ 5 microm 30×100 mm, temperature: 25° C., eluent: gradient from 5-100% acetonitrile in 0.05% aqueous trifluoroacetic acid over 20 minutes, flow rate: 30 ml/minute, detection: UV 254 nm.

Method C (analytical Hplc/MS) Instrument: Hewlett Packard Agilent 1100 series, column: XBridge™ C18 2.5 microm 3.0×30 mm, temperature: 50° C., eluent: 2 channel system: Channel A 5% acetonitrile in water, Channel B acetonitrile containing 0.2% formic acid

| Time (minutes) | % channel B | Flow (ml/minute) |
|---|---|---|
| 0 | 1 | 0.6 |
| 3.5 | 95 | 0.7 |
| 4.0 | 95 | 0.7 |
| 4.5 | 95 | 0.8 | detection: Agilent 1100 DAD 210-350 nm and Waters Micromass ZQ 2000 ESI+ and ESI−.

Method D (analytical MS) Instrument: Micromass Platform II, eluent: 15% methanol in water containing 0.2% of a 25% ammonium hydroxide solution Method E (analytical Hplc/MS) Instrument: Hewlett Packard Agilent 1100 series, column: XBridge™ C18 2.5 microm 3.0×30 mm, temperature: 50° C., eluent: 2 channel system: Channel A 5% acetonitrile in water, Channel B acetonitrile containing 1.0% formic acid

| Time (minutes) | % channel B | Flow (ml/minute) |
|---|---|---|
| 0 | 5 | 1.4 |
| 3.7 | 95 | 1.6 |
| 4.4 | 95 | 2.4 |
| 4.45 | 95 | 2.4 | detection: Agilent 1100 DAD 210-350 nm and Waters Micromass ZQ 2000 ESI+ and ESI−.

Method F (analytical HPLC) Instrument: Shimadzu LC-10AD System; RF-10 spectrofluorometric detector; Column: Nucleosil OD-5-100 C18 (150×4.6 mm); detection at 215 nm, flow rate 2 mL/min at RT; Linear gradient 2-100% $CH_3CN$ (0.1% TFA) and $H_2O$ (0.1% TFA) in 4 min+2 min 100% $CH_3CN$ (0.1% TFA); back to −100% $CH_3CN$ (0.1% TFA) in 3 min.

Analytical HPLC conditions:

System 1

Linear gradient 20-100% solvent A in 5 min+1.5 min 100% solvent A; detection at 215 nm, flow rate 1 mL/min at 30° C. Column: Nucleosil 100-3 C18 (70×4.0 mm). Solvent A=$CH_3CN$+0.1% TFA; Solvent B=$H_2O$+0.1% TFA.

System 2

Linear gradient 2-100% $CH_3CN$ (0.1% TFA) and $H_2O$ (0.1% TFA) in 7 min+2 min 100% $CH_3CN$ (0.1% TFA); detection at 215 nm, flow rate 1 mL/min at 30° C. Column: Nucleosil 100-3 C18HD (125×4 mm)

Intermediate A 5-[4-methanesulfonyl-3-(2-propyl-imidazol-1-yl)-phenyl]-4-methyl-thiazol-2-ylamine hydrochloride Trimethylsilylchloride (1 ml) is added at room temperature to a suspension of N-{5-[4-methanesulfonyl-3-(2-propyl-imidazol-1-yl)-phenyl]-4-methyl-thiazol-2-yl}-acetamide (0.1 g, prepared as described in WO 03/072557) in ethanol (5 ml) at room temperature. The mixture is stood at room temperature for 3.5 hours and is then heated at 65° C. for 18 hours. Following cooing the mixture is stood at 4° C. for 4 hours and the title compound isolated as an off-white solid by filtration. Hplc/MS (Method A) RT 1.62 minutes, M+H 377.1.

Intermediate B (2S,4R)-4-hydroxy-pyrrolidine-2-carboxylic acid amide

A solution of (2S,4R)-4-hydroxy-pyrrolidine-2-carboxylic acid benzyl ester (1 g) in 880 ammonia (5 ml) is stirred for 18 hours then evaporated and triturated with diethyl ether to give the title compound as a white solid. $^1$H nmr ($d_6$-DMSO, 400 MHz) 9.15 (s, br, 1H), 8.04 (s, 1H), 7.63 (s, 1H), 5.56 (s, 1H), 4.40 (s, 1H), 4.27-4.16 (m, 1H), 3.27 (d, J=7 Hz, 1H), 3.02 (d, J=7 Hz, 1H), 2.33-2.19 (m, 1H), 1.89-1.76 (m, 1H).

Intermediate C (2S,4S)-4-hydroxy-pyrrolidine-2-carboxylic acid amide

A solution of (2S,4S)-4-hydroxy-pyrrolidine-2-carboxylic acid methyl ester hydrochloride (1 g) in a 7M solution of ammonia in methanol (10 ml) is stirred for 18 hours then evaporated and triturated with diethyl ether. The residue is dissolved in the minimum volume of hot methanol and stood at 4° C. for 4 hours. The title compound is isolated by filtration as a white solid.

Intermediate D imidazole-1-carboxylic acid [5-(2-tert-butyl-pyridin-4-yl)-4-methyl-thiazol-2-yl]-amide To a solution of the hydrobromide salt of 2-amino-4-methyl-5-(2-tert-butyl-4-pyridyl)-1,3-thiazole (2.62 g) in triethylamine (1.07 ml) and DMF (100 ml) at room temperature is added carbonyl diimidazole (2.38 g) and the reaction mixture is heated at 70° C. for 2.5 hours. Cooling of the reaction mixture, filtration and washing with acetonitrile gives the title compound.

Intermediate D1 2-amino-4-methyl-5-(2-tert-butyl-4-pyridyl)-1,3-thiazole

N-[4-methyl-5-(2-tert-butyl-4-pyridyl)-1,3-thiazol-2-yl] acetamide (90 mg) in ethanol (4.5 ml) and 6N hydrochloric acid (0.5 ml) is heated in a Emrys Optimiser personal chemistry microwave at 100° C. for 90 minutes. Cooling of the reaction mixture and filtration gives the title compound.

Intermediate D2 N-[4-methyl-5-(2-tert.butyl-4-pyridyl)-1,3-thiazol-2-yl]acetamide A mixture of 2-acetamido-4-methylthiazole (92 mg), 4-chloro-2-tert.butylpyridine (83 mg), palladium acetate (10.4 mg), tri-tert-butylphosphonium tetrafluoroborate (28.3 mg) and cesium carbonate (319 mg) in DMF under an argon atmosphere is heated for 3 hours at 150° C. The reaction mixture is cooled, filtered through celite, evaporated and purified by normal and then reversed phase chromatography to give the title compound Intermediate D3 4-chloro-2-tert-butylpyridine Phosphorous oxychloride (21.8 ml) and 2-tert.butylpyridin-4-one (2.36 g) is heated at reflux in chloroform (15 ml) for 24 hours and then stood at room temperature for 48 hours before pouring onto ice (100 g). Extraction with CH2Cl2 (3 times 250 ml) is followed by drying of the combined organic layers over magnesium sulphate. Evaporation of the organic layers gives the title compound.

Intermediate D4 2-tert-butylpyridin-4-one 2-tert.butyl gama-pyrone, (3.02 g, prepared by the procedure of Koreeda and Akagi Tetrahedron Letters 1980, 21, 1197-1200.) is heated for 18 hours at 80° C. in 35% aqueous ammonia (50 ml). The reaction mixture is cooled to room temperature, partitioned with CH2Cl2, and the organic layer washed with water. Drying of the organic layer over magnesium sulphate followed by evaporation gives the title compound.

Intermediate E
(2S,4R)-4-fluoro-pyrrolidine-2-carboxylic acid amide

A 1.25 M solution of HCl in ethanol (2.3 ml) is added to a suspension of (2S,4R)-4-fluoro-pyrrolidine-2-carboxylic acid (0.25 g) in ethanol (2 ml) at room temperature and the mixture heated for 62 hours at 55° C. The reaction mixture is evaporated and a 7 M solution of ammonia in methanol (5.6 ml) added. The reaction mixture is stood at room temperature for 36 hours then evaporated, the residue triturated with methanol (0.5 ml) and filtered to give the title compound as a white solid. $^1$H nmr (d$_6$-DMSO, 400 MHz) 7.68 (s, 1H), 7.37 (s, 1H), 5.30 (d, J=50 Hz, 1H), 3.96 (t, J=8 Hz, 1H), 3.40-3.12 (m, 2H), 2.48-2.31 (m, 1H), 2.02-1.81 (m, 1H).

Intermediate F
(2S,3S)-3-hydroxy-pyrrolidine-2-carboxylic acid amide

A 4 M solution of HCl in 1,4-dioxan (3 ml) is added to a suspension of (2S,3S)-3-hydroxypyrrolidine-2-carboxylic acid (1 g) in ethanol (10 ml) at room temperature and the mixture heated at reflux for 21 hours. The reaction mixture is evaporated and a 7 M solution of ammonia in methanol (10.5 ml) added. The reaction mixture is stood at room temperature for 2 days then evaporated, the residue triturated with ethanol (2 ml) and filtered and washed cold mixture of 9:1 ethanol/methanol (2 ml) to give the title compound as a pale pink solid. $^1$H nmr (d$_6$-DMSO, 400 MHz) 8.27 (s, 1H), 7.76 (s, 1H), 5.85 (d, J=4 Hz, 1H), 4.38-4.32 (m, 1H), 3.97 (d, J=2 Hz, 1H), 3.36-3.15 (m, 3H), 1.90-1.80 (m, 2H).

Intermediate G
(2S,3S)-3-methyl-pyrrolidine-2-carboxylic acid amide

A 4 M solution of HCl in 1,4-dioxan (1.5 ml) is added to a suspension of (2S,3S)-3-methylpyrrolidine-2-carboxylic acid (0.5 g) in ethanol (5 ml) at room temperature and the mixture heated at reflux for 20 hours. The reaction mixture is evaporated and a 7 M solution of ammonia in methanol (5.6 ml) added. The reaction mixture is stood at room temperature for 6 days then evaporated, the residue triturated with methanol (0.5 ml) and filtered and washed with cold methanol (2 ml) to give the title compound as a white solid. $^1$H nmr (d$_6$-DMSO, 400 MHz) 8.06 (s, 1H), 7.67 (s, 1H), 3.60 (d, J=10 Hz, 1H), 3.25-3.14 (m, 2H), 2.24-2.15 (m, 1H), 2.09-1.98 (m, 1H), 1.57-1.45 (m, 1H), 1.13 (d, J=8 Hz, 3H).

Intermediate H
(1R,2S,5S)-3-aza-bicyclo[3.1.0]hexane-2-carboxylic acid amide

Thionyl chloride (0.70 ml) is added dropwise over 1 minute to a suspension of (1R,2S,5S)-3-aza-bicyclo[3.1.0]hexane-2-carboxylic acid (0.7 g) in ethanol (7 ml) at 60° C. After the initial vigorous reaction heating is continued at 60° C. for a further 50 minutes and the cooled reaction then partitioned between CH2Cl2 and aqueous ammonia, extracting twice with CH2Cl2, the organic extracts are dried over Na2SO4 and evaporated. The isolated oil is taken up in a 7 M solution of ammonia in methanol (8 ml) and stood at room temperature for 18 hours. Evaporation and crystallization from CHCl3/methanol gives the title compound as a white solid. $^1$H nmr (d$_6$-DMSO, 400 MHz) 7.36 (s, 1H), 6.96 (s, 1H), 3.44 (d, J=4 Hz, 1H), 2.88 (d, J=10 Hz, 1H), 2.75 (dd, J=4 and 10 Hz, 1H), 1.58-1.51 (m, 1H), 1.36-1.28 (m, 1H), 0.33-0.20 (m, 2H).

Intermediate I (S)-2-methyl-pyrrolidine-2-carboxylic acid amide

A solution of (S)-2-methyl-pyrrolidine-2-carboxylic acid butyl ester (2.3 g) in a 7 M solution of ammonia in methanol (22.2 ml) is heated in a bomb at 70° C. for 10 days. Evaporation of the reaction mixture and trituration with hexanes (20 ml) gives the title compound as an off-white solid. $^1$H nmr (d$_6$-DMSO, 400 MHz) 7.40 (s, 1H), 6.89 (s, 1H), 2.95-2.84 (m, 1H), 2.72-2.60 (m, 1H), 2.06-1.95 (m, 1H), 1.66-1.44 (m, 2H), 1.42-1.30 (m, 1H), 1.22 (s, 3H).

Intermediate I1
(S)-2-methyl-pyrrolidine-2-carboxylic acid butyl ester

Concentrated HCl (2 ml) is added to a suspension of (S)-2-methyl-pyrrolidine-2-carboxylic acid (2 g) in butan-1-ol (50 ml) which is heated at 60° C. for 18 hours then at reflux for 4 days. The reaction mixture is evaporated, partitioned between saturated aqueous NaHCO3 and CH2Cl2, extracted 3×CH2Cl2, dried over Na2SO4 and evaporated. The isolated oil is then kugelrohr distilled at 10 mbar to give the title compound as a clear colorless oil from the fraction distilling at an oven temperature of 100-120° C.

Intermediate J N'-[5-((E)-3-dimethylamino-acryloyl)-4-methyl-thiazol-2-yl]-N,N-dimethyl-formamidine A mixture of 5-acetyl-2-amino-4-methylthiazole (12.5 g) and N,N-dimethylformamide-dimethylacetal (35.4 ml) is heated for 15 hours at 100° C. After cooling to room temperature the reaction mixture is evaporated, triturated with ethyl acetate, and filtered to give the title compound as an orange solid. MS (Method D) M+H 267.

Intermediate K imidazole-1-carboxylic acid {5-[2-(2,6-dichloro-benzyl)-pyrimidin-4-yl]-4-methyl-thiazol-2-yl}-amide Carbonyl diimidazole (0.63 g) is added to a solution of 5-[2-(2,6-dichloro-benzyl)-pyrimidin-4-yl]-4-methyl-thiazol-2-ylamine (0.68 g) in a mixture of triethylamine (0.30 ml) and DMF (2 ml) and heated at 80° C. for 18 hours. The reaction mixture is then evaporated at room temperature, suspended in CHCl3 and stood at 4° C. for 2 hours and then filtered to give the title compound as a yellow solid.

Intermediate K1 5-[2-(2,6-dichloro-benzyl)-pyrimidin-4-yl]-4-methyl-thiazol-2-ylamine A mixture of N'-[5-((E)-3-dimethylamino-acryloyl)-4-methyl-thiazol-2-yl]-N,N-dimethyl-formamidine (1 g), 2,6-dichlorophenylacetamidine (0.90 g) and 2-methoxyethanol (3.8 ml) is stirred at room temperature for 30 minutes. NaOH (0.3 g) is added and the mixture stirred at 125° C. for 1 hr. After cooling to room temperature water is added and the

Intermediate L imidazole-1-carboxylic acid [5-(2-cyclopropyl-pyrimidin-4-yl)-4-methyl-thiazol-2-yl]-amide The tile compound is prepared in an analogous manner to Intermediate K except cyclopropanecarboxamidine is used in place of 2,6-dichlorophenylacetamidine. The title compound is obtained as a yellow solid.

Intermediate M imidazole-1-carboxylic acid {5-[2-(2-fluoro-phenyl)-pyrimidin-4-yl]-4-methyl-thiazol-2-yl}-amide The tile compound is prepared in an analogous manner to Intermediate K except 2-flouro-benzamidine hydrochloride is used in place of 2,6-dichlorophenylacetamidine. The title compound is obtained as a yellow solid.

Intermediate N imidazole-1-carboxylic acid [4-methyl-5-(2-methyl-pyrimidin-4-yl)-thiazol-2-yl]-amide Carbonyl diimidazole (22 mg) is added to a solution of 4-methyl-5-(2-methyl-pyrimidin-4-yl)-thiazol-2-ylamine (24 mg) in DMF (1 ml) at room temperature. After standing 18 hours at room temperature the reaction mixture is diluted with CH2Cl2 (2 ml) and the title compound isolated by filtration as a brown amorphous solid.

Intermediate N1 4-methyl-5-(2-methyl-pyrimidin-4-yl)-thiazol-2-ylamine

Trimethylsilylchloride (0.3 ml) is added at room temperature to a suspension of N-[4-methyl-5-(2-methyl-pyrimidin-4-yl)-thiazol-2-yl]-acetamide (29 mg, prepared as described in WO 04/096797) in ethanol (2 ml) at room temperature. The mixture is heated at 50° C. for 18 hours, conc. HCl (0.2 ml) is added and the heating at 50° C. is continued for a further 46 hours. Following cooing the mixture is partitioned between saturated aqueous NaHCO3 and CH2Cl2 containing 10% methanol and extracted a further 2×CH2Cl2. Evaporation of the organic layers gives the title compound as a beige solid. $^1$H nmr (d$_4$-methanol, 400 MHz) 8.44 (d, J=7 hz, 1H), 7.33 (d, J=7 Hz, 1H), 2.58 (s, 3H), 2.51 (s, 3H).

Intermediate O N-(5-iodo-4-methyl-thiazol-2-yl)-acetamide

N-Iodosuccinimide (4.75 g) is added portion wise to a solution of N-(4-methyl-thiazol-2-yl)-acetamide (3 g) in acetonitrile (60 ml) at room temperature. After 5 minutes a precipitate forms which is collected by filtration and washed with cold acetonitrile to give the title compound as a white solid.

Intermediate P imidazole-1-carboxylic acid [5-(6-imidazol-1-yl-pyridin-2-yl)-4-methyl-thiazol-2-yl]-amide Carbonyl diimidazole (17 mg) is added to a solution of 5-(6-imidazol-1-yl-pyridin-2-yl)-4-methyl-thiazol-2-ylamine (24 mg) in DMF (1 ml) at room temperature. After standing 18 hours at room temperature the reaction mixture is evaporated, CH2Cl2 (2 ml) added, and the title compound isolated by filtration as an off-white solid.

Intermediate P1 5-(6-imidazol-1-yl-pyridin-2-yl)-4-methyl-thiazol-2-ylamine

Conc. HCl (0.3 ml) is added to a suspension of N-[5-(6-imidazol-1-yl-pyridin-2-yl)-4-methyl-thiazol-2-yl]-acetamide (30 mg) in ethanol (2 ml) at room temperature. The mixture is heated at reflux for 7 hours. Following cooing the mixture is partitioned between saturated aqueous NaHCO3 and CH2Cl2 containing 10% methanol and extracted a further 4×CH2Cl2 containing 10% methanol. Evaporation of the organic layers gives the title compound as a beige solid. $^1$H nmr (d$_4$-methanol, 400 MHz) 8.50 (s, 1H), 7.94-7.86 (m, 2H), 7.45-7.37 (m, 2H), 7.16 (s, 1H), 2.51 (s, 3H).

Intermediate P2 N-[5-(6-imidazol-1-yl-pyridin-2-yl)-4-methyl-thiazol-2-yl]-acetamide A mixture of N-(5-iodo-4-methyl-thiazol-2-yl)-acetamide (312 mg), 6-(imidazol-1-yl)pyridine-2-boronic acid pinacol ester (600 mg), 1,1'-bis(diphenylphosphino)ferrocene-dichloropalladium (II) (45 mg) and sodium carbonate (594 mg) in DME (3.1 ml) and water (3.1 ml) is heated in a Emrys Optimiser personal chemistry microwave at 85° C. for 45 minutes. Water is added (5 ml) and the mixture extracted with 3×10% methanol in CH2Cl2, the combined organic layers evaporated and purified by reversed phase chromatography (Method B) collecting the 12.8 minute retention time component. Partial evaporation of the fractions, neutralization with NaHCO3, extraction with 10% methanol in CH2Cl2 (5×) and evaporation gives a white solid. Further purification of this material by normal phase chromatography on silica gel eluting with a gradient from EtOAc to 10% methanol in EtOAc gives the title compound as a white solid. Hplc/MS (Method C) RT 1.31 minutes, M+H 299.9 and M−H 298.0.

Intermediate Q imidazole-1-carboxylic acid [5-(2-methoxymethyl-pyrimidin-4-yl)-4-methyl-thiazol-2-yl]-amide The tile compound is prepared in an analogous manner to Intermediate K except 2-methoxy-acetamidine hydrochloride is used in place of 2,6-dichlorophenylacetamidine. The title compound is obtained as a beige solid.

Intermediate R imidazole-1-carboxylic acid [5-(2-isobutyl-pyrimidin-4-yl)-4-methyl-thiazol-2-yl]-amide The tile compound is prepared in an analogous manner to Intermediate K except 3-methylbutyramidine is used in place of 2,6-dichlorophenylacetamidine. The title compound is obtained as a beige solid.

Intermediate S imidazole-1-carboxylic acid [5-(2-benzyl-pyrimidin-4-yl)-4-methyl-thiazol-2-yl]-amide The tile compound is prepared in an analogous manner to Intermediate K except 2-phenyl acetamidine acetate is used in place of 2,6-dichlorophenylacetamidine. The title compound is obtained as a yellow solid.

Intermediate T imidazole-1-carboxylic acid [5-(2-ethyl-pyrimidin-4-yl)-4-methyl-thiazol-2-yl]-amide The tile compound is prepared in an analogous manner to Intermediate K except propionamidine is used in place of 2,6-dichlorophenylacetamidine. The title compound is obtained as a yellow solid.

Intermediate U imidazole-1-carboxylic acid [5-(2-triflouromethyl-pyrimidin-4-yl)-4-methyl-thiazol-2-yl]-amide The tile compound is prepared in an analogous manner to Intermediate K except triflouroacetamidine is used in place of 2,6-dichlorophenylacetamidine. The title compound is obtained as a yellow solid.

Intermediate V imidazole-1-carboxylic acid [5-(3-tert-butyl-phenyl)-4-methyl-thiazol-2-yl]-amide Carbonyl diimidazole (11 mg) is added to a solution of 5-(3-tert-butyl-phenyl)-4-methyl-thiazol-2-ylamine (20 mg) in CH2Cl2 (1 ml) at room temperature. After standing 18 hours at room temperature the reaction mixture is filtered, washing with cold CH2Cl2 (2 ml) to give the title compound as a white solid.

Intermediate V1 5-(3-tert-butyl-phenyl)-4-methyl-thiazol-2-ylamine

Trimethylsilylchloride (0.3 ml) is added at room temperature to a suspension of N-[4-methyl-5-(2-methyl-pyrimidin-4-yl)-thiazol-2-yl]-acetamide (19 mg) in ethanol (2 ml) at room temperature. The mixture is heated at 50° C. for 18 hours, conc. HCl (0.1 ml) is added and the heating at 50° C. is continued for a further 48 hours. Following cooing the mixture is partitioned between saturated aqueous NaHCO3 and CH2Cl2 and extracted a further 4×CH2Cl2. Evaporation of the organic layers gives the title compound as a clear pale brown glass. $^1$H nmr (d$_4$-methanol, 400 MHz) 7.37-7.24 (m, 3H), 7.26-7.22 (m, 1H), 2.21 (s, 3H), 1.34 (s, 9H).

Intermediate W Imidazole-1-carboxylic acid {4-methyl-5-[2-(1,1,2-trimethyl-propyl)-pyrimidin-4-yl]-thiazol-2-yl}-amide The tile compound is prepared in an analogous manner to Intermediate K except 2,2,3-trimethylbutyramidine is used in place of 2,6-dichlorophenyllacetamidine. The title compound is obtained as a white solid.

Intermediate X Imidazole-1-carboxylic acid {5-[2-(4-methoxy-phenoxymethyl)-pyrimidin-4-yl]-4-methyl-thiazol-2-yl}-amide The tile compound is prepared in an analogous manner to Intermediate K except 2-(4-methoxyphenoxy)-acetamidine is used in place of 2,6-dichlorophenyllacetamidine. The title compound is obtained as a beige solid.

Intermediate Y Imidazole-1-carboxylic acid (5-{2-[2-(4-methoxy-phenyl)-1,1-dimethyl-ethyl]-pyrimidin-4-yl}-4-methyl-thiazol-2-yl)-amide The tile compound is prepared in an analogous manner to Intermediate K except 3-(4-methoxyphenyl)-2,2-dimethyl-propionamidine is used in place of 2,6-dichlorophenyllacetamidine. The title compound is obtained as a white solid.

Intermediate Z (2S,4R)-4-hydroxy-2-methyl-pyrrolidine-2-carboxylic acid amide A solution of (2S,4R)-4-hydroxy-2-methyl-pyrrolidine-1,2-dicarboxylic acid 1-tert-butyl ester 2-methyl ester (400 mg) in 1.25 M hydrogen chloride in ethanol (2 ml) is stood for 18 hours at room temperature. The mixture is then evaporated and the residue taken up in methanol (5 ml) and a solution of 7M ammonia in methanol (5 ml) is added and the mixture heated for 10 days at 65° C. in a sealed vessel. After evaporation the isolated material is used directly in the following reactions.

Intermediate AA (2S,4S)-4-Fluoro-pyrrolidine-2-carboxylic acid amide

A mixture of (2S,4S)-2-carbamoyl-4-fluoro-pyrrolidine-1-carboxylic acid tert-butyl ester (1.0 g), conc. Hydrochoric acid (0.6 ml) and 1-butanol (10 ml) is heated for 48 hours at 50° C. The reaction mixture is evaporated and partitioned dichloromethane and aqueous sodium bicarbonate, the dichloromethane layers are dried over sodium sulphate and evaporated. A solution of 7M ammonia in methanol (10 ml) is added to the residue and the mixture is stood for 60 hours at room temperature in a sealed vessel. Evaporation and trituration with ethanol gives the title compound as a white solid.

Intermediate AB Imidazole-1-carboxylic acid {5-[2-(4-ethyl-tetrahydro-pyran-4-yl)-pyrimidin-4-yl]-4-methyl-thiazol-2-yl}-amide The tile compound is prepared in an analogous manner to Intermediate K except 4-ethyltetrahydro-pyran-4-carboxamidine is used in place of 2,6-dichlorophenyllacetamidine.

Intermediate AC Imidazole-1-carboxylic acid {4-methyl-5-[2-(1-phenyl-cyclopentyl)-pyrimidin-4-yl]-thiazol-2-yl}-amide The tile compound is prepared in an analogous manner to Intermediate K except 1-phenyl-cyclopentanecarboxamidine is used in place of 2,6-dichlorophenyllacetamidine. The title compound is obtained as a beige solid.

Intermediate AD Imidazole-1-carboxylic acid {5-[2-(1,1-dimethyl-2-p-tolyl-ethyl)-pyrimidin-4-yl]-4-methyl-thiazol-2-yl}-amide The tile compound is prepared in an analogous manner to Intermediate K except 2,2-dimethyl-3-p-tolyl-propionamidine is used in place of 2,6-dichlorophenyllacetamidine. The title compound is obtained as a white solid.

Intermediate AE (2S,4R)-4-Dimethylamino-pyrrolidine-2-carboxylic acid amide

A solution of (2S,4R)-4-Dimethylamino-pyrrolidine-2-carboxylic acid methyl ester (225 mg) and 7M ammonia in methanol (7 ml) is stood for 18 hours at room temperature in a sealed vessel. Evaporation and trituration with diethyl ether gives the title compound as a white solid.

Intermediate AE1
(2S,4R)-4-Dimethylamino-pyrrolidine-2-carboxylic acid methyl ester A mixture of (2S,4R)-4-dimethylamino-pyrrolidine-1,2-dicarboxylic acid 1-benzyl ester 2-methyl ester (420 mg), 10% palladium on carbon (80 mg) and methanol (10 ml) is stirred for 16 hours under an atmosphere of hydrogen. Filtration and evaporation gives the title compound which is used without purification in the following steps.

Intermediate AE2 (2S,4R)-4-Dimethylamino-pyrrolidine-1,2-dicarboxylic acid 1-benzyl ester 2-methyl ester Sodium cyanoborohydride (200 mg) is added to a mixture of (2S,4R)-4-amino-pyrrolidine-1,2-dicarboxylic acid 1-benzyl ester 2-methyl ester (400 mg), formalin (0.68 ml), acetic acid (0.72 ml), triethylamine (0.2 ml) and methanol (2 ml) and the mixture is stirred for 2 hours at room temperature. The reaction mixture is then partitioned between dicloromethane and aqueous sodium bicarbonate solution, the dichloromethane layers evaporated and purified by normal phase chromatography, eluent; gradient from ethyl acetate to 20% ethanol in ethyl acetate, to give the predominant UV-active component. The chromatographed material is taken up 1M hydrochloric acid, washed 2× with diethyl ether, the aqueous layer basified with sodium bicarbonate, 3× extracted with diethyl ether, dried over sodium sulphate and evaporated to give the title compound as a pale yellow oil.

Intermediate AF Imidazole-1-carboxylic acid [5-(2-diethylamino-pyrimidin-4-yl)-4-methyl-thiazol-2-yl]-amide Carbonyl diimidazole (437 mg) is added to a solution of [4-(2-Amino-4-methyl-thiazol-5-yl)-pyrimidin-2-yl]-diethyl-amine (355 mg) and triethylamine (207 µl) in DMF (1.4 ml) at room temperature and then heated for 18 hours at 80° C. The reaction mixture is evaporated and triturated with chloroform. The title compound is isolated by filtration.

Intermediate AF1 [4-(2-Amino-4-methyl-thiazol-5-yl)-pyrimidin-2-yl]-diethyl-amine Powdered sodium hydroxide (150 mg) is added to a solution of N'-[5-(3-dimethylamino-acryloyl)-4-methyl-thiazol-2-yl]-N,N-dimethyl-formamidine (0.5 g, prepared as described by S. Wang et al J. Med. Chem. 2004, 47, 1662-1675.) and 1,1-diethylguanidine (259 mg) in 2-methoxyethanol (1.9 ml) and the mixture heated at 125° C. for 1 hour with stirring. The reaction mixture is concentrated under vacuum and purified by normal phase chromatography, eluent; DCM/EtOAc, to give the title compound. ESI-MS: M+H 264 and M-H 262.

Intermediate AG
(2S,4S)-4-Dimethylamino-pyrrolidine-2-carboxylic acid amide A solution of (2S,4S)-4-Dimethylamino-pyrrolidine-2-carboxylic acid butyl ester (326 mg) and 7M ammonia in methanol (8 ml) is stood for 18 hours at room temperature in a sealed vessel. Filtration, evaporation and trituration with diethyl ether/methanol gives the title compound as a beige solid.

Intermediate AG1
(2S,4S)-4-Dimethylamino-pyrrolidine-2-carboxylic acid butyl ester Concentrated hydrochloric acid (0.3 ml) is added to a mixture of (2S,4S)-4-dimethylamino-pyrrolidine-2-carboxylic acid methyl ester dihydrochloride (400 mg) and 1-butanol (4 ml) and heated for 18 hours at 115° C. After cooling the reaction mixture is evaporated then partitioned between dicloromethane and aqueous sodium bicarbonate solution and the dichloromethane layers dried and evaporated to give the title compound as a brown oil which is used without further purification.

Intermediate AH Imidazole-1-carboxylic acid {5-[2-isopropyl-pyrimidin-4-yl]-4-methyl-thiazol-2-yl}-amide The tile compound is prepared in an analogous manner to Intermediate K except 2-methylpropionamidine is used in place of 2,6-dichiorophenyllacetamidine. The title compound is obtained as a beige solid.

Intermediate AI Imidazole-1-carboxylic acid {4-methyl-5-[2-methylsulphanyl-pyrimidin-4-yl]-thiazol-2-yl}-amide Carbonyl diimidazole (1.77 g) is added to a solution of 4-methyl-5-(2-methylsulphanyl-pyrimidin-4-yl)-thiazol-2-ylamine (1.3 g) in triethylamine (0.84 ml) and DMF (5.5 ml) at room temperature and stirred for 2 hours at 80° C. After cooling the title compound is isolated by filtration.

Intermediate AI1 4-Methyl-5-(2-methylsulphanyl-pyrimidin-4-yl)-thiazol-2-ylamine Powdered sodium hydroxide (1.09 g) is added to a solution of N'-[5-(3-dimethylamino-acryloyl)-4-methyl-thiazol-2-yl]-N,N-dimethyl-formamidine (2.0 g, prepared as described by S. Wang et al J. Med. Chem. 2004, 47, 1662-1675.) and thiourea (0.57 g) in ethanol (25 ml) and the mixture is heated at reflux for 3 hour with stirring. The reaction mixture is cooled to room temperature and water then methyliodide (0.47 ml) is added. After 1 hour at room temperature the ethanol is removed by evaporation and water is added and the pH is adjusted to 7 with 2N aqueous hydrochloric acid. The title compound is then obtained by filtration. ESI-MS: M+H 239 and M-H 237.

Intermediate AJ (S)-2-Methyl-pyrrolidine-1,2-dicarboxylic acid 2-amide 1-{[5-(2-methanesulphinyl-pyrimidin-4-yl)-4-methyl-thiazol-2-yl]-amide} meta-Chloroperoxybenzoic acid (0.78 g) was added to a solution of (S)-2-methyl-pyrrolidine-1,2-dicarboxylic acid 2-amide 1-{[4-methyl-5-(2-methylsulphanyl-pyrimidin-4-yl)-thiazol-2-yl]-amide} (1.7 g) in dichloromethane (10 ml) at 0° C. After 10 minutes the reaction mixture is evaporated and purified by normal phase chromatography, eluting with a dichloromethane/methanol gradient, to give the title compound as a orange solid. ESI-MS: M+H 409 and M-H 407.

Intermediate AK Imidazole-1-carboxylic acid [5-(2-cyclobutyl-pyrimidin-4-yl)-4-methyl-thiazol-2-yl]-amide The tile compound is prepared in an analogous manner to Intermediate K except cyclobutanecarboxamidine is used in place of 2,6-dichlorophenyllacetamidine. The title compound is obtained as a beige solid.

Intermediate AL (1S,5R)-2-Aza-bicyclo[3.1.0]hexane-1-carboxylic acid amide

A mixture of (1S,5R)-2-aza-bicyclo[3.1.0]hexane-1-carboxylic acid ethyl ester (2.5 g, prepared by the procedure of Hercouet Tetrahedron Assymmetry 1996, 7, 1267-1268.) and 7M ammonia in methanol (20 ml) are heated in a sealed vessel at 80° C. for 5 days. The cooled reaction mixture is evaporated and triturated with hexanes/dichloromethane to give the title compound as a beige solid.

Intermediate AM Imidazole-1-carboxylic acid {4-methyl-5-[2-(1-methyl-cyclopropyl)-pyrimidin-4-yl]-thiazol-2-yl}-amide Carbonyl diimidazole (4.56 g) is added to a solution of 4-methyl-5-[2-(1-methyl-cyclopropyl)-pyrimidin-4-yl]-thiazol-2-ylamine (10.5 g) and triethylamine (4.28 ml) in DMF (26 ml) at room temperature and then heated for 2 hours at 80° C. After cooling the title compound is isolated by filtration.

Intermediate AM1 4-Methyl-5-[2-(1-methyl-cyclopropyl)-pyrimidin-4-yl]-thiazol-2-ylamine Powdered sodium hydroxide (5.86 g) is added to a solution of N'-[5-(3-dimethylamino-acryloyl)-4-methyl-thiazol-2-yl]-N,N-dimethyl-formamidine (13 g, prepared as described by S. Wang et al J. Med. Chem. 2004, 47, 1662-1675.) and 1-methyl-cyclopropanecarboxamidine hydrochloride (7.2 g, prepared as described in EP0227415) in 2-methoxyethanol (98 ml) and the mixture heated at 125° C. for 1 hour with stirring. The reaction mixture is cooled, water is added, and the title compound isolated by filtration. ESI-MS: M+H 247 and M−H 245.

Intermediate AN (R)-2-Benzyl-pyrrolidine-2-carboxylic acid amide

A mixture of (3R,7aR)-7a-benzyl-3-trichloromethyl-tetrahydro-pyrrolo[1,2-c]oxazol-1one (1.40 g, prepared as described by Wang and Germanas Synlett 1999, 33-36.) and 7M ammonia in methanol (15 ml) is heated at 50° C. for 3 days in a sealed vessel. The cooled reaction mixture is then evaporated and triturated with chloroform to give the title compound as a white solid.

Intermediate AO (R)-2-Dimethylaminomethyl-pyrrolidine-2-carboxylic acid amide A mixture of (3R,7aR)-7a-dimethylaminomethyl-3-trichloromethyl-tetrahydro-pyrrolo[1,2-c]oxazol-1-one (0.26 g) and 7M ammonia in methanol (4 ml) is heated at 50° C. for 3 days in a sealed vessel. The cooled reaction mixture is then evaporated to give the title compound as a brown oil which is used without further purification.

Intermediate AO1 (3R,7aR)-7a-Dimethylaminomethyl-3-trichloromethyl-tetrahydro-pyrrolo[1,2-c]oxazol-1-one A 1M of solution of lithium diisopropylamide in a 3:5 mixture of hexanes/THF (8.25 ml) is added dropwise to (3R,7aS)-3-trichloromethyl-tetrahydro-pyrrolo[1,2-c]oxazol-1-one (1.51 g, prepared as described by Wang and Germanas Synlett 1999, 33-36.) in THF (5 ml) at −78° C. After stirring 30 minutes at −78° C. Eschenmoser's salt (2.78 g) is added. The reaction mixture is then allowed to warm to −40° C. with vigorous stirring over 1 hour and maintained for 2 hours at −40° C. Water is then added and the aqueous layer extracted with dichloromethane, the combined organic layers dried over sodium sulphate and evaporated. The residue is then purified by mormal phase chromatography eluting with a gradient from dichloromethane to 20% ethyl acetate in dichloromethane to give the title compound as a pale yellow oil.

Intermediate AP Imidazole-1-carboxylic acid {4-methyl-5-[2-(1,1-dimethyl-propyl)-pyrimidin-4-yl]-thiazol-2-yl}-amide The tile compound is prepared in an analogous manner to Intermediate AM except 2,2-dimethyl-butyramidine is used in place of 1-methyl-cyclopropanecarboxamidine. The title compound is obtained as a white solid.

Intermediate AQ (2S,4R)-4-Cyano-pyrrolidine-2-carboxylic acid amide

A mixture of (2S,4R)-4-cyano-pyrrolidine-2-carboxylic acid methyl ester (22 mg) and 7M ammonia in methanol (0.24 ml) is stirred at room temperature for 1 hour. The reaction mixture is then evaporated to give the title compound which is used without further purification. MS (Method D) M+H 140.

Intermediate AR Imidazole-1-carboxylic acid [5-(2-cyclopropylmethyl-pyrimidin-4-yl)-4-methyl-thiazol-2-yl]-amide The title compound is prepared in analogy to the procedure described for Intermediate AM, but using 5-(2-cyclopropylmethyl-pyrimidin-4-yl)-4-methyl-thiazol-2-ylamine in place of 4-methyl-5-[2-(1-methyl-cyclopropyl)-pyrimidin-4-yl]-thiazol-2-ylamine and the reaction is stirred for 15 h. M.p. 240-243° C., ESI-MS [M+H]' 305.1, TLC: $R_f$=0.35 (DCM/EtOH 95:5).

Intermediate AR1 5-(2-Cyclopropylmethyl-pyrimidin-4-yl)-4-methyl-thiazol-2-ylamine The title compound is prepared in analogy to the procedure described for Intermediate AM1, but using 2-cyclopropyl-acetamidine hydrochloride in place of 1-methyl-cyclopropanecarboxamidine hydrochloride. M.p. 198-200° C., ESI-MS [M+H]⁺247.1, TLC: $R_f$=0.25 (DCM/EtOH 95:5).

Intermediate AS Imidazole-1-carboxylic acid [5-(2-d₉-tert-butyl-pyrimidin-4-yl)-4-methyl-thiazol-2-yl]-amide Carbonyl diimidazole (0.77 g) is added to a stirred solution of 5-(2-d₉-tert-butyl-pyrimidin-4-yl)-4-methyl-thiazol-2-ylamine (1.11 g) in DMF (4.3 ml) at room temperature. The

Intermediate AS1 5-(2-d$_9$-tert-Butyl-pyrimidin-4-yl)-4-methyl-thiazol-2-ylamine Powdered sodium hydroxide (3.71 g) is added to a solution of N'-[5-(3-dimethylamino-acryloyl)-4-methyl-thiazol-2-yl]-N,N-dimethyl-formamidine (5.51 g) and d$_9$-2,2-dimethyl-propionamidine hydrochloride (4.50 g) in 2-methoxyethanol (41 ml) and the mixture is heated at 125° C. for 1 hour with stirring. The reaction mixture is cooled, water is added, and the crude product is isolated by filtration. The crude product is purified by preparative HPLC and the fractions containing the title compound partitioned between dichloromethane and aqueous sodium bicarbonate. The title compound is obtained as a yellow solid after evaporation of the dried dichloromethane layers. HPLC/MS (Method C): retention time 1.12 minutes, M+H 258.4.

Intermediate AS2 d$_9$-2,2-Dimethyl-propionamidine hydrochloride

A 2M solution of trimethylaluminium in toluene (61 ml) is added dropwise to a suspension of ammonium chloride (6.53 g) in toluene (46 ml) cooled with an ice bath. The reaction mixture is stirred for 4 hours at room temperature and d$_9$-2,2-dimethyl-propionic acid butyl ester (6.3 g) is added. After heating at 80° C. for 4 days the reaction mixture is cooled to 0° C. and methanol (200 ml) is added drop wise. After stirring and sonication for 1 hour at room temperature the reaction mixture is filtered through Hyflo, washing with methanol, and the filtrate is evaporated to give the title compound as an off-white solid.

Intermediate AS3 d$_9$-2,2-Dimethyl-propionic acid butyl ester d$_9$-tert-Butylchloride (5.0 g) is added portion wise to a suspension of magnesium (1.50 g) in tetrahydrofuran (20 ml), activated with a catalytic amount of iodine, over 1 hour with heating as required to maintain a steady reflux. The reaction mixture is then heated for a further one hour to ensure complete Grignard formation. The above Grignard solution is then added dropwise to a solution of imidazole-1-carboxylic acid butyl ester (7.5 g, prepared as described by T. Werner and A. G. M. Barrett J. Org. Chem. 2006, 71, 4302-4304.) in tetrahydrofuran (40 ml) cooled with an ice bath. The reaction mixture is stirred for 18 hours at room temperature, water (200 ml) is added, the mixture is filtered through Hyflo, the filtrate is extracted with diethyl ether and the diethyl ether layers dried over sodium sulphate and evaporated to give the tile compound.

Intermediate AT (R)-2-Methoxymethyl-pyrrolidine-2-carboxylic acid amide

A mixture of (3R,7aR)-7a-methoxymethyl-trichloromethyl-tetrahydro-pyrrolo[1,2-c]oxazol-1-one (0.6 g) and 7M ammonia in methanol (6 ml) is stood at room temperature for 2 days in a sealed vessel. The reaction mixture is then evaporated to give the title compound as a pale yellow oil which is used without further purification.

Intermediate AT1 (3R,7aR)-7a-Methoxymethyl-3-trichloromethyl-tetrahydro-pyrrolo[1,2-c]oxazol-1-one A 1M of solution of lithium diisopropylamide in a 3:5 mixture of hexanes/THF (8.25 ml) is added dropwise to (3R,7aS)-3-trichloromethyl-tetrahydro-pyrrolo[1,2-c]oxazol-1-one (1.51 g, prepared as described by Wang and Germanas Synlett 1999, 33-36.) in THF (5 ml) at −78° C. After stirring 30 minutes at −78° C. methoxymethylchloride (1.14 ml) is added. The reaction mixture is then allowed to warm to −30° C. over 3 hours and water is added. The aqueous layer is extracted with dichloromethane, the combined organic layers evaporated and the residue is then purified by normal phase chromatography, eluting with dichloromethane, to give the title compound as a pale yellow oil.

Intermediate AU (S)-Azetidine-2-carboxylic acid amide

A mixture of (S)-2-carbamoyl-azetidine-1-carboxylic acid benzyl ester (1.8 g), 10% palladium on carbon (0.2 g) and methanol (25 ml) was stirred under a hydrogen atmosphere at room temperature for 5 hours. Filtration and evaporation gives the title compound which is used without further purification.

Intermediate AU1 (S)-2-Carbamoyl-azetidine-1-carboxylic acid benzyl ester

A mixture of (S)-azetidine-1,2-dicarboxylic acid 1-benzyl ester 2-methyl ester (2.5 g) and 7M ammonia in methanol (10 ml) is stood at room temperature for 18 hours in a sealed vessel. The reaction mixture is then evaporated to give the title compound as a white solid which is used without further purification. MS M+H 235.1 and M−H 233.1.

Intermediate AV (S)-2-Difluoromethyl-pyrrolidine-2-carboxylic acid amide

A mixture of (3R,7aS)-7a-difluoromethyl-3-trichloromethyl-tetrahydro-pyrrolo[1,2-c]oxazol-1-one (0.19 g) and 7M ammonia in methanol (4 ml) is stood at room temperature for 3 days in a sealed vessel. The reaction mixture is then filtered and evaporated to give the title compound as a pale brown oil which is used without further purification. MS (Method D) M+H 165.

Intermediate AV1 (3R,7aS)-7a-Difluoromethyl-3-trichloromethyl-tetrahydro-pyrrolo[1,2-c]oxazol-1-one DAST (0.36 ml) is added dropwise to a solution of (3R,7aR)-1-oxo-3-trichloromethyl-dihydro-pyrrolo[1,2-c]oxazole-7a-carbaldehyde (0.25 g, prepared as described by Davis et al J. Org. Chem. 1993, 58, 6843-6850.) in dichloromethane (1 ml) at 0° C. The reaction mixture is stirred for 18 hours at room temperature, partitioned between aqueous sodium bicarbonate solution and dichloromethane and the dichloromethane extracts evaporated. The residue is then purified by normal phase chromatography, eluting with a gradient from dichloromethane to 20% ethyl acetate in dichloromethane to give the title compound as a pale yellow oil.

Intermediate AS1 begins at the top of column 1; at the very top of column 1 the following sentence appears:

reaction mixture is then stood for 18 hours at 25° C. after which time the title compound is isolated by filtration.

Intermediate AW (R)-Thiazolidine-4-carboxylic acid amide

Ethyl chloroformate (2.26 ml) is added dropwise to a mixture of (S)—N-(tert.butoxycarbonyl)-thiazolidine-4-carboxylic acid (5 g), triethylamine (3.14 ml) and THF (75 ml) cooled at −15° C. After 15 minutes 25% ammonium hydroxide solution is added (7.5 ml) and the mixture stirred for 2 hours at 0° C. Saturated aqueous ammonium chloride is then added, extracted with THF, the combined organic layers dried over magnesium sulphate and evaporated. The residue is triturated with diethyl ether to remove a white solid and the solution evaporated. 4M Hydrochloric acid in dioxane is added at room temperature. After 1 hour the mixture is evaporated to give the title compound which is used without further purification.

Intermediate AX imidazole-1-carboxylic acid (2-tert-butyl-4'-methyl-[4,5']bithiazolyl-2'-yl)-amide Carbonyl diimidazole (337 mg) is added to a solution of 2-tert-butyl-4'-methyl-[4,5]bithiazolyl-2'-ylamine (480 mg) in triethylamine (0.66 ml) and CH2Cl2 (19 ml) at room temperature. After standing for 7 hours at room temperature the reaction mixture is filtered to give the title compound as a white needles.

Intermediate AX1 2-tert-butyl-4'-methyl-[4,5]bithiazolyl-2'-ylamine

A mixture of 1-(2-amino-4-methyl-thiazol-5-yl)-2-bromo-ethanone (7.0 g, prepared as described in WO 2006/125805), 2,2-dimethylpropanethioamide (2.25 g, prepared as described by Boys and Downs in Synthetic Communications 2006, 36, 295-298.), triethylamine (7.2 ml) and ethanol (173 ml) are heated at reflux for 3.5 hours. On cooling to room temperature the reaction mixture is filtered, the filtrate evaporated and then partitioned between aqueous NaHCO3 and CH2Cl2, extracting 3×CH2Cl2. The organic layers are dried and evaporated then triturated 4× with diethyl ether (50 ml), the diethyl ether layers combined and extracted with 1M HCl (100 ml). The HCl layer is then washed 3× diethyl ether, basified with aqueous NaOH and extracted 4× diethyl ether and 2×CH2Cl2. The organic layers dried over Na2SO4 and evaporated to give the title compound as a red solid. Hplc/MS (Method B) RT 1.95 minutes, M+H 253.9.

Intermediate AY Imidazole-1-carboxylic acid (2,4"-dimethyl-[4,2';4',5"]terthiazol-2"-yl)-amide The title compound is prepared as described for Intermediate BO using 2-methyl-1,3-thiazol-4-carbonylthiamide in place of 3-pyridylthiourea. Title compound: HPLC (Method F) RT 5.86 minutes; MS (Method D) M+H 389.0.

Intermediate AZ Imidazole-1-carboxylic acid [4'-methyl-2-(2-methyl-1H-imidazol-4-yl)-[4,5]bithiazolyl-2'-yl]-amide The title compound is prepared as described for Intermediate BO using 2-methyl-1H-imidazol-4-carbonylthioamide in place of 3-pyridylthiourea. Title compound: HPLC (Method F) RT 3.55 minutes; MS (Method D) M+H 372.1 and M−H 370.1.

Intermediate BA Imidazole-1-carboxylic acid (2-cyclopropylamino-4'-methyl-[4,5]bithiazolyl-2'-yl)-amide The title compound is prepared as described for Intermediate BO using cyclopropyl-thiourea in place of 3-pyridylthiourea. Title compound: HPLC: (Method F) RT 4.13 minutes; MS (Method D) M+H 347.1

Intermediate BB Imidazole-1-carboxylic acid (2-dimethylamino-4'-methyl-[4,5]bithiazolyl-2'-yl)-amide The title compound is prepared as described for Intermediate BO using 1,1-dimethyl-thiourea in place of 3-pyridylthiourea. Title compound: HPLC (Method F) RT 4.20 minutes; MS (Method D) sample prepared in methanol leads to detection of the corresponding urethane only (NH—CO—OCH3): M+H 299.1.

Intermediate BC Imidazole-1-carboxylic acid [2-(3-aza-bicyclo[3.2.2]non-3-yl)-4'-methyl-[4,5]bithiazolyl-2'-yl]-amide The title compound is prepared as described for Intermediate BO using 3-aza-bicyclo[3.2.2]nonane-3-carbothioic acid amide in place of 3-pyridylthiourea. Title compound: HPLC (Method F) RT 5.43 minutes; MS (Method D) sample prepared in methanol leads to detection of the corresponding urethane only (NH—CO—OCH3): M+H 379.1.

Intermediate BD Imidazole-1-carboxylic acid (2-ethyl-4'-methyl-[4,5]bithiazolyl-2'-yl)-amide The title compound is prepared as described for Intermediate BO using N-(2-ethyl-4'-methyl-[4,5]bithiazolyl-2'-yl)-acetamide in place of N-[4'-methyl-2-(pyridin-3-ylamino)-[4,5']bithiazolyl-2'-yl]-acetamide. Title compound: HPLC (Method F) RT 5.05 minutes; MS (Method D) sample prepared in methanol leads to detection of the corresponding urethane only (NH—CO—OCH3): M+H 283.8.

Intermediate BD1 N-(2-Ethyl-4'-methyl-[4,5]bithiazolyl-2'-yl)-acetamide

N-[5-(2-Bromo-acetyl)-4-methyl-thiazol-2-yl]-acetamide (71.6 mg) (prepared by the procedure of WO 2005/068444) is dissolved in CH3OH (5 mL) at RT, followed by addition of thiopropionamide (21.4 mg) and ammonium phosphomolybdate×H2O (37.5 mg). After completion of the reaction, water is added (25 mL) and the precipitate is filtered off to obtain the title compound as a dark green powder. Title compound: HPLC (Method F) RT 4.86 minutes; MS (Method D) M+H 268.2 and M−H 266.2.

Intermediate BE Imidazole-1-carboxylic acid (4'-methyl-2-pyridin-3-yl-[4,5]bithiazolyl-2'-yl)-amide The title compound is prepared as described for Intermediate BO using thionicotinamide in place of 3-pyridylthiourea. Title compound: HPLC (Method F) RT 4.13 minutes; MS (Method D) sample prepared in methanol leads to detection of the corresponding urethane only (NH—CO—OCH3): M+H 382.8.

Intermediate BF Imidazole-1-carboxylic acid [4'-methyl-2-(1-methyl-cyclopropyl)-[4,5']bithiazolyl-2'-yl]-amide The title compound is prepared as described for Intermediate BD using 1-methyl-cyclopropanecarbothioic acid amide in place of thiopropionamide. Title compound: HPLC (Method F) RT 5.80 minutes; MS (Method D) sample prepared in methanol leads to detection of the corresponding urethane only (NH—CO—OCH3): M+H 309.8.

Intermediate BG (2S,4R)-4-Dimethylamino-pyrrolidine-2-carboxylic acid amide

A solution of (2S,4R)-4-Dimethylamino-pyrrolidine-2-carboxylic acid methyl ester (225 mg) and 7M ammonia in methanol (7 ml) is stood for 18 hours at room temperature in a sealed vessel. Evaporation and trituration with diethyl ether gives the title compound as a white solid.

Intermediate BG1 (2S,4R)-4-Dimethylamino-pyrrolidine-2-carboxylic acid methyl ester A mixture of (2S,4R)-4-dimethylamino-pyrrolidine-1,2-dicarboxylic acid 1-benzyl ester 2-methyl ester (420 mg), 10% palladium on carbon (80 mg) and methanol (10 ml) is stirred for 16 hours under an atmosphere of hydrogen. Filtration and evaporation gives the title compound which is used without purification in the following steps.

Intermediate BG2 (2S,4R)-4-Dimethylamino-pyrrolidine-1,2-dicarboxylic acid 1-benzyl ester 2-methyl ester Sodium cyanoborohydride (200 mg) is added to a mixture of (2S,4R)-4-amino-pyrrolidine-1,2-dicarboxylic acid 1-benzyl ester 2-methyl ester (400 mg), formalin (0.68 ml), acetic acid (0.72 ml), triethylamine (0.2 ml) and methanol (2 ml) and the mixture is stirred for 2 hours at room temperature. The reaction mixture is then partitioned between dicloromethane and aqueous sodium bicarbonate solution, the dichloromethane layers evaporated and purified by normal phase chromatography, eluent; gradient from ethyl acetate to 20% ethanol in ethyl acetate, to give the predominant UV-active component. The chromatographed material is taken up 1M hydrochloric acid, washed 2× with diethyl ether, the aqueous layer basified with sodium bicarbonate, 3× extracted with diethyl ether, dried over sodium sulphate and evaporated to give the title compound as a pale yellow oil.

Intermediate BH (2S,4S)-4-Dimethylamino-pyrrolidine-2-carboxylic acid amide

A solution of (2S,4S)-4-Dimethylamino-pyrrolidine-2-carboxylic acid butyl ester (326 mg) and 7M ammonia in methanol (8 ml) is stood for 18 hours at room temperature in a sealed vessel. Filtration, evaporation and trituration with diethyl ether/methanol gives the title compound as a beige solid.

Intermediate BH1 (2S,4S)-4-Dimethylamino-pyrrolidine-2-carboxylic acid butyl ester Concentrated hydrochloric acid (0.3 ml) is added to a mixture of (2S,4S)-4-dimethylamino-pyrrolidine-2-carboxylic acid methyl ester dihydrochloride (400 mg) and 1-butanol (4 ml) and heated for 18 hours at 115° C. After cooling the reaction mixture is evaporated then partitioned between dicloromethane and aqueous sodium bicarbonate solution and the dichloromethane layers dried and evaporated to give the title compound as a brown oil which is used without further purification.

Intermediate BI Imidazole-1-carboxylic acid (2-cyclobutyl-4'-methyl-[4,5']bithiazolyl-2'-yl)-amide The title compound is prepared as described for Intermediate BD using cyclobutanecarbothioic acid amide in place of thiopropionamide. Title compound: HPLC (Method F) RT 5.58 minutes; MS (Method D) sample prepared in methanol leads to detection of the corresponding urethane only (NH—CO—OCH3): M+H 310.1 and M−H 308.1.

Intermediate BJ Imidazole-1-carboxylic acid [4'-methyl-2-(1-trifluoromethyl-cyclopropyl)-[4,5']bithiazolyl-2'-yl]amide The title compound is prepared as described for Intermediate BD using 1-trifluoromethyl-cyclopropanecarbothioic acid amide in place of thiopropionamide. Title compound: HPLC (Method F) RT 3.533 minutes; MS (Method D) sample prepared in methanol leads to detection of the corresponding urethane only (NH—CO—OCH3): M+H 364.0 and M−H 362.1.

Intermediate BK (1S,5R)-2-Aza-bicyclo[3.1.0]hexane-1-carboxylic acid amide

A mixture of (1S,5R)-2-aza-bicyclo[3.1.0]hexane-1-carboxylic acid ethyl ester (2.5 g, prepared by the procedure of Hercouet Tetrahedron Assymmetry 1996, 7, 1267-1268.) and 7M ammonia in methanol (20 ml) are heated in a sealed vessel at 80° C. for 5 days. The cooled reaction mixture is evaporated and triturated with hexanes/dichloromethane to give the title compound as a beige solid.

Intermediate BL Imidazole-1-carboxylic acid [2-(1-ethyl-propyl)-4'-methyl-[4,5']bithiazolyl-2'-yl]-amide The title compound is prepared as described for Intermediate BD using 2-ethyl-thiobutyramide in place of thiopropionamide. HPLC (Method F) RT 5.892 minutes; MS (Method D) sample prepared in methanol leads to detection of the corresponding urethane only (NH—CO—OCH3): M+H 326.1 and M−H 324.2.

Intermediate BM Imidazole-1-carboxylic acid (2-dimethylaminomethyl-4'-methyl-[4,5']bithiazolyl-2'-yl)-amide The title compound is prepared as described for Intermediate BD using 2-ethyl-thiobutyramide in place of thiopropionamide. HPLC (Method F) RT 3.433 minutes; MS (Method D) sample prepared in methanol leads to detection of the corresponding urethane only (NH—CO—OCH3): M+H 313.1 and M−H 311.2.

Intermediate BN Imidazole-1-carboxylic acid (2-cyclopropylmethyl-4'-methyl-[4,5]bithiazolyl-2'-yl)-amide The title compound is prepared as described for Intermediate BD using 2-cyclopropanethanethioamide in place of thiopropionamide. Title compound: HPLC: (Method F) RT 5.17 minutes; MS (Method D) M+H 294.2 and M−H 292.2.

Intermediate BO imidazole-1-carboxylic acid [4'-methyl-2-(pyridin-3-ylamino)-[4,5']bithiazolyl-2'-yl]-amide Carbonyl diimidazole (506 mg) is added to 4'-methyl-N*2*-pyridin-3-yl-[4,5]bithiazolyl-2,2'-diamine (740 mg) in DMF (10 ml) at room temperature. After standing for 18 hours at room temperature the reaction mixture is filtered and the solid washed with CH2Cl2 to give the title compound as a gray powder.

Intermediate BO1 4'-methyl-N*2*-pyridin-3-yl-[4,5]bithiazolyl-2,2'-diamine

N-[4'-Methyl-2-(pyridin-3-ylamino)-[4,5']bithiazolyl-2'-yl]-acetamide (0.9 g) is refluxed in a mixture of ethanol (30 ml) and concentrated hydrochloric acid (3 ml) for 18 hours then additional hydrochloric acid is added (1.5 ml). After a further 24 hours at reflux the reaction mixture is cooled and the pH adjusted to 8-9 by the addition of 5% aqueous NaHCO3. The title compound is collected by filtration, washed with water and dried to give a light brown solid.

Intermediate BO2 N-[4'-methyl-2-(pyridin-3-ylamino)-[4,5']bithiazolyl-2'-yl]-acetamide 3-Pyridylthiourea (0.62 g) is added to N-[5-(2-bromoacetyl)-4-methyl-thiazol-2-yl]-acetamide (1.1 g, prepared as described in WO 2005/068444) and triethylamine (1.68 ml) in ethanol (10 ml) at −10° C. After 30 minutes stirring at room temperature water is added (50 ml) and the title compound is collected by filtration, washed with water and dried to give an orange solid.

EXAMPLE 1

(2S,4R)-4-hydroxy-pyrrolidine-1,2-dicarboxylic acid 2-amide 1-({5-[4-methanesulfonyl-3-(2-propyl-imidazol-1-yl)-phenyl]-4-methyl-thiazol-2-yl}-amide) triflouroacetate Carbonyldiimidazole (35 mg) is added to a solution of Intermediate A (80 mg) in a mixture of triethylamine (0.054 ml) and DMF (3 ml) at room temperature. The reaction mixture is allowed to stand overnight at room temperature and then one third by volume is added to a mixture of triethylamine (0.01 ml) and (2S,4R)-4-hydroxy-pyrrolidine-2-carboxylic acid amide (10 mg) at room temperature. After 18 hours standing at room temperature the reaction mixture is evaporated then absorbed onto silica gel and purified by flash column chromatography eluting with a gradient from CH2Cl2 to 12% methanol in CH2Cl2. The fraction containing the predominant UV-active component (254 nm) is then further purified by reverse phase chromatography (Method B) to give the title compound as a white foam. Hplc/MS (Method C) RT 1.18 minutes, M+H 533.2.

EXAMPLE 2

(2S,4S)-4-hydroxy-pyrrolidine-1,2-dicarboxylic acid 2-amide 1-({5-[4-methanesulfonyl-3-(2-propyl-imidazol-1-yl)-phenyl]-4-methyl-thiazol-2-yl}-amide) triflouroacetate The tile compound is prepared in an analogous manner to Example 1 except (2S,4S)-4-hydroxy-pyrrolidine-2-carboxylic acid amide is used in place of (2S,4R)-4-hydroxy-pyrrolidine-2-carboxylic acid amide. The title compound is obtained as a colorless glass. Hplc/MS (Method C) RT 1.28 minutes, M+H 533.2 and M−H 531.3.

EXAMPLE 3

(2S,4R)-4-hydroxy-pyrrolidine-1,2-dicarboxylic acid 2-amide 1-{[5-(2-tert-butyl-pyrimidin-4-yl)-4-methyl-thiazol-2-yl]-amide}triflouroacetate A mixture of imidazole-1-carboxylic acid [5-(2-tert-butyl-pyrimidin-4-yl)-4-methylthiazol-2-yl]-amide (100 mg, prepared as described in WO 04/096797), (2S,4R)-4-hydroxy-pyrrolidine-2-carboxylic acid amide (49 mg) and triethylamine (0.049 ml) in DMF (1 ml) is allowed to stand at room temperature for 18 hours. Following evaporation of the reaction mixture purification by reversed phase chromatography (Method B) gives the title compound as a yellow solid. Hplc/MS (Method C) RT 1.68 minutes, M+H 405.1 and M−H 403.3.

EXAMPLE 4

(2S,4S)-4-hydroxy-pyrrolidine-1,2-dicarboxylic acid 2-amide 1-{[5-(2-tert-butyl-pyrimidin-4-yl)-4-methyl-thiazol-2-yl]-amide}triflouroacetate The tile compound is prepared in an analogous manner to Example 3 except (2S,4S)-4-hydroxy-pyrrolidine-2-carboxylic acid amide is used in place of (2S,4R)-4-hydroxy-pyrrolidine-2-carboxylic acid amide. The title compound is obtained as a colorless glass. Hplc/MS (Method C) RT 1.82 minutes, M+H 405.2 and M−H 403.4.

EXAMPLE 5

(S)-2,5-dihydro-pyrrole-1,2-dicarboxylic acid 2-amide 1-{[5-(2-tert-butyl-pyrimidin-4-yl)-4-methyl-thiazol-2-yl]-amide}

A mixture of imidazole-1-carboxylic acid [5-(2-tert-butyl-pyrimidin-4-yl)-4-methylthiazol-2-yl]-amide (100 mg), (S)-2,5-dihydro-1H-pyrrole-2-carboxylic acid amide (43 mg) and triethylamine (0.049 ml) in DMF (1 ml) is allowed to stand at room temperature for 18 hours. Following evaporation of the reaction mixture purification by recrystallisation from aqueous methanol gives the title compound as a white solid. Hplc/MS (Method C) RT 1.99 minutes, M+H 386.9 and M−H 385.1.

EXAMPLE 6

(2S,4R)-4-hydroxy-pyrrolidine-1,2-dicarboxylic acid 2-amide 1-{[5-(2-tert-butyl-pyridin-4-yl)-4-methyl-thiazol-2-yl]-amide}

A mixture of imidazole-1-carboxylic acid [5-(2-tert-butyl-pyridin-4-yl)-4-methyl-thiazol-2-yl]-amide (50 mg), (2S,4R)-4-hydroxy-pyrrolidine-2-carboxylic acid amide (27 mg) and triethylamine (0.051 ml) in DMA (3 ml) is allowed to stand at room temperature for 18 hours. The reaction mixture is partitioned between water/CH2Cl2, extracted 2×CH2Cl2, dried over Na2SO4, and evaporated. Purification of the isolated material by reversed phase chromatography (Method B) with neutralization of the fractions with NaHCO3 prior to evaporation gives a residue which is taken up in DMF, filtered

EXAMPLE 7

(2S,4S)-4-hydroxy-pyrrolidine-1,2-dicarboxylic acid 2-amide 1-{[5-(2-tert-butyl-pyridin-4-yl)-4-methyl-thiazol-2-yl]-amide}

A mixture of imidazole-1-carboxylic acid [5-(2-tert-butyl-pyridin-4-yl)-4-methyl-thiazol-2-yl]amide (55 mg), (2S,4S)-4-hydroxy-pyrrolidine-2-carboxylic acid amide (30 mg) and triethylamine (0.056 ml) in DMA (3 ml) is allowed to stand at room temperature for 18 hours. The reaction mixture is evaporated and purified by normal phase chromatography on silica gel eluting with a gradient from CH2Cl2 to 70:24:6 CH2Cl2/EtOAc/CH3OH to give the title compound as a white solid. MS (Method D) M+H 404 and M−H 402.

EXAMPLE 8

(2S,4R)-4-fluoro-pyrrolidine-1,2-dicarboxylic acid 2-amide 1-{[5-(2-tert-butyl-pyrimidin-4-yl)-4-methyl-thiazol-2-yl]-amide}

A mixture of imidazole-1-carboxylic acid [5-(2-tert-butyl-pyrimidin-4-yl)-4-methylthiazol-2-yl]-amide (45 mg), (2S,4R)-4-fluoro-pyrrolidine-2-carboxylic acid amide (19 mg) and triethylamine (0.022 ml) in DMF (1 ml) is allowed to stand at room temperature for 18 hours. The reaction mixture is filtered through an Acrodisc™ 0.45 microm PTFE membrane filter, evaporated and then purification by recrystallisation from aqueous methanol gives the title compound as a white solid. Hplc/MS (Method C) RT 2.01 minutes, M+H 407.1 and M−H 405.3.

EXAMPLE 9

(2S,3S)-3-hydroxy-pyrrolidine-1,2-dicarboxylic acid 2-amide 1-{[5-(2-tert-butyl-pyrimidin-4-yl)-4-methyl-thiazol-2-yl]-amide}triflouroacetate A mixture of imidazole-1-carboxylic acid [5-(2-tert-butyl-pyrimidin-4-yl)-4-methylthiazol-2-yl]-amide (50 mg), (2S,3S)-3-hydroxy-pyrrolidine-2-carboxylic acid amide (19 mg) and triethylamine (0.025 ml) in DMF (1 ml) is allowed to stand at room temperature for 18 hours. The reaction mixture is filtered through an Acrodisc™ 0.45 microm PTFE membrane filter, evaporated and then purification by reversed phase chromatography (Method B) gives the title compound as a yellow solid. Hplc/MS (Method C) RT 1.76 minutes, M+H 405.2 and M−H 403.3.

EXAMPLE 10

(2S,3S)-3-methyl-pyrrolidine-1,2-dicarboxylic acid 2-amide 1-{[5-(2-tert-butyl-pyrimidin-4-yl)-4-methyl-thiazol-2-yl]-amide}

A mixture of imidazole-1-carboxylic acid [5-(2-tert-butyl-pyrimidin-4-yl)-4-methylthiazol-2-yl]-amide (50 mg), (2S,3S)-3-methyl-pyrrolidine-2-carboxylic acid amide (19 mg) and triethylamine (0.025 ml) in DMF (1 ml) is allowed to stand at room temperature for 18 hours. The reaction mixture is filtered through an Acrodisc™ 0.45 μm PTFE membrane filter, evaporated and then purification by recrystallisation from aqueous methanol gives the title compound as a white solid. Hplc/MS (Method C) RT 2.07 minutes, M+H 403.2 and M−H 401.3.

EXAMPLE 11

(1R,2S,5S)-3-aza-bicyclo[3.1.0]hexane-2,3-dicarboxylic acid 2-amide 3-{[5-(2-tert-butyl-pyrimidin-4-yl)-4-methyl-thiazol-2-yl]-amide}

A mixture of imidazole-1-carboxylic acid [5-(2-tert-butyl-pyrimidin-4-yl)-4-methylthiazol-2-yl]-amide (37 mg), (1R,2S,5S)-3-aza-bicyclo[3.1.0]hexane-2-carboxylic acid amide (15 mg) and triethylamine (0.018 ml) in DMF (1 ml) is allowed to stand at room temperature for 18 hours. The reaction mixture is evaporated and then purification by recrystallisation from aqueous methanol gives the title compound as a white solid. Hplc/MS (Method C) RT 1.93 minutes, M+H 401.2 and M−H 399.4.

EXAMPLE 12

(S)-2-methyl-pyrrolidine-1,2-dicarboxylic acid 2-amide 1-{[5-(2-tert-butyl-pyrimidin-4-yl)-4-methyl-thiazol-2-yl]-amide}

A mixture of imidazole-1-carboxylic acid [5-(2-tert-butyl-pyrimidin-4-yl)-4-methylthiazol-2-yl]-amide (45 mg), (S)-2-methyl-pyrrolidine-2-carboxylic acid amide (19 mg) and triethylamine (0.022 ml) in DMF (1 ml) is allowed to stand at room temperature for 18 hours. The reaction mixture is filtered through an Acrodisc™ 0.45 microm PTFE membrane filter, evaporated and then purification by recrystallisation from aqueous methanol gives the title compound as a white solid. Hplc/MS (Method C) RT 2.09 minutes, M+H 403.0 and M−H 401.1.

EXAMPLE 13

2S,3S)-3-methyl-pyrrolidine-1,2-dicarboxylic acid 2-amide 1-({5-[2-(2,6-dichloro-benzyl)-pyrimidin-4-yl]-4-methyl-thiazol-2-yl}-amide A mixture of imidazole-1-carboxylic acid {5-[2-(2,6-dichloro-benzyl)-pyrimidin-4-yl]-4-methyl-thiazol-2-yl}-amide (50 mg), (2S,3S)-3-methyl-pyrrolidine-2-carboxylic acid amide (15 mg) and triethylamine (0.011 ml) in DMF (0.10 ml) is swirled at 40° C. for 18 hours. The reaction mixture is evaporated and then purification by recrystallisation from aqueous methanol gives the title compound as a beige solid. MS (Method D): M+H 505/507 and M−H 503/505.

EXAMPLE 14

(2S,3S)-3-methyl-pyrrolidine-1,2-dicarboxylic acid 2-amide 1-{[5-(2-cyclopropyl-pyrimidin-4-yl)-4-methyl-thiazol-2-yl]-amide}

A mixture of imidazole-1-carboxylic acid [5-(2-cyclopropyl-pyrimidin-4-yl)-4-methyl-thiazol-2-yl]-amide (50 mg), (2S,3S)-3-methyl-pyrrolidine-2-carboxylic acid amide (16 mg) and triethylamine (0.019 ml) in DMF (0.11 ml) is swirled at 40° C. for 18 hours. The reaction mixture is evaporated and then purification by recrystallisation from aqueous methanol gives the title compound as a beige solid. MS (Method D) M+H 387 and M−H 385.

EXAMPLE 15

2S,3S)-3-methyl-pyrrolidine-1,2-dicarboxylic acid 2-amide 1-({5-[2-(2-fluoro-phenyl)-pyrimidin-4-yl]-4-methyl-thiazol-2-yl}-amide A mixture of imidazole-1-carboxylic acid {5-[2-(2-fluoro-phenyl)-pyrimidin-4-yl]-4-methyl-thiazol-2-yl}-amide (50 mg), (2S,3S)-3-methyl-pyrrolidine-2-carboxylic acid amide (19 mg) and triethylamine (0.016 ml) in DMF (0.13 ml) is swirled at 40° C. for 18 hours. The reaction mixture is evaporated and then purification by recrystallisation from aqueous methanol gives the title compound as a beige solid. MS (Method D) M+H 441 and M−H 439.

EXAMPLE 16 azetidine-1,2-dicarboxylic acid 2-amide 1-{[5-(2-tert-butyl-pyrimidin-4-yl)-4-methyl-thiazol-2-yl]-amide}

A mixture of imidazole-1-carboxylic acid [5-(2-tert-butyl-pyrimidin-4-yl)-4-methylthiazol-2-yl]-amide (75 mg), azetidine-2-carboxylic acid amide (24 mg) and triethylamine (0.037 ml) in DMF (2 ml) is allowed to stand at room temperature for 18 hours. The reaction mixture is evaporated and then purification by recrystallisation from aqueous methanol gives the title compound as a white solid. Hplc/MS (Method C) RT 1.90 minutes, M+H 375.2 and M−H 373.3.

EXAMPLE 17

(S)-2-methyl-pyrrolidine-1,2-dicarboxylic acid 2-amide 1-{[4-methyl-5-(2-methyl-pyrimidin-4-yl)-thiazol-2-yl]-amide}

A mixture of imidazole-1-carboxylic acid [4-methyl-5-(2-methyl-pyrimidin-4-yl)-thiazol-2-yl]-amide (27 mg), (S)-2-methyl-pyrrolidine-2-carboxylic acid amide (13 mg) and triethylamine (0.031 ml) in DMF (1 ml) is allowed to stand at room temperature for 18 hours. The reaction mixture is evaporated and then purification by recrystallisation from aqueous methanol gives the title compound as an off-white solid. Hplc/MS (Method E) RT 0.73 minutes, M+H 360.9 and M−H 359.0.

EXAMPLE 18

(S)-2-methyl-pyrrolidine-1,2-dicarboxylic acid 2-amide 1-{[5-(2-tert-butyl-pyridin-4-yl)-4-methyl-thiazol-2-yl]-amide}

A mixture of imidazole-1-carboxylic acid [5-(2-tert-butyl-pyridin-4-yl)-4-methyl-thiazol-2-yl]-amide. (100 mg), (S)-2-methyl-pyrrolidine-2-carboxylic acid amide (42 mg) and triethylamine (0.102 ml) in DMF (2 ml) is allowed to stand at room temperature for 18 hours. The reaction mixture is evaporated and then purification by recrystallisation from aqueous methanol gives the title compound as a white solid. Hplc/MS (Method E) RT 0.98 minutes, M+H 401.9 and M−H 400.1.

EXAMPLE 19

(S)-2-methyl-pyrrolidine-1,2-dicarboxylic acid 2-amide 1-{[5-(6-imidazol-1-yl-pyridin-2-yl)-4-methyl-thiazol-2-yl]-amide}

A mixture of imidazole-1-carboxylic acid [5-(6-imidazol-1-yl-pyridin-2-yl)-4-methyl-thiazol-2-yl]-amide (27 mg), (S)-2-methyl-pyrrolidine-2-carboxylic acid amide (11 mg) and triethylamine (0.027 ml) in DMF (1 ml) is allowed to stand at room temperature for 18 hours. The reaction mixture is evaporated and then purification by recrystallisation from aqueous methanol gives the title compound as a white solid. Hplc/MS (Method E) RT 0.83 minutes, M+H 411.9 and M−H 409.9.

EXAMPLE 20

(2S,3S)-3-methyl-pyrrolidine-1,2-dicarboxylic acid 2-amide 1-{[5-(2-methoxymethyl-pyrimidin-4-yl)-4-methyl-thiazol-2-yl]-amide}

A mixture of imidazole-1-carboxylic acid [5-(2-methoxymethyl-pyrimidin-4-yl)-4-methyl-thiazol-2-yl]-amide (25 mg), (2S,3S)-3-methyl-pyrrolidine-2-carboxylic acid amide (11 mg) and triethylamine (0.013 ml) in DMF (0.08 ml) is swirled at 40° C. for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a yellow solid. MS (Method D) M+H 391 and M−H 389.

EXAMPLE 21

(2S,3S)-3-methyl-pyrrolidine-1,2-dicarboxylic acid 2-amide 1-{[5-(2-isobutyl-pyrimidin-4-yl)-4-methyl-thiazol-2-yl]-amide}

A mixture of imidazole-1-carboxylic acid [5-(2-isobutyl-pyrimidin-4-yl)-4-methyl-thiazol-2-yl]-amide (30 mg), (2S,3S)-3-methyl-pyrrolidine-2-carboxylic acid amide (12 mg) and triethylamine (0.015 ml) in DMF (0.09 ml) is swirled at 40° C. for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a yellow solid. MS (Method D) M+H 403 and M−H 401.

EXAMPLE 22

(S)-2-methyl-pyrrolidine-1,2-dicarboxylic acid 2-amide 1-{[5-(2-benzyl-pyrimidin-4-yl)-4-methyl-thiazol-2-yl]-amide}

A mixture of imidazole-1-carboxylic acid [5-(2-benzyl-pyrimidin-4-yl)-4-methyl-thiazol-2-yl]-amide (30 mg), (S)-2-methyl-pyrrolidine-2-carboxylic acid amide (11 mg) and triethylamine (0.013 ml) in DMF (0.08 ml) is swirled at 40° C. for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a yellow solid. MS (Method D) M+H 437 and M−H 435.

EXAMPLE 23

(S)-2-methyl-pyrrolidine-1,2-dicarboxylic acid 2-amide 1-{[5-(2-ethyl-pyrimidin-4-yl)-4-methyl-thiazol-2-yl]-amide}

A mixture of imidazole-1-carboxylic acid [5-(2-ethyl-pyrimidin-4-yl)-4-methyl-thiazol-2-yl]-amide (25 mg), (S)-2- methyl-pyrrolidine-2-carboxylic acid amide (11 mg) and triethylamine (0.013 ml) in DMF (0.08 ml) is swirled at 40° C. for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a beige solid. MS (Method D) M+H 375 and M−H 373.

EXAMPLE 24

(S)-2-methyl-pyrrolidine-1,2-dicarboxylic acid 2-amide 1-{[5-(2-cyclopropyl-pyrimidin-4-yl)-4-methyl-thiazol-2-yl]-amide}

A mixture of imidazole-1-carboxylic acid [5-(2-cyclopropyl-pyrimidin-4-yl)-4-methyl-thiazol-2-yl]-amide (30 mg), (S)-2-methyl-pyrrolidine-2-carboxylic acid amide (13 mg) and triethylamine (0.015 ml) in DMF (0.09 ml) is swirled at 40° C. for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a beige solid. MS (Method D) M+H 387 and M−H 385.

EXAMPLE 25

(S)-2-methyl-pyrrolidine-1,2-dicarboxylic acid 2-amide 1-{[5-(2-methoxymethyl-pyrimidin-4-yl)-4-methyl-thiazol-2-yl]-amide}

A mixture of imidazole-1-carboxylic acid [5-(2-methoxymethyl-pyrimidin-4-yl)-4-methyl-thiazol-2-yl]-amide (30 mg), (S)-2-methyl-pyrrolidine-2-carboxylic acid amide (13 mg) and triethylamine (0.015 ml) in DMF (0.09 ml) is swirled at 40° C. for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a beige solid. MS (Method D) M+H 391 and M−H 389.

EXAMPLE 26

S)-2-methyl-pyrrolidine-1,2-dicarboxylic acid 2-amide 1-({5-[2-(2-fluoro-phenyl)-pyrimidin-4-yl]-4-methyl-thiazol-2-yl}-amide A mixture of imidazole-1-carboxylic acid {5-[2-(2-fluoro-phenyl)-pyrimidin-4-yl]-4-methyl-thiazol-2-yl}-amide (30 mg), (S)-2-methyl-pyrrolidine-2-carboxylic acid amide (11 mg) and triethylamine (0.013 ml) in DMF (0.08 ml) is swirled at 40° C. for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a beige solid. MS (Method D) M+H 441 and M−H 439.

EXAMPLE 27

S)-2-methyl-pyrrolidine-1,2-dicarboxylic acid 2-amide 1-({5-[2-(2,6-dichloro-benzyl)-pyrimidin-4-yl]-4-methyl-thiazol-2-yl}-amide A mixture of imidazole-1-carboxylic acid {5-[2-(2,6-dichloro-benzyl)-pyrimidin-4-yl]-4-methyl-thiazol-2-yl}-amide (30 mg), (S)-2-methyl-pyrrolidine-2-carboxylic acid amide (10 mg) and triethylamine (0.011 ml) in DMF (0.07 ml) is swirled at 40° C. for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a beige solid. MS (Method D) M+H 505 and M−H 503.

EXAMPLE 28

(S)-2-methyl-pyrrolidine-1,2-dicarboxylic acid 2-amide 1-{[5-(2-isobutyl-pyrimidin-4-yl)-4-methyl-thiazol-2-yl]-amide}

A mixture of imidazole-1-carboxylic acid [5-(2-isobutyl-pyrimidin-4-yl)-4-methyl-thiazol-2-yl]-amide (30 mg), (S)-2-methyl-pyrrolidine-2-carboxylic acid amide (10 mg) and triethylamine (0.015 ml) in DMF (0.09 ml) is swirled at 40° C. for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a beige solid. MS (Method D) M+H 403 and M−H 401.

EXAMPLE 29

(2S,3S)-3-methyl-pyrrolidine-1,2-dicarboxylic acid 2-amide 1-{[5-(2-benzyl-pyrimidin-4-yl)-4-methyl-thiazol-2-yl]-amide}

A mixture of imidazole-1-carboxylic acid [5-(2-benzyl-pyrimidin-4-yl)-4-methyl-thiazol-2-yl]-amide (30 mg), (2S,3S)-3-methyl-pyrrolidine-2-carboxylic acid amide (11 mg) and triethylamine (0.013 ml) in DMF (0.08 ml) is swirled at 40° C. for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a yellow solid. MS (Method D) M+H 437 and M−H 435.

EXAMPLE 30

(2S,3S)-3-methyl-pyrrolidine-1,2-dicarboxylic acid 2-amide 1-{[5-(2-ethyl-pyrimidin-4-yl)-4-methyl-thiazol-2-yl]-amide}

A mixture of imidazole-1-carboxylic acid [5-(2-ethyl-pyrimidin-4-yl)-4-methyl-thiazol-2-yl]-amide (30 mg), (2S,3S)-3-methyl-pyrrolidine-2-carboxylic acid amide (13 mg) and triethylamine (0.016 ml) in DMF (0.10 ml) is swirled at 40° C. for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a yellow solid. MS (Method D) M+H 375 and M−H 373.

EXAMPLE 31

(2S,3S)-3-methyl-pyrrolidine-1,2-dicarboxylic acid 2-amide 1-{[4-methyl-5-(2-trifluoromethyl-pyrimidin-4-yl)-thiazol-2-yl]-amide}

A mixture of imidazole-1-carboxylic acid [5-(2-trifluoromethyl-pyrimidin-4-yl)-4-methyl-thiazol-2-yl]-amide (25 mg), (2S,3S)-3-methyl-pyrrolidine-2-carboxylic acid amide (10 mg) and triethylamine (0.012 ml) in DMF (0.07 ml) is swirled at 40° C. for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a yellow solid. MS (Method D) M+H 415 and M−H 413.

EXAMPLE 32

(S)-2-methyl-pyrrolidine-1,2-dicarboxylic acid 2-amide 1-{[5-(3-tert-butyl-phenyl)-4-methyl-thiazol-2-yl]-amide}

A mixture of imidazole-1-carboxylic acid [5-(3-tert-butyl-phenyl)-4-methyl-thiazol-2-yl]-amide (13 mg), (S)-2-methyl-pyrrolidine-2-carboxylic acid amide (5 mg) and triethylamine (0.013 ml) in DMF (1.0 ml) is stood at room temperature for 18 hours. The reaction mixture is evaporated and then purified by reversed phase chromatography (Method B), partial evaporation of the fractions containing the 15.0 minute retention time component, neutralization with NaHCO3, extraction with CH2Cl2 (5×) and evaporation gives the title compound as a colourless glass. MS (Method E) RT 2.11 minutes, M+H 401.0 and M−H 399.0.

EXAMPLE 33

(2S,4R)-4-hydroxy-pyrrolidine-1,2-dicarboxylic acid 2-amide 1-[(2-tert-butyl-4'-methyl-[4,5]bithiazolyl-2'-yl)-amide]

A mixture of imidazole-1-carboxylic acid (2-tert-butyl-4'-methyl-[4,5]bithiazolyl-2'-yl)amide (139 mg), (2S,4R)-4-hydroxy-pyrrolidine-2-carboxylic acid amide (73 mg) and triethylamine (0.14 ml) in DMF (2 ml) is allowed to stand at room temperature for 18 hours. The reaction mixture is evaporated and the residue purified by reversed phase chromatography (Method A). Fractions containing the 12.3 minute retention component are evaporated, aqueous NaHCO3 added, and the solid formed is collected by filtration washing with CH2Cl2 and water. Crystallisation from aqueous ethanol gives the title compound as an off-white solid. Hplc/MS (Method E) RT 1.59 minutes, M+H 409.8 and M−H 408.0.

EXAMPLE 34

(2S,4S)-4-hydroxy-pyrrolidine-1,2-dicarboxylic acid 2-amide 1-[(2-tert-butyl-4'-methyl-[4,5]bithiazolyl-2'-yl)-amide]

A mixture of imidazole-1-carboxylic acid (2-tert-butyl-4'-methyl-[4,5']bithiazolyl-2'-yl)-amide (139 mg), (2S,4S)-4-hydroxy-pyrrolidine-2-carboxylic acid amide (73 mg) and triethylamine (0.14 ml) in DMF (2 ml) is allowed to stand at room temperature for 18 hours. The reaction mixture is evaporated and the residue purified by reversed phase chromatography (Method A). Fractions containing the 12.9 minute retention component are evaporated, partitioned between aqueous NaHCO3 and CH2Cl2, extracted 4×CH2Cl2, the combined organic layer evaporated and crystallised from aqueous ethanol to give the title compound as an white solid. Hplc/MS (Method E) RT 1.65 minutes, M+H 409.8 and M−H 408.0.

EXAMPLE 35

(2S,3S)-3-hydroxy-pyrrolidine-1,2-dicarboxylic acid 2-amide 1-[(2-tert-butyl-4'-methyl-[4,5]bithiazolyl-2'-yl)amide]triflouroacetate A mixture of imidazole-1-carboxylic acid (2-tert-butyl-4'-methyl-[4,5]bithiazolyl-2'-yl)amide (37 mg), (2S,3S)-3-hydroxy-pyrrolidine-2-carboxylic acid amide (15 mg) and triethylamine (0.037 ml) in DMF (1 ml) is allowed to stand at room temperature for 18 hours. Following filtration and evaporation of the reaction mixture purification by crystallisation from aqueous methanol gives the title compound as a beige solid. Hplc/MS (Method C) RT 2.21 minutes, M+H 409.9 and M−H 408.1.

EXAMPLE 36

(S)-2-methyl-pyrrolidine-1,2-dicarboxylic acid 2-amide 1-[(2-tert-butyl-4'-methyl-[4,5]bithiazolyl-2'-yl)-amide]

A mixture of imidazole-1-carboxylic acid (2-tert-butyl-4'-methyl-[4,5']bithiazolyl-2'-yl)amide (70 mg), (S)-2-methyl-pyrrolidine-2-carboxylic acid amide (28 mg) and triethylamine (0.07 ml) in DMF (1 ml) is allowed to stand at room temperature for 18 hours. The reaction mixture evaporated and the residue purified by crystallisation from aqueous methanol to give the title compound as an white solid. Hplc/MS (Method C) RT 2.57 minutes, M+H 407.9 and M−H 406.0.

EXAMPLE 37

(2S,3S)-3-methyl-pyrrolidine-1,2-dicarboxylic acid 2-amide 1-[(2-tert-butyl-4'-methyl-[4,5']bithiazolyl-2'-yl)-amide]

A mixture of imidazole-1-carboxylic acid (2-tert-butyl-4'-methyl-[4,5']bithiazolyl-2'-yl)-amide (60 mg), (2S,3S)-3-methyl-pyrrolidine-2-carboxylic acid amide (24 mg) and triethylamine (0.06 ml) in DMF (1 ml) is allowed to stand at room temperature for 18 hours. The reaction mixture is filtered and evaporated and the residue purified by reversed phase chromatography (Method A). Fractions containing the 15.3 minute retention component are evaporated, partitioned between aqueous NaHCO3 and CH2Cl2, extracted 4×CH2Cl2, the combined organic layer evaporated and crystallised from aqueous methanol to give the title compound as an white solid. Hplc/MS (Method C) RT 2.48 minutes, M+H 407.9 and M−H 406.0.

EXAMPLE 38

(2S,4R)-4-fluoro-pyrrolidine-1,2-dicarboxylic acid 2-amide 1-[(2-tert-butyl-4'-methyl-[4,5']bithiazolyl-2'-yl)-amide]

A mixture of imidazole-1-carboxylic acid (2-tert-butyl-4'-methyl-[4,5]bithiazolyl-2'-yl)-amide (60 mg), (2S,4R)-4-fluoro-pyrrolidine-2-carboxylic acid amide (25 mg) and triethylamine (0.06 ml) in DMF (1 ml) is allowed to stand at room temperature for 18 hours. The reaction mixture is filtered and evaporated and the residue purified by reversed phase chromatography (Method A). Fractions containing the 15.2 minute retention component are evaporated, partitioned between aqueous NaHCO3 and CH2Cl2, extracted 3×CH2Cl2, the combined organic layer evaporated and crystallised from aqueous methanol with a hot filtration to give the title compound as an white solid. Hplc/MS (Method C) RT 2.42 minutes, M+H 411.8 and M−H 410.0.

EXAMPLE 39

(S)-2-methyl-pyrrolidine-1,2-dicarboxylic acid 2-amide 1-{[4'-methyl-2-(pyridin-3-ylamino)-[4,5']bithiazolyl-2'-yl]-amide}

A mixture of imidazole-1-carboxylic acid [4'-methyl-2-(pyridin-3-ylamino)-[4,5']bithiazolyl-2'-yl]-amide (115 mg), (S)-2-methyl-pyrrolidine-2-carboxylic acid amide (42 mg) and triethylamine (0.10 ml) in DMF (1.5 ml) is stirred at room temperature for 3.5 hours. The reaction mixture is then evaporated and the title compound precipitated from methanol and water to give a grey powder. MS (Method D) M+H 444.1 and M−H 442.2.

EXAMPLE 40

S)-2-Methyl-pyrrolidine-1,2-dicarboxylic acid 2-amide 1-({4-methyl-5-[2-(1-methyl-cyclopropyl)-pyridin-4-yl]-thiazol-2-yl}-amide

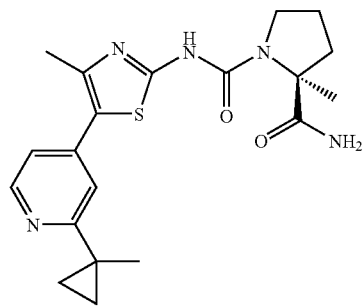 [SMILES: Cc1nc(NC(=O)N2CCC[C@@]2(C)C(N)=O)sc1-c1ccnc(C2(C)CC2)c1]

Et$_3$N (0.117 mL, 0.84 mmol, 3 eq) is added to a solution of imidazole-1-carboxylic acid {4-methyl-5-[2-(1-methyl-cyclopropyl)-1,2-dihydro-pyridin-4-yl]-thiazol-2-yl}-amide (Step 40.1) (94 mg, 0.28 mmol) and (S)-2-methyl-pyrrolidine-2-carboxylic acid amide (Intermediate I) (54 mg, 4.8 mmol, 1.5 eq) in DMF (2 mL), under an argon atmosphere. The reaction mixture is stirred for 6 h at rt, quenched by addition of a saturated solution of NaHCO$_3$ and extracted with EtOAc. The organic phase is washed with a saturated solution of NaHCO$_3$, dried (Na$_2$SO$_4$), filtered and concentrated. The residue is purified by silica gel column chromatography (DCM/MeOH, 1:0→94:6), followed by trituration in Et$_2$O to afford 73 mg of the title compound as a white solid: ESI-MS: 400.1 [M+H]$^+$; TLC: R$_f$=0.45 (DCM/MeOH, 9:1).

Step 40.1: Imidazole-1-carboxylic acid {4-methyl-5-[2-(1-methyl-cyclopropyl)-pyridin-4-yl]-thiazol-2-yl}-amide A mixture of 4-methyl-5-[2-(1-methyl-cyclopropyl)-pyridin-4-yl]-thiazol-2-ylamine (Step 40.2) (211 mg, 0.86 mmol) and 1,1'-carbonyldiimidazole (210 mg, 1.3 mmol, 1.5 eq) in DCM (10 mL) is stirred for 14 h at reflux and allowed to cool. The resulting precipitate is collected by filtration to provide 275 mg of the title compound as white solid: ESI-MS: 338.2 [M−H]$^-$.

Step 40.2: 4-Methyl-5-[2-(1-methyl-cyclopropyl)-pyridin-4-yl]-thiazol-2-ylamine

A mixture of N-{4-methyl-5-[2-(1-methyl-cyclopropyl)-pyridin-4-yl]-thiazol-2-yl}-acetamide (Step 401.3) (565 mg, 7 mmol), a 6N aqueous solution of HCl (3 mL) and EtOH (15 mL) is stirred for 3.5 h at 85° C., allowed to cool, quenched by addition of a saturated solution of NaHCO$_3$ and extracted with DCM. The organic phase is washed with a saturated solution of NaHCO$_3$, dried (Na$_2$SO$_4$), filtered and concentrated. The residue is purified by silica gel column chromatography (DCM/MeOH, 1:0→98:2) to afford 366 mg of the title compound as a yellow solid: ESI-MS: 246.1 [M+H]$^+$; TLC: R$_f$=0.40 (DCM/MeOH, 9:1).

Step 40.3: N-{4-Methyl-5-[2-(1-methyl-cyclopropyl)-pyridin-4-yl]-thiazol-2-yl}-acetamide A mixture of 2-acetamido-4-methylthiazole (405 mg, 2.6 mmol, 1.1 eq), cesium carbonate (1.54 g, 4.72 mmol, 2 eq), tri-tert-butylphosphinium tetrafluoroborate (137 mg, 0.47 mmol, 0.2 eq), palladium (II) acetate (51 mg, 0.24 mmol, 0.1 eq) and 4-bromo-2-(1-methyl-cyclopropyl)-pyridine (Step 40.4) (500 mg, 2.36 mmol) in DMF (10 mL) is stirred for 3.5 h at 100° C. under an argon atmosphere, allowed to cool, quenched by addition of a saturated solution of NaHCO$_3$ and filtered through a pad of celite. The filtrate is extracted with EtOAc. The organic phase is washed with a saturated solution of NaHCO$_3$, dried (Na$_2$SO$_4$), filtered and concentrated. The residue is purified by silica gel column chromatography (DCM/MeOH, 1:0→99:1) to afford 569 mg of the title compound as a yellow solid: ESI-MS: 288.1 [M+H]$^+$; TLC: R$_f$=0.40 (DCM/MeOH, 9:1).

Step 40.4: 4-Bromo-2-(1-methyl-cyclopropyl)-pyridine

A mixture of 2-(1-methyl-cyclopropyl)I-1H-pyridin-4-one (Step 40.5) (330 mg, 2.21 mmol) and POBr$_3$ (700 mg, 2.44 mmol, 1.1 eq) is heated to 120° C., stirred for 15 min, allowed to cool, quenched by addition of a saturated solution of NaHCO$_3$ and extracted with DCM/MeOH (9:1, v/v). The organic phase is washed with a saturated solution of NaHCO$_3$, dried (Na$_2$SO$_4$), filtered and concentrated. The residue is purified by silica gel column chromatography (Hex/EtOAc, 95:5) to afford 335 mg of the title compound as a yellow oil: ESI-MS: 212.0/214.0 [M+H]$^+$; t$_R$=2.39 min (System 1); TLC: R$_f$=0.23 (Hex/EtOAc, 9:1).

Step 40.5: 2-(1-Methyl-cyclopropyl)-1H-pyridin-4-one

A mixture of 2-(1-methyl-cyclopropyl)-pyran-4-one (Step 40.6) (440 mg, 2.93 mmol) and a 30% aqueous solution of ammonium hydroxide (100 mL) is stirred for 1 h at reflux, allowed to cool and concentrated. The residue is purified by silica gel column chromatography (DCM/MeOH/NH$_3^{aq}$, 94:5:1→92:7:1) to afford 333 mg of the title compound as a yellow solid: ESI-MS: 150.0 [M+H]$^+$; t$_R$=1.25 min (System 1).

Step 40.6: 2-(1-Methyl-cyclopropyl)-pyran-4-one

A mixture of 1-hydroxy-5-methoxy-1-(1-methyl-cyclopropyl)-penta-1,4-dien-3-one (Step 40.7) (1.07 g, 5.9 mmol) and TFA (0.9 mL, 11.7 mmol, 2 eq) in toluene (50 mL) is stirred for 14 h at rt and concentrated. Purification of the residue by silica gel column chromatography (Hex/EtOAc, 1:0→3:7) provides 442 mg of the title compound as a red solid: ESI-MS: 151.1 [M+H]$^+$; t$_R$=2.89 min (System 1); TLC: R$_f$=0.19 (Hex/EtOAc, 1:1).

Step 40.7: 1-Hydroxy-5-methoxy-1-(1-methyl-cyclopropyl)-penta-1,4-dien-3-one

LiHMDS (1M in THF, 88 mL, 2 eq) is added dropwise to a cold (−78° C.) solution of 4-methoxy-3-buten-2-one (8.8 mL, 88 mmol, 2 eq) in THF (300 mL). After a 30 min stirring at −78° C., a solution of 1-methyl-cyclopropanecarbonyl chloride (Step 40.8) (5.19 g, 44 mmol) in THF (100 mL) is added. The resulting mixture is allowed to warm to rt over 2 h and quenched by addition of a saturated solution of NH$_4$Cl. THF is removed under vacuum. The concentrated mixture is extracted with Et$_2$O. The organic phase is washed with brine (2×150 mL), dried (Na$_2$SO$_4$), filtered and concentrated. The residue is purified by silica gel column chromatography (Hex/EtOAc, 1:0→95:5) to afford 5.68 g of the title compound as a yellow oil: ESI-MS: 183.1 [M+H]$^+$; TLC: R$_f$=0.32 (Hex/EtOAc, 9:1).

Step 40.8: 1-Methyl-cyclopropanecarbonyl chloride

A mixture of 1-methyl-cyclopropanecarboxylic acid (10 g, 100 mmol) and oxalyl chloride (10.49 ml, 120 mmol, 1.2 eq) in CHCl$_3$ (80 ml) is stirred for 4 h at 70° C. The reaction mixture is concentrated to afford 11.8 g of the title compound as a yellow oil which is used without further purification.

EXAMPLE 41

(S)-2-Methyl-pyrrolidine-1,2-dicarboxylic acid 2-amide 1-{[5-(2-cyclopropyl-pyridin-4-yl)-4-methyl-thiazol-2-yl]-amide}

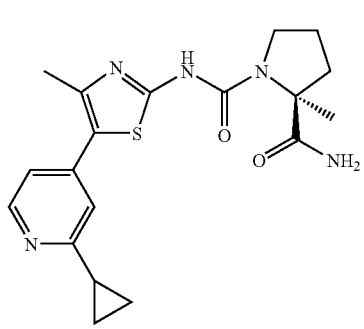 [SMILES: Cc1nc(NC(=O)N2CCC[C@@]2(C)C(N)=O)sc1-c1ccnc(C2CC2)c1]

The title compound is prepared in analogy to the procedure described in Example 40 but with the following modifications. In Example 40, the reaction mixture is stirred for 14 h at rt. In Step 40.1, the reaction mixture is stirred for 4 h at reflux. In Step 1.2, the reaction mixture is stirred for 2 h at 85° C. In Step 1.3, 4-chloro-2-(1-methyl-cyclopropyl)-pyridine (Step 41.1) is used and the reaction mixture is stirred for 2 h at 150° C. Title compound: ESI-MS: 386.1 [M+H]$^+$; TLC: R$_f$=0.33 (DCM/MeOH, 9:1).

Step 41.1: 4-Chloro-2-cyclopropyl-pyridine

The title compound is prepared according to a modification of a procedure described in the literature [Comins, D. L.; Mantlo, N. B., Journal of Organic Chemistry, (1985), 50, 4410-4411]. Cyclopropylmagnesium bromide (0.5M in THF, 100 mL, 50 mmol, 2.2 eq) is added in one portion to a cold (−78° C.) suspension of 4-chloropyridine hydrochloride (3.4 g, 22 mmol) in THF (68 mL).

After a 10 min stirring at −78° C., phenyl chloroformate (2.76 mL, 22 mmol) is added dropwise. The reaction mixture is stirred at −78° C. for 15 min, allowed to warm to rt, quenched by addition of a 20% aqueous solution of NH$_4$Cl and extracted with Et$_2$O (2×100 mL). The organic phase is washed with a saturated solution of NaHCO$_3$ (50 mL), dried (Na$_2$SO$_4$), filtered and concentrated. To the residue dissolved in toluene (100 mL), a solution of o-chloranil (6 g, 24.2 mmol, 1.1 eq) in glacial AcOH (50 mL) is added. The reaction mixture is stirred for 14 h at rt, cooled to 0° C., basified by addition of a 10% aqueous solution of NaOH and filtered through a pad of celite. The organic layer from the filtrate is washed with H$_2$O (20 mL) and extracted with a 10% aqueous solution of HCl (3×25 mL). The combined acidic layers are basified by addition of 20% aqueous solution of NaOH and extracted with DCM (3×25 mL). The organic phase is washed with H$_2$O (50 mL), dried (Na$_2$SO$_4$), filtered and concentrated. The residue purified by silica gel column chromatography (DCM/MeOH, 1:0→99:1) to afford 0.951 g of the title compound as a colorless oil: ESI-MS: 154.1 [M+H]$^+$; t$_R$=1.41 min (System 1); TLC: R$_f$=0.85 (DCM/MeOH, 9:1).

EXAMPLE 42

S)-2-Methyl-pyrrolidine-1,2-dicarboxylic acid 2-amide 1-({5-[2-(2-fluoro-phenyl)-pyridin-4-yl]-4-methyl-thiazol-2-yl}-amide

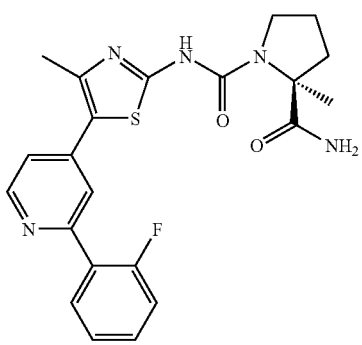 [SMILES: Cc1nc(NC(=O)N2CCC[C@@]2(C)C(N)=O)sc1-c1ccnc(-c2ccccc2F)c1]

The title compound is prepared in analogy to the procedure described in Example 40 but with the following modifications. In Example 40, the reaction mixture is stirred for 2 h at rt. In Step 40.1, the reaction mixture is stirred for 3 h at reflux. In Step 40.3, 4-chloro-2-(2-fluoro-phenyl)-pyridine (Step 42.1) is used and the reaction mixture is stirred for 2 h at 150° C. Title compound: ESI-MS: 440.1 [M+H]$^+$; t$_R$=2.85 min (System 1); TLC: R$_f$=0.36 (DCM/MeOH, 9:1).

Step 42.1: 4-Chloro-2-(2-fluoro-phenyl)-pyridine

A mixture of 2-fluorophenylboronic acid (141 mg, 1 mmol, 1.2 eq) in EtOH (1 mL) is added to a mixture of 4-chloro-2-iodo-pyridine [Choppin, S.; Gros, P.; Fort, Y., European Journal of Organic Chemistry (2001), (3), 603-606] (200 mg, 0.84 mmol), PdCl$_2$(dppf) (18 mg, 0.025 mmol, 0.03 equiv) and Na$_2$CO$_3$ (2 M solution in H$_2$O, 1.68 mL, 3.36 mmol, 4 equiv) in toluene (2 mL) at 105° C., under an argon atmosphere. The reaction mixture is stirred at 105° C. for 1 h, allowed to cool to rt, quenched by addition of a saturated solution of NaHCO$_3$ and extracted with EtOAc. The organic phase is washed with a saturated solution of NaHCO$_3$, dried (Na$_2$SO$_4$), filtered and concentrated. The residue is purified by silica gel column chromatography (Hex/EtOAc, 1:0→97:3) to afford 127 mg of the title compound as a white solid: ESI-MS: 208.1 [M+H]$^+$; t$_R$=4.66 min (System 1); TLC: R$_f$=0.27 (Hex/EtOAc, 9:1).

EXAMPLE 43

(S)-2-Methyl-pyrrolidine-1,2-dicarboxylic acid 2-amide 1-{[5-(2-cyclobutyl-pyridin-4-yl)-4-methyl-thiazol-2-yl]-amide}

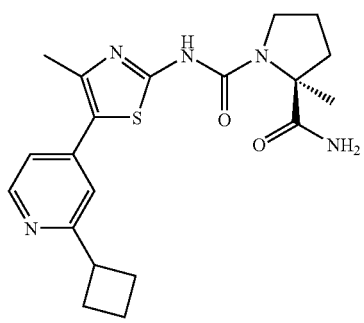 [SMILES: Cc1nc(NC(=O)N2CCC[C@@]2(C)C(N)=O)sc1-c1ccnc(C2CCC2)c1]

The title compound is prepared in analogy to the procedure described in Example 40 but with the following modifications. In Example 40, the reaction mixture is stirred for 18 h at rt, diluted with EtOAc and H$_2$O, and extracted with EtOAc. In Step 40.3, the reaction mixture is stirred for 2 h at 120° C., cooled, diluted with EtOAc and H$_2$O, filtered through a pad of celite and extracted with EtOAc. After drying and concentration of the organic phase, the residue is purified by trituration in Et$_2$O. In Step 40.5, the reaction mixture is stirred for 1 h at 80° C. In Step 40.7, 4-methoxy-3-buten-2-one in THF is added to a cold (−78° C.) solution of LiHMDS in THF. After 30 min, cyclobutylcarbonyl chloride in THF is added and the reaction mixture is allowed to reach rt over 18 h.

Title compound: ESI-MS: 400.1 [M+H]$^+$; t$_R$=2.55 min (System 1); TLC: R$_f$=0.37 (DCM/MeOH/NH$_3$$^{aq}$, 89:10:1).

EXAMPLE 44

S)-2-Methyl-pyrrolidine-1,2-dicarboxylic acid 2-amide 1-({4-methyl-5-[2-(1-methyl-cyclobutyl)-pyridin-4-yl]-thiazol-2-yl}-amide

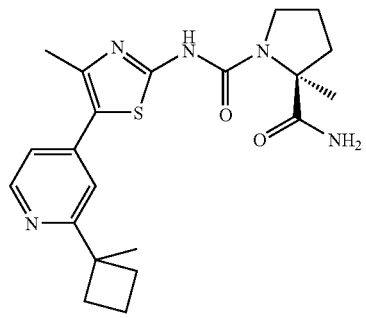 [SMILES: Cc1nc(NC(=O)N2CCC[C@@]2(C)C(N)=O)sc1-c1ccnc(C2(C)CCC2)c1]

The title compound is prepared in analogy to the procedure described in Example 40 but with the following modifications. In Example 40, the reaction mixture is stirred for 18 h at rt, quenched by dilution with EtOAc and H$_2$O, and extracted with EtOAc. In Step 40.1, the reaction mixture is stirred for 4 h at reflux. In Step 40.2, the reaction mixture is stirred for 2 h at 100° C. In Step 40.3, the reaction mixture is stirred for 3 h at 100° C., diluted with EtOAc/H$_2$O, and extracted with EtOAc. After drying and concentration of the organic phase, the residue is purified by silica gel column chromatography (Hex/EtOAc, 1:4). In Step 40.5, the reaction mixture is stirred for 2 h at 80° C. In Step 40.7, 4-methoxy-3-buten-2-one (50 mmol) in THF (100 mL) is added to a cold (−78° C.) solution of LiHMDS (1M in THF, 100 mL) in THF (200 mL). After 30 min, 1-methyl-cyclobutane chloride (Step 44.1) is added and the reaction mixture is allowed to reach rt over 18 h.

Title compound: ESI-MS: 414.1 [M+H]$^+$; t$_R$=2.72 min (System 1); TLC: R$_f$=0.13 (DCM/MeOH/NH$_3$$^{aq}$, 94:5:1).

Step 44.1: 1-Methyl-cyclobutanecarbonyl chloride

The title compound is prepared in analogy to the procedure described in Step 40.8 but using 1-methyl-cyclobutanecarboxylic acid [Cowling, S. J.; Goodby, J. W., Chemical Communications, (2006), (39), 4107-4109].

EXAMPLE 45

(S)-2-Methyl-pyrrolidine-1,2-dicarboxylic acid 2-amide 1-{[5-(2-isopropyl-pyridin-4-yl)-4-methyl-thiazol-2-yl]-amide}

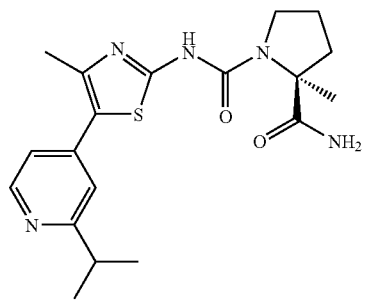 [SMILES: Cc1nc(NC(=O)N2CCC[C@@]2(C)C(N)=O)sc1-c1ccnc(C(C)C)c1]

The title compound is prepared in analogy to the procedure described in Example 40 but with the following modifications. In Example 40, the reaction mixture is stirred for 16 h at rt, quenched by dilution with EtOAc/H₂O, and extracted with EtOAc. In Step 40.1, the reaction mixture is stirred for 4 h at reflux. In Step 40.2, the reaction mixture is stirred for 2 h at 100° C. In Step 1.3, 4-chloro-2-isopropyl-pyridine (Step 45.1) is used. The reaction mixture is stirred for 3 h at 150° C., diluted with EtOAc/H₂O, and extracted with EtOAc. After drying and concentration of the organic phase, the residue is purified by silica gel column chromatography (Hex/EtOAc, 25:75).

Title compound: ESI-MS: 388.1 [M+H]⁺; $t_R$=2.39 min (System 1); TLC: $R_f$=0.15 (DCM/MeOH/NH₃$^{aq}$, 94:5:1).

Step 45.1: 4-Chloro-2-isopropyl-pyridine

The title compound is prepared in analogy to the procedure described in Step 41.1 but using isopropylmagnesium chloride (2M in THF): ESI-MS: 156.0 [M+H]⁺; TLC: $R_f$=0.32 (DCM).

EXAMPLE 46

S)-2-Methyl-pyrrolidine-1,2-dicarboxylic acid 2-amide 1-({4-methyl-5-[2-(1-trifluoromethyl-cyclopropyl)-pyridin-4-yl]-thiazol-2-yl}-amide

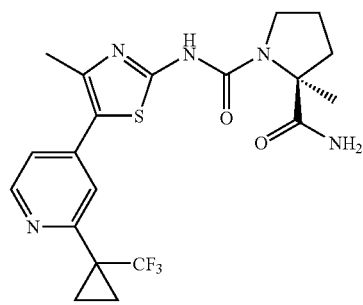

The title compound is prepared in analogy to the procedure described in Example 40 but with the following modifications. In Example 40, the reaction mixture is stirred for 14 h at rt. In Step 40.2, the reaction mixture is stirred for 1 h at 85° C. and extracted with EtOAc after being quenched. In Step 40.3, the reaction mixture is stirred for 2 h at 120° C. In Step 40.4, 1,2-dichloroethane (2.55 mL per mmol of pyridin-4-one) is used as the solvent. The reaction mixture is stirred for 1 h at 83° C. and extracted with EtOAc after being quenched. In Step 40.5, the reaction mixture is stirred for 1 h at 65° C. In Step 40.7, 1-trifluoromethyl-cyclopropanecarbonyl chloride (Step 46.1) is used.

Title compound: ESI-MS: 453.9 [M+H]⁺; $t_R$=2.89 min (System 1); TLC: $R_f$=0.30 (DCM/MeOH, 9:1).

Step 46.1: 1-Trifluoromethyl-cyclopropanecarbonyl chloride

The title compound is prepared in analogy to the procedure described in Step 40.8 but using 1-trifluoromethyl-cyclopropanecarboxylic acid.

EXAMPLE 47

S)-2-Methyl-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide

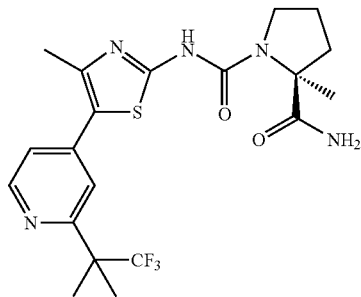 [SMILES: Cc1nc(NC(=O)N2CCC[C@@]2(C)C(N)=O)sc1-c1ccnc(C(C)(C)C(F)(F)F)c1]

The title compound is prepared in analogy to the procedure described in Example 40 but with the following modifications. In Example 40, the reaction mixture is stirred for 14 h at rt. In Step 40.2, the reaction mixture is stirred for 1 h at 85° C. and extracted with EtOAc after being quenched. In Step 40.3, N-thiazol-2-yl-acetamide is used. The reaction mixture is stirred for 2.5 h at 120° C. In Step 40.4, the reaction mixture is stirred for 1 h at 83° C. and extracted with EtOAc after being quenched. In Step 40.5, the reaction mixture is stirred for 1 h at 65° C. In Step 40.6, the crude product is not purified. In Step 40.7, 3,3,3-trifluoro-2,2-dimethyl-propionyl chloride (Step 47.1) is used.

Title compound: ESI-MS: 456.1 [M+H]⁺; $t_R$=3.25 min (System 1); TLC: $R_f$=0.31 (DCM/MeOH, 9:1).

Step 47.1: 3,3,3-Trifluoro-2,2-dimethyl-propionyl chloride

The title compound is prepared in analogy to the procedure described in Step 40.8 but using 3,3,3-trifluoro-2,2-dimethyl-propionic acid.

EXAMPLE 48

S)-2-Methyl-pyrrolidine-1,2-dicarboxylic acid 2-amide 1-({4-methyl-5-[2-(1-trifluoromethyl-cyclobutyl)-pyridin-4-yl]-thiazol-2-yl}-amide

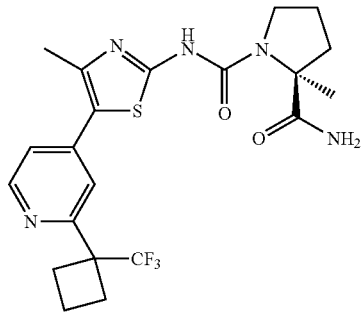 [SMILES: Cc1nc(NC(=O)N2CCC[C@@]2(C)C(N)=O)sc1-c1ccnc(C2(C(F)(F)F)CCC2)c1]

The title compound is prepared in analogy to the procedure described in Example 40 but with the following modifications. In Example 40, the reaction mixture is stirred for 18 h at rt, quenched by dilution with DCM/H$_2$O and extracted with DCM. In Step 40.1, the reaction mixture is stirred for 1 h at reflux. In Step 40.2, the reaction mixture is stirred for 2 h at 100° C. and extracted with DCM after being quenched. In Step 40.3, the reaction mixture is stirred for 6 h at 120° C., quenched by dilution with EtOAc/H$_2$O, filtered through a pad of celite and extracted with EtOAc. In Step 40.4, 1,2-dichloroethane (2.26 mL per mmol of pyridin-4-one) is used as the solvent. The reaction mixture is stirred for 1 h at reflux and extracted with DCM after being quenched. In Step 40.5, the reaction mixture is stirred for 1 h at rt. In Step 40.6, the reaction mixture is stirred for 18 h at rt. In Step 1.7, 4-methoxy-3-buten-2-one in THF is added to a cold (−78° C.) solution of LiHMDS in THF. After 30 min, 1-trifluoromethyl-cyclobutanecarbonyl chloride (Step 48.1) in THF is added and the reaction mixture is allowed to reach rt over 18 h and extracted with EtOAc after being quenched.

Title compound: ESI-MS: 468.1 [M+H]$^+$; $t_R$=3.16 min (System 1); TLC: R$_f$=0.21 (DCM/MeOH/NH$_3$$^{aq}$, 91.5:7.5:1).

Step 48.1: 1-Trifluoromethyl-cyclobutanecarbonyl chloride

The title compound is prepared in analogy to the procedure described in Step 1.8 but using 1-trifluoromethyl-cyclobutanecarboxylic acid and stirring the reaction mixture for 2 h at reflux.

EXAMPLE 49

S)-2-Methyl-pyrrolidine-1,2-dicarboxylic acid 2-amide 1-({5-[2-(1-cyano-cyclopropyl)-pyridin-4-yl]-4-methyl-thiazol-2-yl}-amide

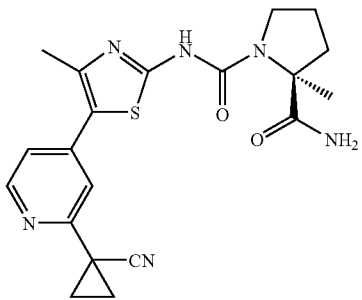 [SMILES: Cc1nc(NC(=O)N2CCC[C@@]2(C)C(N)=O)sc1-c1ccnc(C2(C#N)CC2)c1]

The title compound is prepared in analogy to the procedure described in Example 40 but with the following modifications. In Example 40, the reaction mixture is stirred for 18 h at rt, quenched by dilution with EtOAc/H$_2$O, and extracted with EtOAc. In Step 40.1, 1-[4-(2-amino-4-methyl-thiazol-5-yl)-pyridin-2-yl]-cyclopropanecarbonitrile (Step 49.1) is used and the reaction mixture is stirred for 2 h at reflux.

Title compound: ESI-MS: 411.1 [M+H]$^+$; $t_R$=3.16 min (System 1); TLC: R$_f$=0.14 (DCM/MeOH/NH$_3$$^{aq}$, 94:5:1).

Step 49.1: 1-[4-(2-Amino-4-methyl-thiazol-5-yl)-pyridin-2-yl]-cyclopropanecarbonitrile A mixture of {5-[2-(1-cyano-cyclopropyl)-pyridin-4-yl]-4-methyl-thiazol-2-yl}-carbamic acid tert-butyl ester (Step 49.2) (295 mg), DCM (4 mL) and TFA (1 mL) is stirred for 2 h at rt and then concentrated. The residue is purified by silica gel column chromatography (DCM/MeOH/NH$_3$$^{aq}$, 94:5:1) to afford 182 mg of the title compound: ESI-MS: 257.1 [M+H]$^+$; $t_R$=2.54 min (System 1); TLC: R$_f$=0.30 ((DCM/MeOH/NH$_3$$^{aq}$, 94:5:1).

Step 49.2: {5-[2-(1-Cyano-cyclopropyl)-pyridin-4-yl]-4-methyl-thiazol-2-yl}-carbamic acid tert-butyl ester The title compound is prepared in analogy to the procedure described in Step 40.3, but using 1-(4-bromo-pyridin-2-yl)-cyclopropanecarbonitrile (Step 49.3) and (4-methyl-thiazol-2-yl)-carbamic acid tert-butyl ester (Step 49.4). The reaction mixture is stirred for 2 h at 100° C., quenched by dilution with EtOAc/H$_2$O, and extracted with EtOAc. The crude product is purified by silica gel column chromatography (Hex/EtOAc, 1:1) to afford 122 mg of the title compound as a white solid: ESI-MS: 357.1 [M+H]$^+$; $t_R$=4.86 min (System 1); TLC: R$_f$=0.29 (Hex/EtOAc, 1:1).

Step 49.3: 1-(4-Bromo-pyridin-2-yl)-cyclopropanecarbonitrile

LiHMDS (1M in toluene, 17.6 mL, 17.6 mmol, 3.1 eq) is added dropwise to a cold (−5° C.) mixture of 4-bromo-2-fluoro-pyridine [Marsais, F. et al, Journal of Organic Chemistry, (1992), 57, 565-573] (1 g, 5.7 mmol), cyclopropanecarbonitrile (1.25 mL, 17 mmol, 3 eq), 4 Å molecular sieves and toluene (20 mL). The reaction mixture is allowed to warm to rt, stirred for 16 h, poured into H$_2$O and filtered. The filtrate is diluted with EtOAc/H$_2$O and extracted with EtOAc. The organic phase is washed with H$_2$O and brine, dried (Na$_2$SO$_4$), filtered and concentrated. The residue is purified by silica gel column chromatography (Hex/EtOAc, 9:1), to afford 620 mg of the title compound as a white solid: ESI-MS: 223.1/225.1 [M+H]$^+$; $t_R$=4.22 min (System 1); TLC: R$_f$=0.25 (Hex/EtOAc, 9:1).

Step 49.4: (4-Methyl-thiazol-2-yl)-carbamic acid tert-butyl ester

A solution of di-tert-butyl-dicarbonate (21 g, 96.5 mmol, 1.1 eq) in t-BuOH (50 mL) is added to a solution of 4-methyl-2-aminothiazole (10 g, 87.7 mmol) and DMAP (1.1 g, 8.8 mmol, 0.1 eq) in t-BuOH (50 mL). The reaction mixture is stirred for 72 h at rt and concentrated. The residue is diluted with EtOAc/H$_2$O and extracted with EtOAc. The organic phase is washed with H$_2$O and brine, dried (Na$_2$SO$_4$), filtered and concentrated. The residue is purified by silica gel column chromatography (DCM/MeOH, 98:2), to afford 15.2 g of the title compound as a white solid: ESI-MS: 215.1 [M+H]$^+$; $t_R$=3.43 min (System 1); TLC: R$_f$=0.30 (DCM/MeOH, 98:2).

EXAMPLE 50

(S)-2-Methyl-pyrrolidine-1,2-dicarboxylic acid 2-amide 1-({5-[2-(1-cyano-cyclobutyl)-pyridin-4-yl]-4-methyl-thiazol-2-yl}-amide)

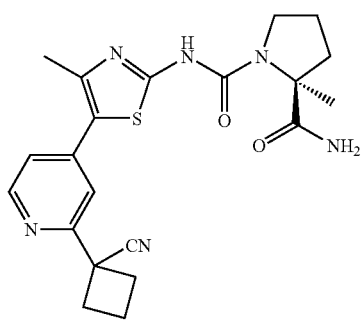 [SMILES: Cc1nc(NC(=O)N2CCC[C@@]2(C)C(N)=O)sc1-c1ccnc(C2(C#N)CCC2)c1]

The title compound is prepared in analogy to the procedure described in Example 40 but with the following modifications. In Step 40.1, 1-[4-(2-amino-4-methyl-thiazol-5-yl)-pyridin-2-yl]-cyclobutanecarbonitrile (Step 50.1) is used and the reaction mixture is stirred for 3 h at reflux. Title compound: ESI-MS: 425.1 [M+H]$^+$; TLC: $R_f$=0.35 (DCM/MeOH, 9:1).

Step 50.1: 1-[4-(2-Amino-4-methyl-thiazol-5-yl)-pyridin-2-yl]-cyclobutanecarbonitrile A mixture of {5-[2-(1-cyano-cyclobutyl)-pyridin-4-yl]-4-methyl-thiazol-2-yl}-carbamic acid tert-butyl ester (Step 50.2) (300 mg), DCM (5 mL) and TFA (1 mL) is stirred for 4 h at rt, quenched by addition of a saturated solution of NaHCO$_3$, and extracted with DCM. The organic phase is washed with a saturated solution of NaHCO$_3$, dried (Na$_2$SO$_4$), filtered and concentrated. The residue is purified by silica gel column chromatography (DCM/MeOH, 1:0→96:4) to afford 181 mg of the title compound as a yellow solid: ESI-MS: 271.1 [M+H]$^+$; $t_R$=2.48 min (System 1); TLC: $R_f$=0.45 (DCM/MeOH, 9:1).

Step 50.2: {5[2-(1-Cyano-cyclobutyl)-pyridin-4-yl]-4-methyl-thiazol-2-yl}-carbamic acid tert-butyl ester The title compound is prepared in analogy to the procedure described in Step 40.3, but using 1-(4-bromo-pyridin-2-yl)-cyclobutanecarbonitrile (Step 50.3) and (4-methyl-thiazol-2-yl)-carbamic acid tert-butyl ester (Step 17.4). The reaction mixture is stirred for 3 h at 100° C. Title compound: ESI-MS: 371.1 [M+H]$^+$; $t_R$=4.86 min (System 1); TLC: $R_f$=0.66 (Hex/EtOAc, 1:1).

Step 50.3: 1-(4-Bromo-pyridin-2-yl)-cyclobutanecarbonitrile

LiHMDS (1M in toluene, 17.7 mL, 17.7 mmol, 3.1 eq) is added dropwise to a cold (−5° C.) solution of 4-bromo-2-fluoro-pyridine [Marsais, F. et al, Journal of Organic Chemistry, (1992), 57, 565-573] (1 g, 5.7 mmol) and cyclobutanecarbonitrile (1.39 g, 17.1 mmol, 3 eq) in toluene (20 mL). The reaction mixture is allowed to warm to rt, stirred for 5 h, quenched by addition of a saturated solution of NaHCO$_3$ and filtered through a pad of celite. The filtrate is extracted with EtOAc. The organic phase is washed with a saturated solution of NaHCO$_3$, dried (Na$_2$SO$_4$), filtered and concentrated. The residue is purified by silica gel column chromatography (Hex/EtOAc, 1:0→95:5) to afford 933 mg of the title compound as a yellow oil: ESI-MS: 237.0/239.0 [M+H]$^+$; $t_R$=4.27 min (System 1); TLC: $R_f$=0.30 (Hex/EtOAc, 9:1).

EXAMPLE 51

(S)-2-Methyl-pyrrolidine-1,2-dicarboxylic acid 2-amide 1-{[5-(2-diethylamino-pyridin-4-yl)-4-methyl-thiazol-2-yl]-amide}

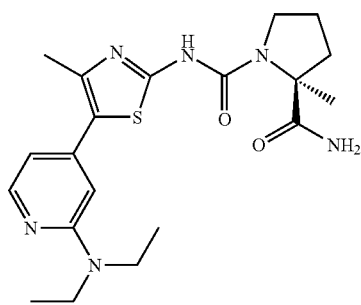 [SMILES: CCN(CC)c1cc(-c2sc(NC(=O)N3CCC[C@@]3(C)C(N)=O)nc2C)ccn1]

The title compound is prepared in analogy to the procedure described in Example 40 but with the following modifications. In Example 40, the reaction mixture is stirred for 18 h at rt, quenched by dilution with DCM/H$_2$O and extracted with DCM. In Step 40.1, the reaction mixture is stirred for 1 h at reflux. In Step 40.2, the reaction mixture is stirred for 1 h at 100° C. and extracted with DCM after being quenched. In Step 40.3, diethyl-(4-iodo-pyridin-2-yl)-amine (Step 51.1) is used. The reaction mixture is stirred for 16 h at 120° C., quenched by dilution with EtOAc/H$_2$O, filtered through a pad of celite and extracted with EtOAc.

Title compound: ESI-MS: 417.2 [M+H]$^+$; $t_R$=2.66 min (System 1); TLC: $R_f$=0.30 (DCM/MeOH/NH$_3^{aq}$, 91.5:7.5:1).

Step 51.1: Diethyl-(4-iodo-pyridin-2-yl)-amine

A mixture of 2-fluoro-4-iodopyridine (2 g, 8.97 mmol), diethyl amine (2.77 ml, 26.9 mmol, 3 eq) and K$_2$CO$_3$ (2.48 g, 17.94 mmol, 2 eq) in DMF (20 mL) is stirred for 18 h at 100° C., allowed to cool to rt, diluted with EtOAc/H$_2$O and extracted with EtOAc. The organic phase is washed with H$_2$O and brine, dried (Na$_2$SO$_4$), filtered and concentrated. The residue purified by silica gel column chromatography (Hex/Et$_2$O, 98:2) to afford 2.3 g of the title compound as a yellow oil: ESI-MS: 277.1 [M+H]$^+$; TLC: $R_f$=0.52 (Hex/Et$_2$O, 98:2).

EXAMPLE 52

(S)-2-Methyl-pyrrolidine-1,2-dicarboxylic acid 2-amide 1-{[5-(3-ethyl-3H-benzoimidazol-5-yl)-4-methyl-thiazol-2-yl]-amide}

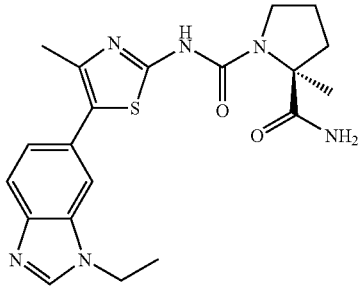 [SMILES: CCn1cnc2ccc(-c3sc(NC(=O)N4CCC[C@@]4(C)C(N)=O)nc3C)cc21]

The title compound is prepared in analogy to the procedure described in Example 40 but with the following modifications. In Example 40, the reaction mixture is stirred for 14 h at rt. In Step 40.1, the reaction mixture is stirred for 15 h at reflux. In Step 40.2, the reaction mixture is stirred for 3 h at 85° C. and extracted with EtOAc after being quenched. In Step 40.3, 6-bromo-1-ethyl-1H-benzoimidazole (Step 52.1) and the reaction mixture is stirred for 14 h at 120° C. Title compound: ESI-MS: 413.1 [M+H]$^+$; $t_R$=2.23 min (System 1); TLC: $R_f$=0.28 (DCM/MeOH, 9:1).

Step 52.1: 6-Bromo-1-ethyl-1H-benzoimidazole

A mixture of 4-bromo-N*2*-ethyl-benzene-1,2-diamine (Step 52.2) (2 g, 9.3 mmol) and triethylortoformate (15.5 mL, 93 mmol, 10 eq) is stirred for 1 h at 148° C., allowed to cool and concentrated. The residue purified by silica gel column chromatography (DCM/MeOH, 1:0→98:2) to afford 2.05 g of the title compound as a white solid: ESI-MS: 225.1/227.1 [M+H]$^+$; $t_R$=2.31 min (System 1); TLC: $R_f$=0.58 (DCM/MeOH, 9:1).

Step 52.2: 4-Bromo-N*2*-ethyl-benzene-1,2-diamine

A suspension of (5-bromo-2-nitro-phenyl)-ethyl-amine (Step 52.3) (6 g, 24.48 mmol) and Raney nickel (2 g) in MeOH/THF (1:1 v/v, 600 mL) is stirred for 9 h at rt, under a hydrogen atmosphere. The reaction mixture is filtered through a pad of celite and concentrated. The residue purified by silica gel column chromatography (Hex/EtOAc, 95:5→85:15) to afford 4.51 g of the title compound as a black oil: ESI-MS: 213.1/215.1 [M–H]$^-$; $t_R$=2.53 min (System 1); TLC: $R_f$=0.57 (Hex/EtOAc, 1:1).

Step 52.3: (5-Bromo-2-nitro-phenyl)-ethyl-amine

A mixture of 4-bromo-2-fluoro-nitrobenzene (6 g, 27.3 mmol), methylamine (2M in MeOH, 34.1 mL, 68.2 mmol, 2.5 eq) and EtOH (80 mL) is stirred for 15 h at 85° C., allowed to cool and concentrated. The residue purified by trituration to afford 6 g of the title compound as an yellow solid: $t_R$=5.13 min (System 1).

EXAMPLE 53

(S)-2-Methyl-pyrrolidine-1,2-dicarboxylic acid 2-amide 1-[(5-{2-[1-(4-methoxy-phenyl)-1-methyl-ethyl]-pyridin-4-yl}-4-methyl-thiazol-2-yl)-amide]

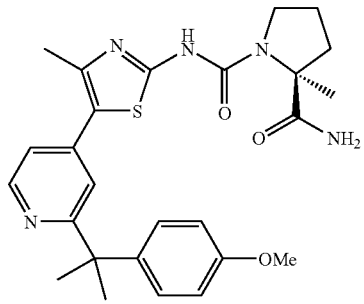 [SMILES: COc1ccc(C(C)(C)c2cc(-c3sc(NC(=O)N4CCC[C@@]4(C)C(N)=O)nc3C)ccn2)cc1]

The title compound is prepared in analogy to the procedure described in Example 40 but with the following modifications. In Example 40, the reaction mixture is stirred for 24 h at rt, quenched by dilution with EtOAc/H$_2$O. In Step 40.1, the reaction mixture is stirred for 4 h at reflux. In Step 40.2, the reaction mixture is stirred for 2 h at 100° C. In Step 40.3, the reaction mixture is stirred for 3 h at 100° C., quenched by dilution with EtOAc/H$_2$O and extracted with EtOAc. In Step 40.4, 1,2-dichloroethane (4.3 mL per mmol of pyridin-4-one) is used as the solvent. The reaction mixture is stirred for 1 h at reflux and extracted with DCM after being quenched. In Step 40.5, the reaction mixture is stirred for 23 h at 80° C. In Step 40.6, the reaction mixture is stirred for 21 h at rt. In Step 40.7, 4-methoxy-3-buten-2-one in THF is added to a cold (−78° C.) solution of LiHMDS in THF. After 30 min, 2-(4-methoxy-phenyl)-2-methyl-propionyl chloride (Step 53.1) in THF is added and the reaction mixture is allowed to reach rt over 16 h.

Title compound: ESI-MS: 494.1 [M+H]$^+$; $t_R$=3.32 min (System 1); TLC: $R_f$=0.18 (DCM/MeOH/NH$_3^{aq}$, 94:5:1).

Step 53.1: 2-(4-Methoxy-phenyl)-2-methyl-propionyl chloride

The title compound is prepared in analogy to the procedure described in Step 40.8 but using 2-(4-methoxy-phenyl)-2-methyl-propionic acid and stirring the reaction mixture for 3 h at reflux.

EXAMPLE 54

(S)-2-Methyl-pyrrolidine-1,2-dicarboxylic acid 2-amide 1-[(5-{2-[1-(4-methoxy-phenyl)-cyclopropyl]-pyridin-4-yl}-4-methyl-thiazol-2-yl)-amide]

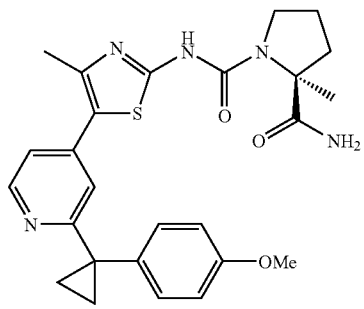 [SMILES: COc1ccc(C2(c3cc(-c4sc(NC(=O)N5CCC[C@@]5(C)C(N)=O)nc4C)ccn3)CC2)cc1]

The title compound is prepared in analogy to the procedure described in Example 40 but with the following modifications. In Example 40, the reaction mixture is stirred for 21 h at rt, quenched by dilution with EtOAc/H$_2$O. In Step 40.1, the reaction mixture is stirred for 5 h at reflux. In Step 40.2, the reaction mixture is stirred for 3 h at 100° C. In Step 40.3, the reaction mixture is stirred for 6 h at 100° C., quenched by dilution with EtOAc/H$_2$O and extracted with EtOAc. In Step 40.4, 1,2-dichloroethane (4.3 mL per mmol of pyridin-4-one) is used as the solvent. The reaction mixture is stirred for 1 h at reflux, poured into a saturated solution of NaHCO$_3$ and extracted with DCM. In Step 40.5, the reaction mixture is stirred for 18 h at 80° C. In Step 40.6, the reaction mixture is stirred for 18 h at rt. In Step 40.7, 4-methoxy-3-buten-2-one in THF is added to a cold (−78° C.) solution of LiHMDS in THF. After 30 min, 1-(4-methoxy-phenyl)-cyclopropanecarbonyl chloride (Step 54.1) in THF is added and the reaction mixture is allowed to reach rt over 16 h. Title compound: ESI-MS: 492.1 [M+H]$^+$; $t_R$=3.21 min (System 1); TLC: R$_f$=0.24 (DCM/MeOH/NH$_3^{aq}$, 94:5:1).

Step 54.1:
1-(4-Methoxy-phenyl)-cyclopropanecarbonyl chloride

The title compound is prepared in analogy to the procedure described in Step 40.8 but using 1-(4-methoxy-phenyl)-cyclopropylcarboxylic acid and stirring the reaction mixture for 3 h at reflux.

EXAMPLE 55

(S)-2-Methyl-pyrrolidine-1,2-dicarboxylic acid 2-amide 1-{[5-(2-{1-[4-(3-dimethylamino-propoxy)-phenyl]-1-methyl-ethyl}-pyridin-4-yl)-4-methyl-thiazol-2-yl]-amide}

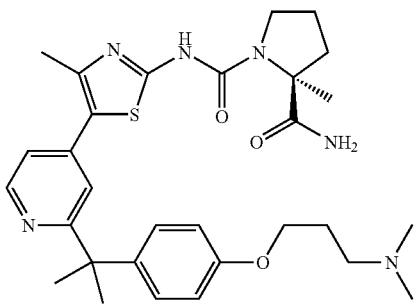 [SMILES: Cc1nc(NC(=O)N2CCC[C@@]2(C)C(N)=O)sc1-c1ccnc(C(C)(C)c2ccc(OCCCN(C)C)cc2)c1]

The title compound is prepared in analogy to the procedure described in Example 40 but with the following modifications. In Example 40, the reaction mixture is stirred for 18 h at rt, quenched by dilution with EtOAc/H$_2$O. In Step 40.1, the reaction mixture is stirred for 4.5 h at reflux. In Step 40.2, the reaction mixture is stirred for 7 h at 100° C. In Step 40.3, (3-{4-[1-(4-bromo-pyridin-2-yl)-1-methyl-ethyl]-phenoxy}-propyl)-dimethyl-amine (Step 55.1) is used. The reaction mixture is stirred for 2 h at 120° C., quenched by dilution with EtOAc/H$_2$O and extracted with EtOAc. Title compound: ESI-MS: 565.1 [M+H]$^+$; $t_R$=2.55 min (System 1); TLC: R$_f$=0.08 (DCM/MeOH/NH$_3^{aq}$, 94:5:1).

Step 55.1: (3-{4-[1-(4-Bromo-pyridin-2-yl)-1-methyl-ethyl]-phenoxy}-propyl)-dimethyl-amine Sodium hydroxide (pellets are finely grinded, 0.488 g, 12.2 mmol, 5 eq) is added to a solution of 4-[1-(4-bromo-pyridin-2-yl)-1-methyl-ethyl]-phenol (Step 55.2) (0.714 g, 2.44 mmol) in DMF (5 mL). The mixture is stirred for 20 min at rt. 3-Dimethylamino-1-propylchloride hydrochloride (0.611 g, 3.87 mmol, 1.6 eq) is added. The reaction mixture is heated to 90° C., stirred for 10 h, allowed to cool, diluted with EtOAc/H$_2$O and extracted with EtOAc. The organic phase is washed with H$_2$O and brine, dried (Na$_2$SO$_4$), filtered and concentrated. The residue purified by silica gel column chromatography (DCM/MeOH/NH$_3^{aq}$, 94:5:1) to afford 0.398 g of the title compound as an impure brown oil which is used without further purification: ESI-MS: 377.1/379.0 [M+H]$^+$; TLC: R$_f$=0.22 (DCM/MeOH/NH$_3^{aq}$, 94:5:1).

Step 55.2: 4-[1-(4-Bromo-pyridin-2-yl)-1-methyl-ethyl]-phenol

BBr$_3$ (1 M in DCM, 23 mmol, 8 eq) is added dropwise to a cold (0° C.) solution of 4-bromo-2-[1-(4-methoxy-phenyl)-1-methyl-ethyl]-pyridine (Step 55.3) (0.878 g, 2.87 mmol) in DCM (42 mL), under an argon atmosphere. The reaction mixture is stirred for 1 h at 0° C., allowed to warm to rt, stirred for 18 h, cooled to 0° C. and quenched by addition of anhydrous MeOH. The mixture is concentrated, diluted with a 6M aqueous solution of HCl, stirred for 1 h, neutralized to pH 7 and extracted with DCM. The organic phase is dried (Na$_2$SO$_4$), filtered and concentrated. The residue is used without purification.

Step 55.3: 4-Bromo-2-[1-(4-methoxy-phenyl)-1-methyl-ethyl]-pyridine

The title compound is prepared in analogy to the procedure described in Steps 40.4 to 40.7 but with the following modifications. In Step 40.4, 1,2-dichloroethane (4.3 mL per mmol of pyridin-4-one) is used as the solvent. The reaction mixture is stirred for 1 h at reflux, poured into a saturated aqueous solution of NaHCO$_3$ and extracted with DCM. In Step 40.5, the reaction mixture is stirred for 23 h at 80° C. In Step 40.6, the reaction mixture is stirred for 21 h at rt. In Step 40.7, 4-methoxy-3-buten-2-one in THF is added to a cold (−78° C.) solution of LiHMDS in THF. After 30 min, 2-(4-methoxy-phenyl)-2-methyl-propionyl chloride (Step 53.1) in THF is added and the reaction mixture is allowed to reach rt over 16 h.

Title compound: ESI-MS: 306.0/308.0 [M+H]$^+$; $t_R$=3.94 min (System 1); TLC: R$_f$=0.55 (Hex/EtOAc, 7:3).

EXAMPLE 56

S-2-Methyl-pyrrolidine-1,2-dicarboxylic acid 2-amide 1-({4-methyl-5-[2-(1-d$_3$-methyl-cyclobutyl)-pyridin-4-yl]-thiazol-2-yl}-amide)

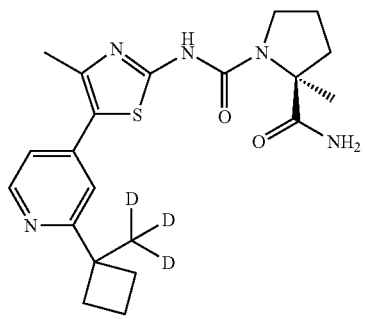 [SMILES: [2H]C([2H])([2H])C1(c2cc(-c3sc(NC(=O)N4CCC[C@@]4(C)C(N)=O)nc3C)ccn2)CCC1]

The title compound is prepared in analogy to the procedure described in Example 40 but with the following modifications. In Example 40, the reaction mixture is stirred for 18 h at rt, quenched by dilution with DCM/H$_2$O, and extracted with DCM. In Step 40.1, the reaction mixture is stirred for 1 h at reflux. In Step 40.2, the reaction mixture is stirred for 1 h at 100° C. In Step 40.3, the palladium catalyst is added to the heated mixture of the remaining reagents and the resulting mixture is stirred for 1 h at 120° C., diluted with EtOAc/H$_2$O and extracted with EtOAc. After drying and concentration of the organic phase, the residue is purified by silica gel column chromatography (Hex/EtOAc, 1:4). In Step 40.4, the reaction mixture is stirred for 30 min at 120° C. In Step 40.5, the reaction mixture is stirred for 3 h at 80° C. In Step 40.7, In Step 40.7, 4-methoxy-3-buten-2-one in THF is added to a cold (−78° C.) solution of LiHMDS in THF. After 30 min, 1-d$_3$-methyl-cyclobutane chloride (Step 56.1) in THF is added and the reaction mixture is allowed to reach rt over 16 h.

Title compound: ESI-MS: 417.2 [M+H]$^+$; t$_R$=2.72 min (System 1); TLC: R$_f$=0.21 (DCM/MeOH/NH$_3$$^{aq}$, 91.5:7.5:1).

Step 56.1: 1-d$_3$-Methyl-cyclobutanecarbonyl chloride

The title compound is prepared in analogy to the procedure described in Step 40.8 but using 1-d$_3$-methyl-cyclobutanecarboxylic acid which is prepared according to a described procedure [Cowling, S. J.; Goodby, J. W., Chemical Communications, (2006), (39), 4107-4109] but using d$_3$-methyl-iodide.

EXAMPLE 57

S)-2-Methyl-pyrrolidine-1,2-dicarboxylic acid 2-amide 1-({4-dimethylaminomethyl-5-[2-(1-d$_3$-methyl-cyclobutyl)-pyridin-4-yl]-thiazol-2-yl}-amide

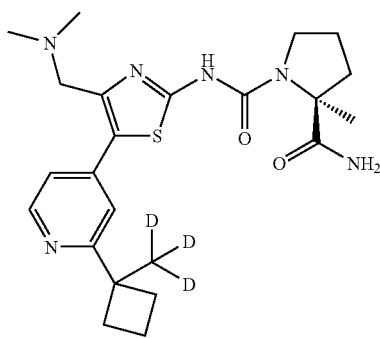 [SMILES: [2H]C([2H])([2H])C1(c2cc(-c3sc(NC(=O)N4CCC[C@@]4(C)C(N)=O)nc3CN(C)C)ccn2)CCC1]

The title compound is prepared in analogy to the procedure described in Example 40 but with the following modifications. In Example 40, the reaction mixture is stirred for 18 h at rt, quenched by dilution with DCM/H$_2$O and extracted with DCM. In Step 40.1, the reaction mixture is stirred for 2 h at reflux. In Step 40.2, N-{4-dimethylaminomethyl-5-[2-(1-d$_3$-methyl-cyclobutyl)-pyridin-4-yl]thiazol-2-yl}-acetamide (Step 57.1) is used. The reaction mixture is stirred for 1 h at 100° C. Title compound: ESI-MS: 460.1 [M+H]$^+$; TLC: R$_f$=0.15 (DCM/MeOH/NH$_3$$^{aq}$, 89:10:1).

Step 57.1: N-(4-Dimethylaminomethyl-5-[2-(1-d$_3$-methyl-cyclobutyl)-pyridin-4-yl]-thiazol-2-acetamide A mixture of N-{4-bromomethyl-5-[2-(1-d$_3$-methyl-cyclobutyl)-pyridin-4-yl]-thiazol-2-yl}-acetamide (Step 57.2) (150 mg, 0.391 mmol), dimethylamine hydrochloride (38.3 mg, 0.470 mmol, 1.2 eq) and cesium carbonate (293 mg, 0.900 mmol, 2.3 eq) in DMF (2 mL) is stirred for 2 h at rt, diluted with EtOAc/H$_2$O, and extracted with EtOAc. The organic phase is washed with H$_2$O and brine, dried (Na$_2$SO$_4$), filtered and concentrated. The residue purified by trituration in Et$_2$O to afford 89 mg of the title compound as a white solid: ESI-MS: 348.2 [M+H]$^+$.

Step 57.2: N-{4-Bromomomethyl-5-[2-(1-d$_3$-methyl-cyclobutyl)-pyridin-4-yl]-thiazol-2-yl}-acetamide NBS (554 mg, 3.06 mmol, 1.1 eq) is added to a solution of N-{4-methyl-5-[2-(1-d$_3$-methyl-cyclobutyl)-pyridin-4-yl]-thiazol-2-yl}-acetamide (Step 57.3) (846 mg, 2.78 mmol) in CCl$_4$ (20 mL) and CHCl$_3$ (16 mL). The reaction mixture is stirred for 1 h at rt, washed with H$_2$O and brine, dried (Na$_2$SO$_4$), filtered and concentrated. The residue purified by silica gel column chromatography (Hex/EtOAc, 1:4) to afford 572 mg of the title compound as a pale yellow solid: ESI-MS: 383.0/385.0 [M+H]$^+$; t$_R$=3.12 min (System 1); TLC: R$_f$=0.45 (Hex/EtOAc, 1:4).

Step 57.3: N-{4-Methyl-5-[2-(1-d$_3$-methyl-pyridin-4-yl]-thiazol-2-yl}acetamide The title compound is prepared in analogy to the procedure described in Steps 40.3 to 40.7 but with the following modifications. In Step 40.3, the reaction mixture is stirred for 1 h at 120° C. and quenched by dilution with EtOAc/H$_2$O. In Step 40.5, the reaction mixture is stirred for 3 h at 80° C. and trituration in MeOH is not performed. In Step 40.7, 4-methoxy-3-buten-2-one in THF is added to a cold (−78° C.) solution of LiHMDS in THF. After 30 min, 1-d$_3$-methyl-cyclobutane chloride (Step 56.1) in THF is added and the reaction mixture is allowed to reach rt over 16 h. Title compound: ESI-MS: 305.2 [M+H]$^+$; TLC: R$_f$=0.24 (Hex/EtOAc, 1:4).

EXAMPLE 58

(S)-2-Methyl-Pyrrolidine-1,2-dicarboxylic acid 2-amide 1-({5-[2-(2-fluoro-1,1-dimethyl-ethyl)-pyridin-4-yl]-4-methyl-thiazol-2-yl}-amide

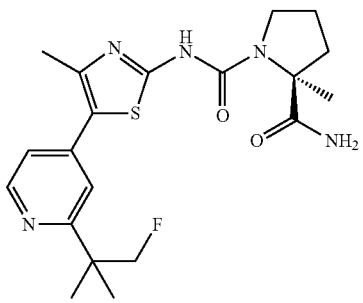 [SMILES: Cc1nc(NC(=O)N2CCC[C@@]2(C)C(N)=O)sc1-c1ccnc(C(C)(C)CF)c1]

The title compound is prepared in analogy to the procedure described in Example 40 but with the following modifications. In Step 40.2, the reaction mixture is stirred for 1 h at 100° C. and extracted with EtOAc after being quenched. In Step 40.3, the reaction mixture is stirred for 4 h at 120° C. In Step 40.4, the reaction mixture is stirred for 30 min at 85° C. and extracted with EtOAc after being quenched. In Step 40.5, the reaction mixture is stirred for 1 h at 70° C. In Step 40.6, the crude product is not purified. In Step 40.7, 3-fluoro-2,2-dimethyl-propionyl chloride (Step 58.1) is used.

Title compound: ESI-MS: 420.1 [M+H]⁺; $t_R$=2.50 min (System 1); TLC: $R_f$=0.31 (DCM/MeOH, 9:1).

Step 58.1: 3-Fluoro-2,2-dimethyl-propionyl chloride

The title compound is prepared in analogy to the procedure described in Step 44.1 but using 3-fluoro-2,2-dimethyl-propionic acid (Step 58.2).

Step 58.2: 3-Fluoro-2,2-dimethyl-propionic acid

A solution of 6.9 g (38.6 mmol) 3-fluoro-2,2-dimethyl-propionic acid methyl ester in 30 mL of methanol is treated with 38.6 mL (77 mmol) 2N NaOH and the mixture heated to reflux for 3 hours. The mixture is cooled to RT and the solvent evaporated. The residue is partitioned between water and DCM. The aqueous phase is acidified by the addition of 50 mL of 2N HCl and extracted with ethyl acetate. The organic phase is washed with brine, dried with sodium sulfate and evaporated. The colorless residue is stirred with hexanes, insoluble material is removed by filtration and the filtrate is evaporated to give the title compound as a colorless solid. ESI-MS: 119.0 [M–H]⁻.

Step 58.3: 3-Fluoro-2,2-dimethyl-propionic acid methyl ester 27 mL of a 1 M solution of tetrabutylammonium fluoride in THF are added slowly and under ice cooling to a solution of 7.25 g (27.4 mmol) 2,2-dimethyl-3-trifluoromethanesulfonyloxy-propionic acid methyl ester in 150 mL of THF. The resulting solution is stirred 6 h at 0° C. and then 10 h at RT. The solvent is evaporated carefully and the residue partitioned between DCM and brine. The organic phase is washed with brine, dried with sodium sulfate and evaporated carefully. The brown oil is distilled in a Kugelrohr-oven (oven temperature 120 to 150° C.) to give the title compound as a colorless liquid.

Step 58.4: 2,2-Dimethyl-3-trifluoromethanesulfonyloxy-propionic acid methyl ester To a solution of 3.64 g (27.5 mmol) 3-hydroxy-2,2-dimethyl-propionic acid methyl ester and (4.82 mL, 41.3 mmol) 2,6-lutidine in 50 mL dry DCM is slowly added trifluoromethanesulfonic acid anhydride (5.12 mL, 30.3 mmol) at −70° C. and under nitrogen. The yellow solution is stirred 5 min. at −70° C. then the cooling bath is removed and the mixture stirred 3 h at RT. Color change from yellow to orange to brown. DCM (50 mL) is added and the solution is washed twice with 2 N HCl, dried with sodium sulfate and evaporated to dryness. The brown residue is dried under vacuum and the title compound used without further purification. TLC: $R_f$=0.72 (EtOAc/hexanes 1:2).

EXAMPLE 59

S)-4,4-Difluoro-pyrrolidine-1,2-dicarboxylic acid 2-amide 1-({4-methyl-5-[2-(1-methyl-cyclopropyl)-pyridin-4-yl]-thiazol-2-yl}-amide

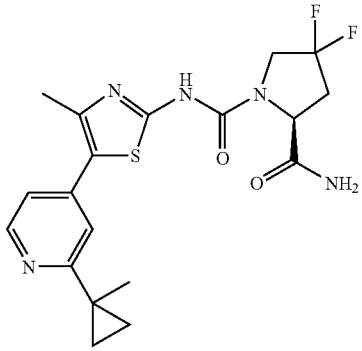 [SMILES: Cc1nc(NC(=O)N2CC(F)(F)C[C@H]2C(N)=O)sc1-c1ccnc(C2(C)CC2)c1]

The title compound is prepared in analogy to the procedure described in Example 40 but using (S)-4,4-Difluoro-pyrrolidine-2-carboxylic acid amide. Title compound: yellow powder; ESI-MS: 422.0 [M+H]⁺; $t_R$=4.26 min (System 2); TLC: $R_f$=0.26 (EtOAc).

EXAMPLE 60

(S)-2-Methyl-pyrrolidine-1,2-dicarboxylic acid 2-amide 1-{[5-(6-imidazol-1-yl-pyridin-2-yl)-4-methyl-thiazol-2-yl]-amide}

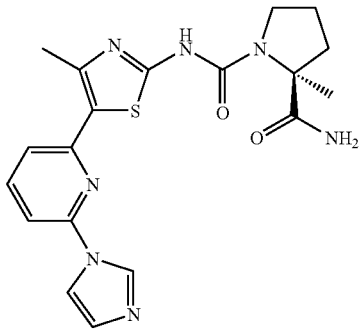 [SMILES: Cc1nc(NC(=O)N2CCC[C@@]2(C)C(N)=O)sc1-c1cccc(-n2ccnc2)n1]

A mixture of imidazole-1-carboxylic acid [5-(6-imidazol-1-yl-pyridin-2-yl)-4-methyl-thiazol-2-yl]-amide (28 mg), (S)-2-methyl-pyrrolidine-2-carboxylic acid amide (11 mg) and triethylamine (0.027 ml) in DMF (1 ml) is allowed to stand at room temperature for 18 hours. The reaction mixture is evaporated and then purification by recrystallisation from aqueous methanol gives the title compound as a white solid. Hplc/MS (Method B) RT 2.09 minutes, M+H 411.9 and M−H 409.9.

Step 60.1: Imidazole-1-carboxylic acid [5-(6-imidazol-1-yl-pyridin-2-yl)-4-methyl-thiazol-2-yl]-amide Carbonyl diimidazole (17 mg) is added to a solution of 5-(6-imidazol-1-yl-pyridin-2-yl)-4-methyl-thiazol-2-ylamine (26 mg) in DMF (1 ml) and stirred at room temperature for 18 hours. The reaction mixture is then filtered to give the title compound as a white solid.

Step 60.2: 5-(6-Imidazol-1-yl-pyridin-2-yl)-4-methyl-thiazol-2-ylamine

Concentrated hydrochloric acid (0.3 ml) is added to N-[5-(6-imidazol-1-yl-pyridin-2-yl)-4-methyl-thiazol-2-yl]-acetamide (30 mg) in ethanol (2 ml) and heated at reflux for 3 hours and then stood for 18 hours at room temperature. The reaction mixture is evaporated and partitioned between aqueous sodium bicarbonate solution and 10% methanol in dichloromethane, extracting a further 4× with 10% methanol in dichloromethane. Evaporation of the combined organic layers gives the title compound which is used in Step. 60.1 without further purification.

Step 60.3: N-[5-(6-Imidazol-1-yl-pyridin-2-yl)-4-methyl-thiazol-2-yl]-acetamide

Argon is bubbled through a mixture of 5-iodo-2-acetylamino-4-methylthiazole (312 mg), 6-imidazol-1-yl)pyridine-2-boronic acid (600 mg), 1,1'-bis(diphenylphosphino) ferrocenedichloro palladium (II) dichloromethane (45 mg), sodium carbonate (594 mg), water (3.1 ml) and dimethoxyethane (3.1 ml) at room temperature for 5 minutes prior to heating for 45 minutes at 85° C. in a Biotage Initiator™ microwave apparatus. The reaction mixture is evaporated and partitioned between aqueous sodium bicarbonate solution and 10% methanol in dichloromethane, extracting a further 2× with 10% methanol in dichloromethane. The combined organic layers are evaporated, purified by preparative reversed phase chromatography and the fractions containing the 12.8 minute component combined and evaporated. Partitioning between aqueous sodium bicarbonate solution and 10% methanol in dichloromethane, extracting a further 2× with 10% methanol in dichloromethane is followed by normal phase chromatography, eluent: 4:1 ethyl acetate:methanol, which gives the title compound as a white solid. Hplc/MS (Method A) RT 1.39 minutes, M+H 300.

EXAMPLE 61

2S,3S)-3-Methyl-pyrrolidine-1,2-dicarboxylic acid 2-amide 1-({4-methyl-5-[2-(1,1,2-trimethyl-propyl)-pyrimidin-4-yl]-thiazol-2-yl}-amide

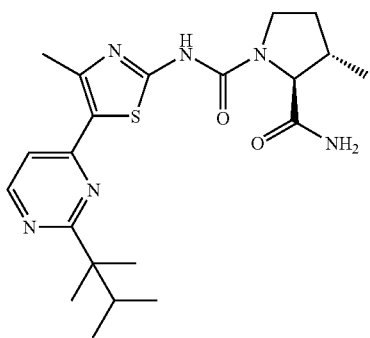 [SMILES: Cc1nc(NC(=O)N2CC[C@H](C)[C@H]2C(N)=O)sc1-c1ccnc(C(C)(C)C(C)C)n1]

A mixture of imidazole-1-carboxylic acid {4-methyl-5-[2-(1,1,2-trimethyl-propyl)-pyrimidin-4-yl]-thiazol-2-yl}-amide (30 mg), (2S,3S)-3-methyl-pyrrolidine-2-carboxylic acid amide (11 mg) and triethylamine (0.014 ml) in DMF (0.08 ml) is swirled at 40° C. for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a yellow solid. MS (Method D) M+H 431 and M−H 429.

EXAMPLE 62

S)-2-Methyl-pyrrolidine-1,2-dicarboxylic acid 2-amide 1-({5-[2-(4-methoxy-phenoxymethyl)-pyrimidin-4-yl]-4-methyl-thiazol-2-yl}-amide

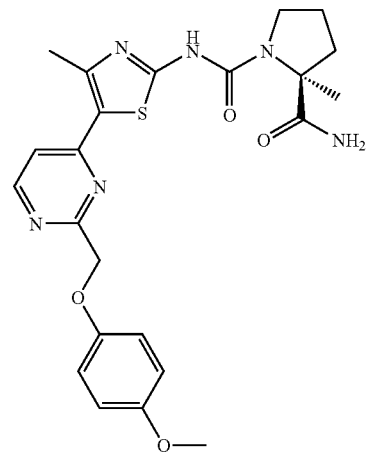 [SMILES: COc1ccc(OCc2nccc(-c3sc(NC(=O)N4CCC[C@@]4(C)C(N)=O)nc3C)n2)cc1]

A mixture of imidazole-1-carboxylic acid {5-[2-(4-methoxy-phenoxymethyl)-pyrimidin-4-yl]-4-methyl-thiazol-2-yl}-amide (30 mg), (2S)-2-methyl-pyrrolidine-2-carboxylic acid amide (10 mg) and triethylamine (0.012 ml) in DMF (0.07 ml) is swirled at 40° C. for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a beige solid. MS (Method D) M+H 483 and M−H 481.

EXAMPLE 63

(S)-2-Methyl-pyrrolidine-1,2-dicarboxylic acid 2-amide 1-[(5-{2-[2-(4-methoxy-phenyl)-1,1-dimethyl-ethyl]-pyrimidin-4-yl}-4-methyl-thiazol-2-yl)-amide]

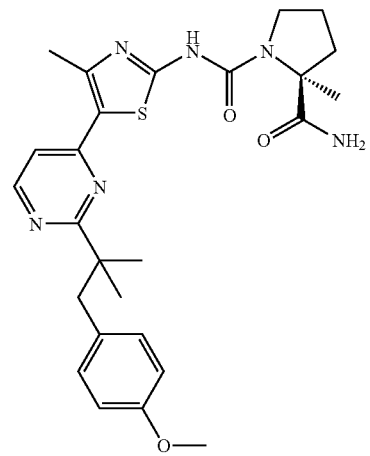 [SMILES: COc1ccc(CC(C)(C)c2nccc(-c3sc(NC(=O)N4CCC[C@@]4(C)C(N)=O)nc3C)n2)cc1]

A mixture of imidazole-1-carboxylic acid (5-{2-[2-(4-methoxy-phenyl)-1,1-dimethyl-ethyl]-pyrimidin-4-yl}-4- methyl-thiazol-2-yl)-amide (30 mg), (2S)-2-methyl-pyrrolidine-2-carboxylic acid amide (9.4 mg) and triethylamine (0.011 ml) in DMF (0.07 ml) is swirled at 40° C. for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a beige solid. MS (Method D) M+H 509 and M−H 507.

EXAMPLE 64

2S)-2-Methyl-pyrrolidine-1,2-dicarboxylic acid 2-amide 1-({4-methyl-5-[2-(1,1,2-trimethyl-propyl)-pyrimidin-4-yl]-thiazol-2-yl}-amide

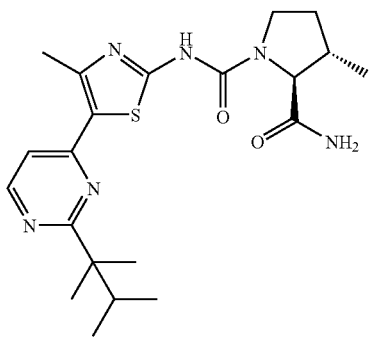 [SMILES: Cc1nc(NC(=O)N2CC[C@H](C)[C@H]2C(N)=O)sc1-c1ccnc(C(C)(C)C(C)C)n1]

A mixture of imidazole-1-carboxylic acid {4-methyl-5-[2-(1,1,2-trimethyl-propyl)-pyrimidin-4-yl]-thiazol-2-yl}-amide (30 mg), (2S)-2-methyl-pyrrolidine-2-carboxylic acid amide (11 mg) and triethylamine (0.014 ml) in DMF (0.08 ml) is swirled at 40° C. for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a beige solid. MS (Method D) M+H 431 and M−H 429.

EXAMPLE 65

(2S,4R)-4-Hydroxy-2-methyl-pyrrolidine-1,2-dicarboxylic acid 2-amide 1-{[5-(2-tert-butyl-pyrimidin-4-yl)-4-methyl-thiazol-2-yl]-amide}

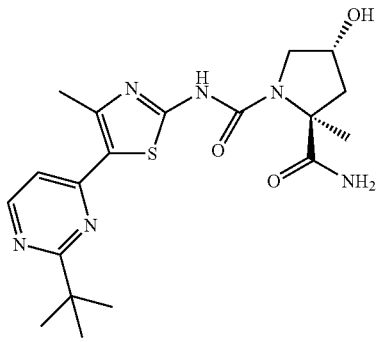 [SMILES: Cc1nc(NC(=O)N2C[C@H](O)C[C@@]2(C)C(N)=O)sc1-c1ccnc(C(C)(C)C)n1]

A mixture of imidazole-1-carboxylic acid {4-methyl-5-[2-tert-butyl-pyrimidin-4-yl]-thiazol-2-yl}-amide (153 mg), (2S,4R)-4-hydroxy-2-methyl-pyrrolidine-2-carboxylic acid amide (71 mg) and triethylamine (0.156 ml) in DMF (2 ml) is stood at room temperature for 18 hours. The reaction mixture is evaporated and then purified by normal phase chromatography eluting with a gradient from ethyl acetate to 10% ethanol in ethyl acetate and the title compound is obtained as a white solid after a further crystallisation step from aqueous methanol. Hplc/MS (Method C) RT 1.13 minutes, M+H 418.9 and M−H 417.1.

EXAMPLE 66

2S,4S)-4-Fluoro-pyrrolidine-1,2-dicarboxylic acid 2-amide 1-{[5-(2-tert-butyl-pyrimidin-4-yl)-4-methyl-thiazol-2-yl]-amide}

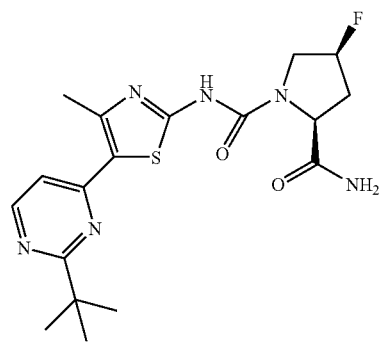 [SMILES: Cc1nc(NC(=O)N2C[C@@H](F)C[C@H]2C(N)=O)sc1-c1ccnc(C(C)(C)C)n1]

A mixture of imidazole-1-carboxylic acid {4-methyl-5-[2-tert-butyl-pyrimidin-4-yl]-thiazol-2-yl}-amide (34 mg), (2S,4S)-4-fluoro-2-methyl-pyrrolidine-2-carboxylic acid amide (14 mg) and triethylamine (0.035 ml) in DMF (1 ml) is stood at room temperature for 18 hours. The reaction mixture is evaporated and crystallisation from aqueous methanol gives the title compound as a yellow/white solid. Hplc/MS (Method C) RT 1.21 minutes, M+H 406.9 and M−H 404.9.

EXAMPLE 67

S)-2-Methyl-pyrrolidine-1,2-dicarboxylic acid 2-amide 1-({5-[2-(4-ethyl-tetrahydro-pyran-4-yl)-pyrimidin-4-yl]-4-methyl-thiazol-2-yl}-amide

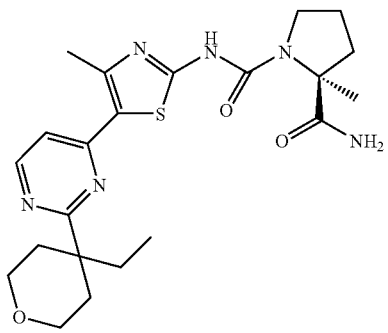 [SMILES: CCC1(c2nccc(-c3sc(NC(=O)N4CCC[C@@]4(C)C(N)=O)nc3C)n2)CCOCC1]

A mixture of imidazole-1-carboxylic acid {5-[2-(4-ethyl-tetrahydro-pyran-4-yl)-pyrimidin-4-yl]-4-methyl-thiazol-2-yl}-amide (50 mg), (2S)-2-methyl-pyrrolidine-2-carboxylic acid amide (18 mg) and triethylamine (0.021 ml) in DMF (0.13 ml) is swirled at 40° C. for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a beige solid. MS (Method D) M+H 459 and M−H 457.

EXAMPLE 68

S)-2-Methyl-pyrrolidine-1,2-dicarboxylic acid 2-amide 1-({4-methyl-5-[2-(1-phenyl-cyclopentyl)-pyrimidin-4-yl]-thiazol-2-yl}-amide

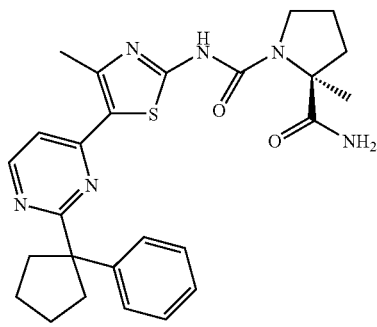 [SMILES: Cc1nc(NC(=O)N2CCC[C@@]2(C)C(N)=O)sc1-c1ccnc(C2(c3ccccc3)CCCC2)n1]

A mixture of imidazole-1-carboxylic acid {4-methyl-5-[2-(1-phenyl-cyclopentyl)-pyrimidin-4-yl]-thiazol-2-yl}-amide (60 mg), (2S)-2-methyl-pyrrolidine-2-carboxylic acid amide (13 mg) and triethylamine (0.015 ml) in DMF (0.13 ml) is swirled at 40° C. for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a solid. MS (Method D) M+H 491 and M−H 489.

EXAMPLE 69

S)-2-Methyl-pyrrolidine-1,2-dicarboxylic acid 2-amide 1-({5-[2-(1,1-dimethyl-2-p-tolyl-ethyl)-pyrimidin-4-yl]-4-methyl-thiazol-2-yl}-amide

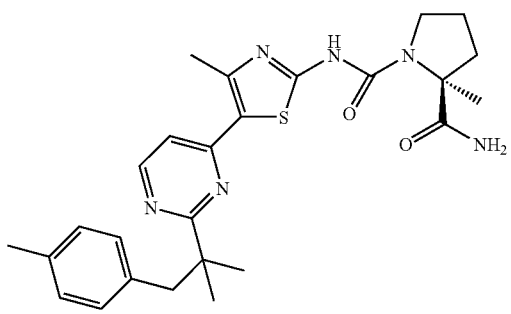 [SMILES: Cc1ccc(CC(C)(C)c2nccc(-c3sc(NC(=O)N4CCC[C@@]4(C)C(N)=O)nc3C)n2)cc1]

A mixture of imidazole-1-carboxylic acid {5-[2-(1,1-dimethyl-2-p-tolyl-ethyl)-pyrimidin-4-yl]-4-methyl-thiazol-2-yl}-amide (40 mg), (2S)-2-methyl-pyrrolidine-2-carboxylic acid amide (13 mg) and triethylamine (0.015 ml) in DMF (0.09 ml) is swirled at 40° C. for 4 hours. The reaction mixture is evaporated and then purified by reversed phase chromatography (Method B), the fractions passed through a Varian Bond Elute SCX 300 mg SPE cartridge followed by elution with 7 M ammonia in methanol. Evaporation of the methanolic ammonia washings gives the title compound as a solid. MS (Method D) M+H 493 and M−H 491.

EXAMPLE 70

(2S,4R)-4-Dimethylamino-pyrrolidine-1,2-dicarboxylic acid 2-amide 1-{[5-(2-tert-butyl-pyrimidin-4-yl)-4-methyl-thiazol-2-yl]-amide}

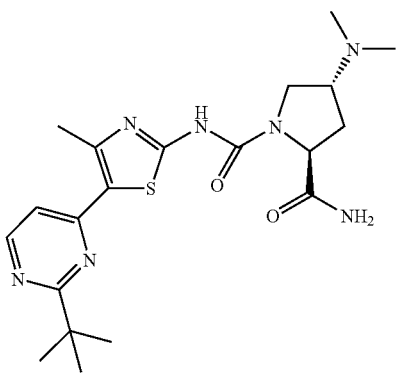 [SMILES: Cc1nc(NC(=O)N2C[C@H](N(C)C)C[C@H]2C(N)=O)sc1-c1ccnc(C(C)(C)C)n1]

A mixture of imidazole-1-carboxylic acid {4-methyl-5-[2-tert-butyl-pyrimidin-4-yl]-thiazol-2-yl}-amide (50 mg), (2S, 4R)-4-dimethylamino-pyrrolidine-2-carboxylic acid amide (25 mg) and triethylamine (0.051 ml) in DMF (1 ml) is stood at room temperature for 18 hours. The reaction mixture is evaporated and crystallisation from aqueous methanol gives the title compound as a yellow/white solid. Hplc/MS (Method C) RT 0.90 minutes, M+H 432.1 and M−H 430.3.

EXAMPLE 71

(S)-2-Methyl-pyrrolidine-1,2-dicarboxylic acid 2-amide 1-{[5-(2-diethylamino-pyrimidin-4-yl)-4-methyl-thiazol-2-yl]-amide}

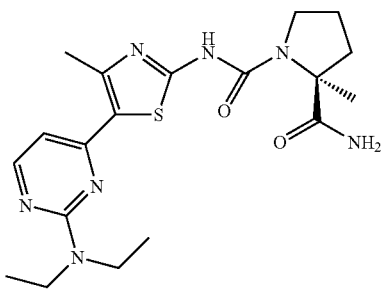 [SMILES: CCN(CC)c1nccc(-c2sc(NC(=O)N3CCC[C@@]3(C)C(N)=O)nc2C)n1]

A mixture of imidazole-1-carboxylic acid [5-(2-diethylamino-pyrimidin-4-yl)-4-methyl-thiazol-2-yl]-amide (40 mg), (2S,4R)-4-dimethylamino-pyrrolidine-2-carboxylic acid amide (16 mg) and triethylamine (0.019 ml) in DMF (0.11 ml) is stirred at 40° C. for 2 hours. The reaction mixture is evaporated and then purified by reversed phase chromatography (Method B), the fractions passed through a Varian Bond Elute SCX 300 mg SPE cartridge followed by elution with 7 M ammonia in methanol. Evaporation of the methanolic ammonia washings gives the title compound as a yellow solid. MS (Method D) M+H 418 and M−H 416.

EXAMPLE 72

(2S,4S)-4-Dimethylamino-pyrrolidine-1,2-dicarboxylic acid 2-amide 1-{[5-(2-tert-butyl-pyrimidin-4-yl)-4-methyl-thiazol-2-yl]-amide}

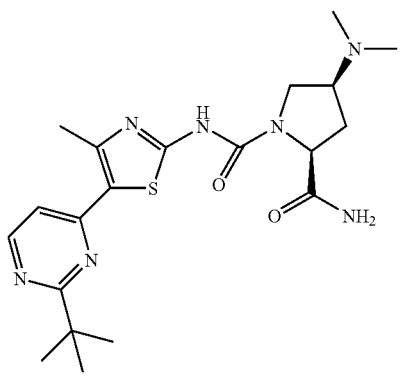 [SMILES: Cc1nc(NC(=O)N2C[C@@H](N(C)C)C[C@H]2C(N)=O)sc1-c1ccnc(C(C)(C)C)n1]

A mixture of imidazole-1-carboxylic acid {4-methyl-5-[2-tert-butyl-pyrimidin-4-yl]-thiazol-2-yl}-amide (50 mg), (2S, 4S)-4-dimethylamino-pyrrolidine-2-carboxylic acid amide (25 mg) and triethylamine (0.051 ml) in DMF (1 ml) is stood at room temperature for 18 hours. The reaction mixture is evaporated and then purified by reversed phase chromatography (Method B), the fractions passed through a Varian Bond Elute SCX 300 mg SPE cartridge followed by elution with 7 M ammonia in methanol. Evaporation of the methanolic ammonia washings gives the title compound as a yellow/white solid. Hplc/MS (Method C) RT 0.93 minutes, M+H 432.1 and M−H 430.2.

EXAMPLE 73

(S)-2-Methyl-pyrrolidine-1,2-dicarboxylic acid 2-amide 1-{[5-(2-isopropyl-pyrimidin-4-yl)-4-methyl-thiazol-2-yl]-amide}

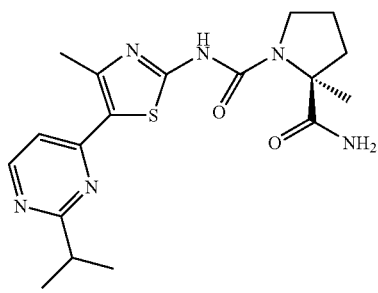

A mixture of imidazole-1-carboxylic acid {4-methyl-5-[2-isopropyl-pyrimidin-4-yl]-thiazol-2-yl}-amide (40 mg), (2S)-2-methyl-pyrrolidine-2-carboxylic acid amide (17 mg) and triethylamine (0.015 ml) in DMF (0.12 ml) is swirled at 40° C. for 18 hours. The reaction mixture is evaporated and then purified by reversed phase chromatography (Method B), the fractions passed through a Varian Bond Elute SCX 300 mg SPE cartridge followed by elution with 7 M ammonia in methanol. Evaporation of the methanolic ammonia washings gives the title compound as a yellow solid. MS (Method D) M+H 389 and M−H 387.

EXAMPLE 74

(S)-2-Methyl-pyrrolidine-1,2-dicarboxylic acid 2-amide 1-{[4-methyl-5-(2-methylsulphanyl-pyrimidin-4-yl)-thiazol-2-yl]-amide}

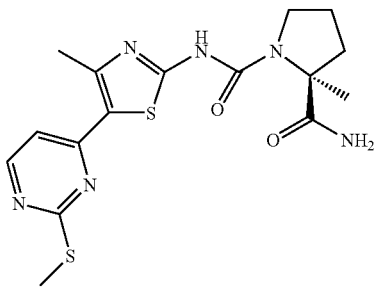 [SMILES: CSc1nccc(-c2sc(NC(=O)N3CCC[C@@]3(C)C(N)=O)nc2C)n1]

A mixture of imidazole-1-carboxylic acid {4-methyl-5-[2-methylsulphanyl-pyrimidin-4-yl]-thiazol-2-yl}-amide (1.41 g), (2S)-2-methyl-pyrrolidine-2-carboxylic acid amide (0.59 g) and triethylamine (0.71 ml) in DMF (4.2 ml) is swirled at 40° C. for 3 hours. The reaction mixture is evaporated and then partitioned between water and 5% methanol in dichloromethane, the organic layers are dried over sodium sulphate and evaporated to give the title compound as an orange solid which is used without further purification. MS (Method D) M+H 393 and M−H 391.

EXAMPLE 75

S)-2-Methyl-pyrrolidine-1,2-dicarboxylic acid 2-amide 1-({5-[2-(4-dimethylamino-piperidin-1-yl)-pyrimidin-4-yl]-4-methyl-thiazol-2-yl}-amide

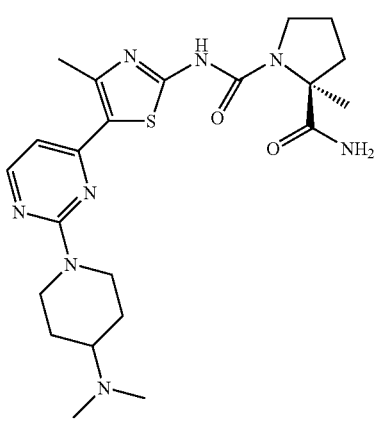 [SMILES: Cc1nc(NC(=O)N2CCC[C@@]2(C)C(N)=O)sc1-c1ccnc(N2CCC(N(C)C)CC2)n1]

A mixture of (S)-2-methyl-pyrrolidine-1,2-dicarboxylic acid 2-amide 1-{[5-(2-methanesulphinyl-pyrimidin-4-yl)-4-methyl-thiazol-2-yl]-amide} (50 mg), 4-(dimethylamino)-piperidine (78 mg) and 1,4-dioxane are heated at 80° C. for 5 hours. The cooled reaction mixture is then purified by reversed phase chromatography (Method B), the fractions passed through a Varian Bond Elute SCX 300 mg SPE cartridge followed by elution with 7 M ammonia in methanol. Evaporation of the methanolic ammonia washings gives the title compound. MS (Method D) M+H 473 and M−H 471.

EXAMPLE 76

(S)-2-Methyl-pyrrolidine-1,2-dicarboxylic acid 2-amide 1-[(4-methyl-5-{2-[methyl-(1-methyl-piperidin-4-yl)-amino]-pyrimidin-4-yl}-thiazol-2-yl)-amide]

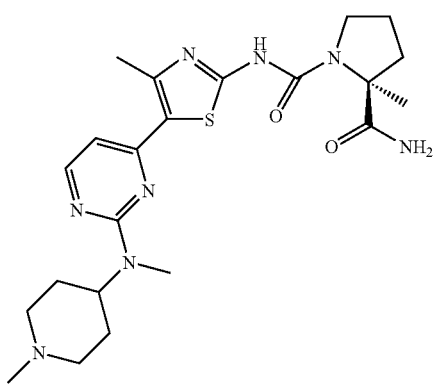

The tile compound is prepared in an analogous manner to Example 75 except 1-methyl-4-(methylamino)-piperidine is used in place of 4-(dimethylamino)-piperidine. The title compound is obtained as a solid. MS (Method D) M+H 473.

EXAMPLE 77

S)-2-Methyl-pyrrolidine-1,2-dicarboxylic acid 2-amide 1-({4-methyl-5-[2-(4-methyl-piperazin-1-yl)-pyrimidin-4-yl]-thiazol-2-yl}-amide

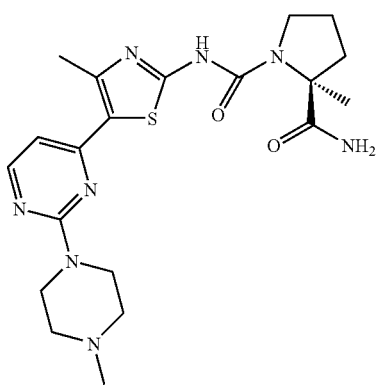 [SMILES: Cc1nc(NC(=O)N2CCC[C@@]2(C)C(N)=O)sc1-c1ccnc(N2CCN(C)CC2)n1]

The tile compound is prepared in an analogous manner to Example 75 except N-methylpiperazine is used in place of 4-(dimethylamino)-piperidine. The title compound is obtained as a solid. MS (Method D) M+H 445 and M−H 443.

EXAMPLE 78

S)-2-Methyl-pyrrolidine-1,2-dicarboxylic acid 2-amide 1-({5-[2-((R)-3-dimethylamino-pyrrolidin-1-yl)-pyrimidin-4-yl]-4-methyl-thiazol-2-yl}-amide

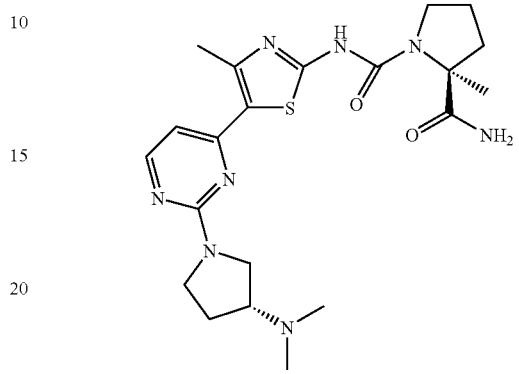

The tile compound is prepared in an analogous manner to Example 75 except (R)-(+)-3-(dimethylamino)-pyrrolidine is used in place of 4-(dimethylamino)-piperidine. The title compound is obtained as a solid. MS (Method D) M+H 459 and M−H 457.

EXAMPLE 79

S)-2-Methyl-pyrrolidine-1,2-dicarboxylic acid 2-amide 1-({5-[2-(isopropyl-methyl-amino)-pyrimidin-4-yl]-4-methyl-thiazol-2-yl}-amide

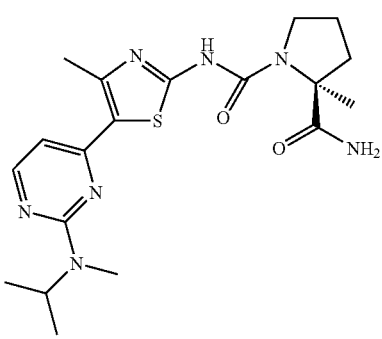 [SMILES: Cc1nc(NC(=O)N2CCC[C@@]2(C)C(N)=O)sc1-c1ccnc(N(C)C(C)C)n1]

The tile compound is prepared in an analogous manner to Example 75 except (R)-(+)-3-(dimethylamino)-pyrrolidine is used in place of 4-(dimethylamino)-piperidine. The title compound is obtained as a yellow solid. MS (Method D) M+H 418 and M−H 416.

EXAMPLE 80

(S)-2-Methyl-pyrrolidine-1,2-dicarboxylic acid 2-amide 1-[(5-{2-[(2-dimethylamino-ethyl)-methyl-amino]-pyrimidin-4-yl}-4-methyl-thiazol-2-yl)-amide]

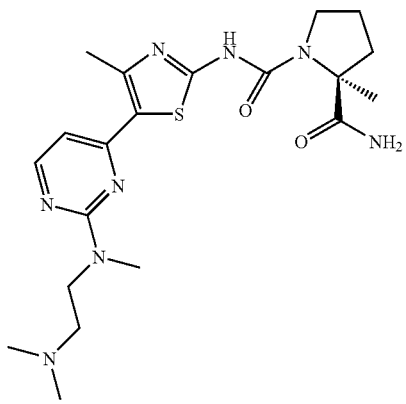 [SMILES: Cc1nc(NC(=O)N2CCC[C@@]2(C)C(N)=O)sc1-c1ccnc(N(C)CCN(C)C)n1]

The tile compound is prepared in an analogous manner to Example 75 except (R)-(+)-3-(dimethylamino)-pyrrolidine is used in place of 4-(dimethylamino)-piperidine. The title compound is obtained as a yellow solid. MS (Method D) M+H 447.

EXAMPLE 81

(S)-2-Methyl-pyrrolidine-1,2-dicarboxylic acid 2-amide 1-{[5-(2-cyclobutyl-pyrimidin-4-yl)-4-methyl-thiazol-2-yl]-amide}

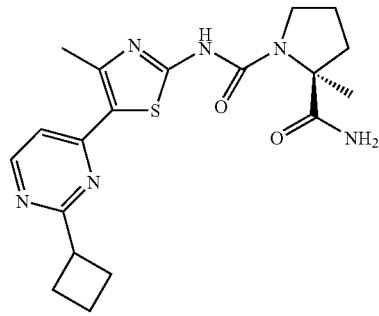 [SMILES: Cc1nc(NC(=O)N2CCC[C@@]2(C)C(N)=O)sc1-c1ccnc(C2CCC2)n1]

A mixture of imidazole-1-carboxylic acid {4-methyl-5-[2-cyclobutyl-pyrimidin-4-yl]-thiazol-2-yl}-amide (42 mg), (2S)-2-methyl-pyrrolidine-2-carboxylic acid amide (17 mg) and triethylamine (0.020 ml) in DMF (0.12 ml) is swirled at 40° C. for 18 hours. The reaction mixture is evaporated and then purified by reversed phase chromatography (Method B), the fractions passed through a Varian Bond Elute SCX 300 mg SPE cartridge followed by elution with 7 M ammonia in methanol. Evaporation of the methanolic ammonia washings gives the title compound as a yellow solid. MS (Method D) M+H 401 and M−H 399.

EXAMPLE 82

(2S,4R)-4-Dimethylamino-pyrrolidine-1,2-dicarboxylic acid 2-amide 1-{[5-(2-isopropyl-pyrimidin-4-yl)-4-methyl-thiazol-2-yl]-amide}

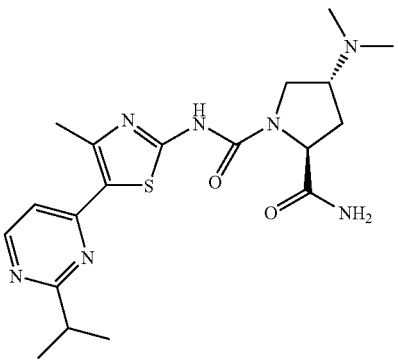 [SMILES: Cc1nc(NC(=O)N2C[C@H](N(C)C)C[C@H]2C(N)=O)sc1-c1ccnc(C(C)C)n1]

A mixture of imidazole-1-carboxylic acid {4-methyl-5-[2-isopropyl-pyrimidin-4-yl]-thiazol-2-yl}-amide (40 mg), (2S,4R)-4-dimethylamino-pyrrolidine-2-carboxylic acid amide (21 mg) and triethylamine (0.020 ml) in DMF (0.12 ml) is swirled at 40° C. for 18 hours. The reaction mixture is evaporated and then purified by reversed phase chromatography (Method B), the fractions passed through a Varian Bond Elute SCX 300 mg SPE cartridge followed by elution with 7 M ammonia in methanol. Evaporation of the methanolic ammonia washings gives the title compound as a yellow solid. MS (Method D) M+H 418 and M−H 416.

EXAMPLE 83

S)-2-Methyl-pyrrolidine-1,2-dicarboxylic acid 2-amide 1-({5-[2-((S)-3-dimethylamino-pyrrolidin-1-yl)-pyrimidin-4-yl]-4-methyl-thiazol-2-yl}-amide

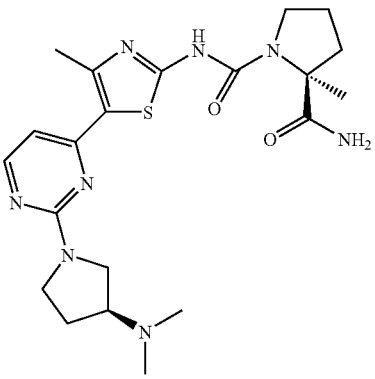 [SMILES: Cc1nc(NC(=O)N2CCC[C@@]2(C)C(N)=O)sc1-c1ccnc(N2CC[C@H](N(C)C)C2)n1]

The tile compound is prepared in an analogous manner to Example 75 except (S)-(+)-3-(dimethylamino)-pyrrolidine is used in place of 4-(dimethylamino)-piperidine. The title compound is obtained as a solid. MS (Method D) M+H 459 and M−H 457.

EXAMPLE 84

(S)-2-Methyl-pyrrolidine-1,2-dicarboxylic acid 2-amide 1-{[5-(2-azetidin-1-yl-pyrimidin-4-yl)-4-methyl-thiazol-2-yl]-amide}

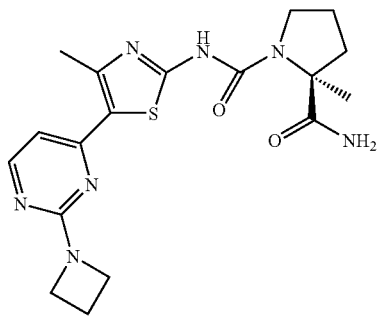 [SMILES: Cc1nc(NC(=O)N2CCC[C@@]2(C)C(N)=O)sc1-c1ccnc(N2CCC2)n1]

The title compound is prepared in an analogous manner to Example 75 except azetidine is used in place of 4-(dimethylamino)-piperidine. The title compound is obtained as a solid. MS (Method D) M+H 402.

EXAMPLE 85

(2S,4S)-4-Fluoro-pyrrolidine-1,2-dicarboxylic acid 2-amide 1-{[5-(2-isopropyl-pyrimidin-4-yl)-4-methyl-thiazol-2-yl]-amide}

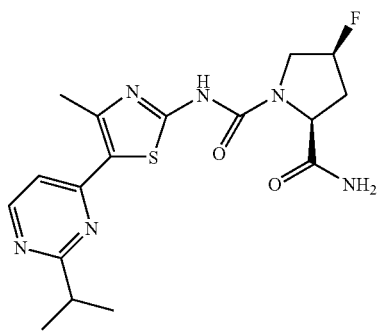 [SMILES: Cc1nc(NC(=O)N2C[C@@H](F)C[C@H]2C(N)=O)sc1-c1ccnc(C(C)C)n1]

A mixture of imidazole-1-carboxylic acid {4-methyl-5-[2-isopropyl-pyrimidin-4-yl]-thiazol-2-yl}-amide (50 mg), (2S,4S)-4-fluoro-pyrrolidine-2-carboxylic acid amide (25 mg) and triethylamine (0.026 ml) in DMF (0.15 ml) is swirled at 40° C. for 2 hours. The reaction mixture is evaporated and then purified by reversed phase chromatography (Method B), the fractions passed through a Varian Bond Elute SCX 300 mg SPE cartridge followed by elution with 7 M ammonia in methanol. Evaporation of the methanolic ammonia washings gives the title compound as a solid. MS (Method D) M+H 393 and M−H 391.

EXAMPLE 86

1S,5R)-2-Aza-bicyclo[3.1.0]hexane-1,2-dicarboxylic acid 1-amide 2-([5-(2-tert-butyl-pyrimidin-4-yl)-4-methyl-thiazol-2-yl]-amide

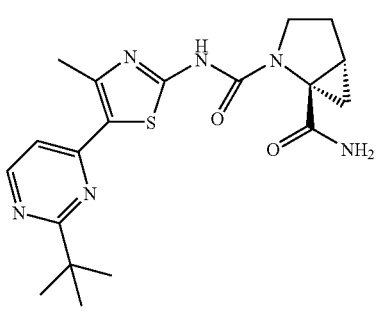 [SMILES: Cc1nc(NC(=O)N2CC[C@@H]3C[C@@]32C(N)=O)sc1-c1ccnc(C(C)(C)C)n1]

A mixture of imidazole-1-carboxylic acid {4-methyl-5-[2-tert-butyl-pyrimidin-4-yl]-thiazol-2-yl}-amide (50 mg), (1S,5R)-2-aza-bicyclo[3.1.0]hexane-1-carboxylic acid amide (20 mg) and triethylamine (0.051 ml) in DMF (1 ml) is stood at room temperature for 18 hours. The reaction mixture is evaporated and crystallisation from aqueous methanol gives the title compound as a yellow/white solid. Hplc/MS (Method C) RT 1.36 minutes, M+H 401.0 and M−H 399.2.

EXAMPLE 87

(1S,5R)-2-Aza-bicyclo[3.1.0]hexane-1,2-dicarboxylic acid 1-amide 2-{[5-(2-isopropyl-pyrimidin-4-yl)-4-methyl-thiazol-2-yl]-amide}

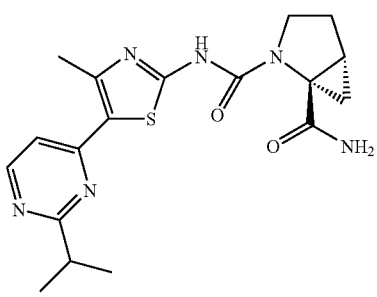 [SMILES: Cc1nc(NC(=O)N2CC[C@@H]3C[C@@]32C(N)=O)sc1-c1ccnc(C(C)C)n1]

A mixture of imidazole-1-carboxylic acid {4-methyl-5-[2-isopropyl-pyrimidin-4-yl]-thiazol-2-yl}-amide (40 mg), (1S,5R)-2-aza-bicyclo[3.1.0]hexane-1-carboxylic acid amide (17 mg) and triethylamine (0.020 ml) in DMF (0.12 ml) is stood at 40° C. for 1 hours. The reaction mixture is evaporated and then purified by reversed phase chromatography (Method B), the fractions passed through a Varian Bond Elute SCX 300 mg SPE cartridge followed by elution with 7 M ammonia in methanol. Evaporation of the methanolic ammonia washings gives the title compound as a beige solid. MS (Method D) M+H 387 and M−H 385.

EXAMPLE 88

(1S,5R)-2-Aza-bicyclo[3.1.0]hexane-1,2-dicarboxylic acid 1-amide 2-{[5-(2-diethylamino-pyrimidin-4-yl)-4-methyl-thiazol-2-yl]-amide}

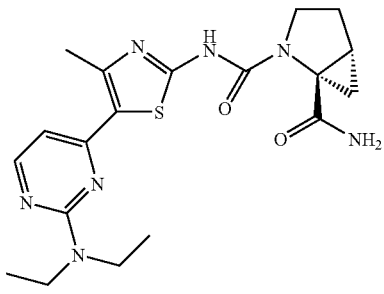 [SMILES: CCN(CC)c1nccc(-c2sc(NC(=O)N3CC[C@@H]4C[C@@]43C(N)=O)nc2C)n1]

A mixture of imidazole-1-carboxylic acid [5-(2-diethylamino-pyrimidin-4-yl)-4-methyl-thiazol-2-yl]-amide (40 mg), (1S,5R)-2-aza-bicyclo[3.1.0]hexane-1-carboxylic acid amide (16 mg) and triethylamine (0.019 ml) in DMF (0.11 ml) is stood at 40° C. for 1 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a beige solid. MS (Method D) M+H 416 and M−H 414.

EXAMPLE 89

(1S,5R)-2-Aza-bicyclo[3.1.0]hexane-1,2-dicarboxylic acid 1-amide 2-{[5-(2-isobutyl-pyrimidin-4-yl)-4-methyl-thiazol-2-yl]-amide}

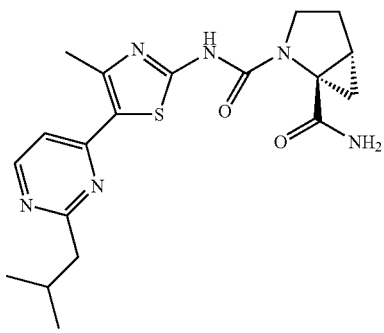 [SMILES: Cc1nc(NC(=O)N2CC[C@@H]3C[C@@]32C(N)=O)sc1-c1ccnc(CC(C)C)n1]

A mixture of imidazole-1-carboxylic acid {4-methyl-5-[2-isobutyl-pyrimidin-4-yl]-thiazol-2-yl}-amide (40 mg), (1S,5R)-2-aza-bicyclo[3.1.0]hexane-1-carboxylic acid amide (16 mg) and triethylamine (0.020 ml) in DMF (0.12 ml) is stood at 40° C. for 1 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a yellow/beige solid. MS (Method D) M+H 401 and M−H 399.

EXAMPLE 90

1S,5R)-2-Aza-bicyclo[3.1.0]hexane-1,2-dicarboxylic acid 1-amide 2-({4-methyl-5-[2-(1,1,2-trimethyl-propyl)-pyrimidin-4-yl]-thiazol-2-yl}-amide

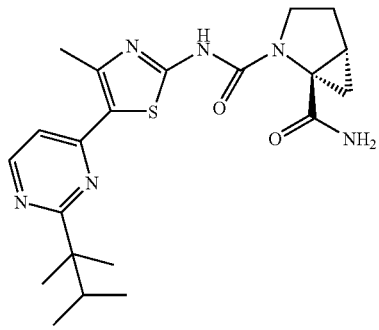 [SMILES: Cc1nc(NC(=O)N2CC[C@@H]3C[C@@]32C(N)=O)sc1-c1ccnc(C(C)(C)C(C)C)n1]

A mixture of imidazole-1-carboxylic acid {4-methyl-5-[2-(1,1,2-trimethyl-propyl)-pyrimidin-4-yl]-thiazol-2-yl}-amide (40 mg), (1S,5R)-2-aza-bicyclo[3.1.0]hexane-1-carboxylic acid amide (15 mg) and triethylamine (0.018 ml) in DMF (0.11 ml) is stood at 40° C. for 1 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a white solid. MS (Method D) M+H 429 and M−H 427.

EXAMPLE 91

(1S,5R)-2-Aza-bicyclo[3.1.0]hexane-1,2-dicarboxylic acid 1-amide 2-{[5-(2-cyclopropyl-pyrimidin-4-yl)-4-methyl-thiazol-2-yl]-amide}

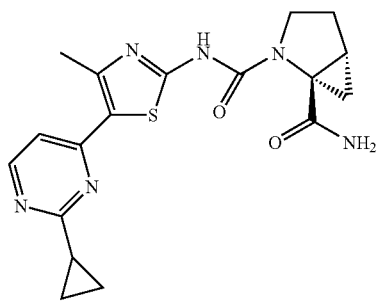 [SMILES: Cc1nc(NC(=O)N2CC[C@@H]3C[C@@]32C(N)=O)sc1-c1ccnc(C2CC2)n1]

A mixture of imidazole-1-carboxylic acid {4-methyl-5-[2-cyclopropyl-pyrimidin-4-yl]-thiazol-2-yl}-amide (40 mg), (1S,5R)-2-aza-bicyclo[3.1.0]hexane-1-carboxylic acid amide (17 mg) and triethylamine (0.020 ml) in DMF (1 ml) is stood at 40° C. for 1 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a white solid. MS (Method D) M+H 385 and M−H 383.

EXAMPLE 92

S)-2-Methyl-pyrrolidine-1,2-dicarboxylic acid 2-amide 1-({5-[2-(7-aza-bicyclo[2.2.1]hept-7-yl)-pyrimidin-4-yl]-4-methyl-thiazol-2-yl}-amide

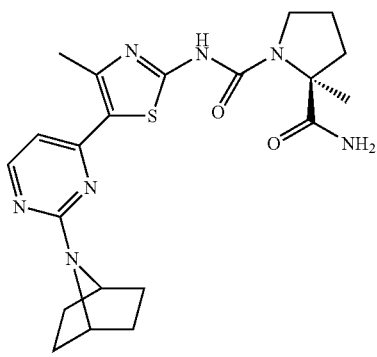 [SMILES: Cc1nc(NC(=O)N2CCC[C@@]2(C)C(N)=O)sc1-c1ccnc(N2C3CCC2CC3)n1]

The tile compound is prepared in an analogous manner to Example 75 except 7-azabicyclo[2.2.1]heptane is used in place of 4-(dimethylamino)-piperidine. The title compound is obtained as a white solid. MS (Method D) M+H 442.

EXAMPLE 93

(2S,4S)-4-Hydroxy-pyrrolidine-1,2-dicarboxylic acid 2-amide 1-{[5-(2-diethylamino-pyrimidin-4-yl)-4-methyl-thiazol-2-yl]-amide}

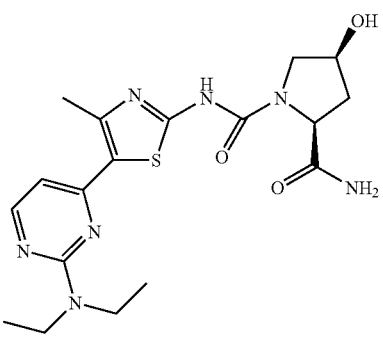 [SMILES: CCN(CC)c1nccc(-c2sc(NC(=O)N3C[C@@H](F)C[C@H]3C(N)=O)nc2C)n1]

A mixture of imidazole-1-carboxylic acid {4-methyl-5-[2-diethylamino-pyrimidin-4-yl]-thiazol-2-yl}-amide (40 mg), (2S,4S)-4-hydroxy-pyrrolidine-2-carboxylic acid amide (21 mg) and triethylamine (0.019 ml) in DMF (0.11 ml) is stood at 40° C. for 1 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a yellow solid. MS (Method D) M+H 420 and M–H 418.

EXAMPLE 94

(2S,4R)-4-Hydroxy-pyrrolidine-1,2-dicarboxylic acid 2-amide 1-{[5-(2-diethylamino-pyrimidin-4-yl)-4-methyl-thiazol-2-yl]-amide}

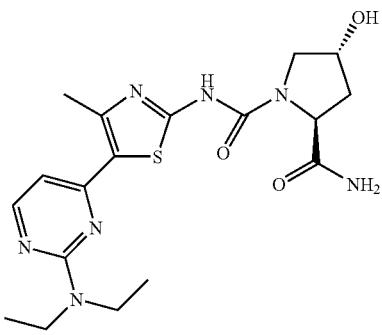 [SMILES: CCN(CC)c1nccc(-c2sc(NC(=O)N3C[C@H](F)C[C@H]3C(N)=O)nc2C)n1]

A mixture of imidazole-1-carboxylic acid {4-methyl-5-[2-diethylamino-pyrimidin-4-yl]-thiazol-2-yl}-amide (40 mg), (2S,4R)-4-hydroxy-pyrrolidine-2-carboxylic acid amide (21 mg) and triethylamine (0.019 ml) in DMF (0.11 ml) is stood at 40° C. for 1 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a yellow solid. MS (Method D) M+H 420 and M–H 418.

EXAMPLE 95

(2S,4S)-4-Fluoro-pyrrolidine-1,2-dicarboxylic acid 2-amide 1-{[5-(2-diethylamino-pyrimidin-4-yl)-4-methyl-thiazol-2-yl]-amide}

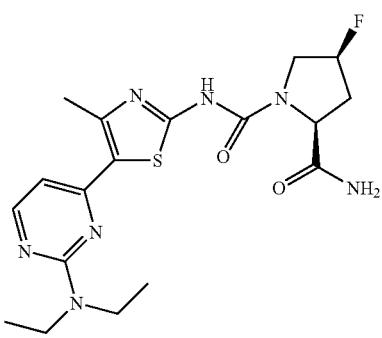

A mixture of imidazole-1-carboxylic acid {4-methyl-5-[2-diethylamino-pyrimidin-4-yl]-thiazol-2-yl}-amide (40 mg), (2S,4S)-4-fluoro-pyrrolidine-2-carboxylic acid amide (16 mg) and triethylamine (0.019 ml) in DMF (0.11 ml) is stood at 40° C. for 1 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a yellow solid.

EXAMPLE 96

(2S,4R)-4-Fluoro-pyrrolidine-1,2-dicarboxylic acid 2-amide 1-{[5-(2-diethylamino-pyrimidin-4-yl)-4-methyl-thiazol-2-yl]-amide}

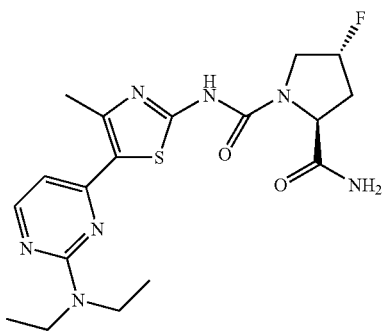

A mixture of imidazole-1-carboxylic acid {4-methyl-5-[2-diethylamino-pyrimidin-4-yl]-thiazol-2-yl}-amide (40 mg), (2S,4R)-4-fluoro-pyrrolidine-2-carboxylic acid amide (16 mg) and triethylamine (0.019 ml) in DMF (0.11 ml) is stood at 40° C. for 1 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a white solid. MS (Method D) M+H 422 and M−H 420.

EXAMPLE 97

S)-2-Methyl-pyrrolidine-1,2-dicarboxylic acid 2-amide 1-({5-[2-(ethyl-methyl-amino)-pyrimidin-4-yl]-4-methyl-thiazol-2-yl}-amide

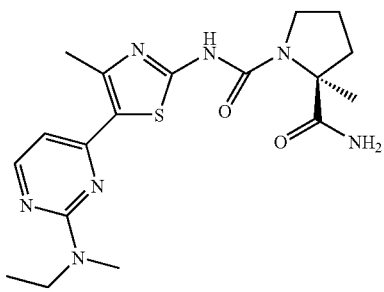 [SMILES: CCN(C)c1nccc(-c2sc(NC(=O)N3CCC[C@@]3(C)C(N)=O)nc2C)n1]

The tile compound is prepared in an analogous manner to Example 75 except N-ethylmethylamine is used in place of 4-(dimethylamino)-piperidine. The title compound is obtained as a solid. MS (Method D) M+H 404.

EXAMPLE 98

S)-2-Methyl-pyrrolidine-1,2-dicarboxylic acid 2-amide 1-({5-[2-(benzyl-ethyl-amino)-pyrimidin-4-yl]-4-methyl-thiazol-2-yl}-amide)

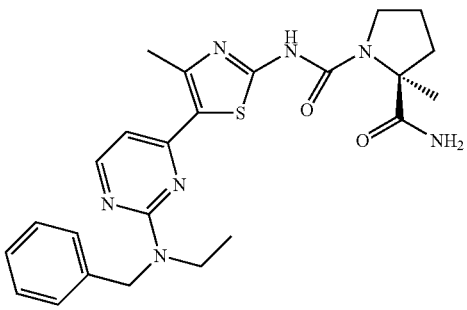 [SMILES: CCN(Cc1ccccc1)c1nccc(-c2sc(NC(=O)N3CCC[C@@]3(C)C(N)=O)nc2C)n1]

The tile compound is prepared in an analogous manner to Example 75 except N-ethylbenzylamine is used in place of 4-(dimethylamino)-piperidine. The title compound is obtained as a solid.

EXAMPLE 99

(S)-2-Methyl-pyrrolidine-1,2-dicarboxylic acid 2-amide 1-{[5-(2-imidazol-1-yl-pyrimidin-4-yl)-4-methyl-thiazol-2-yl]-amide}

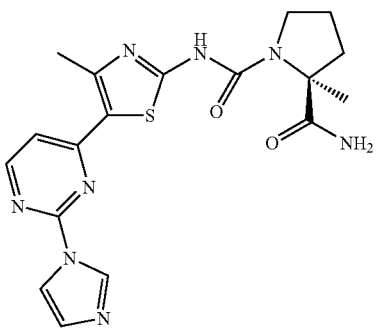 [SMILES: Cc1nc(NC(=O)N2CCC[C@@]2(C)C(N)=O)sc1-c1ccnc(-n2ccnc2)n1]

A mixture of (S)-2-methyl-pyrrolidine-1,2-dicarboxylic acid 2-amide 1-{[5-(2-methanesulphinyl-pyrimidin-4-yl)-4-methyl-thiazol-2-yl]-amide} (20 mg), imidazole (17 mg) and 1,4-dioxane (0.5 ml) are heated at 100° C. for 10 minutes in an Emrys Optimizer microwave apparatus. The cooled reaction mixture is then purified by reversed phase chromatography (Method B), the fractions passed through a Varian Bond Elute SCX 300 mg SPE cartridge followed by elution with 7 M

EXAMPLE 100

S)-2-Methyl-pyrrolidine-1,2-dicarboxylic acid 2-amide 1-({5-[2-(ethyl-propyl-amino)-pyrimidin-4-yl]-4-methyl-thiazol-2-yl}-amide

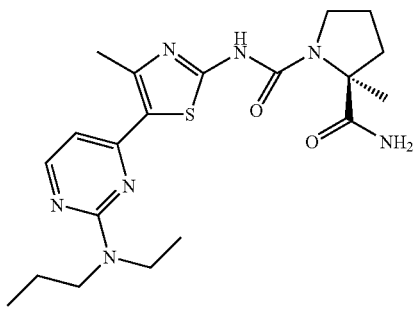 [SMILES: CCCN(CC)c1nccc(-c2sc(NC(=O)N3CCC[C@@]3(C)C(N)=O)nc2C)n1]

The tile compound is prepared in an analogous manner to Example 75 except N-ethyl-N-propylamine is used in place of 4-(dimethylamino)-piperidine. The title compound is obtained as a solid.

EXAMPLE 101

(S)-2-Methyl-pyrrolidine-1,2-dicarboxylic acid 2-amide 1-[(5-{2-[ethyl-(2-methoxy-ethyl)-amino]-pyrimidin-4-yl}-4-methyl-thiazol-2-yl)-amide]

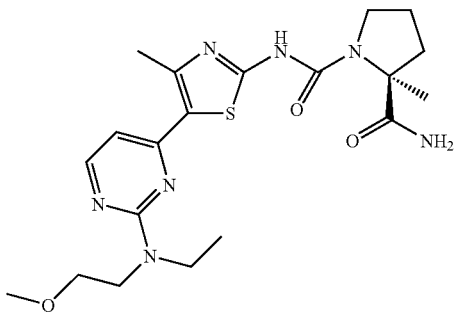

The tile compound is prepared in an analogous manner to Example 75 except N-(2-methoxyethyl)-ethylamine is used in place of 4-(dimethylamino)-piperidine. The title compound is obtained as a yellow solid. MS (Method D) M+H 448 and M−H 446.

EXAMPLE 102

S)-2-Methyl-pyrrolidine-1,2-dicarboxylic acid 2-amide 1-({4-methyl-5-[2-(2-methyl-imidazol-1-yl)-pyrimidin-4-yl]-thiazol-2-yl}-amide

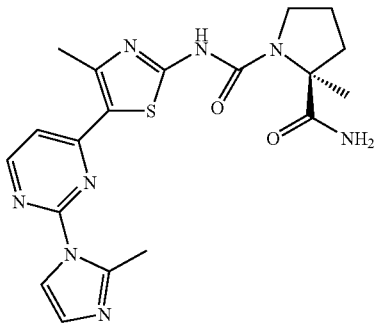 [SMILES: Cc1nc(NC(=O)N2CCC[C@@]2(C)C(N)=O)sc1-c1ccnc(-n2ccnc2C)n1]

A mixture of (S)-2-methyl-pyrrolidine-1,2-dicarboxylic acid 2-amide 1-{[5-(2-methanesulphinyl-pyrimidin-4-yl)-4-methyl-thiazol-2-yl]-amide} (50 mg), 2-methylimidazole (50 mg) and 1,4-dioxane (0.2 ml) are heated at 100° C. for 1 hour in an Emrys Optimizer microwave apparatus. The cooled reaction mixture is then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a white solid. MS (Method D) M+H 427 and M−H 425.

EXAMPLE 103

S)-2-Methyl-pyrrolidine-1,2-dicarboxylic acid 2-amide 1-({4-methyl-5-[2-(1-methyl-cyclopropyl)-pyrimidin-4-yl]-thiazol-2-yl}-amide

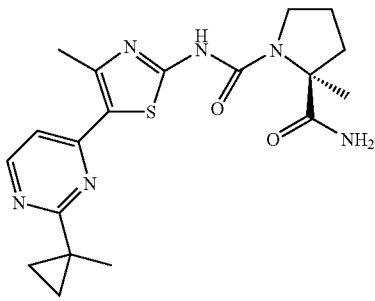 [SMILES: Cc1nc(NC(=O)N2CCC[C@@]2(C)C(N)=O)sc1-c1ccnc(C2(C)CC2)n1]

A mixture of imidazole-1-carboxylic acid {4-methyl-5-[2-(1-methyl-cyclopropyl)-pyrimidin-4-yl]-thiazol-2-yl}-amide (80 mg), (2S)-2-methyl-pyrrolidine-2-carboxylic acid amide (33 mg) and triethylamine (0.039 ml) in DMF (0.24 ml) is swirled at 40° C. for 1 hour. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a yellow solid. MS (Method D) M+H 401 and M−H 399.

EXAMPLES 104

(S)-2-Methyl-pyrrolidine-1,2-dicarboxylic acid 2-amide 1-({4-methyl-5-[2-(cis-2-methyl-cyclopropyl)-pyrimidin-4-yl]-thiazol-2-yl}-amide) and

EXAMPLE 105

(S)-2-Methyl-pyrrolidine-1,2-dicarboxylic acid 2-amide 1-({4-methyl-5-[2-(trans-2-methyl-cyclopropyl)-pyrimidin-4-yl]-thiazol-2-yl}-amide)

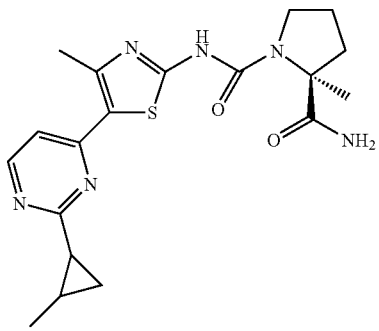 [SMILES: Cc1nc(NC(=O)N2CCC[C@@]2(C)C(N)=O)sc1-c1ccnc(C2CC2C)n1]

A mixture of imidazole-1-carboxylic acid {4-methyl-5-[2-(2-methyl-cyclopropyl)-pyrimidin-4-yl]-thiazol-2-yl}-amide (50 mg), (2S)-2-methyl-pyrrolidine-2-carboxylic acid amide (21 mg) and triethylamine (0.025 ml) in DMF (0.15 ml) is swirled at 40° C. for 2 hours. The reaction mixture is evaporated and then purified by reversed phase chromatography to give two components, the fractions containing each component are passed through a Varian Bond Elut® SCX 300 mg SPE cartridge followed by elution with 7 M ammonia in methanol. Evaporation of the methanolic ammonia washings gives the title compound as a mixture of cis-cyclopropyl diastereoisomers from the first eluting component and as a mixture of trans-cyclopropyl diastereoisomers from the second eluting component. MS (Method D) M+H 401 and M−H 399.

EXAMPLE 106

(R)-2-Benzyl-pyrrolidine-1,2-dicarboxylic acid 2-amide 1-{[5-(2-tert-butyl-pyrimidin-4-yl)-4-methyl-thiazol-2-yl]-amide}

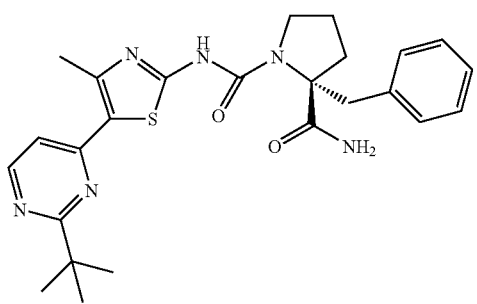 [SMILES: Cc1nc(NC(=O)N2CCC[C@@]2(Cc2ccccc2)C(N)=O)sc1-c1ccnc(C(C)(C)C)n1]

A mixture of imidazole-1-carboxylic acid {4-methyl-5-[2-tert-butyl-pyrimidin-4-yl]-thiazol-2-yl}-amide (50 mg), (R)-2-benzyl-pyrrolidine-2-carboxylic acid amide (33 mg) and triethylamine (0.051 ml) in DMF (1 ml) is stood at room temperature for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a yellow/white solid. Hplc/MS (Method C) RT 1.94 minutes, M+H 479.1 and M−H 477.2.

EXAMPLE 107

(R)-2-Dimethylaminomethyl-pyrrolidine-1,2-dicarboxylic acid 2-amide 1-{[5-(2-tert-butyl-pyrimidin-4-yl)-4-methyl-thiazol-2-yl]-amide}

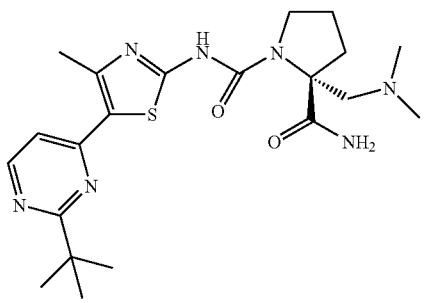 [SMILES: Cc1nc(NC(=O)N2CCC[C@@]2(CN(C)C)C(N)=O)sc1-c1ccnc(C(C)(C)C)n1]

A mixture of imidazole-1-carboxylic acid {4-methyl-5-[2-tert-butyl-pyrimidin-4-yl]-thiazol-2-yl}-amide (50 mg), (R)-2-dimethylaminomethyl-pyrrolidine-2-carboxylic acid amide (28 mg) and triethylamine (0.051 ml) in DMF (1 ml) is stood at room temperature for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a yellow/white solid. Hplc/MS (Method C) RT 1.94 minutes, M+H 446.1 and M−H 444.2.

EXAMPLE 108

S)-2-Methyl-pyrrolidine-1,2-dicarboxylic acid 2-amide 1-({5-[2-(1,1-dimethyl-propyl)-pyrimidin-4-yl]-4-methyl-thiazol-2-yl}-amide

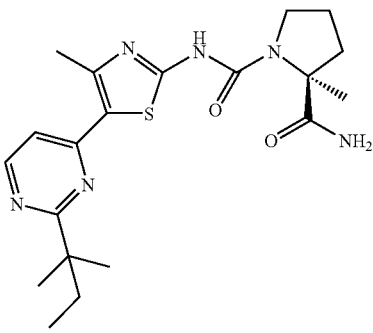 [SMILES: CCC(C)(C)c1nccc(-c2sc(NC(=O)N3CCC[C@@]3(C)C(N)=O)nc2C)n1]

A mixture of imidazole-1-carboxylic acid {4-methyl-5-[2-(1,1-dimethyl-propyl)-pyrimidin-4-yl]-thiazol-2-yl}-amide (50 mg), (2S)-2-methyl-pyrrolidine-2-carboxylic acid amide (20 mg) and triethylamine (0.024 ml) in DMF (0.1 ml) is swirled at 40° C. for 2 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic ammonia washings gives the title compound as a beige solid. MS (Method D) M−H 415.

EXAMPLE 109

(2S,4R)-4-Cyano-pyrrolidine-1,2-dicarboxylic acid 2-amide 1-{[5-(2-tert-butyl-pyrimidin-4-yl)-4-methyl-thiazol-2-yl]-amide}

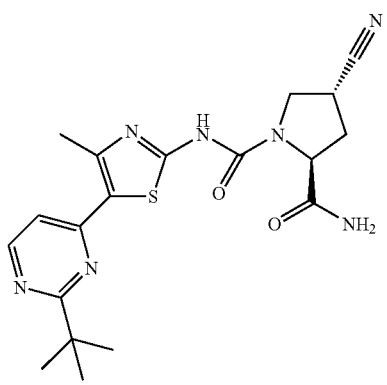 [SMILES: Cc1nc(NC(=O)N2C[C@H](C#N)C[C@H]2C(N)=O)sc1-c1ccnc(C(C)(C)C)n1]

A mixture of imidazole-1-carboxylic acid {4-methyl-5-[2-tert-butyl-pyrimidin-4-yl]-thiazol-2-yl}-amide (40 mg), (2S, 4R)-4-cyano-pyrrolidine-2-carboxylic acid amide (18 mg) and triethylamine (0.016 ml) in DMF (0.2 ml) is stood at 40 C.° for 2 hours. The reaction mixture is evaporated and then purified by reversed phase chromatography (Method B), the fractions passed through a Varian Bond Elute SCX 300 mg SPE cartridge followed by elution with 7 M ammonia in methanol. Evaporation of the methanolic ammonia washings gives the title compound as a solid.

EXAMPLE 110

(S)-2-Methyl-pyrrolidine-1,2-dicarboxylic acid 2-amide 1-{[5-(2-cyclopropylmethyl-pyrimidin-4-yl)-4-methyl-thiazol-2-yl]-amide}

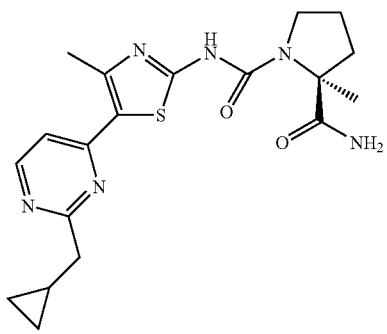 [SMILES: Cc1nc(NC(=O)N2CCC[C@@]2(C)C(N)=O)sc1-c1ccnc(CC2CC2)n1]

The title compound is prepared in analogy to the procedure described for Example 40, but using imidazole-1-carboxylic acid [5-(2-cyclopropylmethyl-pyrimidin-4-yl)-4-methyl-thiazol-2-yl]-amide in place of imidazole-1-carboxylic acid {4-methyl-5-[2-(1-methyl-cyclopropyl)-pyridin-4-yl]-thiazol-2-yl}-amide. M.p. 168-170° C.

EXAMPLE 111

(S)-2-methyl-pyrrolidine-1,2-dicarboxylic acid 2-amide 1-({[5-(2-d$_9$-tert-butyl-pyrimidin-4-yl)-4-methyl-thiazol-2-yl]-amide}

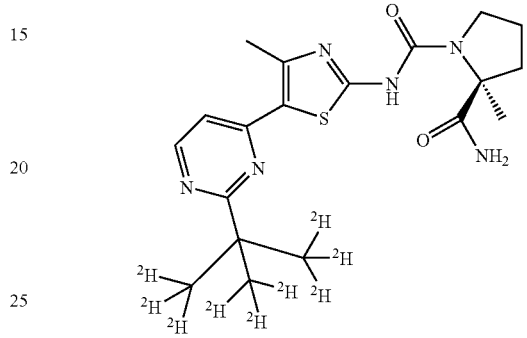

A mixture of imidazole-1-carboxylic acid [5-(2-d$_9$-tert-butyl-pyrimidin-4-yl)-4-methyl-thiazol-2-yl]-amide (176 mg), (2S)-2-methyl-pyrrolidine-2-carboxylic acid amide (71 mg) and triethylamine (0.17 ml) in DMF (2 ml) is stood at room temperature for 18 hours. The reaction mixture is evaporated and crystallisation from aqueous methanol gives the title compound as a yellow/white solid. Hplc/MS (Method C) RT 1.44 minutes, M+H 412.2 and M−H 410.3.

EXAMPLE 112

(R)-2-Methoxymethyl-pyrrolidine-1,2-dicarboxylic acid 2-amide 1-{[5-(2-tert-butyl-pyrimidin-4-yl)-4-methyl-thiazol-2-yl]-amide}

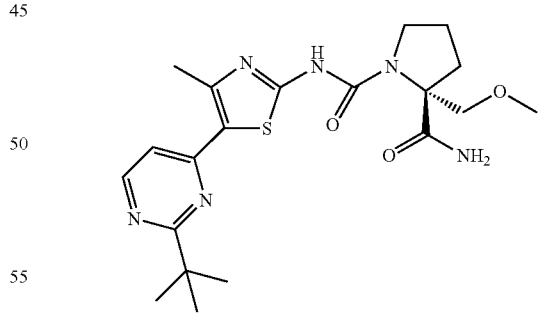

A mixture of imidazole-1-carboxylic acid {4-methyl-5-[2-tert-butyl-pyrimidin-4-yl]-thiazol-2-yl}-amide (100 mg), (R)-2-methoxymethyl-pyrrolidine-2-carboxylic acid amide (51 mg) and triethylamine (0.102 ml) in DMF (1 ml) is stood at room temperature for 18 hours. The reaction mixture is evaporated and then purified by reversed phase chromatography (Method B), the fractions passed through a Varian Bond Elut® SCX 300 mg SPE cartridge followed by elution with 7 M ammonia in methanol. Evaporation of the methanolic

EXAMPLE 113

(S)-Azetidine-1,2-dicarboxylic acid 2-amide 1-{[5-(2-tert-butyl-pyrimidin-4-yl)-4-methyl-thiazol-2-yl]-amide}

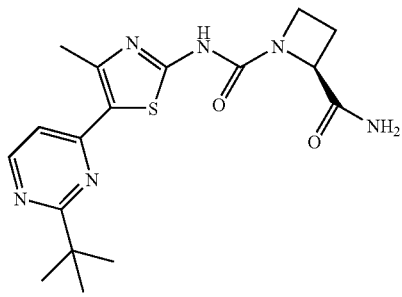 [SMILES: Cc1nc(NC(=O)N2CC[C@H]2C(N)=O)sc1-c1ccnc(C(C)(C)C)n1]

A mixture of imidazole-1-carboxylic acid [5-(2-tert-butyl-pyrimidin-4-yl)-4-methyl-thiazol-2-yl]-amide (300 mg), (S)-azetidine-2-carboxylic acid amide (96 mg) and triethylamine (0.31 ml) in DMF (2.5 ml) is stood at room temperature for 17 hours. The reaction mixture is evaporated and crystallisation from methanol gives the title compound as a yellow solid. MS M+H 375.1 and M−H 373.2.

EXAMPLE 114

(S)-2-Difluoromethyl-pyrrolidine-1,2-dicarboxylic acid 2-amide 1-{[5-(2-tert-butyl-pyrimidin-4-yl)-4-methyl-thiazol-2-yl]-amide}

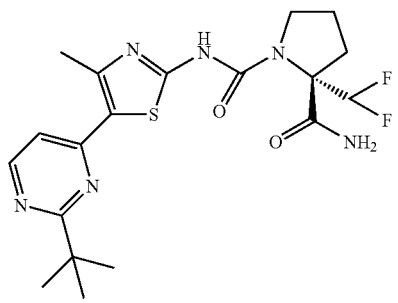 [SMILES: Cc1nc(NC(=O)N2CCC[C@]2(C(N)=O)C(F)F)sc1-c1ccnc(C(C)(C)C)n1]

A mixture of imidazole-1-carboxylic acid {4-methyl-5-[2-tert-butyl-pyrimidin-4-yl]-thiazol-2-yl}-amide (156 mg), (S)-2-difluoromethyl-pyrrolidine-2-carboxylic acid amide (100 mg) and triethylamine (0.159 ml) in DMF (1 ml) is stood at room temperature for 36 hours.

The reaction mixture is evaporated and then purified by reversed phase chromatography (Method B), the fractions passed through a Varian Bond Elute SCX 300 mg SPE cartridge followed by elution with 7 M ammonia in methanol. Evaporation of the methanolic ammonia washings gives the title compound as a yellow/white solid. Hplc/MS (Method C) RT 1.71 minutes, M+H 439.1 and M−H 437.2.

EXAMPLE 115

(S)-2-Methyl-pyrrolidine-1,2-dicarboxylic acid 2-amide 1-{[5-(2-tert-butyl-pyridin-4-yl)-thiazol-2-yl]-amide}

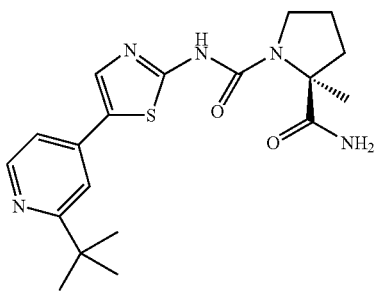 [SMILES: CC(C)(C)c1cc(-c2cnc(NC(=O)N3CCC[C@@]3(C)C(N)=O)s2)ccn1]

The title compound is prepared in analogy to the procedure described in Example 40 with the following modifications. In Example 40, the reaction mixture is stirred for 3 h at rt, quenched by dilution with EtOAc/H$_2$O, and extracted with EtOAc. In Step 40.1, the reaction mixture is stirred for 2 h at reflux. In Step 40.2, the reaction mixture is stirred for 1 h at 100° C. In Step 1.3, N-thiazol-2-yl-acetamide is used. The reaction mixture is stirred for 2 h at 120° C., diluted with EtOAc/H$_2$O and extracted with EtOAc. After drying and concentration of the organic phase, the residue is purified by silica gel column chromatography (Hex/EtOAc, 1:1), followed by trituration in Et$_2$O. In Step 40.7, pivaloyl chloride is used.

Title compound: ESI-MS: 388.1 [M+H]$^+$; t$_R$=2.48 min (System 1); TLC: R$_f$=0.15 (DCM/MeOH/NH$_3^{aq}$, 94:5:1).

EXAMPLE 116

(S)-2-Methyl-pyrrolidine-1,2-dicarboxylic acid 2-amide 1-{[5-(2-cyclobutyl-pyridin-4-yl)-thiazol-2-yl]-amide}

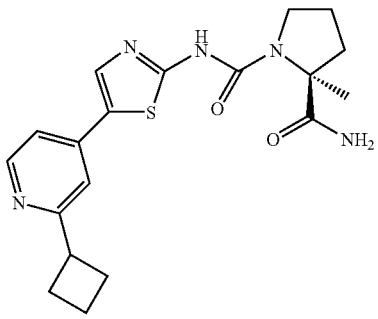 [SMILES: C[C@@]1(C(N)=O)CCCN1C(=O)Nc1ncc(-c2ccnc(C3CCC3)c2)s1]

The title compound is prepared in analogy to the procedure described in Example 40 but with the following modifications. In Example 40, the reaction mixture is stirred for 16 h at rt, diluted with DCM/H$_2$O and extracted with DCM. In Step 40.1, the reaction mixture is stirred for 4 h at reflux. In Step 40.2, the crude product is not purified. In Step 40.3, N-thiazol-2-yl-acetamide is used. The reaction mixture is stirred for 3 h at 120° C., quenched by dilution with EtOAc/H$_2$O, and extracted with EtOAc. After drying and concentration of the organic phase, the residue is purified by silica gel column chromatography (Hex/EtOAc, 2:3). In Step 40.5, the reaction mixture is stirred for 1 h at 80° C. In Step 40.7, 4-methoxy-3-buten-2-one (50 mmol) in THF (100 mL) is added to a cold (−78° C.) solution of LiHMDS (1M in THF, 100 mL) in THF (200 mL). After 30 min, cyclobutylcarbonyl chloride is added and the reaction mixture is allowed to reach rt over 18 h.

Title compound: ESI-MS: 386.1 [M+H]$^+$; $t_R$=2.42 min (System 1); TLC: $R_f$=0.22 (DCM/MeOH/NH$_3$$^{aq}$, 91.5:7.5:1).

EXAMPLE 117

S)-2-Methyl-pyrrolidine-1,2-dicarboxylic acid 2-amide 1-({5-[2-(1-methyl-cyclopropyl)-pyridin-4-yl]-thiazol-2-yl}amide

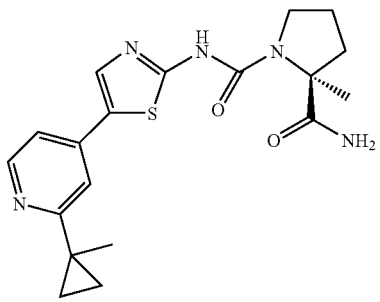 [SMILES: CC1(c2cc(-c3cnc(NC(=O)N4CCC[C@@]4(C)C(N)=O)s3)ccn2)CC1]

The title compound is prepared in analogy to the procedure described in Example 40 but with the following modifications. In Example 40, the reaction mixture is stirred for 14 h at rt. In Step 40.2, the reaction mixture is stirred for 1 h at 85° C. In Step 1.3, N-thiazol-2-yl-acetamide is used and the reaction mixture is stirred for 4 h at 120° C.

Title compound: ESI-MS: 386.1 [M+H]$^+$; $t_R$=2.35 min (System 1); TLC: $R_f$=0.28 (DCM/MeOH, 9:1).

EXAMPLE 118

S)-2-Methyl-pyrrolidine-1,2-dicarboxylic acid 2-amide 1-({5-[2-(1-trifluoromethyl-cyclopropyl)-pyridin-4-yl]-thiazol-2-yl}-amide

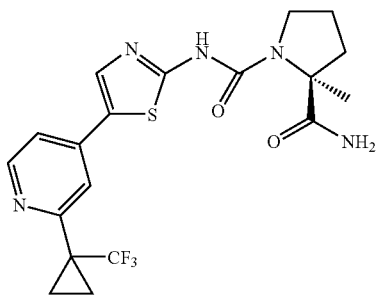 [SMILES: C[C@@]1(C(N)=O)CCCN1C(=O)Nc1ncc(-c2ccnc(C3(C(F)(F)F)CC3)c2)s1]

The title compound is prepared in analogy to the procedure described in Example 40 but with the following modifications. In Example 40, the reaction mixture is stirred for 14 h at rt. In Step 40.2, the reaction mixture is stirred for 2 h at 85° C. and extracted with EtOAc after being quenched. In Step 40.3, N-thiazol-2-yl-acetamide is used. The reaction mixture is stirred for 2 h at 120° C. In Step 40.4, 1,2-dichloroethane (2.55 mL per mmol of pyridin-4-one) is used as the solvent. The reaction mixture is stirred for 1 h at 83° C. and extracted with EtOAc after being quenched. In Step 40.5, the reaction mixture is stirred for 1 h at 65° C. In Step 40.7, 1-trifluoromethyl-cyclopropanecarbonyl chloride (Step 118.1) is used.

Title compound: ESI-MS: 440.0 [M+H]$^+$; $t_R$=2.61 min (System 1); TLC: $R_f$=0.50 (DCM/MeOH, 9:1).

Step 118.1: 1-Trifluoromethyl-cyclopropanecarbonyl chloride

The title compound is prepared in analogy to the procedure described in Step 40.8 but using 1-trifluoromethyl-cyclopropanecarboxylic acid.

EXAMPLE 119

S)-2-Methyl-pyrrolidine-1,2-dicarboxylic acid 2-amide 1-({5-[2-(2,2,2-trifluoro-1,1-dimethyl-ethyl)-pyridin-4-yl}-thiazol-2-yl]-amide

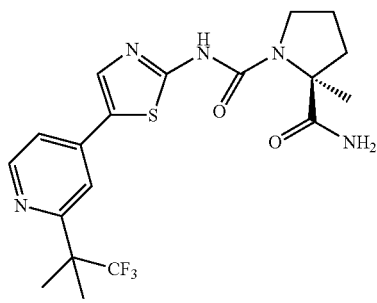 [SMILES: CC(C)(c1cc(-c2cnc(NC(=O)N3CCC[C@@]3(C)C(N)=O)s2)ccn1)C(F)(F)F]

The title compound is prepared in analogy to the procedure described in Example 40 but with the following modifications. In Example 40, the reaction mixture is stirred for 5 h at rt. In Step 40.2, the reaction mixture is stirred for 1 h at 85° C. and extracted with EtOAc after being quenched. In Step 40.3, N-thiazol-2-yl-acetamide is used. The reaction mixture is stirred for 2.5 h at 120° C. In Step 40.4, the reaction mixture is stirred for 1 h at 83° C. and extracted with EtOAc after being quenched. In Step 40.5, the reaction mixture is stirred for 1 h at 65° C. In Step 40.6, the crude product is not purified. In Step 40.7, 3,3,3-trifluoro-2,2-dimethyl-propionyl chloride (Step 119.1) is used.

Title compound: ESI-MS: 442.0 [M+H]$^+$; $t_R$=2.98 min (System 1); TLC: $R_f$=0.47 (DCM/MeOH, 9:1).

Step 119.1: 3,3,3-Trifluoro-2,2-dimethyl-propionyl chloride

The title compound is prepared in analogy to the procedure described in Step 40.8 but using 3,3,3-trifluoro-2,2-dimethyl-propionic acid.

EXAMPLE 120

S)-2-Methyl-pyrrolidine-1,2-dicarboxylic acid 2-amide 1-({5-[2-(1-trifluoromethyl-cyclobutyl)-pyridin-4-yl]-thiazol-2-yl}-amide

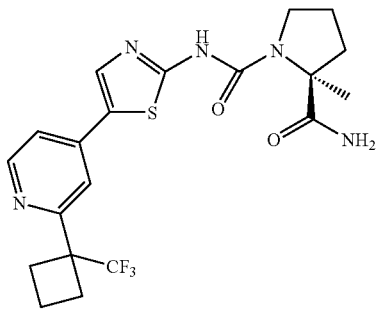 [SMILES: C[C@@]1(C(N)=O)CCCN1C(=O)Nc1ncc(-c2ccnc(C3(C(F)(F)F)CCC3)c2)s1]

The title compound is prepared in analogy to the procedure described in Example 40 but with the following modifications. In Example 40, the reaction mixture is stirred for 18 h at rt, quenched by dilution with DCM/H$_2$O and extracted with DCM. In Step 40.1, the reaction mixture is stirred for 1 h at reflux. In Step 40.2, the reaction mixture is stirred for 1 h at 100° C. and extracted with DCM after being quenched. In Step 40.3, N-thiazol-2-yl-acetamide is used. The reaction mixture is stirred for 5 h at 120° C., quenched by dilution with EtOAc/H$_2$O and extracted with EtOAc. In Step 40.4, 1,2-dichloroethane (2.26 mL per mmol of pyridin-4-one) is used as the solvent. The reaction mixture is stirred for 1 h at reflux and extracted with DCM after being quenched. In Step 40.5, the reaction mixture is stirred for 1 h at rt. In Step 40.6, the reaction mixture is stirred for 18 h at rt. In Step 1.7, 4-methoxy-3-buten-2-one in THF is added to a cold (−78° C.) solution of LiHMDS in THF. After 30 min, 1-trifluoromethyl-cyclobutanecarbonyl chloride (Step 120.1) in THF is added. The reaction mixture is allowed to reach rt over 18 h and extracted with EtOAc after being quenched.

Title compound: ESI-MS: 454.1 [M+H]$^+$; $t_R$=2.90 min (System 1); TLC: R$_f$=0.18 (DCM/MeOH/NH$_3$$^{aq}$, 91.5:7.5:1).

Step 120.1: 1-Trifluoromethyl-cyclobutanecarbonyl chloride

The title compound is prepared in analogy to the procedure described in Step 40.8 but using 1-trifluoromethyl-cyclobutanecarboxylic acid and stirring the reaction mixture for 2 h at reflux.

EXAMPLE 121

S)-2-Methyl-pyrrolidine-1,2-dicarboxylic acid 2-amide 1-({5-[2-(1-methyl-cyclobutyl)-pyridin-4-yl]-thiazol-2-yl}-amide

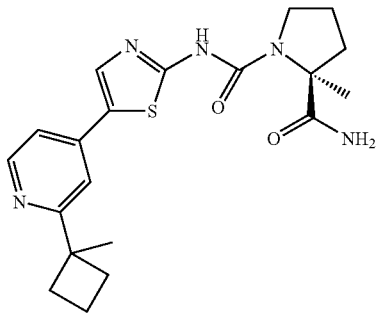 [SMILES: CC1(c2cc(-c3cnc(NC(=O)N4CCC[C@@]4(C)C(N)=O)s3)ccn2)CCC1]

The title compound is prepared in analogy to the procedure described in Example 40 but with the following modifications. In Example 40, the reaction mixture is stirred for 24 h at rt, quenched by dilution with EtOAc/H$_2$O, and extracted with EtOAc. In Step 40.1, the reaction mixture is stirred for 4 h at reflux. In Step 40.2, the reaction mixture is stirred for 2 h at 100° C. and extracted with DCM after being quenched. In Step 40.3, N-thiazol-2-yl-acetamide is used. The reaction mixture is stirred for 3 h at 100° C., diluted with EtOAc/H$_2$O, and extracted with EtOAc. After drying and concentration of the organic phase, the residue is purified by silica gel column chromatography (Hex/EtOAc, 25:75). In Step 40.5, the reaction mixture is stirred for 2 h at 80° C. In Step 40.7, 4-methoxy-3-buten-2-one in THF is added to a cold (−78° C.) solution of LiHMDS in THF. After 30 min, 1-methyl-cyclobutane chloride (Step 44.1) in THF is added and the reaction mixture is allowed to reach rt over 18 h.

Title compound: ESI-MS: 400.1 [M+H]$^+$; $t_R$=2.60 min (System 1); TLC: R$_f$=0.08 (DCM/MeOH/NH$_3$$^{aq}$, 94:5:1).

EXAMPLE 122

(S)-2-Methyl-pyrrolidine-1,2-dicarboxylic acid 2-amide 1-{[5-(2-diethylamino-pyridin-4-yl)-thiazol-2-yl]-amide}

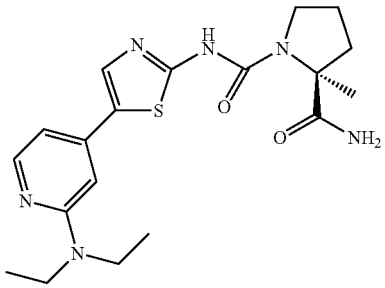 [SMILES: CCN(CC)c1cc(-c2cnc(NC(=O)N3CCC[C@@]3(C)C(N)=O)s2)ccn1]

The title compound is prepared in analogy to the procedure described in Example 40 but with the following modifications. In Example 40, the reaction mixture is stirred for 18 h at rt, quenched by dilution with DCM/H$_2$O and extracted with DCM. In Step 40.1, the reaction mixture is stirred for 1 h at reflux. In Step 40.2, the reaction mixture is stirred for 1 h at 100° C. and extracted with DCM after being quenched. In Step 40.3, diethyl-(4-iodo-pyridin-2-yl)-amine (Step 51.1) and N-thiazol-2-yl-acetamide are used. The reaction mixture is stirred for 5 h at 120° C., quenched by dilution with EtOAc/H$_2$O, filtered through a pad of celite and extracted with EtOAc.

Title compound: ESI-MS: 403.2 [M+H]$^+$; $t_R$=2.60 min (System 1); TLC: R$_f$=0.37 (DCM/MeOH/NH$_3$$^{aq}$, 91.5:7.5:1).

EXAMPLE 123

(S)-2-Methyl-pyrrolidine-1,2-dicarboxylic acid 2-amide 1-{[5-(3-tert-butyl-3H-benzoimidazol-5-yl)-thiazol-2-yl]-amide}

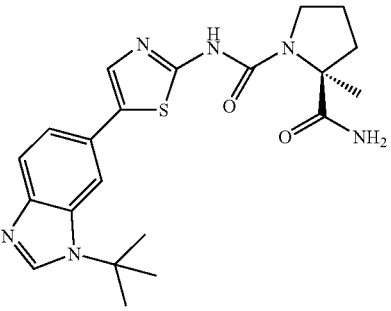 [SMILES: CC(C)(C)n1cnc2ccc(-c3cnc(NC(=O)N4CCC[C@@]4(C)C(N)=O)s3)cc21]

The title compound is prepared in analogy to the procedure described in Example 40 but with the following modifications. In Example 40, the reaction mixture is stirred for 5 h at rt. In Step 40.2, the reaction mixture is stirred for 1 h at 85° C. and extracted with EtOAc after being quenched. In Step 1.3, 6-bromo-1-tert-butyl-1H-benzoimidazole (Step 123.1) and N-thiazol-2-yl-acetamide are used. The reaction mixture is stirred for 7 h at 120° C.

Title compound: ESI-MS: 427.1 [M+H]'; $t_R$=2.56 min (System 1); TLC: $R_f$=0.39 (DCM/MeOH, 9:1).

Step 123.1:
6-Bromo-1-tert-butyl-1H-benzoimidazole

A mixture of 4-bromo-N*2*-tert-butyl-benzene-1,2-diamine (Step 123.2) (2.14 g, 8.80 mmol) and triethylortoformate (14.7 mL, 88 mmol) is stirred for 1 h at 148° C., allowed to cool and concentrated. The residue purified by silica gel column chromatography (DCM/MeOH, 1:0→99:1) to afford 1.74 g of the title compound as a white solid: ESI-MS: 253.0/255.0 [M+H]$^+$; $t_R$=2.88 min (System 1); TLC: $R_f$=0.54 (DCM/MeOH, 9:1).

Step 123.2:
4-Bromo-N*2*-tert-butyl-benzene-1,2-diamine

A suspension of (5-bromo-2-nitro-phenyl)-tert-butyl-amine (Step 123.3) (6 g, 21.97 mmol) and Raney nickel (2 g) in MeOH/THF (1:1 v/v, 600 mL) is stirred for 9 h at rt, under a hydrogen atmosphere. The reaction mixture is filtered through a pad of celite and concentrated. The residue purified by silica gel column chromatography (Hex/EtOAc, 97:3→3:1) to afford 4.4 g of the title compound as a black oil: ESI-MS: 243.0/245.0 [M+H]$^+$; $t_R$=2.75 min (System 1); TLC: $R_f$=0.89 (Hex/EtOAc, 1:1).

Step 123.3:
(5-Bromo-2-nitro-phenyl)-tert-butyl-amine

A mixture of 4-bromo-2-fluoro-nitrobenzene (4 g, 18.2 mmol) and tert-butylamine (4.78 mL, 45.5 mmol, 2.5 eq) in EtOH (80 mL) is stirred for 15 h at 85° C., allowed to cool and concentrated. The residue purified by silica gel column chromatography (Hex/EtOAc, 1:0→99:1) to afford 4.8 g of the title compound as an orange solid: ESI-MS: 273.0/275.0 [M+H]$^+$; $t_R$=5.68 min (System 1); TLC: $R_f$=0.49 (Hex/EtOAc, 9:1).

EXAMPLE 124

(S)-2-Methyl-pyrrolidine-1,2-dicarboxylic acid 2-amide 1-[(5-{2-[1-(4-methoxy-phenyl)-1-methyl-ethyl]-pyridin-4-yl}-thiazol-2-yl)-amide]

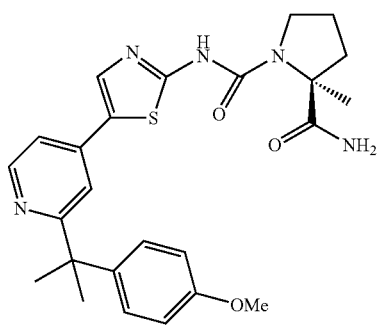 [SMILES: COc1ccc(C(C)(C)c2cc(-c3cnc(NC(=O)N4CCC[C@@]4(C)C(N)=O)s3)ccn2)cc1]

The title compound is prepared in analogy to the procedure described in Example 40 but with the following modifications. In Example 40, the reaction mixture is stirred for 16 h at rt, quenched by dilution with EtOAc/H$_2$O. In Step 40.1, the reaction mixture is stirred for 4 h at reflux. In Step 40.2, the reaction mixture is stirred for 2 h at 100° C. In Step 40.3, N-thiazol-2-yl-acetamide is used. The reaction mixture is stirred for 5 h at 100° C., quenched by dilution with EtOAc/H$_2$O and extracted with EtOAc. In Step 1.4, 1,2-dichloroethane (4.3 mL per mmol of pyridin-4-one) is used as the solvent. The reaction mixture is stirred for 1 h at reflux, poured into a saturated solution of NaHCO$_3$ and extracted with DCM. In Step 40.5, the reaction mixture is stirred for 23 h at 80° C. In Step 40.6, the reaction mixture is stirred for 21 h at rt. In Step 40.7, 4-methoxy-3-buten-2-one in THF is added to a cold (−78° C.) solution of LiHMDS in THF. After 30 min, 2-(4-methoxy-phenyl)-2-methyl-propionyl chloride (Step 53.1) in THF is added and the reaction mixture is allowed to reach rt over 16 h.

Title compound: ESI-MS: 480.0 [M+H]$^+$; $t_R$=3.10 min (System 1); TLC: $R_f$=0.06 (DCM/MeOH/NH$_3^{aq}$, 94:5:1).

EXAMPLE 125

(S)-2-Methyl-pyrrolidine-1,2-dicarboxylic acid 2-amide 1-[(5-{2-[1-(4-methoxy-phenyl)-cyclopropyl]-pyridin-4-yl}-thiazol-2-yl)-amide]

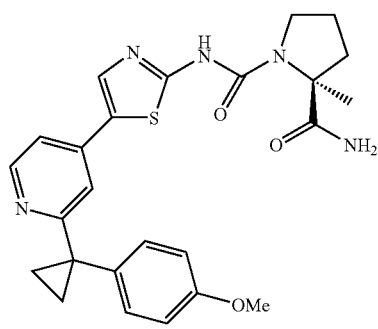 [SMILES: COc1ccc(C2(c3cc(-c4cnc(NC(=O)N5CCC[C@@]5(C)C(N)=O)s4)ccn3)CC2)cc1]

The title compound is prepared in analogy to the procedure described in Example 40 but with the following modifications. In Example 40, the reaction mixture is stirred for 16 h at rt, quenched by dilution with EtOAc/H$_2$O. In Step 40.1, the reaction mixture is stirred for 4.5 h at reflux. In Step 40.2, the reaction mixture is stirred for 3 h at 100° C. and extracted with DCM after being quenched. In Step 40.3, N-thiazol-2-yl-acetamide is used. The reaction mixture is stirred for 28 h at 100° C., quenched by dilution with EtOAc/H$_2$O and extracted with EtOAc. In Step 40.4, 1,2-dichloroethane (4.3 mL per mmol of pyridin-4-one) is used as the solvent. The reaction mixture is stirred for 1 h at reflux, poured into a saturated solution of NaHCO$_3$ and extracted with DCM. In Step 40.5, the reaction mixture is stirred for 18 h at 80° C. In Step 40.6, the reaction mixture is stirred for 18 h at rt. In Step 1.7, 4-methoxy-3-buten-2-one in THF is added to a cold (−78° C.) solution of LiHMDS in THF. After 30 min, 1-(4-methoxy-phenyl)-cyclopropanecarbonyl chloride (Step 54.1) in THF is added and the reaction mixture is allowed to reach rt over 16 h.

Title compound: ESI-MS: 478.1 [M+H]$^+$; $t_R$=3.11 min (System 1); TLC: $R_f$=0.08 (DCM/MeOH/NH$_3^{aq}$, 94:5:1).

EXAMPLE 126

S)-2-Methyl-pyrrolidine-1,2-dicarboxylic acid 2-amide 1-({5-[2-(1-d$_3$-methyl-cyclobutyl)-pyridin-4-yl]-thiazol-2-yl}-amide

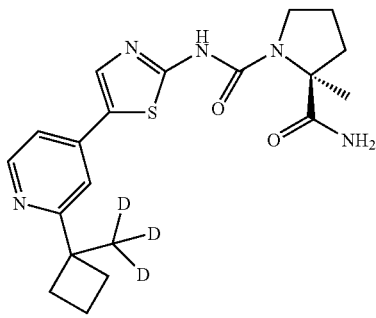 [SMILES: [2H]C([2H])([2H])C1(c2cc(-c3cnc(NC(=O)N4CCC[C@@]4(C)C(N)=O)s3)ccn2)CCC1]

The title compound is prepared in analogy to the procedure described in Example 40 but with the following modifications. In Example 40, the reaction mixture is stirred for 18 h at rt, quenched by dilution with DCM/H$_2$O and extracted with DCM. In Step 40.1, the reaction mixture is stirred for 1 h at reflux. In Step 40.2, the reaction mixture is stirred for 1 h at 100° C. In Step 40.3, N-thiazol-2-yl-acetamide is used. The palladium catalyst is added to the heated mixture of the remaining reagents. The resulting mixture is stirred for 7 h at 120° C., diluted with EtOAc/H$_2$O, filtered through a pad of celite and extracted with EtOAc. After drying and concentration of the organic phase, the residue is purified by silica gel column chromatography (Hex/EtOAc, 1:4). In Step 40.5, the reaction mixture is stirred for 3 h at 80° C. In Step 40.7, 4-methoxy-3-buten-2-one in THF is added to a cold (−78° C.) solution of LiHMDS in THF. After 30 min, 1-d$_3$-methyl-cyclobutane chloride (Step 56.1) in THF is added and the reaction mixture is allowed to reach rt over 16 h.

Title compound: ESI-MS: 403.2 [M+H]$^+$; t$_R$=2.60 min (System 1); TLC: R$_f$=0.20 (DCM/MeOH/NH$_3$$^{aq}$, 91.5:7.5:1).

EXAMPLE 127

(S)-2-Methyl-pyrrolidine-1,2-dicarboxylic acid 2-amide 1-({4-d$_3$-methyl-5-[2-(1-methyl-cyclopropyl)-pyridin-4-yl]thiazol-2-yl}-amide

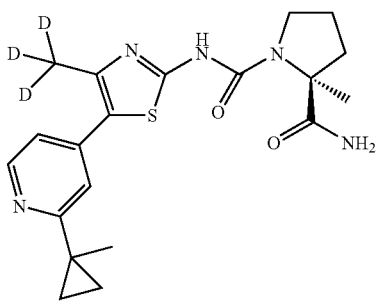 [SMILES: [2H]C([2H])([2H])c1nc(NC(=O)N2CCC[C@@]2(C)C(N)=O)sc1-c1ccnc(C2(C)CC2)c1]

The title compound is prepared in analogy to the procedure described in Example 40 but with the following modifications. In Example 40, the reaction mixture is stirred for 14 h at rt. In Step 40.1, the reaction mixture is stirred for 8 h at reflux. In Step 40.2, the reaction mixture is stirred for 1 h at 85° C. and extracted with EtOAc after being quenched. In Step 40.3, 2-acetamido-4-d$_3$-methyl-thiazole (Step 127.1) is used. The reaction mixture is stirred for 2 h at 120° C.

Title compound: ESI-MS: 403.2 [M+H]$^+$; t$_R$=2.40 min (System 1); TLC: R$_f$=0.25 (DCM/MeOH, 9:1).

Step 127.1: 2-Acetamido-4-d$_3$-methyl-thiazole

A mixture of 1-bromo-propan-2-one-d$_5$ [Challacombe, K. et al, Journal of the Chemical Society Perkin Trans. I, (1988), 2213-2218] (1.25 g, 8.8 mmol) and 1-acetyl-2-thiourea (1 g, 8.8 mmol) in EtOH (20 mL) is stirred for 2 h at 85° C., allowed to cool and concentrated. The residue is purified by silica gel column chromatography (Hex/EtOAc, 85:15→1:1) to provide 1.08 g of the title compound as an orange solid: ESI-MS: 160.0 [M+H]$^+$; TLC: R$_f$=0.25 (Hex/EtOAc, 1:1).

EXAMPLE 128

S)-2-Methyl-pyrrolidine-1,2-dicarboxylic acid 2-amide 1-({4-d$_3$-methyl-5-[2-(2,2,2-trifluoro-1,1-dimethyl-ethyl)-pyridin-4-yl]-thiazol-2-yl}-amide

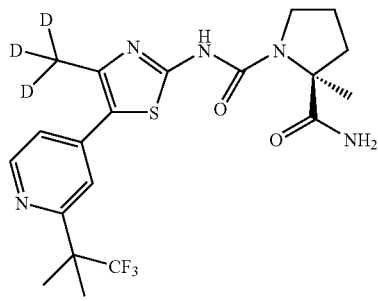 [SMILES: [2H]C([2H])([2H])c1nc(NC(=O)N2CCC[C@@]2(C)C(N)=O)sc1-c1ccnc(C(C)(C)C(F)(F)F)c1]

The title compound is prepared in analogy to the procedure described in Example 40 but with the following modifications. In Example 40, the reaction mixture is stirred for 14 h at rt. In Step 40.1, the reaction mixture is stirred for 8 h at reflux. In Step 40.2, the reaction mixture is stirred for 1 h at 85° C. and extracted with EtOAc after being quenched. In Step 40.3, 2-acetamido-4-d$_3$-methyl-thiazole (Step 127.1) is used. The reaction mixture is stirred for 2 h at 120° C. In Step 40.4, the reaction mixture is stirred for 1 h at 83° C. and extracted with EtOAc after being quenched. In Step 40.5, the reaction mixture is stirred for 1 h at 65° C. In Step 40.6, the crude product is not purified. In Step 40.7, 3,3,3-trifluoro-2,2-dimethyl-propionyl chloride (Step 119.1) is used.

Title compound: ESI-MS: 459.0 [M+H]$^+$; t$_R$=3.21 min (System 1); TLC: R$_f$=0.55 (DCM/MeOH, 9:1).

EXAMPLE 129

S)-2-Methyl-pyrrolidine-1,2-dicarboxylic acid 2-amide 1-({4-chloro-5-[2-(1-methyl-cyclopropyl)-pyridin-4-yl]-thiazol-2-yl}-amide

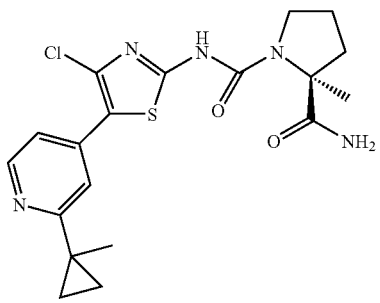 [SMILES: CC1(c2cc(-c3sc(NC(=O)N4CCC[C@@]4(C)C(N)=O)nc3Cl)ccn2)CC1]

The title compound is prepared in analogy to the procedure described in Example 40 but with the following modifications. In Example 40, the reaction mixture is stirred for 72 h at rt. In Step 40.1, DCM/DMF (3:1, v/v) is used as the solvent system. The reaction mixture is stirred for 28 h at reflux and concentrated. The residue is used without purification. In Step 40.2, the reaction mixture is stirred for 4 h at 85° C. and extracted with EtOAc after being quenched. In Step 40.3, N-(4-chloro-thiazol-2-yl)-acetamide (Step 129.1) is used. The reaction mixture is stirred for 2 h at 120° C.

Title compound: ESI-MS: 420.0 [M+H]$^+$; $t_R$=2.60 min (System 1); TLC: $R_f$=0.39 (DCM/MeOH, 9:1).

Step 129.1: N-(4-Chloro-thiazol-2-yl)-acetamide

A mixture of N-(4-oxo-4,5-dihydro-thiazol-2-yl)-acetamide (Step 129.2) (14.8 g, 94 mmol) and POCl$_3$ (175 mL, 20 eq) is heated to 105° C., stirred for 15 min, allowed to cool and concentrated. The residue is poured onto ice-H$_2$O and extracted with EtOAc (2×100 mL). The organic phase is washed with a saturated solution of NaHCO$_3$ (2×100 mL), dried (Na$_2$SO$_4$), filtered and concentrated. The residue is purified by silica gel column chromatography (DCM/MeOH, 99:1) to afford 13.9 g of the title compound as a white solid: ESI-MS: 177.0 [M+H]$^+$; $t_R$=2.74 min (System 1); TLC: $R_f$=0.66 (DCM/MeOH, 9:1).

Step 129.2: N-(4-Oxo-4,5-dihydro-thiazol-2-yl)-acetamide

A mixture of pseudothiohydanthoin (16 g, 138 mmol) and acetic anhydride (16.9 mL, 179 mmol, 1.3 eq) in pyridine (150 mL) is heated to 115° C., stirred for 1 h and allowed to cool. The resulting precipitate is collected by filtration to provide 12.64 g of the title compound as a brown solid: ESI-MS: 159.0 [M+H]$^+$.

EXAMPLE 130

(S)-2-Methyl-pyrrolidine-1,2-dicarboxylic acid 2-amide 1-[(2,4"-dimethyl[4,2';4',5"]terthiazol-2"-yl)-amide]

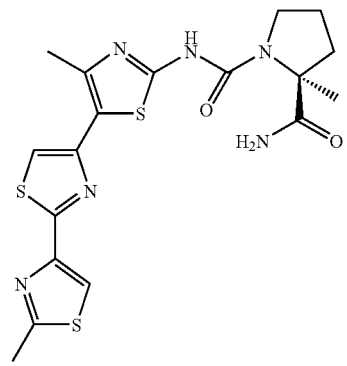 [SMILES: Cc1nc(-c2nc(-c3sc(NC(=O)N4CCC[C@@]4(C)C(N)=O)nc3C)cs2)cs1]

Imidazole-1-carboxylic acid (2,4"-dimethyl-[4,2';4',5"]terthiazol-2"-yl)-amide (25 mg) is suspended in DMF (1 mL), followed by addition of (S)-2-methyl-pyrrolidine-2-carboxylic acid amide (9.1 mg) and triethylamine (0.022 ml) at RT. The reaction mixture is stirred until completion of the reaction (30 min.) EtOAc (50 mL) is added and the mixture is washed with water (2×). The layer is freed from solvent under reduced pressure and the residue is taken up into dioxane and freeze-dried. The title compound is obtained as a as a white powder; HPLC (Method F) RT 4.65 minutes; MS (Method D) M+H 449.0 and M−H 447.1.

EXAMPLE 131

(S)-2-Methyl-pyrrolidine-1,2-dicarboxylic acid 2-amide 1-{[4'-methyl-2-(2-methyl-1H-imidazol-4-yl)-[4,5']bithiazolyl-2'-yl]-amide}

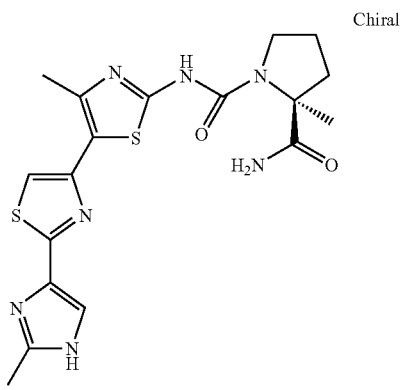 [SMILES: Cc1nc(-c2nc(-c3sc(NC(=O)N4CCC[C@@]4(C)C(N)=O)nc3C)cs2)c[nH]1]

The title compound is prepared as described as in Example 130, using imidazole-1-carboxylic acid [4'-methyl-2-(2-methyl-1H-imidazol-4-yl)-[4,5']bithiazolyl-2'-yl]-amide in place of imidazole-1-carboxylic acid (2,4"-dimethyl-[4,2';4',5"]terthiazol-2"-yl)amide and (S)-2-methyl-pyrrolidine-2-carboxylic acid amide. Title compound: HPLC (Method F) RT 3.73 minutes; MS (Method D) M+H 432.1 and M−H 430.2

EXAMPLE 132

(S)-2-Methyl-pyrrolidine-1,2-dicarboxylic acid 2-amide 1-[(2-cyclopropyl amino-4'-methyl-[4,5'] bithiazolyl-2'-yl)-amide]

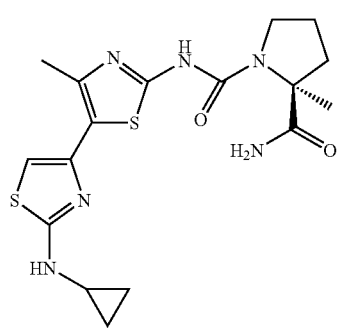 [SMILES: Cc1nc(NC(=O)N2CCC[C@@]2(C)C(N)=O)sc1-c1csc(NC2CC2)n1]

The title compound is prepared as described as in Example 130, using imidazole-1-carboxylic acid (2-cyclopropylamino-4'-methyl-[4,5]bithiazolyl-2'-yl)-amide in place of imidazole-1-carboxylic acid (2,4"-dimethyl-[4,2';4',5"]terthiazol-2"-yl)amide. Title compound: HPLC (Method F) RT 3.90 minutes; MS (Method D) M+H 407.1 and M−H 405.2.

EXAMPLE 133

(S)-2-Methyl-pyrrolidine-1,2-dicarboxylic acid 2-amide 1-[(2-dimethylamino-4'-methyl-[4,5']bithiazolyl-2'-yl)-amide]

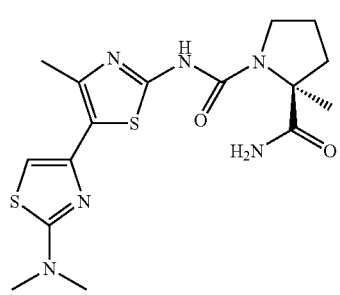 [SMILES: Cc1nc(NC(=O)N2CCC[C@@]2(C)C(N)=O)sc1-c1csc(N(C)C)n1]

The title compound is prepared as described as in Example 130, using imidazole-1-carboxylic acid (2-dimethylamino-4'-methyl-[4,5]bithiazolyl-2'-yl)-amide in place of imidazole-1-carboxylic acid (2,4"-dimethyl-[4,2';4',5"]terthiazol-2"-yl)-amide. Title compound: HPLC: (Method F) RT 3.87 minutes; MS (Method D) M+H 395.1 and M−H 393.2.

EXAMPLE 134

(S)-2-Methyl-pyrrolidine-1,2-dicarboxylic acid 2-amide 1-{[2-(3-aza-bicyclo[3.2.2]non-3-yl)-4'-methyl-[4,5']bithiazolyl-2'-yl]-amide}

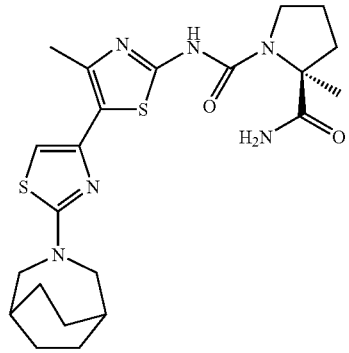 [SMILES: Cc1nc(NC(=O)N2CCC[C@@]2(C)C(N)=O)sc1-c1csc(N2CC3CCC(CC3)C2)n1]

The title compound is prepared as described as in Example 16, using imidazole-1-carboxylic acid [2-(3-aza-bicyclo[3.2.2]non-3-yl)-4'-methyl-[4,5]bithiazolyl-2'-yl]-amide in place of imidazole-1-carboxylic acid (2,4"-dimethyl-[4,2';4',5"]terthiazol-2"-yl)amide. Title compound: HPLC: (Method F) RT 4.78 minutes; MS (Method D) M+H 474.9.

EXAMPLE 135

(S)-2-Methyl-pyrrolidine-1,2-dicarboxylic acid 2-amide 1-[(2-ethyl-4'-methyl-[4.5']bithiazolyl-2'-yl)-amide]

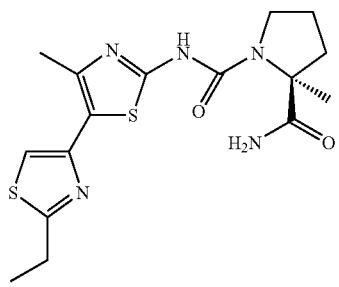

The title compound is prepared as described as in Example 130, using imidazole-1-carboxylic acid (2-ethyl-4'-methyl-[4,5']bithiazolyl-2'-yl)-amide in place of imidazole-1-carboxylic acid (2,4"-dimethyl-[4,2';4',5"]terthiazol-2"-yl)-amide and (S)-2-methyl-pyrrolidine-2-carboxylic acid amide. Title compound: HPLC (Method F) RT 4.27 minutes; MS (Method D) M+H 379.8.

EXAMPLE 136

(S)-2-Methyl-pyrrolidine-1,2-dicarboxylic acid 2-amide 1-[(4'-methyl-2-pyridin-3-yl-[4,5']bithiazolyl-2'-yl)-amide]

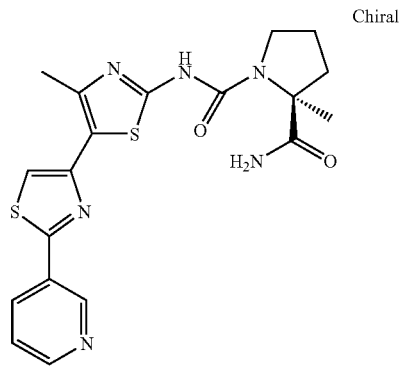 [SMILES: Cc1nc(NC(=O)N2CCC[C@@]2(C)C(N)=O)sc1-c1csc(-c2cccnc2)n1]

The title compound is prepared as described as in Example 16, using imidazole-1-carboxylic acid (4'-methyl-2-pyridin-3-yl-[4,5']bithiazolyl-2'-yl)-amide in place of imidazole-1-carboxylic acid (2,4"-dimethyl-[4,2';4',5"]terthiazol-2"-yl)-amide. Title compound: HPLC: (Method F) RT 3.78 minutes; MS (Method D) M+H 428.8.

EXAMPLE 137

(S)-2-Methyl-pyrrolidine-1,2-dicarboxylic acid 2-amide 1-{[4'-methyl-2-(1-methyl-cyclopropyl)-[4,5']bithiazolyl-2'-yl]-amide}

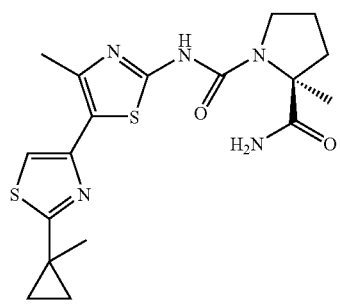 [SMILES: Cc1nc(NC(=O)N2CCC[C@@]2(C)C(N)=O)sc1-c1csc(C2(C)CC2)n1]

The title compound is prepared as described as in Example 130, using imidazole-1-carboxylic acid [4'-methyl-2-(1-methyl-cyclopropyl)-[4,5]bithiazolyl-2'-yl]-amide in place of imidazole-1-carboxylic acid (2,4"-dimethyl-[4,2';4',5"]terthiazol-2"-yl)-amide. Title compound: HPLC: (Method F) RT 4.83 minutes; MS (Method D) M+H 405.8.

EXAMPLE 138

(2S,4R)-4-Hydroxy-pyrrolidine-1,2-dicarboxylic acid 2-amide 1-{[4'-methyl-2-(1-methyl-cyclopropyl)-[4,5']bithiazolyl-2'-yl]-amide}

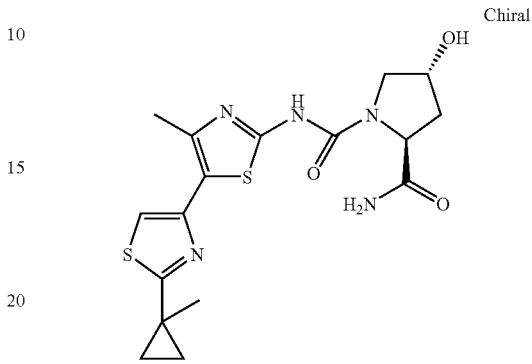

The title compound is prepared as described as in Example 137, using (2S,4R)-4-hydroxy-pyrrolidine-2-carboxylic acid amide in place of (S)-2-methyl-pyrrolidine-2-carboxylic acid amide. Title compound: HPLC (Method F) RT 4.21 minutes; MS (Method D) M+H 407.8.

EXAMPLE 139

(2S,4S)-4-Hydroxy-pyrrolidine-1,2-dicarboxylic acid 2-amide 1-{[4'-methyl-2-(1-methyl-cyclopropyl)-[4,5']bithiazolyl-2'-yl]-amide}

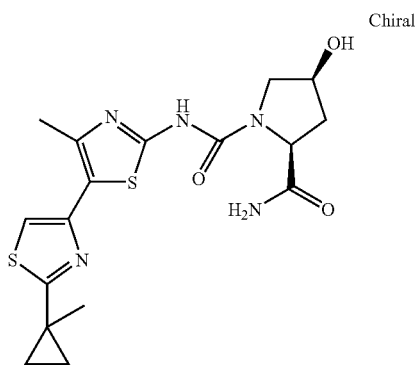 [SMILES: Cc1nc(NC(=O)N2C[C@@H](O)C[C@H]2C(N)=O)sc1-c1csc(C2(C)CC2)n1]

The title compound is prepared as described as in Example 137, using (2S,4S)-4-hydroxy-pyrrolidine-2-carboxylic acid amide in place of (S)-2-methyl-pyrrolidine-2-carboxylic acid amide. Title compound: HPLC: (Method F) RT 4.35 minutes; MS (Method D) M+H 407.8.

EXAMPLE 140

(2S,4R)-4-Dimethylamino-pyrrolidine-1,2-dicarboxylic acid 2-amide 1-[(2-tert-butyl-4'-methyl-[4,5']bithiazolyl-2'-yl)-amide]

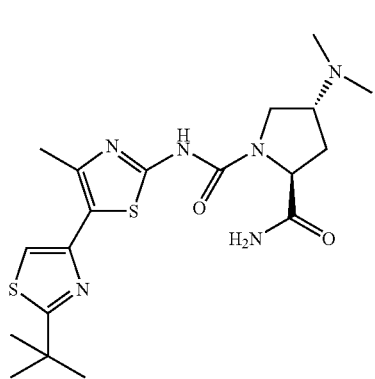

The title compound is prepared as described as in Example 37, using (2S,4R)-4-dimethylamino-pyrrolidine-2-carboxylic acid amide in place of (2S,3S)-3-methyl-pyrrolidine-2-carboxylic acid amide. Purification is done by chromatography over silica gel, eluting with $CH_2Cl_2/CH_3OH$ (82/18%). Title compound: HPLC (Method F) RT 4.20 minutes; MS (Method D) M+H 437.1 and M−H 435.2.

EXAMPLE 141

(2S,4R)-4-Dimethylamino-pyrrolidine-1,2-dicarboxylic acid 2-amide 1-{[4'-methyl-2-(1-methyl-cyclopropyl)-[4,5']bithiazolyl-2'-yl]-amide}

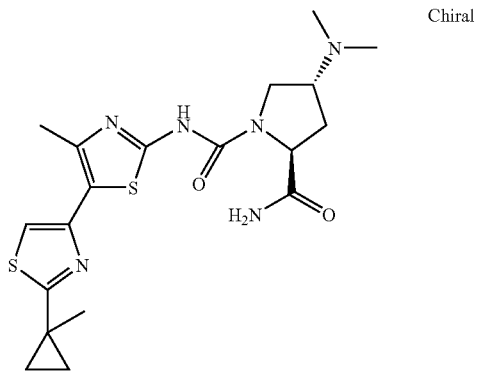 [SMILES: Cc1nc(NC(=O)N2C[C@H](N(C)C)C[C@H]2C(N)=O)sc1-c1csc(C2(C)CC2)n1]

The title compound is prepared as described as in Example 137, using (2S,4R)-4-dimethylamino-pyrrolidine-2-carboxylic acid amide in place of (S)-2-methyl-pyrrolidine-2-carboxylic acid amide. Title compound: HPLC: (Method F) RT 4.13 minutes; MS (Method D) M+H 435.1 and M−H 433.1.

EXAMPLE 142

(2S,4S)-4-Dimethylamino-pyrrolidine-1,2-dicarboxylic acid 2-amide 1-[(2-tert-butyl-4'-methyl-[4,5']bithiazolyl-2'-yl)-amide]

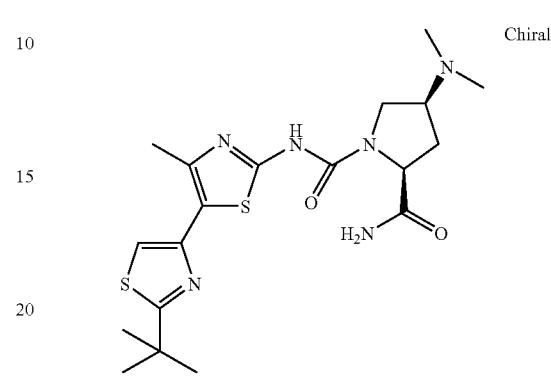

The title compound is prepared as described as in Example 37, using (2S,4S)-4-dimethylamino-pyrrolidine-2-carboxylic acid amide in place of (2S,3S)-3-methyl-pyrrolidine-2-carboxylic acid amide. Title compound: HPLC: (Method F) RT 4.23 minutes; MS (Method D) M+H 437.2 and M−H 435.2.

EXAMPLE 143

(2S,4S)-4-Dimethylamino-pyrrolidine-1,2-dicarboxylic acid 2-amide 1-{[4'-methyl-2-(1-methyl-cyclopropyl)-[4,5']bithiazolyl-2'-yl]-amide}

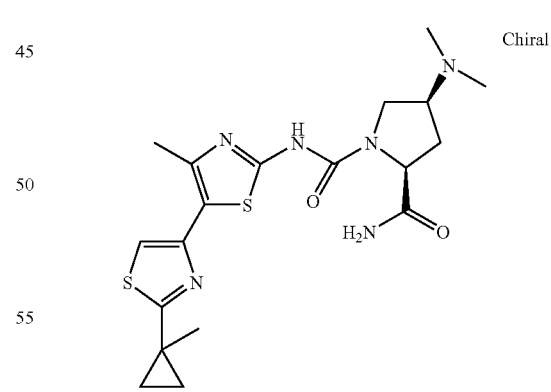

The title compound is prepared as described as in Example 137, using (2S,4S)-4-dimethylamino-pyrrolidine-2-carboxylic acid amide in place of (S)-2-methyl-pyrrolidine-2-carboxylic acid amide. Title compound: HPLC: (Method F) RT 4.17 minutes; MS (Method D) M+H 435.2 and M−H 433.2.

EXAMPLE 144

(S)-2-Methyl-pyrrolidine-1,2-dicarboxylic acid 2-amide 1-[(2-cyclobutyl-4'-methyl-[4,5']bithiazolyl-2'-yl)-amide]

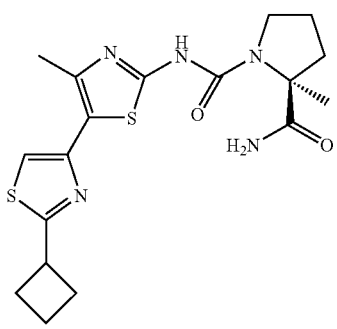

The title compound is prepared as described as in Example 130, using imidazole-1-carboxylic acid (2-cyclobutyl-4'-methyl-[4,5]bithiazolyl-2'-yl)-amide in place of imidazole-1-carboxylic acid (2,4"-dimethyl-[4,2';4',5"]terthiazol-2"-yl)-amide. Title compound: HPLC: (Method F) RT 4.71 minutes; MS (Method D) M+H 406.1 and M−H 404.2.

EXAMPLE 145

(S)-2-Methyl-pyrrolidine-1,2-dicarboxylic acid 2-amide 1-{[4'-methyl-2-(1-trifluoromethyl-cyclopropyl)-[4,5']bithiazolyl-2'-yl]-amide}

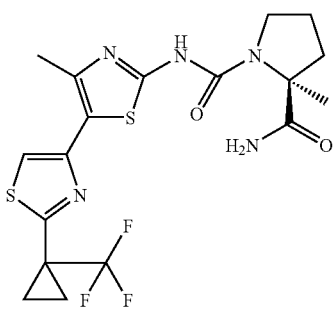 [SMILES: Cc1nc(NC(=O)N2CCC[C@@]2(C)C(N)=O)sc1-c1csc(C2(C(F)(F)F)CC2)n1]

The title compound is prepared as described as in Example 130, using imidazole-1-carboxylic acid [4'-methyl-2-(1-trifluoromethyl-cyclopropyl)-[4,5]bithiazolyl-2'-yl]-amide in place of imidazole-1-carboxylic acid (2,4"-dimethyl-[4,2';4',5"]terthiazol-2"-yl)-amide. Title compound: HPLC: (Method F) RT 4.88 minutes; MS (Method D) M+H 460.0 and M−H 458.0.

EXAMPLE 146

(1S,5R)-2-Aza-bicyclo[3.1.0]hexane-1,2-dicarboxylic acid 1-amide 2-[(2-tert-butyl-4'-methyl-[4,5']bithiazolyl-2'-yl)-amide]

The title compound is prepared as described as in Example 37, using (1S,5R)-2-aza-bicyclo[3.1.0]hexane-1-carboxylic acid amide in place of (2S,3S)-3-methyl-pyrrolidine-2-carboxylic acid amide. Title compound: HPLC: (Method F) RT 4.90 minutes; MS (Method D) M+H 406.1 and M−H 404.1.

EXAMPLE 147

(1S,5R)-2-Aza-bicyclo[3.1.0]hexane-1,2-dicarboxylic acid 1-amide 2-[(2-cyclobutyl-4'-methyl-[4,5']bithiazolyl-2'-yl)-amide]

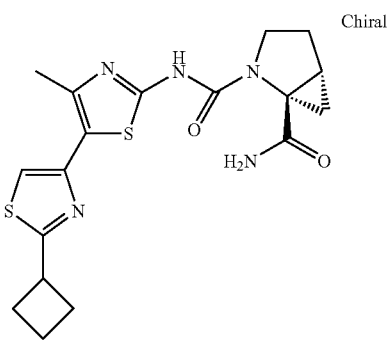 [SMILES: Cc1nc(NC(=O)N2CC[C@@H]3C[C@@]32C(N)=O)sc1-c1csc(C2CCC2)n1]

The title compound is prepared as described as in Example 130, using imidazole-1-carboxylic acid (2-cyclobutyl-4'-methyl-[4,5']bithiazolyl-2'-yl)-amide and (1S,5R)-2-aza-bicyclo[3.1.0]hexane-1-carboxylic acid amide in place of imidazole-1-carboxylic acid (2,4"-dimethyl-[4,2';4',5"]terthiazol-2"-yl)-amide and (S)-2-methyl-pyrrolidine-2-carboxylic acid amide. Title compound: HPLC: (Method F) RT 4.68 minutes; MS (Method D) M+H 404.1 and M−H 402.1.

EXAMPLE 148

(S)-2-Methyl-pyrrolidine-1,2-dicarboxylic acid 2-amide 1-{[2-(1-ethyl-propyl)-4'-methyl-[4,5']bithiazolyl-2'-yl]-amide}

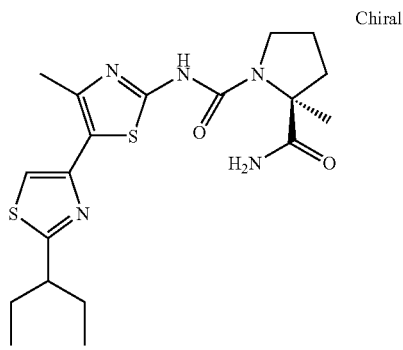 [SMILES: CCC(CC)c1nc(-c2sc(NC(=O)N3CCC[C@@]3(C)C(N)=O)nc2C)cs1]

The title compound is prepared as described as in Example 16, using imidazole-1-carboxylic acid [2-(1-ethyl-propyl)-4'-methyl-[4,5]bithiazolyl-2'-yl]amide in place of imidazole-1-carboxylic acid (2,4"-dimethyl-[4,2';4',5"]terthiazol-2"-yl)-amide. Title compound: HPLC: (Method F) RT 5.05 minutes; MS (Method D) M+H 422.1 and M−H 420.2.

EXAMPLE 149

(1S,5R)-2-Aza-bicyclo[3.1.0]hexane-1,2-dicarboxylic acid 1-amide 2-{[2-(1-ethyl-propyl)-4'-methyl-[4,5']bithiazolyl-2'-yl]-amide}

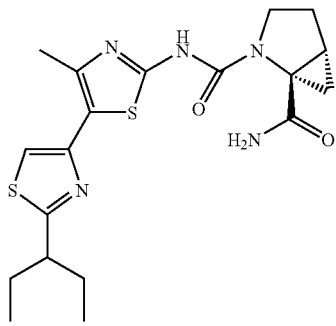 [SMILES: CCC(CC)c1nc(-c2sc(NC(=O)N3CC[C@@H]4C[C@@]43C(N)=O)nc2C)cs1]

The title compound is prepared as described as in Example 130, using imidazole-1-carboxylic acid [2-(1-ethyl-propyl)-4'-methyl-[4,5]bithiazolyl-2'-yl]-amide and (1S,5R)-2-aza-bicyclo[3.1.0]hexane-1-carboxylic acid amide in place of imidazole-1-carboxylic acid (2,4"-dimethyl-[4,2';4',5"]terthiazol-2"-yl)-amide and (S)-2-methyl-pyrrolidine-2-carboxylic acid amide. Title compound: HPLC: (Method F) RT 5.00 minutes; MS (Method D) M+H 420.1 and M−H 418.1.

EXAMPLE 150

(S)-2-Methyl-pyrrolidine-1,2-dicarboxylic acid 2-amide 1-[(2-dimethylaminomethyl-4'-methyl-[4,5']bithiazolyl-2'-yl)-amide]

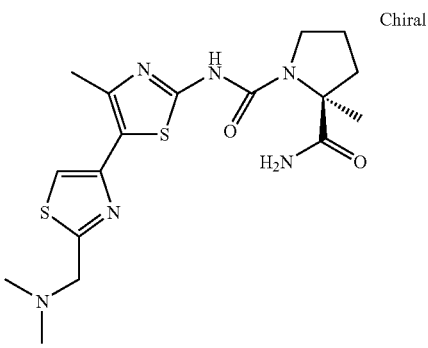

The title compound is prepared as described as in Example 130, using Imidazole-1-carboxylic acid (2-dimethylaminomethyl-4'-methyl-[4,5']bithiazolyl-2'-yl)-amide in place of imidazole-1-carboxylic acid (2,4"-dimethyl-[4,2';4',5"]terthiazol-2"-yl)-amide. Title compound: HPLC: (Method F) RT 3.54 minutes; MS (Method D) M+H 409.1 and M−H 407.2.

EXAMPLE 151

(S)-2-Methyl-pyrrolidine-1,2-dicarboxylic acid 2-amide 1-[(2-cyclopropylmethyl-4'-methyl-[4,5']bithiazolyl-2'-yl)-amide]

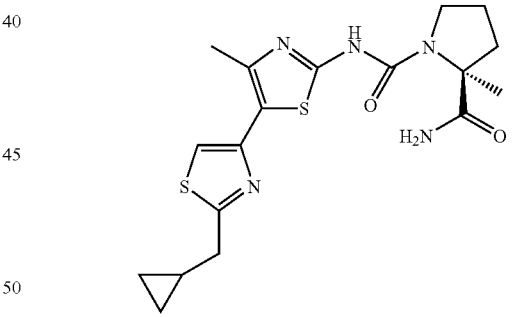

The title compound is prepared as described as in Example 130, using imidazole-1-carboxylic acid (2-cyclopropylmethyl-4'-methyl-[4,5]bithiazolyl-2'-yl)amide in place of imidazole-1-carboxylic acid (2,4"-dimethyl-[4,2';4',5"]terthiazol-2"-yl)-amide. Title compound: HPLC: (Method F) RT 4.59 minutes; MS (Method D) M+H 406.1 and M−H 404.2.

EXAMPLE A

Efficiency as PI3 Kinase Inhibitors

PI3K KinaseGlo Assay:
50 nL of compound dilutions were dispensed onto black 384-well low volume Non Binding Styrene (NBS) plates (Costar Cat. No. NBS#3676). L-a-phosphatidylinositol (PI), provided as 10 mg/ml solution in methanol, was transferred into a glass tube and dried under nitrogen beam. It was then resuspended in 3% OctylGlucoside (OG) by vortexing and stored at 4° C. The KinaseGlo Luminescent Kinase Assay (Promega, Madison/WI, USA) is a homogeneous HTS method of measuring kinase activity by quantifying the amount of ATP remaining in solution following a kinase reaction.

5 μL of a mix of PI/OG with the PI3K subtype were added (Table 1). Kinase reactions were started by addition of 5 μl of ATP-mix containing in a final volume 10 μL 10 mM TRIS-HCl pH 7.5, 3 mM $MgCl_2$, 50 mM NaCl, 0.05% CHAPS, 1 mM DTT and 1 μM ATP, and occurred at room temperature. Reactions were stopped with 10 μl of KinaseGlo and plates were read 10 mins later in a Synergy2 reader using an integration time of 0.1 seconds per well. 2.5 μM of a pan-class 1 PI3 kinase inhibitor (standard) was added to the assay plates to generate the 100% inhibition of the kinase reaction, and the 0% inhibition was given by the solvent vehicle (90% DMSO in water). The standard was used as a reference compound and included in all assay plates in the form of 16 dilution points in duplicate.

BV1075: The construct for Baculovirus BV-1075 was generated by a three-part ligation comprised of a p85 fragment and a p110α fragment cloned into vector pBlueBac4.5. The p85 fragment was derived from plasmid p1661-2 digested with Nhe/Spe. The p110α fragment derived from is clone was verified by sequencing and used in a LR410 as a SpeI/HindIII fragment. For the generation of the baculovirus expression vector LR410 the gateway LR reaction to transfer the insert into the Gateway adapted pBlueBac4.5 (Invitrogen) vector was used. The cloning vector pBlueBac4.5 (Invitrogen) was digested with Nhe/HindIII. This resulted in the construct PED 153.8. The p85 component (iSH2) was generated by PCR using ORF 318 (described above) as a template and one forward primer KAC1028 (5'-GCTAGCATGCGAGAATAT-GATAGAT-TATATGAAG-AATATACC) and two reverse primers, KAC1029 (5'-GCCTCCACCAC-CTCCGCCTG-GTTTAATGCTGTTCATACGTTTGTC) and KAC1039 (5'-TACTAGTC-CGCCTCCAC-CACCTCCGCCTCCAC-CACCTCCGCC). The two reverse primers overlap and incorporate the 12× Gly linker and the N-terminal sequence of the p110α gene to the SpeI site. The 12× Gly linker replaces the single Gly linker in the BV1052 construct. The

TABLE 1

PI3Ks by KinaseGlo: assay conditions and reagent protocol

| Vol (10 μL) | Enzyme (nM) | ATP (μM) | PI/OG (μM/μg/ml) | NaCl (mM) | $Mg^{2+}$ (mM) | CHAPS (%) | DTT (mM) | time (mins) |
|---|---|---|---|---|---|---|---|---|
| PI3Kα | 10 | 1 | 11/10 | 50 | 3 | 0.05 | 1 | 30 |
| PI3Kβ | 25 | 1 | 11/10 | 50 | 3 | 0.05 | 1 | 30 |
| PI3Kγ | 150 | 1 | 22/20 | 50 | 3 | 0.05 | 1 | 90 |
| PI3Kd | 10 | 1 | 11/10 | 50 | 3 | 0.05 | 1 | 30 |

Cloning of PI3Ks

The PI3Kα, PI3Kβ and PI3Kδ constructs are fusion of p85α iSH2 domain and the respective p110 isoforms. The p85α fragment and p110 isoform genes were generated by PCR from first strand cDNA generated by RT-PCR from commercial RNA from placenta, testis and brain as described below. The PI3Kγ construct was obtained from Roger Williams lab, MRC Laboratory of Molecular Biology, Cambridge, UK (November, 2003) and is described (Pacold, Michael E.; Suire, Sabine; Perisic, Olga; Lara-Gonzalez, Samuel; Davis, Colin T.; Walker, Edward H.; Hawkins, Philip T.; Stephens, Len; Eccleston, John F.; Williams, Roger L. Crystal structure and functional analysis of Ras binding to its effector phosphoinositide 3-kinase gamma. Cell (2000), 103 (6), 931-943).

PI3Kα Constructs and Proteins

| | | |
|---|---|---|
| PI3Kα wt | BV1075 | p85iSH2(461-568)-GGGGGGGGGGGG-p110α(21-1068)-His |

PCR fragment was cloned into pCR2.1 TOPO (Invitrogen). Of the resulting clones, p1661-2 was determined to be correct by sequencing. This plasmid was digested with Nhe and SpeI and the resulting fragment was gel-isolated and purified for sub-cloning.

The p110α cloning fragment was generated by enzymatic digest of clone LR410 (see above) with Spe I and HindIII. The SpeI site is in the coding region of the p110α ☐ gene. The resulting fragment was gel-isolated and purified for sub-cloning. The cloning vector, pBlueBac4.5 (Invitrogen) was prepared by enzymatic digestion with Nhe and HindIII.

The cut vector was purified with Qiagen column and then dephosphorylated with Calf Intestine alkaline phosphatase (CIP) (BioLabs). After completion of the CIP reaction the cut vector was again column purified to generate the final vector. A three-part ligation was performed using Roche Rapid ligase and the vendor specifications. The final plasmid was verified by sequencing.

Kinase Domain.

Protein Sequence of BV 1075:

```
  1 MREYDRLYEE YTRTSQEIQM KRTAIEAFNE TIKIFEEQCQ TQERYSKEYI EKFKREGNEK

61 EIQRIMHNYD KLKSRISEII DSRRRLEEDL KKQAAEYREI DKRMNSIKPG GGGGGGGGGG

121 GLVECLLPNG MIVTLECLRE ATLITIKHEL FKEARKYPLH QLLQDESSYI FVSVTQEAER

181 EEFFDETRRL CDLRLFQPFL KVIEPVGNRE EKILNREIGF AIGMPVCEFD MVKDPEVQDF

241 RRNILNVCKE AVDLRDLNSP HSRAMYVYPP NVESSPELPK HIYNKLDKGQ IIVVIWVIVS

301 PNNDKQKYTL KINHDCVPEQ VIAEAIRKKT RSMLLSSEQL KLCVLEYQGK YILKVCGCDE
```

```
 361 YFLEKYPLSQ YKYIRSCIML GRMPNLMLMA KESLYSQLPM DCFTMPSYSR RISTATPYMN

421 GETSTKSLWV INSALRIKIL CATYVNVNIR DIDKIYVRTG IYHGGEPLCD NVNTQRVPCS

481 NPRWNEWLNY DIYIPDLPRA ARLCLSICSV KGRKGAKEEH CPLAWGNINL FDYTDTLVSG

541 KMALNLWPVP HGLEDLLNPI GVTGSNPNKE TPCLELEFDW FSSVVKFPDM SVIEEHANWS

601 VSREAGFSYS HAGLSNRLAR DNELRENDKE QLKAISTRDP LSEITEQEKD FLWSHRHYCV

661 TIPEILPKLL LSVKWNSRDE VAQMYCLVKD WPPIKPEQAM ELLDCNYPDP MVRGFAVRCL

721 EKYLTDDKLS QYLIQLVQVL KYEQYLDNLL VRFLLKKALT NQRIGHFFFW HLKSEMHNKT

781 VSQRFGLLLE SYCRACGMYL KHLNRQVEAM EKLINLTDIL KQEKKDETQK VQMKFLVEQM

841 RRPDFMDALQ GFLSPLNPAH QLGNLRLEEC RIMSSAKRPL WLNWENPDIM SELLFQNNEI

901 IFKNGDDLRQ DMLTLQIIRI MENIWQNQGL DLRMLPYGCL SIGDCVGLIE VVRNSHTIMQ

961 IQCKGGLKGA LQFNSHTLHQ WLKDKNKGEI YDAAIDLFTR SCAGYCVATF ILGIGDRHNS

1021 NIMVKDDGQL FHIDFGHFLD HKKKKFGYKR ERVPFVLTQD FLIVISKGAQ ECTKTREFER

1081 FQEMCYKAYL AIRQHANLFI NLFSMMLGSG MPELQSFDDI AYIRKTLALD KTEQEALEYF

1141 MKQMNDAHHG GWTTKMDWIF HTIKQHALNE LGGAHHHHHH
```

PI3Kβ Constructs and Proteins

| PI3Kβ | BV949 | p85iSH2(461-N58K-568)-GGGGGG-p110β(2-1070)-His |
|---|---|---|

BV949: PCR products for the inter SH2 domain (iSH2) of the p85 PI3Kα, PI3Kβ and PI3Kδ subunit and for the full-length p110β subunit were generated and fused by overlapping PCR. The iSH2 PCR product was obtained from first strand cDNA generated by RT-PCR from commercial human RNA from placenta, testis and brain (Clontech), initiallyusing primers gwG130-p01 (5-CGAGAATATGATAGAT-TATATGAAGAAT-3') and gwG130-p02 (5'-TGGTTT-AAT-GCTGTTCATACGTTTGTCAAT-3'). Subsequently, in a secondary PCR reaction Gateway recombination AttB1 sites and linker sequences were added at the 5' end and 3' end of the p85 iSH2 fragment respectively, using primers gwG130-p03 (5'-GGGACAAGTT-TGTACAAAAAAGCAGGCTAC-GAAGGAGATATACATATGCGAGAATATGATAGATTAT ATGAAGAAT-3') and gwG130-p05 (5'-ACTGAAGCATC-CTCCTC-CTCCTCCT-CCTGGTTTAATGCTGTTCAT-ACGTTTGTC-3'). The p110β fragment was obtained by PCR using as template a p110β clone (from unknown source that was sequence verified) using primers gwG130-p04 (5'-ATTAAACCAGGAGGAGGAGGAGGAGGATGCTT-CAGTTTCATAATGCCTCCTGCT-3') which contains linker sequences and the 5' end of p110β and gwG130-p06 (5'-AGCTCCGTGATGGTGATGGTGATGT-GCTCCAGATC-TGTAGTCTTTCCGAA-CTGTGTG-3') which contains sequences of the 3' end of p110-β fused to a Histidine tag. The p85-iSH2/p11013 fusion protein was assembled by an overlapping PCR a reaction of the linkers at the 3' end of the iSH2 fragment and the 5' end of the p110β fragment, using the above mentioned gwG130-p03 primer and a primer containing an overlapping Histidine tag and the AttB2 recombination sequences (5'-GGGACCACTTTGTA-CAAGAAAGCTGGGTTTAAGCTCCGT-GATGGTGATGGTGATGT GCTCC-3'). This final product was recombined in a Gateway (Invitrogen) OR reaction into the donor vector pDONR201 (Invitrogen) to generate the ORF253 entry clone. This clone was verified by sequencing and used in a Gateway LR reaction (Invitrogen) to transfer the insert into the Gateway adapted pBlueBac4.5 (Invitrogen) vector for generation of the baculovirus expression vector LR280. This LR280 has an amino acid mutation in the p85 sequence.

Kinase Domain.

Protein Sequence of BV949:

```
   1 MREYDRLYEE YTRTSQEIQM KRTAIEAFNE TIKIFEEQCQ TQERYSKEYI EKFKREGKEK

61 EIQRIMHNYD KLKSRISEII DSRRRLEEDL KKQAAEYREI DKRMNSIKPG GGGGGCFSFI

121 MPPAMADILD IWAVDSQIAS DGSIPVDFLL PTGIYIQLEV PREATISYIK QMLWKQVHNY

181 PMFNLLMDID SYMFACVNQT AVYEELEDET RRLCDVRPFL PVLKLVTRSC DPGEKLDSKI

241 GVLIGKGLHE FDSLKDPEVN EFRRKMRKFS EEKILSLVGL SWMDWLKQTY PREHEPSIPE

301 NLEDKLYGGK LIVAVHFENC QDVFSFQVSP NMNPIKVNEL AIQKRLTIHG KEDEVSPYDY

361 VLQVSGRVEY VFGDHPLIQF QYIRNCVMNR ALPHFILVEC CKIKKMYEQE MIAIEAAINR

421 NSSNLPLPLP PKKTRIISHV WENNNPFQIV LVKGNKLNTE ETVKVHVRAG LFHGTELLCK
```

-continued

```
 481 TIVSSEVSGK NDHIWNEPLE FDINICDLPR MARLCFAVYA VLDKVKTKKS TKTINPSKYQ

541 TIRKAGKVHY PVAWVNTMVF DFKGQLRTGD IILHSWSSFP DELEEMLNPM GTVQTNPYTE

601 NATALHVKFP ENKKQPYYYP PFDKIIEKAA EIASSDSANV SSRGGKKFLP VLKEILDRDP

661 LSQLCENEMD LIWTLRQDCR EIFPQSLPKL LLSIKWNKLE DVAQLQALLQ IWPKLPPREA

721 LELLDFNYPD QYVREYAVGC LRQMSDEELS QYLLQLVQVL KYEPFLDCAL SRFLLERALG

781 NRRIGQFLFW HLRSEVHIPA VSVQFGVILE AYCRGSVGHM KVLSKQVEAL NKLKTLNSLI

841 KLNAVKLNRA KGKEAMHTCL KQSAYREALS DLQSPLNPCV ILSELYVEKC KYMDSKMKPL

801 WLVYNNKVFG EDSVGVIFKN GDDLRQDMLT LQMLRLMDLL WKEAGLDLRM LPYGCLATGD

861 RSGLIEVVST SETIADIQLN SSNVAAAAAF NKDALLNWLK EYNSGDDLDR AIEEFTLSCA

1021 GYCVASYVLG IGDRHSDNIM VKKTGQLFHI DFGHILGNFK SKFGIKRERV PFILTYDFIH

1081 VIQQGKTGNT EKFGRFRQCC EDAYLILRRH GNLFITLFAL MLTAGLPELT SVKDIQYLKD

1141 SLALGKSEEE ALKQFKQKFD EALRESWTTK VNWMAHTVRK DYRSGAHHHH HHGA
```

Kinase Domain.
PI3Kγ Construct and Protein

| PI3Kγ | BV950 | p110γ(Δ143-[Met144-1102])-His |

Construct obtained from Roger Williams lab, MRC Laboratory of Molecular Biology, Cambridge, UK (November, 2003). Description of the construct in (Pacold, Michael E.; Suire, Sabine; Perisic, Olga; Lara-Gonzalez, Samuel; Davis, Colin T.; Walker, Edward H.; Hawkins, Phillip T.; Stephens, Len; Eccleston, John F.; Williams, Roger L. Crystal structure and functional analysis of Ras binding to its effector phosphoinositide 3-kinase gamma. Cell (2000), 103(6), 931-943). Constructs lacking the N-terminal 144 aa. Protein sequence of BV950:

```
  1 MSEESQAFQR QLTALIGYDV TDVSNVHDDE LEFTRRGLVT PRMAEVASRD PKLYAMHPWV

61 TSKPLPEYLW KKIANNCIFI VIHRSTTSQT IKVSPDDTPG AILQSFFTKM AKKKSLMDIP

121 ESQSEQDFVL RVCGRDEYLV GETPIKNFQW VRHCLKNGEE IHVVLDTPPD PALDEVRKEE

181 WPLVDDCTGV TGYHEQLTIH GKDHESVFTV SLWDCDRKFR VKIRGIDIPV LPRNTDLTVF

241 VEANIQHGQQ VLCQRRTSPK PFTEEVLWNV WLEFSIKIKD LPKGALLNLQ IYCGKAPALS

301 SKASAESPSS ESKGKVRLLY YVNLLLIDHR FLLRRGEYVL HMWQISGKGE DQGSFNADKL

361 TSATNPDKEN SMSISILLDN YCHPIALPKH QPTPDPEGDR VRAEMPNQLR KQLEAIIATD

421 PLNPLTAEDK ELLWHFRYES LKHPKAYPKL FSSVKWGQQE IVAKTYQLLA RREVWDQSAL

481 DVGLTMQLLD CNFSDENVRA IAVQKLESLE DDDVLHYLLQ LVQAVKFEPY HDSALARFLL

541 KRGLRNKRIG HFLFWFLRSE IAQSRHYQQR FAVILEAYLR GCGTAMLHDF TQQVQVIEML

601 QKVTLDIKSL SAEKYDVSSQ VISQLKQKLE HLQNSQLPES FRVPYDPGLK AGALAIEKCK

661 VMASKKKPLW LEFKCADPTA LSNETIGIIF KHGDDLRQDM LILQILRIME SIWETESLDL

721 CLLPYGCIST GDKIGMIEIV KDATTIAKIQ QSTVGNTGAF KDEVLNHWLK EKSPTEEKFQ

781 AAVERFVYSC AGYCVATFVL GIGDRHNDNI MITETGNLFH IDFGHILGNY KSFLGINKER

841 VPFVLTPDFL FVMGTSGKKT SPHFQKFQDI CVKAYLALRH HTNLLIILFS MMLMTGMPQL

901 TSKEDIEYIR DALTVGKNEE DAKKYFLDQI EVCRDKGWTV QFNWFLHLVL GIKQGEKHSA

961 HHHHHH
```

PI3Kδ Construct and Protein

| PI3Kδ | BV1060 | p85iSH2(461-568)-GGGGGG-p110δ(2-1044)-His |

BV1060: PCR products for the inter SH2 domain (iSH2) of the p85 subunit and for the full-length p110δ subunit were generated and fused by overlapping PCR. The iSH2 PCR product was generated by using as a template the ORF318 (see above) and the primers gwG130-p03 (5'-GGGACAAG-TTTGTACAAAAAAGCAGGCTACGAAG-GAGATATACATATGC-GAGAATATGATAGATTATAT-GAAGAAT-3') and gwG154-p04 (5'-TCCTCCTCCT-CCTCCTCCTGGTTTAATGCTGTTCATACGTTTGTC-3'). The p110δ fragment was obtained from first strand cDNA generated by RT-PCR from commercial human RNA from placenta, testis and brain (Clontech), using initially primers gwG154-p01 (5'-ATGCCCCCTGGGGTGGACTGC-CCCAT-3') and gwG154-p02 (5'-CTACTGCCTGT-TGTCTTTGGACACGT-3'). In a subsequent PCR reaction linker sequences and a Histidine tag was added at the 5' end and 3' end of the p110δ fragment respectively, using primers gw154-p03 (5'-ATTAAACCAGGAGGAGGAGGAGGAG-GACCCCCTGGGGTGGAC-TGCCCCATGGA-3') and gwG154-p06 (5'-AGCTCCGTGATGGTGATGGTGAT-GT-GCT-CCCTGCCTGTTGTCTTTGGACACGTTGT-3'). The p85-iSH2/p110δ fusion protein was assembled in a third PCR reaction by the overlapping linkers at the 3' end of the iSH2 fragment and the 5' end of the p110δ fragment, using the above mentioned gwG130-p03 primer and a primer containing an overlapping Histidine tag and the Gateway (Invitrogen) AttB2 recombination sequences (5'-GGG-AC-CACTTTGTACAAGAAAGCTGGGTTTAA-GCTCCGTGATGGTGATGGTGAGTGCTCC-3'). This final product was recombined in a Gateway OR reaction into the donor vector pDONR201 (Invitrogen) to generate the ORF319 entry clone. This clone was verified by sequencing and used in a Gateway LR reaction (Invitrogen) to transfer the insert into the Gateway adapted pBlueBac4.5 (Invitrogen) vector for generation of the baculovirus expression vector LR415.

Protein Sequence of BV1060:

room temperature. All buffers used to purify PI3Kβ contained 0.05% Triton X100 in addition to what is described below.

Typically frozen cells from 10 L of Tn5 cell culture were resuspended in "Lysis Buffer" 20 mM Tris-Cl, pH 7.5, 500 mM NaCl, 5% glycerol, 5 mM imidazole, 1 mM NaF, 0.1 ug/mL okadaic acid (OAA), 5 mM BME, 1× Complete protease inhibitor cocktail—EDTA-free (20 tablets/1 L buffer, Roche Applied Sciences), benzonase (25 U/mL buffer, EMD Biosciences) at a ratio of 1:6 v/v pellet to Lysis Buffer ratio, and mechanically lysed by douncing 20 strokes using a tight-fitting pestle. The lysate was centrifuged at 45,000 g for 30 minutes, and the supernatant was loaded onto a pre-equilibrated IMAC column (3 mL resin/100 mL lysate). The column was washed with 3-5 column volumes of Lysis Buffer, followed by a second wash of 3-5 column volumes with 20 mM Tris-Cl, pH 7.5, 500 mM NaCl, 5% glycerol, 45 mM imidazole, 1 mM NaF, 0.1 μg/mL OAA, 5 mM BME, 1× Complete protease inhibitor cocktail—EDTA-free. Protein was eluted with 20 mM Tris-Cl, pH 7.5, 0.5 M NaCl, 5% glycerol, 250 mM imidazole, 1 mM NaF, 0.1 μg/mL OAA, 5 mM BME, 1× Complete protease inhibitor cocktail—EDTA-free. Pertinent fractions were analyzed by SDS-PAGE and pooled accordingly. The protein was further purified by gel filtration on a Superdex 200 26/60 column equilibrated in 20 mM Tris-Cl, pH 7.5, 0.5 M NaCl, 5% glycerol, 1 mM NaF, 5

```
   1 MREYDRLYEE YTRTSQEIQM KRTAIEAFNE TIKIFEEQCQ TQERYSKEYI EKFKREGNEK

61 EIQRIMHNYD KLKSRISEII DSRRRLEEDL KKQAAEYREI DKRMNSIKPG GGGGGPPGVD

121 CPMEFWTKEE NQSVVVDFLL PTGVYLNFPV SRNANLSTIK QLLWHRAQYE PLFHMLSGPE

181 AYVFTCINQT AEQQELEDEQ RRLCDVQPFL PVLRLVAREG DRVKKLINSQ ISLLIGKGLH

241 EFDSLCDPEV NDFRAKMCQF CEEAAARRQQ LGWEAWLQYS FPLQLEPSAQ TWGPGTLRLP

301 NRALLVNVKF EGSEESFTFQ VSTKDVPLAL MACALRKKAT VFRQPLVEQP EDYTLQVNGR

361 HEYLYGSYPL CQFQYICSCL HSGLTPHLTM VHSSSILAMR DEQSNPAPQV QKPRAKPPPI

421 PAKKPSSVSL WSLEQPFRIE LIQGSKVNAD ERMKLVVQAG LFHGNEMLCK TVSSSEVSVC

481 SEPVWKQRLE FDINICDLPR MARLCFALYA VIEKAKKARS TKKKSKKADC PIAWANLMLF

541 DYKDQLKTGE RCLYMWPSVP DEKGELLNPT GTVRSNPNTD SAAALLICLP EVAPHPVYYP

601 ALEKILELGR HSECVHVTEE EQLQLREILE RRGSGELYEH EKDLVWKLRH EVQEHFPEAL

661 ARLLLVTKWN KHEDVAQMLY LLCSWPELPV LSALELLDFS FPDCHVGSFA IKSLRKLTDD

721 ELFQYLLQLV QVLKYESYLD CELTKFLLDR ALANRKIGHF LFWHLRSEMH VPSVALRFGL

781 ILEAYCRGST HHMKVLMKQG EALSKLKALN DFVKLSSQKT PKPQTKELMH LCMRQEAYLE

841 ALSHLQSPLD PSTLLAEVCV EQCTFMDSKM KPLWIMYSNE EAGSGGSVGI IFKNGDDLRQ

901 DMLTLQMIQL MDVLWKQEGL DLRMTPYGCL PTGDRTGLIE VVLRSDTIAN IQLNKSNMAA

961 TAAFNKDALL NWLKSKNPGE ALDRAIEEFT LSCAGYCVAT YVLGIGDRHS DNIMIRESGQ

1021 LFHIDFGHFL GNFKTKFGIN RERVPFILTY DFVHVIQQGK TNNSEKFERF RGYCERAYTI

1081 LRRHGLLFLH LFALMRAAGL PELSCSKDIQ YLKDSLALGK TEEEALKHFR VKFNEALRES

1141 WKTKVNWLAH NVSKDNRQEL GGAHHHHHH
```
                                                            60

Purification of PI3Kα, PI3Kβ and PI3Kγ Constructs

PI3Kα, PI3Kβ and PI3Kγ were purified in two chromatographic steps: immobilized metal affinity chromatography (IMAC) on a Ni sepharose resin (GE Healthcare) and gel filtration utilizing a Superdex 200 26/60 column (GE Healthcare). All buffers were chilled to 4° C. and lysis was performed chilled on ice. Column fractionation was performed at mM DTT, 1× Complete protease inhibitor cocktail—EDTA-free. Pertinent fractions were analyzed by SDS-PAGE and pooled accordingly. An equal volume of Dialysis Buffer (20 mM Tris-Cl, pH 7.5, 500 mM NaCl, 50% glycerol, 5 mM NaF, 5 mM DTT) was added to the pool and than dialyzed against Dialysis Buffer two changes (one change overnight). Protein was stored at −20° C.

Purification of PI3Kα

PI3Kδ was purified in three chromatographic steps: immobilized metal affinity chromatography on a Ni Sepharose resin (GE Healthcare), gel filtration utilizing a Superdex 200 26/60 column (GE Healthcare), and finally a ion exchange step on a Q-HP column (GE Healthcare). All buffers were chilled to 4° C. and lysis was performed chilled on ice. Column fractionation was performed at room temperature.

Typically frozen cells from 10 L of Tn5 cell culture were resuspended in "Lysis Buffer" 20 mM Tris-Cl, pH 7.5, 500 mM NaCl, 5% glycerol, 5 mM imidazole, 1 mM NaF, 0.1 µg/mL okadaic acid (OAA), 5 mM BME, 1× Complete protease inhibitor cocktail—EDTA-free (20 tablets/1 L buffer, Roche Applied Sciences), benzonase (25 U/mL lysis buffer, EMD Biosciences) at a ratio of 1:10 v/v pellet to Lysis Buffer ratio, and mechanically lysed by douncing 20 strokes using a tight-fitting pestle. The lysate was centrifuged at 45,000 g for 30 minutes, and the supernatant was loaded onto a pre-equilibrated IMAC column (5 mL resin/100 mL lysate). The column was washed with 3-5 column volumes of Lysis Buffer, followed by a second wash of 3-5 column volumes with 20 mM Tris-Cl, pH 7.5, 500 mM NaCl, 5% glycerol, 40 mM imidazole, 1 mM NaF, 0.1 µg/mL OAA, 5 mM BME, 1× Complete protease inhibitor cocktail—EDTA-free. Protein was eluted with 20 mM Tris-Cl, pH 7.5, 500 mM NaCl, 5% glycerol, 250 mM imidazole, 1 mM NaF, 0.1 µg/mL OAA, 5 mM BME, 1× Complete protease inhibitor cocktail—EDTA-free. Pertinent fractions were analyzed by SDS-PAGE and pooled accordingly. The protein was further purified by gel filtration on a Superdex 200 equilibrated in 20 mM Tris-Cl, pH 7.5, 500 mM NaCl, 5% glycerol, 1 mM NaF, 0.1 µg/mL OAA, 5 mM DTT, 1× Complete protease inhibitor cocktail—EDTA-free. Pertinent fractions were analyzed by SDS-PAGE and pooled accordingly. These fractions were diluted 1:10 v/v pool volume to buffer ratio with "Buffer A" 20 mM Tris-Cl, pH 8.2, 5% glycerol, 1 mM NaF, 0.1 µg/mL OAA, 5 mM DTT and loaded onto a prepared Q-HP column. After sample loading is completed we wash with Buffer A and 5% "Buffer B" 20 mM Tris-Cl, pH 8.2, 1 M NaCl, 5% glycerol, 1 mM NaF, 0.1 ug/mL OAA, 5 mM DTT for 3-5 column volumes. We elute the protein using a 5%-30% gradient of Buffer B. Typically the protein elutes at ~200 mM NaCl. Pertinent fractions were analyzed by SDS-PAGE and pooled accordingly. An equal volume of Dialysis Buffer (20 mM Tris-Cl, pH 7.5, 500 mM NaCl, 50% glycerol, 1 mM NaF, 0.1 µg/mL OAA, 5 mM DTT) was added to the pool and then dialyzed against Dialysis Buffer two changes (one change overnight). Protein was stored at −20° C.

The following results were obtained using the above described assays.

| Example # | PI3Kalpha IC50 [µM] |
|---|---|
| 117 | 0.026 |
| 124 | 0.028 |
| 107 | 0.044 |
| 88 | 0.076 |
| 122 | 0.050 |
| 46 | 0.009 |
| 47 | 0.040 |
| 102 | 0.21 |
| 48 | 0.005 |
| 119 | 0.008 |
| 40 | 0.037 |
| 49 | 0.017 |
| 65 | 0.031 |
| 80 | 0.25 |
| 110 | 0.071 |
| 114 | 0.13 |
| 74 | 0.13 |
| 54 | 0.19 |
| 98 | 0.14 |
| 111 | 0.052 |
| 112 | 0.049 |
| 129 | 0.024 |
| 101 | 0.099 |
| 11 | 0.048 |
| 66 | 0.040 |
| 1 | 0.17 |
| 7 | 0.015 |
| 3 | 0.013 |
| 59 | 0.071 |

The following further results were obtained using the above described assays.

| Example no. | PI3Kalpha/IC50 [umol l−1] | PI3Kdelta/ IC50 [umol l−1] | Selectivity PI3Kalpha vs. PI3Kdelta |
|---|---|---|---|
| Example 133 WO 2004/096797 | 0.011 | 0.099 | 9-fold |
| 9 | 0.012 | 452 | 38-fold |
| 12 | 0.015 | 0.974 | 65-fold |
| 35 | 0.024 | 1.739 | 72-fold |
| 66 | 0.040 | 1.273 | 32-fold |
| 70 | 0.014 | 3.450 | 246-fold |

The following further results were also obtained using the above described assays.

| Example no. | PI3Kalpha/IC50 [umol l−1] | PI3Kbeta/IC50 [umol l−1] | PI3Kgamma/ IC50 [umol l−1] | PI3Kdelta/ IC50 [umol l−1] |
|---|---|---|---|---|
| 34 | 0.083 | >9.1 | 1.98 | 2.15 |
| 35 | 0.024 | 7.15 | 2.32 | 1.74 |
| 37 | 0.022 | 7.10 | 1.70 | 0.494 |
| 151 | 0.078 | 0.885 | 0.928 | 1.26 |

The invention claimed is:

1. A compound of formula:

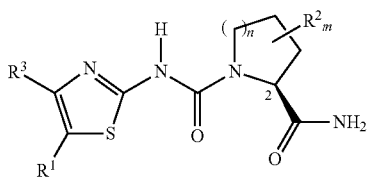

wherein $R^1$ is pyridin-4-yl substituted with one substituent said substituent is attached to the 2-position of the pyridinyl ring;

n represents 1 and m represents 1, 2, 3 or 4;

$R^2$ represents halo, cyano, nitro, hydroxy, lower alkyl, lower alkoxy, lower alkylamino, lower dialkylamino, lower dialkylamino lower alkyl, cycloalkyl, or cycloalkoxy wherein each alkyl or cycloalkyl may be mono or poly-substituted by halo, cyano, nitro, hydroxy, or phenyl and wherein each phenyl may be mono or poly-substituted by halo, cyano, nitro, hydroxy, or lower alkyl; or two substituents R² together form an alkandiyl or alkenediyl, each optionally substituted by hydroxy or halo, to form a cyclic moiety; or two R² substituents together form a double bond; and R³ represents hydrogen, lower alkyl, mono-, poly- or per-deutero lower alkyl, halo, halo lower alkyl, hydroxy lower alkyl, or lower dialkylamino lower alkyl;

or a pharmaceutically acceptable salt thereof.

2. The compound according to claim 1 wherein the R¹ substituent is selected from the group consisting of: halogen, hydroxy, cyano, nitro $C_1$-$C_7$-alkyl, per-deutero $C_1$-$C_7$-alkyl, $C_3$-$C_{12}$-cycloalkyl, amino-$C_1$-$C_7$-alkyl, halo-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, pyrrolidino-$C_1$-$C_7$-alkyl, oxo-pyrrolidino-$C_1$-$C_7$-alkyl, $C_1$-$C_7$-alkanesulfinyl, $C_1$-$C_7$-alkanesulfonyl, $C_1$-$C_7$-alkoxy, amino, N-mono- or N,N-di($C_1$-$C_7$-alkyl)-amino, $C_1$-$C_7$-alkanoylamino, pyrrolidino, oxo-pyrrolidino, piperidine, piperazin-1-yl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl, 4-(amino-$C_1$-$C_7$-alkyl)-piperazin-1-yl, 4-[N-mono- or N,N-di-($C_1$-$C_7$-alkylamino)-$C_1$-$C_7$-alkyl]piperazin-1-yl, morpholino, thiomorpholino, S-oxo- or S,S-dioxothiomorpholino, $C_1$-$C_7$-alkane-sulfonylamino, carbamoyl, N-mono- or N,N-di-($C_1$-$C_7$-alkyl, $C_1$-$C_7$-alkoxy-$C_1$-$C_7$-alkyl, amino-$C_1$-$C_7$-alkyl, (N'-mono- or N',N'-di-($C_1$-$C_7$-alkyl)-amino-$C_1$-$C_7$-alkyl)-carbamoyl, pyrrolidin-1-carbonyl, piperidin-1-carbonyl, piperazin-1-carbonyl, 4-($C_1$-$C_7$-alkyl)piperazin-1-carbonyl, morpholin-1-carbonyl, thiomorpholin-1-carbonyl, S-oxo- or S,S-dioxothio-morpholin-1-carbonyl, sulfa, $C_1$-$C_7$-alkanesulfonyl, $C_1$-$C_7$-alkane-sulfinyl, sulfamoyl, N-mono- or N,N-di-($C_1$-$C_7$-alkyl)-sulfamoyl, morpholinosulfonyl, thiomorpholinosulfonyl, and thiazolyl; or a pharmaceutically acceptable salt thereof.

3. The compound according to claim 2 wherein R³ represents hydrogen, methyl, $d_3$-methyl, chloro, or dimethylamino methyl; or a pharmaceutically acceptable salt thereof.

4. The compound according to claim 3 wherein R² represents hydroxy, methyl, fluoro, or chloro; or a pharmaceutically acceptable salt thereof.

5. A compound of claim 1, selected from, (2S,4R)-4-hydroxy-pyrrolidine-1,2-dicarboxylic acid 2-amide 1-{[5-(2-tert-butyl-pyridin-4-yl)-4-methyl-thiazol-2-yl]-amide}, (2S,4S)-4-hydroxy-pyrrolidine-1,2-dicarboxylic acid 2-amide 1-{[5-(2-tert-butyl-pyridin-4-yl)-4-methyl-thiazol-2-yl]-amide}, (S)-2-Methyl-pyrrolidine-1,2-dicarboxylic acid 2-amide 1-{[5-(2-cyclopropyl-pyridin-4-yl)-4-methyl-thiazol-2-yl]-amide}, (S)-2-Methyl-pyrrolidine-1,2-dicarboxylic acid 2-amide 1-({5-[2-(2-fluoro-phenyl)-pyridin-4-yl]-4-methyl-thiazol-2-yl}-amide), (S)-2-Methyl-pyrrolidine-1,2-dicarboxylic acid 2-amide 1-{[5-(2-cyclobutyl-pyridin-4-yl)-4-methyl-thiazol-2-yl]-amide}, (S)-2-Methyl-pyrrolidine-1,2-dicarboxylic acid 2-amide 1-({4-methyl-5-[2-(1-methyl-cyclobutyl)-pyridin-4-yl]-thiazol-2-yl}-amide), (S)-2-Methyl-pyrrolidine-1,2-dicarboxylic acid 2-amide 1-{[5-(2-isopropyl-pyridin-4-yl)-4-methyl-thiazol-2-yl]-amide}, (S)-2-Methyl-pyrrolidine-1,2-dicarboxylic acid 2-amide 1-({4-methyl-5-[2-(1-trifluoromethyl-cyclopropyl)-pyridin-4-yl]-thiazol-2-yl}-amide), (S)-2-Methyl-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), (S)-2-Methyl-pyrrolidine-1,2-dicarboxylic acid 2-amide 1-({4-methyl-5-[2-(1-trifluoromethyl-cyclobutyl)-pyridin-4-yl]-thiazol-2-yl}-amide), (S)-2-Methyl-pyrrolidine-1,2-dicarboxylic acid 2-amide 1-({5-[2-(1-cyano-cyclopropyl)-pyridin-4-yl]-4-methyl-thiazol-2-yl}-amide), (S)-2-Methyl-pyrrolidine-1,2-dicarboxylic acid 2-amide 1-({5-[2-(1-cyano-cyclobutyl)-pyridin-4-yl]-4-methyl-thiazol-2-yl}-amide), (S)-2-Methyl-pyrrolidine-1,2-dicarboxylic acid 2-amide 1-{[5-(2-diethylamino-pyridin-4-yl)-4-methyl-thiazol-2-yl]-amide}, (S)-2-Methyl-pyrrolidine-1,2-dicarboxylic acid 2-amide 1-[(5-{2-[1-(4-methoxy-phenyl)-1-methyl-ethyl]-pyridin-4-yl}-4-methyl-thiazol-2-yl)-amide], (S)-2-Methyl-pyrrolidine-1,2-dicarboxylic acid 2-amide 1-[(5-{2-[1-(4-methoxy-phenyl)-cyclopropyl]-pyridin-4-yl}-4-methyl-thiazol-2-yl)-amide], (S)-2-Methyl-pyrrolidine-1,2-dicarboxylic acid 2-amide 1-{[5-(2-{1-[4-(3-dimethylamino-propoxy)-phenyl]-1-methyl-ethyl}-pyridin-4-yl)-4-methyl-thiazol-2-yl]-amide}, (S)-2-Methyl-pyrrolidine-1,2-dicarboxylic acid 2-amide 1-({4-methyl-5-[2-(1-$d_3$-methyl-cyclobutyl)-pyridin-4-yl]-thiazol-2-yl}-amide), (S)-2-Methyl-pyrrolidine-1,2-dicarboxylic acid 2-amide 1-({4-dimethylaminomethyl-5-[2-(1-$d_3$-methyl-cyclobutyl)-pyridin-4-yl]-thiazol-2-yl}-amide), (S)-2-Methyl-Pyrrolidine-1,2-dicarboxylic acid 2-amide 1-({5-[2-(2-fluoro-1,1-dimethyl-ethyl)-pyridin-4-yl]-4-methyl-thiazol-2-yl}-amide), (S)-4,4-Difluoro-pyrrolidine-1,2-dicarboxylic acid 2-amide 1-({4-methyl-5-[2-(1-methyl-cyclopropyl)-pyridin-4-yl]-thiazol-2-yl}-amide), (S)-2-Methyl-pyrrolidine-1,2-dicarboxylic acid 2-amide 1-{[5-(2-tert-butyl-pyridin-4-yl)-thiazol-2-yl]-amide}, (S)-2-Methyl-pyrrolidine-1,2-dicarboxylic acid 2-amide 1-{[5-(2-cyclobutyl-pyridin-4-yl)-thiazol-2-yl]-amide}, (S)-2-Methyl-pyrrolidine-1,2-dicarboxylic acid 2-amide 1-({5-[2-(1-methyl-cyclopropyl)-pyridin-4-yl]-thiazol-2-yl}-amide), (S)-2-Methyl-pyrrolidine-1,2-dicarboxylic acid 2-amide 1-({5-[2-(1-trifluoromethyl-cyclopropyl)-pyridin-4-yl]-thiazol-2-yl}-amide), (S)-2-Methyl-pyrrolidine-1,2-dicarboxylic acid 2-amide 1-({5-[2-(2,2,2-trifluoro-1,1-dimethyl-ethyl)-pyridin-4-yl]-thiazol-2-yl}-amide), (S)-2-Methyl-pyrrolidine-1,2-dicarboxylic acid 2-amide 1-({5-[2-(1-trifluoromethyl-cyclobutyl)-pyridin-4-yl]-thiazol-2-yl}-amide), (S)-2-Methyl-pyrrolidine-1,2-dicarboxylic acid 2-amide 1-({5-[2-(1-methyl-cyclobutyl)-pyridin-4-yl]-thiazol-2-yl}-amide), (S)-2-Methyl-pyrrolidine-1,2-dicarboxylic acid 2-amide 1-{[5-(2-diethylamino-pyridin-4-yl)-thiazol-2-yl]-amide}, (S)-2-Methyl-pyrrolidine-1,2-dicarboxylic acid 2-amide 1-[(5-{2-[1-(4-methoxy-phenyl)-1-methyl-ethyl]-pyridin-4-yl}-thiazol-2-yl)-amide], (S)-2-Methyl-pyrrolidine-1,2-dicarboxylic acid 2-amide 1-[(5-{2-[1-(4-methoxy-phenyl)-cyclopropyl]-pyridin-4-yl}-thiazol-2-yl)-amide], (S)-2-Methyl-pyrrolidine-1,2-dicarboxylic acid 2-amide 1-({5-[2-(1-$d_3$-methyl-cyclobutyl)-pyridin-4-yl]-thiazol-2-yl}-amide), (S)-2-Methyl-pyrrolidine-1,2-dicarboxylic acid 2-amide 1-({4-d₃-methyl-5-[2-(1-methyl-cyclopropyl)-pyridin-4-yl]-thiazol-2-yl}-amide), (S)-2-Methyl-pyrrolidine-1,2-dicarboxylic acid 2-amide 1-({4-d₃-methyl-5-[2-(2,2,2-trifluoro-1,1-dimethyl-ethyl)-pyridin-4-yl]-thiazol-2-yl}-amide), and (S)-2-Methyl-pyrrolidine-1,2-dicarboxylic acid 2-amide 1-({4-chloro-5-[2-(1-methyl-cyclopropyl)-pyridin-4-yl]-thiazol-2-yl}-amide).

6. A pharmaceutical composition comprising a compound of claim 1, or a pharmaceutically acceptable salt thereof, and one or more pharmaceutically acceptable excipients.

7. A combined pharmaceutical composition, adapted for simultaneous or sequential administration, comprising a compound of claim 1, or a pharmaceutically acceptable salt thereof, one or more combination partners, and one or more pharmaceutically acceptable excipients.

8. A compound selected from the group consisting of (2S,4R)-4-hydroxy-pyrrolidine-1,2-dicarboxylic acid 2-amide 1-[(2-tert-butyl-4'-methyl-[4,5']bithiazolyl-2'-yl)-amide], (2S,4S)-4-hydroxy-pyrrolidine-1,2-dicarboxylic acid 2-amide 1-[(2-tert-butyl-4'-methyl-[4,5']bithiazolyl-2'-yl)-amide], (2S,3S)-3-hydroxy-pyrrolidine-1,2-dicarboxylic acid 2-amide 1-[(2-tert-butyl-4'-methyl-[4,5']bithiazolyl-2'-yl)-amide]triflouroacetate, (S)-2-methyl-pyrrolidine-1,2-dicarboxylic acid 2-amide 1-[(2-tert-butyl-4'-methyl-[4,5']bithiazolyl-2'-yl)-amide], (2S,3S)-3-methyl-pyrrolidine-1,2-dicarboxylic acid 2-amide 1-[(2-tert-butyl-4'-methyl-[4,5']bithiazolyl-2'-yl)-amide], (2S,4R)-4-fluoro-pyrrolidine-1,2-dicarboxylic acid 2-amide 1-[(2-tert-butyl-4'-methyl-[4,5']bithiazolyl-2'-yl)-amide], (S)-2-methyl-pyrrolidine-1,2-dicarboxylic acid 2-amide 1-{[4'-methyl-2-(pyridin-3-ylamino)-[4,5']bithiazolyl-2'-yl]-amide}, (S)-2-Methyl-pyrrolidine-1,2-dicarboxylic acid 2-amide 1-[(2,4''-dimethyl[4,2';4',5'']terthiazol-2''-yl)-amide], (S)-2-Methyl-pyrrolidine-1,2-dicarboxylic acid 2-amide 1-{[4'-methyl-2-(2-methyl-1H-imidazol-4-yl)-[4,5']bithiazolyl-2'-yl]-amide}, (S)-2-Methyl-pyrrolidine-1,2-dicarboxylic acid 2-amide 1-[(2-cyclopropyl amino-4'-methyl-[4,5']bithiazolyl-2'-yl)-amide], (S)-2-Methyl-pyrrolidine-1,2-dicarboxylic acid 2-amide 1-[(2-dimethylamino-4'-methyl-[4,5']bithiazolyl-2'-yl)-amide], (S)-2-Methyl-pyrrolidine-1,2-dicarboxylic acid 2-amide 1-{[2-(3-aza-bicyclo[3.2.2]non-3-yl)-4'-methyl-[4,5']bithiazolyl-2'-yl]-amide}, (S)-2-Methyl-pyrrolidine-1,2-dicarboxylic acid 2-amide 1-[(2-ethyl-4'-methyl-[4,5']bithiazolyl-2'-yl)-amide], (S)-2-Methyl-pyrrolidine-1,2-dicarboxylic acid 2-amide 1-[(4'-methyl-2-pyridin-3-yl-[4,5']bithiazolyl-2'-yl)-amide], (S)-2-Methyl-pyrrolidine-1,2-dicarboxylic acid 2-amide 1-{[4'-methyl-2-(1-methyl-cyclopropyl)-[4,5']bithiazolyl-2'-yl]-amide}, (2S,4R)-4-Hydroxy-pyrrolidine-1,2-dicarboxylic acid 2-amide 1-{[4'-methyl-2-(1-methyl-cyclopropyl)-[4,5']bithiazolyl-2'-yl]-amide}, (2S,4S)-4-Hydroxy-pyrrolidine-1,2-dicarboxylic acid 2-amide 1-{[4'-methyl-2-(1-methyl-cyclopropyl)-[4,5']bithiazolyl-2'-yl]-amide}, (2S,4R)-4-Dimethylamino-pyrrolidine-1,2-dicarboxylic acid 2-amide 1-[(2-tert-butyl-4'-methyl-[4,5']bithiazolyl-2'-yl)-amide], (2S,4R)-4-Dimethylamino-pyrrolidine-1,2-dicarboxylic acid 2-amide 1-{[4'-methyl-2-(1-methyl-cyclopropyl)-[4,5']bithiazolyl-2'-yl]-amide}, (2S,4S)-4-Dimethylamino-pyrrolidine-1,2-dicarboxylic acid 2-amide 1-[(2-tert-butyl-4'-methyl-[4,5']bithiazolyl-2'-yl)-amide], (2S,4S)-4-Dimethylamino-pyrrolidine-1,2-dicarboxylic acid 2-amide 1-{[4'-methyl-2-(1-methyl-cyclopropyl)-[4,5']bithiazolyl-2'-yl]-amide}, (S)-2-Methyl-pyrrolidine-1,2-dicarboxylic acid 2-amide 1-[(2-cyclobutyl-4'-methyl-[4,5']bithiazolyl-2'-yl)-amide], (S)-2-Methyl-pyrrolidine-1,2-dicarboxylic acid 2-amide 1-{[4'-methyl-2-(1-trifluoromethyl-cyclopropyl)-[4,5']bithiazolyl-2'-yl]-amide}, (1S,5R)-2-Aza-bicyclo[3.1.0]hexane-1,2-dicarboxylic acid 1-amide 2-[(2-tert-butyl-4'-methyl-[4,5']bithiazolyl-2'-yl)-amide], (1S,5R)-2-Aza-bicyclo[3.1.0]hexane-1,2-dicarboxylic acid 1-amide 2-[(2-cyclobutyl-4'-methyl-[4,5']bithiazolyl-2'-yl)-amide], (S)-2-Methyl-pyrrolidine-1,2-dicarboxylic acid 2-amide 1-{[2-(1-ethyl-propyl)-4'-methyl-[4,5']bithiazolyl-2'-yl]-amide}, (1S,5R)-2-Aza-bicyclo[3.1.0]hexane-1,2-dicarboxylic acid 1-amide 2-{[2-(1-ethyl-propyl)-4'-methyl-[4,5']bithiazolyl-2'-yl]-amide}, (S)-2-Methyl-pyrrolidine-1,2-dicarboxylic acid 2-amide 1-[(2-dimethylaminomethyl-4'-methyl-[4,5']bithiazolyl-2'-yl)-amide], and (S)-2-Methyl-pyrrolidine-1,2-dicarboxylic acid 2-amide 1-[(2-cyclopropylmethyl-4'-methyl-[4,5']bithiazolyl-2'-yl)-amide].

* * * * *

SEQUENCE LISTING

<160> NUMBER OF SEQ ID NOS: 20

<210> SEQ ID NO 1
<211> LENGTH: 42
<212> TYPE: DNA
<213> ORGANISM: Artificial
<220> FEATURE:

-continued

<223> OTHER INFORMATION: PCR Primer

<400> SEQUENCE: 1
gctagcatgc gagaatatga tagattatat gaagaatata cc                42

<210> SEQ ID NO 2
<211> LENGTH: 45
<212> TYPE: DNA
<213> ORGANISM: Artificial
<220> FEATURE:
<223> OTHER INFORMATION: PCR primer

<400> SEQUENCE: 2
gcctccacca cctccgcctg gtttaatgct gttcatacgt ttgtc            45

<210> SEQ ID NO 3
<211> LENGTH: 42
<212> TYPE: DNA
<213> ORGANISM: Artificial
<220> FEATURE:
<223> OTHER INFORMATION: PCR primer

<400> SEQUENCE: 3
tactagtccg cctccaccac ctccgcctcc accacctccg cc               42

<210> SEQ ID NO 4
<211> LENGTH: 1180
<212> TYPE: PRT
<213> ORGANISM: Artificial
<220> FEATURE:
<223> OTHER INFORMATION: PI3K kinase construct

<400> SEQUENCE: 4

Met Arg Glu Tyr Asp Arg Leu Tyr Glu Tyr Thr Arg Thr Ser Gln
1               5                  10                  15

Glu Ile Gln Met Lys Arg Thr Ala Ile Glu Ala Phe Asn Glu Thr Ile
                20                  25                  30

Lys Ile Phe Glu Glu Gln Cys Gln Thr Gln Glu Arg Tyr Ser Lys Glu
        35                  40                  45

Tyr Ile Glu Lys Phe Lys Arg Glu Gly Asn Glu Lys Glu Ile Gln Arg
    50                  55                  60

Ile Met His Asn Tyr Asp Lys Leu Lys Ser Arg Ile Ser Glu Ile Ile
65                  70                  75                  80

Asp Ser Arg Arg Arg Leu Glu Glu Asp Leu Lys Lys Gln Ala Ala Glu
                85                  90                  95

Tyr Arg Glu Ile Asp Lys Arg Met Asn Ser Ile Lys Pro Gly Gly Gly
            100                 105                 110

Gly Gly Gly Gly Gly Gly Gly Gly Leu Val Glu Cys Leu Leu Pro
        115                 120                 125

Asn Gly Met Ile Val Thr Leu Glu Cys Leu Arg Glu Ala Thr Leu Ile
    130                 135                 140

Thr Ile Lys His Glu Leu Phe Lys Glu Ala Arg Lys Tyr Pro Leu His
145                 150                 155                 160

Gln Leu Leu Gln Asp Glu Ser Ser Tyr Ile Phe Val Ser Val Thr Gln
                165                 170                 175

Glu Ala Glu Arg Glu Glu Phe Phe Asp Glu Thr Arg Arg Leu Cys Asp
            180                 185                 190

Leu Arg Leu Phe Gln Pro Phe Leu Lys Val Ile Glu Pro Val Gly Asn
        195                 200                 205

-continued

Arg Glu Glu Lys Ile Leu Asn Arg Glu Ile Gly Phe Ala Ile Gly Met
210                 215                 220

Pro Val Cys Glu Phe Asp Met Val Lys Asp Pro Glu Val Gln Asp Phe
225                 230                 235                 240

Arg Arg Asn Ile Leu Asn Val Cys Lys Glu Ala Val Asp Leu Arg Asp
            245                 250                 255

Leu Asn Ser Pro His Ser Arg Ala Met Tyr Val Tyr Pro Pro Asn Val
            260                 265                 270

Glu Ser Ser Pro Glu Leu Pro Lys His Ile Tyr Asn Lys Leu Asp Lys
        275                 280                 285

Gly Gln Ile Ile Val Val Ile Trp Val Ile Val Ser Pro Asn Asn Asp
290                 295                 300

Lys Gln Lys Tyr Thr Leu Lys Ile Asn His Asp Cys Val Pro Glu Gln
305                 310                 315                 320

Val Ile Ala Glu Ala Ile Arg Lys Lys Thr Arg Ser Met Leu Leu Ser
            325                 330                 335

Ser Glu Gln Leu Lys Leu Cys Val Leu Glu Tyr Gln Gly Lys Tyr Ile
        340                 345                 350

Leu Lys Val Cys Gly Cys Asp Glu Tyr Phe Leu Glu Lys Tyr Pro Leu
            355                 360                 365

Ser Gln Tyr Lys Tyr Ile Arg Ser Cys Ile Met Leu Gly Arg Met Pro
370                 375                 380

Asn Leu Met Leu Met Ala Lys Glu Ser Leu Tyr Ser Gln Leu Pro Met
385                 390                 395                 400

Asp Cys Phe Thr Met Pro Ser Tyr Ser Arg Arg Ile Ser Thr Ala Thr
            405                 410                 415

Pro Tyr Met Asn Gly Glu Thr Ser Thr Lys Ser Leu Trp Val Ile Asn
        420                 425                 430

Ser Ala Leu Arg Ile Lys Ile Leu Cys Ala Thr Tyr Val Asn Val Asn
            435                 440                 445

Ile Arg Asp Ile Asp Lys Ile Tyr Val Arg Thr Gly Ile Tyr His Gly
450                 455                 460

Gly Glu Pro Leu Cys Asp Asn Val Asn Thr Gln Arg Val Pro Cys Ser
465                 470                 475                 480

Asn Pro Arg Trp Asn Glu Trp Leu Asn Tyr Asp Ile Tyr Ile Pro Asp
            485                 490                 495

Leu Pro Arg Ala Ala Arg Leu Cys Leu Ser Ile Cys Ser Val Lys Gly
        500                 505                 510

Arg Lys Gly Ala Lys Glu His Cys Pro Leu Ala Trp Gly Asn Ile
            515                 520                 525

Asn Leu Phe Asp Tyr Thr Asp Thr Leu Val Ser Gly Lys Met Ala Leu
530                 535                 540

Asn Leu Trp Pro Val Pro His Gly Leu Glu Asp Leu Leu Asn Pro Ile
545                 550                 555                 560

Gly Val Thr Gly Ser Asn Pro Asn Lys Glu Thr Pro Cys Leu Glu Leu
            565                 570                 575

Glu Phe Asp Trp Phe Ser Ser Val Val Lys Phe Pro Asp Met Ser Val
        580                 585                 590

Ile Glu Glu His Ala Asn Trp Ser Val Ser Arg Glu Ala Gly Phe Ser
            595                 600                 605

Tyr Ser His Ala Gly Leu Ser Asn Arg Leu Ala Arg Asp Asn Glu Leu
610                 615                 620

Arg Glu Asn Asp Lys Glu Gln Leu Lys Ala Ile Ser Thr Arg Asp Pro

```
                625                 630                 635                 640
Leu Ser Glu Ile Thr Glu Gln Glu Lys Asp Phe Leu Trp Ser His Arg
                    645                 650                 655
His Tyr Cys Val Thr Ile Pro Glu Ile Leu Pro Lys Leu Leu Leu Ser
                    660                 665                 670
Val Lys Trp Asn Ser Arg Asp Glu Val Ala Gln Met Tyr Cys Leu Val
                675                 680                 685
Lys Asp Trp Pro Pro Ile Lys Pro Glu Gln Ala Met Glu Leu Leu Asp
            690                 695                 700
Cys Asn Tyr Pro Asp Pro Met Val Arg Gly Phe Ala Val Arg Cys Leu
705                 710                 715                 720
Glu Lys Tyr Leu Thr Asp Asp Lys Leu Ser Gln Tyr Leu Ile Gln Leu
                    725                 730                 735
Val Gln Val Leu Lys Tyr Glu Gln Tyr Leu Asp Asn Leu Leu Val Arg
                740                 745                 750
Phe Leu Leu Lys Lys Ala Leu Thr Asn Gln Arg Ile Gly His Phe Phe
                755                 760                 765
Phe Trp His Leu Lys Ser Glu Met His Asn Lys Thr Val Ser Gln Arg
            770                 775                 780
Phe Gly Leu Leu Leu Glu Ser Tyr Cys Arg Ala Cys Gly Met Tyr Leu
785                 790                 795                 800
Lys His Leu Asn Arg Gln Val Glu Ala Met Glu Lys Leu Ile Asn Leu
                    805                 810                 815
Thr Asp Ile Leu Lys Gln Glu Lys Lys Asp Glu Thr Gln Lys Val Gln
                820                 825                 830
Met Lys Phe Leu Val Glu Gln Met Arg Arg Pro Asp Phe Met Asp Ala
            835                 840                 845
Leu Gln Gly Phe Leu Ser Pro Leu Asn Pro Ala His Gln Leu Gly Asn
        850                 855                 860
Leu Arg Leu Glu Glu Cys Arg Ile Met Ser Ser Ala Lys Arg Pro Leu
865                 870                 875                 880
Trp Leu Asn Trp Glu Asn Pro Asp Ile Met Ser Glu Leu Leu Phe Gln
                885                 890                 895
Asn Asn Glu Ile Ile Phe Lys Asn Gly Asp Asp Leu Arg Gln Asp Met
                900                 905                 910
Leu Thr Leu Gln Ile Ile Arg Ile Met Glu Asn Ile Trp Gln Asn Gln
            915                 920                 925
Gly Leu Asp Leu Arg Met Leu Pro Tyr Gly Cys Leu Ser Ile Gly Asp
        930                 935                 940
Cys Val Gly Leu Ile Glu Val Val Arg Asn Ser His Thr Ile Met Gln
945                 950                 955                 960
Ile Gln Cys Lys Gly Gly Leu Lys Gly Ala Leu Gln Phe Asn Ser His
                965                 970                 975
Thr Leu His Gln Trp Leu Lys Asp Lys Asn Lys Gly Glu Ile Tyr Asp
            980                 985                 990
Ala Ala Ile Asp Leu Phe Thr Arg  Ser Cys Ala Gly Tyr  Cys Val Ala
        995                 1000                1005
Thr Phe Ile Leu Gly Ile Gly  Asp Arg His Asn Ser  Asn Ile Met
    1010                1015                1020
Val Lys Asp Asp Gly Gln Leu  Phe His Ile Asp Phe  Gly His Phe
    1025                1030                1035
Leu Asp His Lys Lys Lys Lys  Phe Gly Tyr Lys Arg  Glu Arg Val
    1040                1045                1050
```

```
Pro Phe Val Leu Thr Gln Asp Phe Leu Ile Val Ile Ser Lys Gly
    1055                1060                1065

Ala Gln Glu Cys Thr Lys Thr Arg Glu Phe Glu Arg Phe Gln Glu
    1070                1075                1080

Met Cys Tyr Lys Ala Tyr Leu Ala Ile Arg Gln His Ala Asn Leu
    1085                1090                1095

Phe Ile Asn Leu Phe Ser Met Met Leu Gly Ser Gly Met Pro Glu
    1100                1105                1110

Leu Gln Ser Phe Asp Asp Ile Ala Tyr Ile Arg Lys Thr Leu Ala
    1115                1120                1125

Leu Asp Lys Thr Glu Gln Glu Ala Leu Glu Tyr Phe Met Lys Gln
    1130                1135                1140

Met Asn Asp Ala His His Gly Gly Trp Thr Thr Lys Met Asp Trp
    1145                1150                1155

Ile Phe His Thr Ile Lys Gln His Ala Leu Asn Glu Leu Gly Gly
    1160                1165                1170

Ala His His His His His His
    1175                1180

<210> SEQ ID NO 5
<211> LENGTH: 28
<212> TYPE: DNA
<213> ORGANISM: Artificial
<220> FEATURE:
<223> OTHER INFORMATION: PCR primer

<400> SEQUENCE: 5
cgagaatatg atagattata tgaagaat                                       28

<210> SEQ ID NO 6
<211> LENGTH: 30
<212> TYPE: DNA
<213> ORGANISM: Artificial
<220> FEATURE:
<223> OTHER INFORMATION: PCR primer

<400> SEQUENCE: 6
tggtttaatg ctgttcatac gtttgtcaat                                     30

<210> SEQ ID NO 7
<211> LENGTH: 76
<212> TYPE: DNA
<213> ORGANISM: Artificial
<220> FEATURE:
<223> OTHER INFORMATION: PCR primer

<400> SEQUENCE: 7
gggacaagtt tgtacaaaaa agcaggctac gaaggagata tacatatgcg agaatatgat   60
agattatatg aagaat                                                    76

<210> SEQ ID NO 8
<211> LENGTH: 54
<212> TYPE: DNA
<213> ORGANISM: Artificial
<220> FEATURE:
<223> OTHER INFORMATION: PCR primer

<400> SEQUENCE: 8
actgaagcat cctcctcctc ctcctcctgg tttaatgctg ttcatacgtt tgtc          54
```

<210> SEQ ID NO 9
<211> LENGTH: 54
<212> TYPE: DNA
<213> ORGANISM: Artificial
<220> FEATURE:
<223> OTHER INFORMATION: PCR primer

<400> SEQUENCE: 9

```
attaaaccag gaggaggagg aggaggatgc ttcagtttca taatgcctcc tgct        54
```

<210> SEQ ID NO 10
<211> LENGTH: 57
<212> TYPE: DNA
<213> ORGANISM: Artificial
<220> FEATURE:
<223> OTHER INFORMATION: PCR primer

<400> SEQUENCE: 10

```
agctccgtga tggtgatggt gatgtgctcc agatctgtag tctttccgaa ctgtgtg     57
```

<210> SEQ ID NO 11
<211> LENGTH: 61
<212> TYPE: DNA
<213> ORGANISM: Artificial
<220> FEATURE:
<223> OTHER INFORMATION: PCR primer

<400> SEQUENCE: 11

```
gggaccactt tgtacaagaa agctgggttt aagctccgtg atggtgatgg tgatgtgctc  60
c                                                                  61
```

<210> SEQ ID NO 12
<211> LENGTH: 1194
<212> TYPE: PRT
<213> ORGANISM: Artificial
<220> FEATURE:
<223> OTHER INFORMATION: PI3K kinase construct

<400> SEQUENCE: 12

```
Met Arg Glu Tyr Asp Arg Leu Tyr Glu Glu Tyr Thr Arg Thr Ser Gln
1               5                   10                  15

Glu Ile Gln Met Lys Arg Thr Ala Ile Glu Ala Phe Asn Glu Thr Ile
            20                  25                  30

Lys Ile Phe Glu Glu Gln Cys Gln Thr Gln Glu Arg Tyr Ser Lys Glu
        35                  40                  45

Tyr Ile Glu Lys Phe Lys Arg Glu Gly Lys Glu Lys Glu Ile Gln Arg
    50                  55                  60

Ile Met His Asn Tyr Asp Lys Leu Lys Ser Arg Ile Ser Glu Ile Ile
65                  70                  75                  80

Asp Ser Arg Arg Arg Leu Glu Glu Asp Leu Lys Lys Gln Ala Ala Glu
                85                  90                  95

Tyr Arg Glu Ile Asp Lys Arg Met Asn Ser Ile Lys Pro Gly Gly Gly
            100                 105                 110

Gly Gly Gly Cys Phe Ser Phe Ile Met Pro Pro Ala Met Ala Asp Ile
        115                 120                 125

Leu Asp Ile Trp Ala Val Asp Ser Gln Ile Ala Ser Asp Gly Ser Ile
    130                 135                 140

Pro Val Asp Phe Leu Leu Pro Thr Gly Ile Tyr Ile Gln Leu Glu Val
145                 150                 155                 160

Pro Arg Glu Ala Thr Ile Ser Tyr Ile Lys Gln Met Leu Trp Lys Gln
                165                 170                 175
```

-continued

```
Val His Asn Tyr Pro Met Phe Asn Leu Leu Met Asp Ile Asp Ser Tyr
            180                 185                 190
Met Phe Ala Cys Val Asn Gln Thr Ala Val Tyr Glu Glu Leu Glu Asp
        195                 200                 205
Glu Thr Arg Arg Leu Cys Asp Val Arg Pro Phe Leu Pro Val Leu Lys
    210                 215                 220
Leu Val Thr Arg Ser Cys Asp Pro Gly Glu Lys Leu Asp Ser Lys Ile
225                 230                 235                 240
Gly Val Leu Ile Gly Lys Gly Leu His Glu Phe Asp Ser Leu Lys Asp
                245                 250                 255
Pro Glu Val Asn Glu Phe Arg Arg Lys Met Arg Lys Phe Ser Glu Glu
            260                 265                 270
Lys Ile Leu Ser Leu Val Gly Leu Ser Trp Met Asp Trp Leu Lys Gln
        275                 280                 285
Thr Tyr Pro Pro Glu His Glu Pro Ser Ile Pro Glu Asn Leu Glu Asp
    290                 295                 300
Lys Leu Tyr Gly Gly Lys Leu Ile Val Ala Val His Phe Glu Asn Cys
305                 310                 315                 320
Gln Asp Val Phe Ser Phe Gln Val Ser Pro Asn Met Asn Pro Ile Lys
                325                 330                 335
Val Asn Glu Leu Ala Ile Gln Lys Arg Leu Thr Ile His Gly Lys Glu
            340                 345                 350
Asp Glu Val Ser Pro Tyr Asp Tyr Val Leu Gln Val Ser Gly Arg Val
        355                 360                 365
Glu Tyr Val Phe Gly Asp His Pro Leu Ile Gln Phe Gln Tyr Ile Arg
    370                 375                 380
Asn Cys Val Met Asn Arg Ala Leu Pro His Phe Ile Leu Val Glu Cys
385                 390                 395                 400
Cys Lys Ile Lys Lys Met Tyr Glu Gln Glu Met Ile Ala Ile Glu Ala
                405                 410                 415
Ala Ile Asn Arg Asn Ser Ser Asn Leu Pro Leu Pro Leu Pro Pro Lys
            420                 425                 430
Lys Thr Arg Ile Ile Ser His Val Trp Glu Asn Asn Pro Phe Gln
        435                 440                 445
Ile Val Leu Val Lys Gly Asn Lys Leu Asn Thr Glu Glu Thr Val Lys
    450                 455                 460
Val His Val Arg Ala Gly Leu Phe His Gly Thr Glu Leu Leu Cys Lys
465                 470                 475                 480
Thr Ile Val Ser Ser Glu Val Ser Gly Lys Asn Asp His Ile Trp Asn
                485                 490                 495
Glu Pro Leu Glu Phe Asp Ile Asn Ile Cys Asp Leu Pro Arg Met Ala
            500                 505                 510
Arg Leu Cys Phe Ala Val Tyr Ala Val Leu Asp Lys Val Lys Thr Lys
        515                 520                 525
Lys Ser Thr Lys Thr Ile Asn Pro Ser Lys Tyr Gln Thr Ile Arg Lys
    530                 535                 540
Ala Gly Lys Val His Tyr Pro Val Ala Trp Val Asn Thr Met Val Phe
545                 550                 555                 560
Asp Phe Lys Gly Gln Leu Arg Thr Gly Asp Ile Ile Leu His Ser Trp
                565                 570                 575
Ser Ser Phe Pro Asp Glu Leu Glu Glu Met Leu Asn Pro Met Gly Thr
            580                 585                 590
```

```
Val Gln Thr Asn Pro Tyr Thr Glu Asn Ala Thr Ala Leu His Val Lys
        595                 600                 605

Phe Pro Glu Asn Lys Lys Gln Pro Tyr Tyr Pro Pro Phe Asp Lys
610                 615                 620

Ile Ile Glu Lys Ala Ala Glu Ile Ala Ser Ser Asp Ser Ala Asn Val
625                 630                 635                 640

Ser Ser Arg Gly Gly Lys Lys Phe Leu Pro Val Leu Lys Glu Ile Leu
            645                 650                 655

Asp Arg Asp Pro Leu Ser Gln Leu Cys Glu Asn Glu Met Asp Leu Ile
                660                 665                 670

Trp Thr Leu Arg Gln Asp Cys Arg Glu Ile Phe Pro Gln Ser Leu Pro
            675                 680                 685

Lys Leu Leu Leu Ser Ile Lys Trp Asn Lys Leu Glu Asp Val Ala Gln
        690                 695                 700

Leu Gln Ala Leu Leu Gln Ile Trp Pro Lys Leu Pro Pro Arg Glu Ala
705                 710                 715                 720

Leu Glu Leu Leu Asp Phe Asn Tyr Pro Asp Gln Tyr Val Arg Glu Tyr
                725                 730                 735

Ala Val Gly Cys Leu Arg Gln Met Ser Asp Glu Glu Leu Ser Gln Tyr
            740                 745                 750

Leu Leu Gln Leu Val Gln Val Leu Lys Tyr Glu Pro Phe Leu Asp Cys
        755                 760                 765

Ala Leu Ser Arg Phe Leu Leu Glu Arg Ala Leu Gly Asn Arg Arg Ile
770                 775                 780

Gly Gln Phe Leu Phe Trp His Leu Arg Ser Glu Val His Ile Pro Ala
785                 790                 795                 800

Val Ser Val Gln Phe Gly Val Ile Leu Glu Ala Tyr Cys Arg Gly Ser
            805                 810                 815

Val Gly His Met Lys Val Leu Ser Lys Gln Val Glu Ala Leu Asn Lys
            820                 825                 830

Leu Lys Thr Leu Asn Ser Leu Ile Lys Leu Asn Ala Val Lys Leu Asn
        835                 840                 845

Arg Ala Lys Gly Lys Glu Ala Met His Thr Cys Leu Lys Gln Ser Ala
850                 855                 860

Tyr Arg Glu Ala Leu Ser Asp Leu Gln Ser Pro Leu Asn Pro Cys Val
865                 870                 875                 880

Ile Leu Ser Glu Leu Tyr Val Glu Lys Cys Lys Tyr Met Asp Ser Lys
                885                 890                 895

Met Lys Pro Leu Trp Leu Val Tyr Asn Asn Lys Val Phe Gly Glu Asp
            900                 905                 910

Ser Val Gly Val Ile Phe Lys Asn Gly Asp Asp Leu Arg Gln Asp Met
            915                 920                 925

Leu Thr Leu Gln Met Leu Arg Leu Met Asp Leu Leu Trp Lys Glu Ala
        930                 935                 940

Gly Leu Asp Leu Arg Met Leu Pro Tyr Gly Cys Leu Ala Thr Gly Asp
945                 950                 955                 960

Arg Ser Gly Leu Ile Glu Val Val Ser Thr Ser Glu Thr Ile Ala Asp
            965                 970                 975

Ile Gln Leu Asn Ser Ser Asn Val Ala Ala Ala Ala Phe Asn Lys
        980                 985                 990

Asp Ala Leu Leu Asn Trp Leu Lys  Glu Tyr Asn Ser Gly  Asp Asp Leu
        995                 1000                1005

Asp Arg  Ala Ile Glu Glu Phe  Thr Leu Ser Cys Ala  Gly Tyr Cys
```

-continued

```
                1010                1015                1020
Val Ala Ser Tyr Val Leu Gly Ile Gly Asp Arg His Ser Asp Asn
            1025                1030                1035

Ile Met Val Lys Lys Thr Gly Gln Leu Phe His Ile Asp Phe Gly
        1040                1045                1050

His Ile Leu Gly Asn Phe Lys Ser Lys Phe Gly Ile Lys Arg Glu
    1055                1060                1065

Arg Val Pro Phe Ile Leu Thr Tyr Asp Phe Ile His Val Ile Gln
1070                1075                1080

Gln Gly Lys Thr Gly Asn Thr Glu Lys Phe Gly Arg Phe Arg Gln
        1085                1090                1095

Cys Cys Glu Asp Ala Tyr Leu Ile Leu Arg Arg His Gly Asn Leu
    1100                1105                1110

Phe Ile Thr Leu Phe Ala Leu Met Leu Thr Ala Gly Leu Pro Glu
1115                1120                1125

Leu Thr Ser Val Lys Asp Ile Gln Tyr Leu Lys Asp Ser Leu Ala
        1130                1135                1140

Leu Gly Lys Ser Glu Glu Glu Ala Leu Lys Gln Phe Lys Gln Lys
    1145                1150                1155

Phe Asp Glu Ala Leu Arg Glu Ser Trp Thr Thr Lys Val Asn Trp
1160                1165                1170

Met Ala His Thr Val Arg Lys Asp Tyr Arg Ser Gly Ala His His
        1175                1180                1185

His His His His Gly Ala
    1190

<210> SEQ ID NO 13
<211> LENGTH: 966
<212> TYPE: PRT
<213> ORGANISM: Artificial
<220> FEATURE:
<223> OTHER INFORMATION: PI3K kinase construct

<400> SEQUENCE: 13

Met Ser Glu Glu Ser Gln Ala Phe Gln Arg Gln Leu Thr Ala Leu Ile
1               5                   10                  15

Gly Tyr Asp Val Thr Asp Val Ser Asn Val His Asp Asp Glu Leu Glu
                20                  25                  30

Phe Thr Arg Arg Gly Leu Val Thr Pro Arg Met Ala Glu Val Ala Ser
            35                  40                  45

Arg Asp Pro Lys Leu Tyr Ala Met His Pro Trp Val Thr Ser Lys Pro
        50                  55                  60

Leu Pro Glu Tyr Leu Trp Lys Lys Ile Ala Asn Asn Cys Ile Phe Ile
65                  70                  75                  80

Val Ile His Arg Ser Thr Thr Ser Gln Thr Ile Lys Val Ser Pro Asp
                85                  90                  95

Asp Thr Pro Gly Ala Ile Leu Gln Ser Phe Phe Thr Lys Met Ala Lys
            100                 105                 110

Lys Lys Ser Leu Met Asp Ile Pro Glu Ser Gln Ser Glu Gln Asp Phe
        115                 120                 125

Val Leu Arg Val Cys Gly Arg Asp Glu Tyr Leu Val Gly Glu Thr Pro
    130                 135                 140

Ile Lys Asn Phe Gln Trp Val Arg His Cys Leu Lys Asn Gly Glu Glu
145                 150                 155                 160

Ile His Val Val Leu Asp Thr Pro Pro Asp Pro Ala Leu Asp Glu Val
```

```
                165                 170                 175
Arg Lys Glu Glu Trp Pro Leu Val Asp Asp Cys Thr Gly Val Thr Gly
                180                 185                 190

Tyr His Glu Gln Leu Thr Ile His Gly Lys Asp His Glu Ser Val Phe
            195                 200                 205

Thr Val Ser Leu Trp Asp Cys Asp Arg Lys Phe Arg Val Lys Ile Arg
        210                 215                 220

Gly Ile Asp Ile Pro Val Leu Pro Arg Asn Thr Asp Leu Thr Val Phe
225                 230                 235                 240

Val Glu Ala Asn Ile Gln His Gly Gln Gln Val Leu Cys Gln Arg Arg
                245                 250                 255

Thr Ser Pro Lys Pro Phe Thr Glu Glu Val Leu Trp Asn Val Trp Leu
            260                 265                 270

Glu Phe Ser Ile Lys Ile Lys Asp Leu Pro Lys Gly Ala Leu Leu Asn
        275                 280                 285

Leu Gln Ile Tyr Cys Gly Lys Ala Pro Ala Leu Ser Ser Lys Ala Ser
    290                 295                 300

Ala Glu Ser Pro Ser Ser Glu Ser Lys Gly Lys Val Arg Leu Leu Tyr
305                 310                 315                 320

Tyr Val Asn Leu Leu Leu Ile Asp His Arg Phe Leu Leu Arg Arg Gly
                325                 330                 335

Glu Tyr Val Leu His Met Trp Gln Ile Ser Gly Lys Gly Glu Asp Gln
            340                 345                 350

Gly Ser Phe Asn Ala Asp Lys Leu Thr Ser Ala Thr Asn Pro Asp Lys
        355                 360                 365

Glu Asn Ser Met Ser Ile Ser Ile Leu Leu Asp Asn Tyr Cys His Pro
    370                 375                 380

Ile Ala Leu Pro Lys His Gln Pro Thr Pro Asp Pro Glu Gly Asp Arg
385                 390                 395                 400

Val Arg Ala Glu Met Pro Asn Gln Leu Arg Lys Gln Leu Glu Ala Ile
                405                 410                 415

Ile Ala Thr Asp Pro Leu Asn Pro Leu Thr Ala Glu Asp Lys Glu Leu
            420                 425                 430

Leu Trp His Phe Arg Tyr Glu Ser Leu Lys His Pro Lys Ala Tyr Pro
        435                 440                 445

Lys Leu Phe Ser Ser Val Lys Trp Gly Gln Gln Glu Ile Val Ala Lys
    450                 455                 460

Thr Tyr Gln Leu Leu Ala Arg Arg Glu Val Trp Asp Gln Ser Ala Leu
465                 470                 475                 480

Asp Val Gly Leu Thr Met Gln Leu Leu Asp Cys Asn Phe Ser Asp Glu
                485                 490                 495

Asn Val Arg Ala Ile Ala Val Gln Lys Leu Glu Ser Leu Glu Asp Asp
            500                 505                 510

Asp Val Leu His Tyr Leu Leu Gln Leu Val Gln Ala Val Lys Phe Glu
        515                 520                 525

Pro Tyr His Asp Ser Ala Leu Ala Arg Phe Leu Leu Lys Arg Gly Leu
    530                 535                 540

Arg Asn Lys Arg Ile Gly His Phe Leu Phe Trp Phe Leu Arg Ser Glu
545                 550                 555                 560

Ile Ala Gln Ser Arg His Tyr Gln Gln Arg Phe Ala Val Ile Leu Glu
                565                 570                 575

Ala Tyr Leu Arg Gly Cys Gly Thr Ala Met Leu His Asp Phe Thr Gln
            580                 585                 590
```

```
Gln Val Gln Val Ile Glu Met Leu Gln Lys Val Thr Leu Asp Ile Lys
            595                 600                 605

Ser Leu Ser Ala Glu Lys Tyr Asp Val Ser Ser Gln Val Ile Ser Gln
610                 615                 620

Leu Lys Gln Lys Leu Glu Asn Leu Gln Asn Ser Gln Leu Pro Glu Ser
625                 630                 635                 640

Phe Arg Val Pro Tyr Asp Pro Gly Leu Lys Ala Gly Ala Leu Ala Ile
            645                 650                 655

Glu Lys Cys Lys Val Met Ala Ser Lys Lys Pro Leu Trp Leu Glu
            660                 665                 670

Phe Lys Cys Ala Asp Pro Thr Ala Leu Ser Asn Glu Thr Ile Gly Ile
            675                 680                 685

Ile Phe Lys His Gly Asp Asp Leu Arg Gln Asp Met Leu Ile Leu Gln
            690                 695                 700

Ile Leu Arg Ile Met Glu Ser Ile Trp Glu Thr Glu Ser Leu Asp Leu
705                 710                 715                 720

Cys Leu Leu Pro Tyr Gly Cys Ile Ser Thr Gly Asp Lys Ile Gly Met
            725                 730                 735

Ile Glu Ile Val Lys Asp Ala Thr Thr Ile Ala Lys Ile Gln Gln Ser
            740                 745                 750

Thr Val Gly Asn Thr Gly Ala Phe Lys Asp Glu Val Leu Asn His Trp
            755                 760                 765

Leu Lys Glu Lys Ser Pro Thr Glu Glu Lys Phe Gln Ala Ala Val Glu
770                 775                 780

Arg Phe Val Tyr Ser Cys Ala Gly Tyr Cys Val Ala Thr Phe Val Leu
785                 790                 795                 800

Gly Ile Gly Asp Arg His Asn Asp Asn Ile Met Ile Thr Glu Thr Gly
            805                 810                 815

Asn Leu Phe His Ile Asp Phe Gly His Ile Leu Gly Asn Tyr Lys Ser
            820                 825                 830

Phe Leu Gly Ile Asn Lys Glu Arg Val Pro Phe Val Leu Thr Pro Asp
            835                 840                 845

Phe Leu Phe Val Met Gly Thr Ser Gly Lys Lys Thr Ser Pro His Phe
            850                 855                 860

Gln Lys Phe Gln Asp Ile Cys Val Lys Ala Tyr Leu Ala Leu Arg His
865                 870                 875                 880

His Thr Asn Leu Leu Ile Ile Leu Phe Ser Met Met Leu Met Thr Gly
            885                 890                 895

Met Pro Gln Leu Thr Ser Lys Glu Asp Ile Glu Tyr Ile Arg Asp Ala
            900                 905                 910

Leu Thr Val Gly Lys Asn Glu Glu Asp Ala Lys Lys Tyr Phe Leu Asp
            915                 920                 925

Gln Ile Glu Val Cys Arg Asp Lys Gly Trp Thr Val Gln Phe Asn Trp
930                 935                 940

Phe Leu His Leu Val Leu Gly Ile Lys Gln Gly Glu Lys His Ser Ala
945                 950                 955                 960

His His His His His His
            965

<210> SEQ ID NO 14
<211> LENGTH: 45
<212> TYPE: DNA
<213> ORGANISM: Artificial
<220> FEATURE:
```

<223> OTHER INFORMATION: PCR primer

<400> SEQUENCE: 14
tcctcctcct cctcctcctg gtttaatgct gttcatacgt ttgtc     45

<210> SEQ ID NO 15
<211> LENGTH: 26
<212> TYPE: DNA
<213> ORGANISM: Artificial
<220> FEATURE:
<223> OTHER INFORMATION: PCR primer

<400> SEQUENCE: 15
atgccccctg gggtggactg ccccat     26

<210> SEQ ID NO 16
<211> LENGTH: 26
<212> TYPE: DNA
<213> ORGANISM: Artificial
<220> FEATURE:
<223> OTHER INFORMATION: PCR primer

<400> SEQUENCE: 16
ctactgcctg ttgtctttgg acacgt     26

<210> SEQ ID NO 17
<211> LENGTH: 53
<212> TYPE: DNA
<213> ORGANISM: Artificial
<220> FEATURE:
<223> OTHER INFORMATION: PCR primer

<400> SEQUENCE: 17
attaaaccag gaggaggagg aggaggaccc cctggggtgg actgccccat gga     53

<210> SEQ ID NO 18
<211> LENGTH: 56
<212> TYPE: DNA
<213> ORGANISM: Artificial
<220> FEATURE:
<223> OTHER INFORMATION: PCR primer

<400> SEQUENCE: 18
agctccgtga tggtgatggt gatgtgctcc ctgcctgttg tctttggaca cgttgt     56

<210> SEQ ID NO 19
<211> LENGTH: 60
<212> TYPE: DNA
<213> ORGANISM: Artificial
<220> FEATURE:
<223> OTHER INFORMATION: PCR primer

<400> SEQUENCE: 19
gggaccactt tgtacaagaa agctgggttt aagctccgtg atggtgatgg tgagtgctcc     60

<210> SEQ ID NO 20
<211> LENGTH: 1169
<212> TYPE: PRT
<213> ORGANISM: Artificial
<220> FEATURE:
<223> OTHER INFORMATION: PI3K kinase construct

<400> SEQUENCE: 20

Met Arg Glu Tyr Asp Arg Leu Tyr Glu Glu Tyr Thr Arg Thr Ser Gln
1               5                   10                  15

```
Glu Ile Gln Met Lys Arg Thr Ala Ile Glu Ala Phe Asn Thr Ile
             20                  25                  30

Lys Ile Phe Glu Glu Gln Cys Gln Thr Gln Arg Tyr Ser Lys Glu
         35                  40                  45

Tyr Ile Glu Lys Phe Lys Arg Glu Gly Asn Glu Lys Glu Ile Gln Arg
     50                  55                  60

Ile Met His Asn Tyr Asp Lys Leu Lys Ser Arg Ile Ser Glu Ile Ile
65                  70                  75                  80

Asp Ser Arg Arg Arg Leu Glu Glu Asp Leu Lys Lys Gln Ala Ala Glu
                 85                  90                  95

Tyr Arg Glu Ile Asp Lys Arg Met Asn Ser Ile Lys Pro Gly Gly Gly
            100                 105                 110

Gly Gly Gly Pro Pro Gly Val Asp Cys Pro Met Glu Phe Trp Thr Lys
        115                 120                 125

Glu Glu Asn Gln Ser Val Val Asp Phe Leu Leu Pro Thr Gly Val
    130                 135                 140

Tyr Leu Asn Phe Pro Val Ser Arg Asn Ala Asn Leu Ser Thr Ile Lys
145                 150                 155                 160

Gln Leu Leu Trp His Arg Ala Gln Tyr Glu Pro Leu Phe His Met Leu
                165                 170                 175

Ser Gly Pro Glu Ala Tyr Val Phe Thr Cys Ile Asn Gln Thr Ala Glu
            180                 185                 190

Gln Gln Glu Leu Glu Asp Glu Arg Arg Leu Cys Asp Val Gln Pro
    195                 200                 205

Phe Leu Pro Val Leu Arg Leu Val Ala Arg Gly Asp Arg Val Lys
210                 215                 220

Lys Leu Ile Asn Ser Gln Ile Ser Leu Leu Ile Gly Lys Gly Leu His
225                 230                 235                 240

Glu Phe Asp Ser Leu Cys Asp Pro Glu Val Asn Asp Phe Arg Ala Lys
                245                 250                 255

Met Cys Gln Phe Cys Glu Glu Ala Ala Arg Arg Gln Gln Leu Gly
            260                 265                 270

Trp Glu Ala Trp Leu Gln Tyr Ser Phe Pro Leu Gln Leu Glu Pro Ser
    275                 280                 285

Ala Gln Thr Trp Gly Pro Gly Thr Leu Arg Leu Pro Asn Arg Ala Leu
    290                 295                 300

Leu Val Asn Val Lys Phe Glu Gly Ser Glu Glu Ser Phe Thr Phe Gln
305                 310                 315                 320

Val Ser Thr Lys Asp Val Pro Leu Ala Leu Met Ala Cys Ala Leu Arg
            325                 330                 335

Lys Lys Ala Thr Val Phe Arg Gln Pro Leu Val Glu Gln Pro Glu Asp
            340                 345                 350

Tyr Thr Leu Gln Val Asn Gly Arg His Glu Tyr Leu Tyr Gly Ser Tyr
        355                 360                 365

Pro Leu Cys Gln Phe Gln Tyr Ile Cys Ser Cys Leu His Ser Gly Leu
    370                 375                 380

Thr Pro His Leu Thr Met Val His Ser Ser Ile Leu Ala Met Arg
385                 390                 395                 400

Asp Glu Gln Ser Asn Pro Ala Pro Gln Val Lys Pro Arg Ala Lys
                405                 410                 415

Pro Pro Pro Ile Pro Ala Lys Lys Pro Ser Ser Val Ser Leu Trp Ser
            420                 425                 430

Leu Glu Gln Pro Phe Arg Ile Glu Leu Ile Gln Gly Ser Lys Val Asn
```

```
            435                 440                 445
Ala Asp Glu Arg Met Lys Leu Val Val Gln Ala Gly Leu Phe His Gly
450                 455                 460

Asn Glu Met Leu Cys Lys Thr Val Ser Ser Glu Val Ser Val Cys
465                 470                 475                 480

Ser Glu Pro Val Trp Lys Gln Arg Leu Glu Phe Asp Ile Asn Ile Cys
                    485                 490                 495

Asp Leu Pro Arg Met Ala Arg Leu Cys Phe Ala Leu Tyr Ala Val Ile
                500                 505                 510

Glu Lys Ala Lys Lys Ala Arg Ser Thr Lys Lys Lys Ser Lys Lys Ala
            515                 520                 525

Asp Cys Pro Ile Ala Trp Ala Asn Leu Met Leu Phe Asp Tyr Lys Asp
        530                 535                 540

Gln Leu Lys Thr Gly Glu Arg Cys Leu Tyr Met Trp Pro Ser Val Pro
545                 550                 555                 560

Asp Glu Lys Gly Glu Leu Leu Asn Pro Thr Gly Thr Val Arg Ser Asn
                565                 570                 575

Pro Asn Thr Asp Ser Ala Ala Leu Leu Ile Cys Leu Pro Glu Val
                580                 585                 590

Ala Pro His Pro Val Tyr Tyr Pro Ala Leu Glu Lys Ile Leu Glu Leu
            595                 600                 605

Gly Arg His Ser Glu Cys Val His Val Thr Glu Glu Glu Gln Leu Gln
610                 615                 620

Leu Arg Glu Ile Leu Glu Arg Gly Ser Gly Glu Leu Tyr Glu His
625                 630                 635                 640

Glu Lys Asp Leu Val Trp Lys Leu Arg His Glu Val Gln Glu His Phe
                645                 650                 655

Pro Glu Ala Leu Ala Arg Leu Leu Val Thr Lys Trp Asn Lys His
                660                 665                 670

Glu Asp Val Ala Gln Met Leu Tyr Leu Leu Cys Ser Trp Pro Glu Leu
            675                 680                 685

Pro Val Leu Ser Ala Leu Glu Leu Leu Asp Phe Ser Phe Pro Asp Cys
690                 695                 700

His Val Gly Ser Phe Ala Ile Lys Ser Leu Arg Lys Leu Thr Asp Asp
705                 710                 715                 720

Glu Leu Phe Gln Tyr Leu Leu Gln Leu Val Gln Val Leu Lys Tyr Glu
                725                 730                 735

Ser Tyr Leu Asp Cys Glu Leu Thr Lys Phe Leu Leu Asp Arg Ala Leu
                740                 745                 750

Ala Asn Arg Lys Ile Gly His Phe Leu Phe Trp His Leu Arg Ser Glu
            755                 760                 765

Met His Val Pro Ser Val Ala Leu Arg Phe Gly Leu Ile Leu Glu Ala
770                 775                 780

Tyr Cys Arg Gly Ser Thr His His Met Lys Val Leu Met Lys Gln Gly
785                 790                 795                 800

Glu Ala Leu Ser Lys Leu Lys Ala Leu Asn Asp Phe Val Lys Leu Ser
                805                 810                 815

Ser Gln Lys Thr Pro Lys Pro Gln Thr Lys Glu Leu Met His Leu Cys
            820                 825                 830

Met Arg Gln Glu Ala Tyr Leu Glu Ala Leu Ser His Leu Gln Ser Pro
835                 840                 845
```

-continued

```
Leu Asp Pro Ser Thr Leu Leu Ala Glu Val Cys Val Glu Gln Cys Thr
    850             855             860
Phe Met Asp Ser Lys Met Lys Pro Leu Trp Ile Met Tyr Ser Asn Glu
865             870             875             880
Glu Ala Gly Ser Gly Gly Ser Val Gly Ile Ile Phe Lys Asn Gly Asp
                885             890             895
Asp Leu Arg Gln Asp Met Leu Thr Leu Gln Met Ile Gln Leu Met Asp
            900             905             910
Val Leu Trp Lys Gln Gly Leu Asp Leu Arg Met Thr Pro Tyr Gly
        915             920             925
Cys Leu Pro Thr Gly Asp Arg Thr Gly Leu Ile Glu Val Val Leu Arg
    930             935             940
Ser Asp Thr Ile Ala Asn Ile Gln Leu Asn Lys Ser Asn Met Ala Ala
945             950             955             960
Thr Ala Ala Phe Asn Lys Asp Ala Leu Leu Asn Trp Leu Lys Ser Lys
                965             970             975
Asn Pro Gly Glu Ala Leu Asp Arg Ala Ile Glu Glu Phe Thr Leu Ser
            980             985             990
Cys Ala Gly Tyr Cys Val Ala Thr Tyr Val Leu Gly Ile Gly Asp Arg
            995             1000            1005
His Ser Asp Asn Ile Met Ile Arg Glu Ser Gly Gln Leu Phe His
    1010            1015            1020
Ile Asp Phe Gly His Phe Leu Gly Asn Phe Lys Thr Lys Phe Gly
    1025            1030            1035
Ile Asn Arg Glu Arg Val Pro Phe Ile Leu Thr Tyr Asp Phe Val
    1040            1045            1050
His Val Ile Gln Gln Gly Lys Thr Asn Asn Ser Glu Lys Phe Glu
    1055            1060            1065
Arg Phe Arg Gly Tyr Cys Glu Arg Ala Tyr Thr Ile Leu Arg Arg
    1070            1075            1080
His Gly Leu Leu Phe Leu His Leu Phe Ala Leu Met Arg Ala Ala
    1085            1090            1095
Gly Leu Pro Glu Leu Ser Cys Ser Lys Asp Ile Gln Tyr Leu Lys
    1100            1105            1110
Asp Ser Leu Ala Leu Gly Lys Thr Glu Glu Ala Leu Lys His
    1115            1120            1125
Phe Arg Val Lys Phe Asn Glu Ala Leu Arg Glu Ser Trp Lys Thr
    1130            1135            1140
Lys Val Asn Trp Leu Ala His Asn Val Ser Lys Asp Asn Arg Gln
    1145            1150            1155
Glu Leu Gly Gly Ala His His His His His
    1160            1165
```